US010463718B2

(12) United States Patent
Colosi et al.

(10) Patent No.: US 10,463,718 B2
(45) Date of Patent: *Nov. 5, 2019

(54) ADENO-ASSOCIATED VIRUS FACTOR VIII VECTORS

(71) Applicants: BIOMARIN PHARMACEUTICAL INC., Novato, CA (US); UCL BUSINESS PLC, London (GB)

(72) Inventors: Peter Cameron Colosi, Novato, CA (US); Amit Nathwani, London (GB); Jenny McIntosh, London (GB); Edward Tuddenham, London (GB)

(73) Assignee: BIOMARIN PHARMACEUTICAL INC., Novato, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/294,310

(22) Filed: Oct. 14, 2016

(65) Prior Publication Data

US 2017/0095538 A1    Apr. 6, 2017

Related U.S. Application Data

(63) Continuation of application No. 14/482,648, filed on Sep. 10, 2014, now Pat. No. 9,504,762.

(60) Provisional application No. 61/877,042, filed on Sep. 12, 2013.

(51) Int. Cl.
| | | |
|---|---|---|
| *A01N 63/00* | (2006.01) | |
| *A61K 38/37* | (2006.01) | |
| *A61K 48/00* | (2006.01) | |
| *C12N 7/00* | (2006.01) | |
| *C07K 14/755* | (2006.01) | |
| *C12N 15/86* | (2006.01) | |

(52) U.S. Cl.
CPC .......... *A61K 38/37* (2013.01); *A61K 48/0058* (2013.01); *A61K 48/0066* (2013.01); *C07K 14/755* (2013.01); *C12N 7/00* (2013.01); *C12N 15/86* (2013.01); *C12N 2750/14132* (2013.01); *C12N 2750/14142* (2013.01); *C12N 2750/14143* (2013.01); *C12N 2750/14151* (2013.01); *C12N 2800/22* (2013.01); *C12N 2830/008* (2013.01)

(58) Field of Classification Search
USPC .................................... 424/93.1, 93.2, 93.21
See application file for complete search history.

(56) References Cited

U.S. PATENT DOCUMENTS

| | | | |
|---|---|---|---|
| 6,200,560 B1 | 3/2001 | Couto et al. | |
| 6,221,349 B1 | 4/2001 | Couto et al. | |
| 6,383,794 B1 * | 5/2002 | Mountz .................. | C12N 15/86 435/235.1 |
| 7,351,577 B2 | 4/2008 | Couto et al. | |
| 8,030,065 B2 | 10/2011 | Gray | |
| 9,393,323 B2 * | 7/2016 | Nathwani ............ | C07K 14/755 |
| 2007/0042462 A1 | 2/2007 | Hildinger | |
| 2008/0131403 A1 * | 6/2008 | Wang .................. | C12N 15/1137 424/93.6 |
| 2013/0024960 A1 | 1/2013 | Nathwani et al. | |

FOREIGN PATENT DOCUMENTS

| | | | |
|---|---|---|---|
| WO | WO-2011/005968 A1 | | 1/2011 |
| WO | WO 2011005968 | * | 1/2011 |

OTHER PUBLICATIONS

Edelstein (Journal Gene Med., 2004, vol. 6, p. 597-602).*
Wu (Mol. Therapy, 2008, vol. 16, No. 2, p. 280-289).*
Lu (Human Gene Therapy, Jun. 2008, vol. 19, No. 6, p. 648-654).*
Ishiwata (J. Gene Med., 2009, vol. 11, p. 1020-1029).*
McIntosh (Blood Apr. 2013, vol. 121, No. 17, p. 3335-3344).*
Rogers (Front Biosci., 2015, vol. 20, p. 556-603).*
De Simone et al., Cis- and trans-acting elements responsible for the cell-specific expression of the human alpha 1-antitrypsin gene, EMBO J., 6(9):2759-66 (1987).
Edelstein et al., Gene therapy clinical trials worldwide 1989-2004—an overview, J. Gene Med., 6(6):597-602 (2004).
Ghosh et al., Expanding adeno-associated viral vector capacity: a tale of two vectors, Biotechnol. Genet. Eng. Rev., 24:165-77 (2007).
Hirsch et al., Little vector, big gene transduction: fragmented genome reassembly of adeno-associated virus, Mol. Ther., 18(1):6-8 (2010).
International Preliminary Report on Patentability, International Application No. PCT/US2014/054960, dated Mar. 15, 2016.
International Search Report and Written Opinion, International Application No. PCT/US2014/054960, dated Dec. 22, 2014.
Ishiwata et al., Liver-restricted expression of the canine factor VIII gene facilitates prevention of inhibitor formation in factor VIII-deficient mice, J. Gene Med., 11(11):1020-9 (2009).
Lu et al., Complete correction of hemophilia A with adeno-associated viral vectors containing a full-size expression cassette, Hum. Gene Ther., 19(6):648-54 (2008).
McIntosh et al., Therapeutic levels of FVIII following a single peripheral vein administration of rAAV vector encoding a novel human factor VIII variant, Blood, 121 (17):3335-44 (2013).
Nathwani et al., Adenovirus-associated virus vector-mediated gene transfer in hemophilia B, N. Engl. J. Med., 365(25):2357-65 (2011).
Rogers et al., Gene therapy for hemophilia, Front Biosci (Landmark Ed.), 20:556-603 (2015).
Sarkar et al., A single adeno-associated virus (AAV)-murine factor VIII vector partially corrects the hemophilia A phenotype, J. Thromb. Haemost., 1(2):220-6 (2003).

(Continued)

*Primary Examiner* — Michael C Wilson
(74) *Attorney, Agent, or Firm* — Marshall, Gerstein & Borun LLP

(57) ABSTRACT

The invention provides improved adeno-associated virus (AAV) Factor VIII (FVIII) vectors, including AAV FVIII vectors that produce a functional Factor VIII polypeptide and AAV FVIII vectors with high expression activity.

10 Claims, 21 Drawing Sheets

Specification includes a Sequence Listing.

(56) References Cited

OTHER PUBLICATIONS

Ward et al., Codon optimization of human factor VIII cDNAs leads to high-level expression, Blood, 117(3):798-807 (2011).

Wu et al., Optimization of self-complementary AAV vectors for liver-directed expression results in sustained correction of hemophilia B at low vector dose, Mol. Ther., 16(2):280-9 (2008).

Yan et al., Inverted terminal repeat sequences are important for intermolecular recombination and circularization of adeno-associated virus genomes, J. Virol., 79(1):364-79 (2005).

Burton et al., Coexpression of factor VIII heavy and light chain adeno-associated viral vectors produces biologically active protein, Proc. Natl. Acad. Sci. USA, 96(22):12725-30 (Oct. 1999).

Youjin et al., The treatment of hemophilia A: from protein replacement to AAV-mediated gene therapy, Biotechnol. Lett., 31(3):321-8 (Mar. 2009).

Chao et al., Sustained expression of human factor VIII in mice using a parvovirus-based vector, Blood, 95(5):1594-9 (Mar. 2000).

Gnatenko et al., Human factor VIII can be packaged and functionally expressed in an adeno-associated virus background: applicability to haemophilia A gene therapy, Br. J. Haematol., 104(1):27-36 (Jan. 1999).

European Patent Application No. 14771729.2, Third Party Observations Communication Pursuant to Rule 114(2) EPC, dated Feb. 18, 2019.

\* cited by examiner

Schematic of Proto 1

Schematic of Proto 1S

Schematic of Proto 4

Schematic of Proto 5

Schematic of Proto 6

Insert ApoE/C1 enhancer (forward orientation) into FVIII intron

Schematic of Proto 7

Insert ApoE/C1 enhancer (reverse orientation) into FVIII intron

ADENO-ASSOCIATED VIRUS FACTOR VIII VECTORS

This application is a continuation of U.S. patent application Ser. No. 14/842,648, filed Sep. 10, 2014, which claims priority to the U.S. Provisional Patent Application Ser. No. 61/877,042, filed Sep. 12, 2013, which are incorporated by reference herein their entirety.

FIELD OF INVENTION

The invention relates to adeno-associated virus (AAV) Factor VIII (FVIII) vectors, including AAV FVIII vectors with high expression activity and AAV FVIII vectors that express full-length or truncated functional FVIII. The invention also relates to methods of making the herein described AAV FVIII vectors and associated therapeutic uses of thereof.

BACKGROUND

Adeno-associated virus (AAV) is a small, replication-defective, non-enveloped animal virus that infects humans and some other primate species. Several features of AAV make this virus an attractive vehicle for delivery of therapeutic proteins by gene therapy, including, for example, that AAV is not known to cause human disease and induces a mild immune response, and that AAV vectors can infect both dividing and quiescent cells without integrating into the host cell genome. Gene therapy vectors using AAV have been successfully used in some clinical trials, for example, for the delivery of human Factor IX (FIX) to the liver for the treatment of Hemophilia B (Nathwani et al., New Engl. J. Med. 365:2357-2365, 2011).

AAV gene therapy vectors do have some drawbacks, however. In particular, the cloning capacity of AAV vectors is limited as a consequence of the DNA packaging capacity of the virus. The single-stranded DNA genome of wild-type AAV is about 4.7 kilobases (kb). In practice, AAV genomes of up to about 5.0 kb appear to be completely packaged, i.e., be full-length, into AAV virus particles. With the requirement that the nucleic acid genome in AAV vectors must have two AAV inverted terminal repeats (ITRs) of about 145 bases, the DNA packaging capacity of an AAV vector is such that a maximum of about 4.4 kb of protein-coding sequence can be encapsidated.

Due to this size constraint, large therapeutic genes, i.e., those greater than about 4.4 kb in length, are generally not suitable for use in AAV vectors. One such therapeutic gene is the Factor VIII (FVIII) gene, which has an mRNA of about 7.0 kb that encodes a polypeptide of 2332 amino acids comprising, from N- to C-terminus, a 19 amino acid signal peptide, and three large domains (i.e., the heavy chain or A domain, the central or B domain, and the light chain or C domain). One strategy that had been employed to overcome the AAV vector size limitation for FVIII was to use two AAV vectors, one encoding the heavy chain or A domain, and the other encoding the light chain or C domain (see, e.g., Coutu et al., U.S. Pat. Nos. 6,221,349, 6,200,560 and 7,351,577). Another strategy to circumvent this size constraint was to generate AAV vectors encoding FVIII in which the central portion or B domain of the protein has been deleted and replaced with a 14 amino acid linker, known as the SQ sequence (Ward et al., Blood, 117:798-807, 2011, and McIntosh et al., Blood 121:3335-3344, 2013).

While AAV vectors have been reported in the literature having AAV genomes of >5.0 kb, in many of these cases the 5' or 3' ends of the encoded genes appear to be truncated (see Hirsch et al., Molec. Ther. 18-6-8, 2010, and Ghosh et al., Biotech. Genet. Engin. Rev. 24:165-178, 2007). It has been shown, however, that overlapping homologous recombination occurs in AAV infected cells between nucleic acids having 5' end truncations and 3' end truncations so that a "complete" nucleic acid encoding the large protein is generated, thereby reconstructing a functional, full-length gene.

There is a need for novel AAV vectors encoding a functional Factor VIII protein useful in gene therapy approaches for the treatment of hemophilia A. As such, the present invention relates to AAV vectors that encode functionally active FVIII such that either the AAV virions encapsidate the entire nucleic acid encoding the therapeutic protein, i.e., completely packaged AAV FVIII vectors, thereby avoiding the above-mentioned problems of oversized genomes, or at least produce a functionally active Factor VIII protein, which may or may not be truncated. Moreover, to avoid capsid directed immune response, AAV vectors should have the highest possible transduction/expression activity of the target protein per capsid particle. This invention also relates to the production of completely AAV FVIII vectors with high expression activity. Finally, the present invention relates to methods for producing the herein described AAV Factor VIII vectors and associated methods for using the same.

SUMMARY OF INVENTION

The present invention provides AAV vectors encoding functionally active FVIII (referred to herein as "AAV FVIII vectors"). The genomes encoding functionally active FVIII are preferably at most 7.0 kb in length, more preferably at most 6.5 kb in length, yet more preferably at most 6.0 kb in length, yet more preferably at most 5.5 kb in length, yet more preferably at most 5.0 kb in length, with enhanced promoter function.

As used herein, a "functionally active FVIII" is a FVIII protein that has the functionality of a wild-type FVIII protein in vitro, when expressed in cultured cells, or in vivo, when expressed in cells or body tissues. This includes, for example, allowing for blood coagulation to occur and decreasing the time that it takes for blood to clot in a subject suffering from Hemophilia A. Wild-type FVIII participates in blood coagulation via the coagulation cascade, acting as a co-factor for activated FIX (FIXa) which, in the presence of calcium ions and phospholipids forms a complex that converts Factor X (FX) into activated FX (FXa). Accordingly, a functionally active FVIII can form a complex with FIXa, which can convert FX to FXa.

As used herein, an "AAV vector" refers to nucleic acids, either single-stranded or double-stranded, having an AAV 5' inverted terminal repeat (ITR) sequence and an AAV 3' ITR flanking a protein-coding sequence operably linked to transcription regulatory elements, i.e., one or more promoters and/or enhancers, and a polyadenylation sequence, and, optionally, one or more introns inserted between exons of the protein-coding sequence. A single-stranded AAV vector refers to nucleic acids that are present in the genome of an AAV virus particle, and can be either the sense strand or the anti-sense strand of the nucleic acid sequences disclosed herein. The size of such single-stranded nucleic acids is provided in bases. A double-stranded AAV vector refers to nucleic acids that are present in the DNA of plasmids, e.g., pUC19, or genome of a double-stranded virus, e.g., baculovirus, used to express or transfer the AAV vector nucleic acids. The size of such double-stranded nucleic acids in provided in base pairs (bp).

The term "inverted terminal repeat (ITR)" as used herein refers to the art-recognized regions found at the 5' and 3' termini of the AAV genome which function in cis as origins of DNA replication and as packaging signals for the viral genome. AAV ITRs, together with the AAV rep coding region, provide for efficient excision and rescue from, and integration of a nucleotide sequence interposed between two flanking ITRs into a host cell genome. Sequences of certain AAV-associated ITRs are disclosed by Yan et al., J. Virol. 79 (1):364-379 (2005) which is herein incorporated by reference in its entirety.

A "transcription regulatory element" refers to nucleotide sequences of a gene involved in regulation of genetic transcription including a promoter, plus response elements, activator and enhancer sequences for binding of transcription factors to aid RNA polymerase binding and promote expression, and operator or silencer sequences to which repressor proteins bind to block RNA polymerase attachment and prevent expression. The term "liver specific transcription regulatory element" refers to a regulatory element that modulates gene expression specifically in the liver tissue. Examples of liver specific regulatory elements include, but are not limited to, the mouse thyretin promoter (mTTR), the endogenous human factor VIII promoter (F8), human alpha-1-antitrypsin promoter (hAAT) and active fragments thereof, human albumin minimal promoter, and mouse albumin promoter. Enhancers derived from liver specific transcription factor binding sites are also contemplated, such as EBP, DBP, HNF1, HNF3, HNF4, HNF6, with Enh1.

In one embodiment, the AAV vector of the invention comprises a nucleic acid encoding functionally active FVIII having the B domain replaced by the 14 amino acid SQ sequence, i.e., encoding FVIII SQ. The SQ sequence is disclosed in Ward et al., Blood, 117:798-807, 2011, and McIntosh et al., Blood 121:3335-3344, 2013. The FVIII coding region sequence is a codon-optimized sequence (see Nathwani et al., US Pat. App. Pub. No. 2013/0024960A1, published Jan. 24, 2013, which is incorporated herein by reference in its entirety, and McIntosh et al., Blood 121: 3335-3344, 2013). This sequence is referred herein as the "UCL SQ FVIII."

In a first aspect, the AAV vector of the invention comprises Proto 1, which is depicted schematically in FIG. 2A, and comprises the nucleic acid sequence set forth in SEQ ID NO: 1.

In a second aspect, the AAV vector of the invention comprises Proto 1S, which is depicted schematically in FIG. 2B, and comprises the nucleic acid sequence set forth in SEQ ID NO: 2.

In a third aspect, the AAV vector of the invention comprises Proto 2S, which is depicted schematically in FIG. 2C, and comprises the nucleic acid sequence set forth in SEQ ID NO: 3.

In a fourth aspect, the AAV vector of the invention comprises Proto 3S, which is depicted schematically in FIG. 2D, and comprises the nucleic acid sequence set forth in SEQ ID NO: 4.

In another embodiment, the AAV vector of the invention comprises a nucleic acid encoding FVIII lacking the entire B domain, including the SQ sequence, and the a3 domain, which is located just N-terminal to the light chain or C domain. The FVIII coding region sequence is a codon-optimized sequence (see Nathwani et al., US Pat. App. Pub. No. 2013/0024960A1, published Jan. 24, 2013, which is incorporated herein by reference in its entirety, and McIntosh et al., Blood 121:3335-3344, 2013).

In a first aspect, the AAV vector of the invention comprises Proto 4, which is depicted schematically in FIG. 3A, and comprises the nucleic acid sequence set forth in SEQ ID NO: 5.

In a second aspect, the AAV vector of the invention comprises Proto 5, which is depicted schematically in FIG. 3B, and comprises the nucleic acid sequence set forth in SEQ ID NO: 6.

In a third aspect, the AAV vector of the invention comprises Proto 6, which is depicted schematically in FIG. 3C, and comprises the nucleic acid sequence set forth inSEQ ID NO: 7.

In a fourth aspect, the AAV vector of the invention comprises Proto 7, which is depicted schematically in FIG. 3D, and comprises the nucleic acid sequence set forth in SEQ ID NO: 8.

In another embodiment, the AAV vector of the invention comprises a nucleic acid comprising an AAV2 5' inverted terminal repeat (ITR), a liver-specific transcription regulatory region, a codon-optimized functionally active FVIII coding region, optionally one or more introns, a polyadenylation sequence, and an AAV2 3' ITR. In a preferred embodiment, the liver-specific transcription regulatory region comprises a shortened ApoE enhancer sequence, a 186 base human alpha anti-trypsin (hAAT) proximal promoter, including 42 bases of the 5' untranslated region (UTR), and one or more enhancers selected from the group consisting of (i) a 34 base human ApoE/C1 enhancer, (ii) a 32 base human AAT promoter distal X region and (iii) 80 additional bases of distal element of the human AAT proximal promoter; and a codon-optimized functionally active FVIII coding regions encodes the FVIII SQ variant. In another preferred embodiment, the liver specific transcription regulatory region comprises a a1 microglobulin enhancer sequence and the 186 base human alpha anti-trypsin (AAT) proximal promoter.

In a first aspect, the AAV vector of the invention comprises Construct 100ATG comprising the nucleic acid sequence forth in SEQ ID NO: 9.

In a second aspect, the AAV vector of the invention comprises Construct 100ATG bGH poly A comprising the nucleic acid sequence set forth in SEQ ID NO: 10.

In a third aspect, the AAV vector of the invention comprises Construct 100ATG short bGH polyA sequence set forth in SEQ ID NO: 11.

In a fourth aspect, the AAV vector of the invention comprises Construct 103ATG comprising the nucleic acid sequence forth in SEQ ID NO: 12.

In a fifth aspect, the AAV vector of the invention comprises Construct 103ATG short bGH poly A comprising the nucleic acid sequence set forth in SEQ ID NO: 13.

In a sixth aspect, the AAV vector of the invention comprises Construct 105ATG bGH poly A comprising the nucleic acid sequence set forth in SEQ ID NO: 14.

In a seventh aspect, the AAV vector of the invention comprises Construct DC172ATG FVIII comprising the nucleic acid sequence set forth in SEQ ID NO: 15.

In an eighth aspect, the AAV vector of the invention comprises Construct DC172ATG FVIII hAAT comprising the nucleic acid sequence set forth in SEQ ID NO: 16.

In a ninth aspect, the AAV vector of the invention comprises Construct DC172 2×HCR ATG FVIII comprising the nucleic acid sequence set forth in SEQ ID NO: 17.

In a tenth aspect, the AAV vector of the invention comprises Construct DC172 2×HCR ATG FVIII hAAT comprising the nucleic acid sequence set forth in SEQ ID NO: 18.

In an eleventh aspect, the AAV vector of the invention comprises Construct 2× SerpinA hAAT ATG FVIII comprising the nucleic acid sequence set forth in SEQ ID NO: 19.

In a twelfth aspect, the AAV vector of the invention comprises Construct 2× SerpinA hAAT ATG FVIII 2× µ-globulin enhancer comprising the nucleic acid sequence set forth in SEQ ID NO: 20.

In a thirteenth aspect, the AAV vector of the invention Construct 100ATG short polyA 2× µ-globulin enhancer comprising the nucleic acid sequence set forth in SEQ ID NO: 21.

In a fourteenth aspect, the AAV vector of the invention comprises Construct Factor VIII-BMN001 comprising the nucleic acid sequence set forth in SEQ ID NO: 22.

In a fifteenth aspect, the AAV vector of the invention comprises Construct Factor VIII-BMN002 sequence set forth in SEQ ID NO: 23.

In a sixteenth aspect, the AAV vector of the invention comprises Construct 99 comprising the nucleic acid sequence set forth in SEQ ID NO: 24.

In a seventeenth aspect, the AAV vector of the invention comprises Construct 100 comprising the nucleic acid sequence set forth in SEQ ID NO: 25.

In an eighteenth aspect, the AAV vector of the invention comprises Construct 100 reverse orientation comprising the nucleic acid sequence set forth in SEQ ID NO: 26.

In a nineteenth aspect, the AAV vector of the invention Construct 100AT comprising the nucleic acid sequence set forth in SEQ ID NO: 27.

In a twentieth aspect, the AAV vector of the invention Construct 100AT 2× MG comprising the nucleic acid sequence set forth in SEQ ID NO: 28.

In a twenty-first aspect, the AAV vector of the invention comprises Construct 100AT 2× MG bGH polyA comprising the nucleic acid sequence set forth in SEQ ID NO: 29.

In a twenty-second aspect, the AAV vector of the invention comprises Construct 100AT 2× MG (reverse) bGH polyA comprising the nucleic acid sequence set forth in SEQ ID NO: 30.

In a twenty-third aspect, the AAV vector of the invention comprises Construct 100 bGH polyA comprising the nucleic acid sequence set forth in SEQ ID NO: 31.

In a twenty-fourth aspect, the AAV vector of the invention comprises Construct 100-400 comprising the nucleic acid sequence set forth in SEQ ID NO: 32.

In a twenty-fifth aspect, the AAV vector of the invention comprises Construct 101 comprising the nucleic acid sequence set forth in SEQ ID NO: 33.

In a twenty-sixth aspect, the AAV vector of the invention comprises Construct 102 sequence comprising the nucleic acid sequence set forth in SEQ ID NO: 34.

In a twenty-seventh aspect, the AAV vector of the invention comprises Construct 103 comprising the nucleic acid sequence set forth in SEQ ID NO: 35.

In a twenty-ninth aspect, the AAV vector of the invention comprises Construct 103 reverse orientation comprising the nucleic acid sequence set forth in SEQ ID NO: 36.

In a thirtieth aspect, the AAV vector of the invention comprises Construct 103AT comprising the nucleic acid sequence set forth in SEQ ID NO: 37.

In a thirty-first aspect, the AAV vector of the invention comprises Construct 103AT 2×MG comprising the nucleic acid sequence set forth in SEQ ID NO: 38.

In a thirty-second aspect, the AAV vector of the invention comprises Construct 103AT 2×MG bGH polyA comprising the nucleic acid sequence set forth in SEQ ID NO: 39.

In a thirty-third aspect, the AAV vector of the invention comprises the Construct 103 bGH polyA comprising the nucleic acid sequence set forth in SEQ ID NO: 40.

In a thirty-fourth aspect, the AAV vector of the invention comprises Construct 104 comprising the nucleic acid comprising the nucleic acid sequence set forth in SEQ ID NO: 41.

In a thirty-fifth aspect, the AAV vector of the invention comprises Construct 105 comprising the nucleic acid sequence set forth in SEQ ID NO: 42.

In a thirty-sixth aspect, the AAV vector of the invention comprises Construct 106 comprising the nucleic acid sequence set forth in SEQ ID NO: 43.

In a thirty-seventh aspect, the AAV vector of the invention comprises Construct 106AT comprising the nucleic acid sequence set forth in SEQ ID NO: 44.

In a thirty-eighth aspect, the AAV vector of the invention comprises Construct 2× SerpinA hAAT comprising the nucleic acid sequence set forth in SEQ ID NO: 45.

In yet other embodiments, the present invention is directed to vector constructs encoding a functional Factor VIII polypeptide, wherein said constructs comprise one or more of the individual elements of the above described constructs and combinations thereof, in one or more different orientation(s). The present invention is also directed to the above described constructs in an opposite orientation.

The AAV vectors of the invention in single strand is less than about 7.0 kb in length, or is less than 6.5 kb in length, or is less than 6.4 kb in length, or is less than 6.3 kb in length, or is less than 6.2 kb in length, or is less than 6.0 kb in length, or is less than 5.8 kb in length, or is less than 5.6 kb in length, or is less than 5.5 kb in length, or is less than 5.4 kb in length, or is less than 5.4 kb in length, or is less than 5.2 kb in length or is less than 5.0 kb in length. The AAV vectors of the invention in single strand ranges from about 5.0 kb to about 6.5 kb in length, or ranges from about 4.8 kb to about 5.2 k in length, or 4.8 kb to 5.3 kb in length, or ranges from about 4.9 kb to about 5.5 kb in length, or about 4.8 kb to about 6.0 kb in length, or about 5.0 kb to 6.2 kb in length or about 5.1 kb to about 6.3 kb in length, or about 5.2 kb to about 6.4 kb in length, or about 5.5 kb to about 6.5 kb in length.

In another embodiment, the invention provides for methods of producing a recombinant adeno-associated virus (AAV) particle comprising any of the AAV vectors of the invention. The methods comprise the steps of culturing a cell that has been transfected with any of the AAV vectors of the invention and recovering recombinant AAV from the supernatant of the transfected cell.

The cells of the invention are any cell type are susceptible to baculovirus infection, including insect cells such as High Five, Sf9, Se301, SeIZD2109, SeUCR1, Sf9, Sf900+, Sf21, BTI-TN-5B1-4, MG-1, Tn368, HzAm1, BM-N, Ha2302, Hz2E5 and Ao38. Preferred mammalian cells used can be HEK293, HeLa, CHO, NS0, SP2/0, PER.C6, Vero, RD, BHK, HT 1080, A549, Cos-7, ARPE-19 and MRC-5 cells, and including mammalian cells such as HEK293, HeLa, CHO, NS0, SP2/0, PER.C6, Vero, RD, BHK, HT 1080, A549, Cos-7, ARPE-19 and MRC-5 cells.

The invention also provides for a viral particle comprising any of the AAV vectors of the invention or any viral particle produced by the forgoing methods of the invention.

An "AAV virion" or "AAV viral particle" or "AAV vector particle" refers to a viral particle composed of at least one AAV capsid protein and an encapsidated polynucleotide AAV vector. If the particle comprises a heterologous polynucleotide (i.e. a polynucleotide other than a wild-type AAV genome such as a transgene to be delivered to a mammalian cell), it is typically referred to as an "AAV vector particle" or simply an "AAV vector". Thus, production of AAV vector particle necessarily includes production of AAV vector, as such a vector is contained within an AAV vector particle.

The invention also provides for cells comprising any of the AAV vectors of the invention, and viral particles produced by these cells of the invention.

In another embodiment, the invention provides for methods of treating a patient suffering from hemophilia A comprising administering to the patient an effective amount of any of the AAV vectors of the invention, or a viral particle of the invention or a viral particles produced by a method of the invention.

In a further embodiment, the invention provides for a use of any of the AAV vectors of the invention for preparation of a medicament for the treatment of hemophilia A. In one aspect, the medicament comprises an amount of AAV vector that expresses human FVIII in an amount effective to treat hemophilia A.

In another embodiment, the invention provides for a composition comprising any of the AAV vectors of the invention for the treatment of hemophilia A. In one aspect, the composition comprises an amount of AAV vector that expresses human FVIII in an amount effective to treat hemophilia A.

In another embodiment, the AAV vectors of the invention are used to produce AAV viral particles that are useful to treat a patient suffering from Hemophilia A.

DESCRIPTION OF DRAWINGS

FIG. 2A provides a schematic of the Proto 1 vector. Starting from the UCL SQ vector (see FIG. 1), the extraneous wild-type AAV2 viral sequences were deleted, and sequences corresponding to restriction sites between the human AAT 5' UTR and the human FVIII coding region, and between the human FVIII termination codon and the synthetic polyadenylation sequence, were removed. FIG. 2B provides a schematic of the Proto 1S vector. Starting from the Proto 1 vector, 10 bases at the 3' end of the AAV2 5'ITR and 10 bases at the 5' end of the 3' ITR were deleted. FIG. 2C provides a schematic of the Proto 2S vector. Starting from the Proto 1S vector, the human ApoE/C1 enhancer and human AAT promoter distal X region were moved into a 100 base synthetic intron that was inserted between exons 1 and 2 of the human FVIII sequence. As indicated by the arrows, the orientation of the human ApoE/C1 enhancer and human AAT promoter distal X region are reversed compared to their orientation in Proto 1S. FIG. 2D provides a schematic of the Proto 3S vector. Starting from Proto 2S, the human AAT promoter distal X region is replaced by a second copy of the human ApoE/C1 enhancer in the reverse orientation.

FIG. 3A provides a schematic of the Proto 4 vector. Starting from the Proto 1 vector, the SQ sequence and a3 domain were deleted. FIG. 3B provides a schematic of the Proto 5 vector. Starting from the Proto 4 vector, a 129 base FVIII intron was inserted between exons 1 and 2 of the human Factor VIII sequence. FIG. 3C provides a schematic of the Proto 6 vector. Starting from the Proto 5 vector, a second copy of the human ApoE/C1 enhancer was inserted in the forward orientation into the FVIII intron. FIG. 3R provides a schematic of the Proto 7 vector. Starting from the Proto 5 vector, a second copy of the human ApoE/C1 enhancer was inserted in the reverse orientation into the FVIII intron.

FIG. 4A provides a schematic of Construct 100ATG. FIG. 4B provides a schematic of Construct 100ATG bGH polyA. FIG. 4C provides a schematic of Construct 100ATG short bGH poly A. FIG. 4D provides a schematic of Construct 103ATG. FIG. 4E provides a schematic of Construct 103ATG short bGH poly A. FIG. 4F provides a schematic of Construct 105ATG bGH polyA. FIG. 4G provides a schematic of Construct DC172ATG FVIII. FIG. 4H provides a schematic of Construct DC172ATG FVIII hAAT. FIG. 4I provides a schematic of Construct DC172 2×HCR ATG FVIII. FIG. 4J provides a schematic of Construct DC 172 2×HCR ATG FVIII hAAT. FIG. 4K provides a schematic of Construct 2× SerpinA hAAT ATG FVIII. FIG. 4AA provides a schematic of Construct 103. FIG. 4BB provides a schematic of Construct 103 reverse orientation. FIG. 4CC provides a schematic of Construct 103AT. FIG. 4DD provides a schematic of Construct 103AT 2× MG. FIG. 4EE provides a schematic of Construct 103AT 2× MG bGH poly A. FIG. 4FF provides a schematic of 103 sbGH poly A. FIG. 4GG provides a schematic of Construct 104. FIG. 4HH provides a schematic of Construct 105. FIG. 4II provides a schematic of Construct 106. FIG. 4JJ provides a schematic of Construct 106AT. FIG. 4KK provides a schematic of Construct 2× SerpinA hAAT.

DETAILED DESCRIPTION

Oversized AAV vectors are randomly truncated at the 5' ends and lack a 5' AAV ITR. Because AAV is a single-stranded DNA virus, and packages either the sense or antisense strand, the sense strand in oversized AAV vectors lacks the 5' AAV ITR and possibly portions of the 5' end of the target protein-coding gene, and the antisense strand in oversized AAV vectors lacks the 3' ITR and possibly portions of the 3' end of the target protein-coding gene. A functional transgene is produced in oversized AAV vector infected cells by annealing of the sense and antisense truncated genomes within the target cell.

The invention provides for AAV vectors encoding functionally active FVIII, i.e., completely packaged AAV FVIII vectors or AAV FVIII vectors with high expression activity. The AAV FVIII vectors of the invention have improved expression/particle, as well as improved AAV virus production yield and simplified purification. Introducing one or more introns into the FVIII protein-coding region enhances expression. Reconfiguring the number and positioning of enhancers also enhances expression.

UCL SQ Vector

Figure 1:
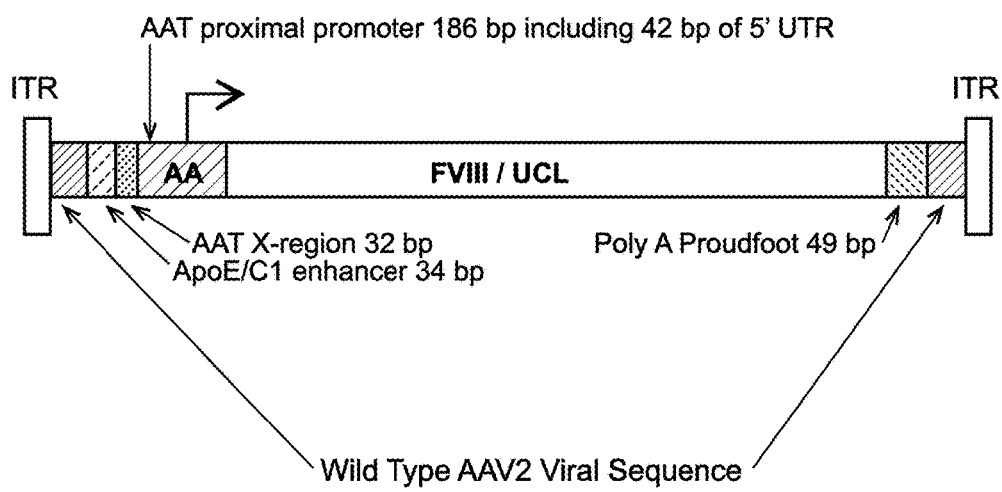
FIG. 1 provides a schematic of the UCL SQ vector. From left to right, the UCL SQ vector comprises the AAV2 5' ITR, wild-type AAV2 viral sequence, the 34 base human ApoE/C1 enhancer, the 32 base human AAT promoter distal X region, the 186 base human AAT promoter, including 42 bases of 5' UTR sequence, the codon-optimized human FVIII SQ sequence (see Nathwani et al., US Pat. App. Pub. No. 2013/0024960A1, published Jan. 24, 2013, which is incorporated herein by reference in its entirety, and McIntosh et al., Blood 121:3335-3344, 2013), the 49 bases synthetic polyadenylation sequence, wild-type AAV2 viral sequence, and the AAV2 3'ITR. The UCL SQ vector is 5081 bases in length.

The UCL SQ vector, which is described in detail in Nathwani et al., US Pat. App. Pub. No. 2013/0024960A1, published Jan. 24, 2013, which is incorporated herein by reference in its entirety, and McIntosh et al., Blood 121: 3335-3344, 2013, is an oversized, i.e., greater than 5.0 kb, AAV vector. As shown in FIG. 1, the UCL SQ vector comprises, from left to right, the AAV serotype 2 (AAV2) 5' ITR, wild-type AAV2 viral sequence, the 34 base human apolipoprotein E (ApoE)/C1 enhancer, the 32 base human alpha anti-trypsin (AAT) promoter distal X region, the 186 base human AAT promoter, including 42 bases of 5' untranslated region (UTR) sequence, the codon-optimized human FVIII sequence in which the B domain is replaced with the 14 amino acid SQ sequence, the 49 bases synthetic polyadenylation sequence, wild-type AAV2 viral sequence, and the AAV2 3'ITR. The UCL SQ vector is 5081 bases in length.

As shown in Nathwani et al., US Pat. App. Pub. No. 2013/0024960A1, published Jan. 24, 2013, and McIntosh et al., Blood 121:3335-3344, 2013, the UCL SQ vector expresses functionally active FVIII in vitro and in vivo.

Proto 1, Proto 1S, Proto 2S and Proto 3S Vectors

To avoid the problem of over-sized AAV vectors and/or to increase the expression of the AAV vectors, the invention provides completely packaged, smaller, i.e., less than 5.0 kb, AAV vectors encoding the FVIII SQ variant. The 4970 bp nucleotide sequence of sequence of Proto 1 is set forth in SEQ ID NO: 1.

To generate the AAV vector Proto 1, sequences that appear to be unnecessary for production of functionally active FVIII were deleted as compared to the UCL SQ vector. As shown in Example 1, 110 bases of extraneous DNA were removed, including 53 bases of AAV2 viral sequence 3' to the AAV2 5'ITR, 46 bases of AAV2 viral sequence 5' to the AAV2 3'ITR, and 11 bases adjacent to the codon-optimized FVIII SQ coding region. The resultant Proto 1 vector is 4970 bases in length. When designed, it was unknown whether the Proto 1 vector would be capable of expressing functional FVIII polypeptide, either in vitro or in vivo.

To generate the AAV vector Proto 1S, 10 bases at the 3' end of the AAV2 5'ITR, and 10 bases at the 5' end of the AAV32 3'ITR, were removed from the Proto 1 vector. The resultant Proto 1S vector is 4950 bases in length. The nucleotide sequence of sequence of Proto 1S is set forth in SEQ ID NO: 2.

To generate the AAV vector Proto 2S, a synthetic 100 base intron was inserted between exons 1 and 2 of the codon-optimized FVIII SQ sequence in the Proto 1S vector. The 34 bases ApoE/C1 enhancer and 32 base human AAT promoter distal X region was removed from upstream of the human AAT promoter and inserted into the synthetic intron in the reverse orientation (as compared to the orientation when these elements are located upstream of the human AAT promoter). The resultant Proto 2S vector is 4983 bases in length. The nucleotide sequence of sequence of Proto 2S is set forth in SEQ ID NO: 3.

To generate the AAV vector Proto 3S, the human AAT promoter distal X region was removed from the Proto 2S vector, and replaced with a second copy of the 34 bases ApoE/C1 enhancer in the reverse orientation. The resultant Proto 3S vector is 4984 bases in length. The nucleotide sequence of sequence of Proto 3S is set forth in SEQ ID NO: 4.

Proto 4, Proto 5, Proto 6 and Proto 7 Vectors

To reduce the size of AAV vectors and/or increase the expression of the AAV vectors, the invention also provides completely packaged, smaller, i.e., less than 5.0 kb, AAV vectors encoding B domain and a3 domain deleted FVIII.

To generate the AAV vector Proto 4, the 14 amino acid SQ sequence and the a3 domain located adjacent to the C domain was removed from the Proto 1 vector. The total amount of FVIII sequence deleted is 55 amino acids or 165 bases. The resultant Proto 4 vector is 4805 bases in length. The nucleotide sequence of sequence of Proto 4 is set forth in SEQ ID NO: 5.

To generate the AAV vector Proto 5, a 129 base truncated FVIII intron was inserted between exons 1 and 2 of the codon-optimized FVIII sequence in the Proto 4 vector. The resultant Proto 5 vector is 4934 bases in length. The nucleotide sequence of sequence of Proto 5 is set forth in SEQ ID NO: 6.

To generate the AAV Proto 6 vector, 34 bases of the FVIII intron were replaced with a second copy of the 34 base human ApoE/C1 enhancer in the forward orientation in the Proto 5 vector. The resultant Proto 6 vector is 4934 bases in length. The nucleotide sequence of sequence of Proto 6 is set forth in SEQ ID NO: 7.

To generate the AAV Proto 7 vector, 34 bases of the FVIII intron were replaced with a second copy of the 34 base human ApoE/C1 enhancer in the reverse orientation in the Proto 5 vector. The resultant Proto 7 vector is 4934 bases in length. The nucleotide sequence of sequence of Proto 7 is set forth in SEQ ID NO: 8.

Additional AAV FVIII Vectors With Improved Promoter/Enhancer Sequences

Oversized AAV vectors with strong promoters were generated to increase expression of B domain and a3 domain deleted FVIII, and these constructs were generated with modified enhancer and/or promoter sequences. In some embodiments, the AAV FVIII vectors express a truncated functional FVIII. These constructs comprised one or more promoter and enhancer sequences such as ApoE HCR or fragments thereof, the μ-globulin enhancer or fragments thereof, the human alpha 1 antitrypsin promoter (hAAT) or fragments thereof, Serpin A enhancer or fragments thereof, the LP1 promoter enhancer or fragments thereof or macro-globulin enhancer or fragment thereof. These constructs comprise a polyadenylation sequence such as the bGH poly A sequence or the synthetic rabbit β-globin poly A sequence.

In some embodiment, the constructs comprise an intron or fragments of an intron such as a hAAT intron or a human β-globin intron.

Construct 100ATG is 5511 bases in length. This construct is set forth in SEQ ID NO: 9 in which bases 1-145 are the 5'AAV2 ITR, bases 160-502 are an ApoE HCR, bases 509-726 are a hAAT promoter, bases 727-910 are a modified human β-globin 2nd intron, bases 923-5296 are a codon optimized SQ FVIII, bases 5305-5352 are a synthetic rabbit β-globin poly A and bases 5367-5511 are the 3' AAV2 ITR.

Construct 100ATG bGH poly A is 5688 bases in length. This construct is set forth in SEQ ID NO: 10 in which bases 1-145 are the 5' AAV2 ITR, bases 160-502 are an ApoE HCR, bases 509-726 are a hAAT promoter, bases 727-910 are a modified human β-globin 2nd intron, bases 923-5296 are a codon optimized SQ FVIII, bases 5305-5529 are a bGH poly A and bases 5544-5688 are the 3' AAV2 ITR.

Construct 100ATG short bGH poly A is 5613 bases in length. This construct is set forth in SEQ ID NO: 11 in which bases 1-145 are the 5' AAV2 ITR, bases 160-502 are an ApoE HCR, bases 509-726 are a hAAT promoter, bases 727-910 are a modified human β-globin 2nd intron, bases 923-5296 are a codon optimized SQ FVIII, bases 5305-5454 are a short bGH poly A and bases 5469-5613 are the 3' AAV2 ITR.

Construct 103ATG is 5362 bases in length. This construct is set forth in SEQ ID NO: 12 in which bases 1-145 are the 5' AAV2 ITR, bases 169-344 are four copies (4×) of a 44 bp ApoE repeat, bases 360-577 are a hAAT promoter, bases 578-761 are a modified human β-globin $2^{nd}$ intron, bases 774-5147 are a codon optimized SQ FVIII, bases 5156-5203 are a synthetic rabbit β-globin poly A and bases 5218-5362 are the 3' AAV2 ITR.

Construct 103ATG short bGH poly A is 5464 bases in length. This construct is set forth in SEQ ID NO: 13 in which bases 1-145 are the 5' AAV2 ITR, bases 169-344 are four copies (4×) of a 44 bp ApoE repeat, bases 360-577 are a hAAT promoter, bases 578-761 are a modified human β-globin $2^{nd}$ intron, bases 774-5147 are a codon optimized SQ FVIII, bases 5156-5305 are a bGH short poly A and bases 5320-5464 are the 3' AAV2 ITR.

Construct 105ATG bGH polyA is 6354 bases in length. This construct is set forth in SEQ ID NO: 14 in which bases 1-145 are the 5' AAV2 ITR, bases 173-512 are two copies (2×) of a 170 bp microglobulin enhancer, bases 519-736 are a hAAT promoter, bases 737-920 are a modified human β-globin $2^{nd}$ intron, bases 933-5306 are a codon optimized SQ FVIII, bases 5315-5539 are a bGH poly A, bases 5546-6195 are two copies (2×) of a 325 bp ApoE HCR and bases 6210-6354 are the 3' AAV2 ITR.

Construct DC172ATG FVIII is 6308 bases in length. This construct is set forth in SEQ ID NO: 15 in which bases 1-145 are the 5' AAV2 ITR, bases 160-449 are two copies (2×) of a 145 bp macroglobulin enhancer, bases 450-1347 are an 898 bp hAAT promoter, bases 1348-1531 are a modified human β-globin $2^{nd}$ intron, bases 1544-5917 are a codon optimized SQ FVIII, bases 5926-6149 are a bGH poly A and bases 6164-6308 are the 3' AAV2 ITR.

Construct DC172ATG FVIII hAAT is 5635 bases in length, This construct is set forth as SEQ ID NO: 16 in which bases 1-145 are the 5' AAV2 ITR, bases 160-449 are two copies (2×) of a 145 bp macroglobulin enhancer, bases 457-674 are a hAAT promoter, bases 675-858 are a modified human β-globin $2^{nd}$ intron, bases 871-5244 are a codon optimized SQ FVIII, bases 5253-5476 are a bGH poly A and bases 5490-5635 are the 3' AAV2 ITR.

Construct DC172 2×HCR ATG FVIII is 6962 bases in length. This construct is set forth in SEQ ID NO: 17 in which bases 1-145 are the 5' AAV2 ITR, bases 160-807 are two copies (2×) of a 321 bp ApoE HCR, bases 814-1103 are two copies (2×) of a 145 bp macroglobulin enhancer, bases 1104-2001 are a 898 bp hAAT promoter, bases 2002-2185 are a modified human β-globin $2^{nd}$ intron, bases 2198-6571 are a codon optimized SQ FVIII, bases 6580-6803 are a bGH poly A and bases 6818-6962 are the 3' AAV2 ITR.

Construct DC172 2×HCR ATG FVIII hAAT is 6289 bases in length. This construct is set forth in SEQ ID NO: 18 in which bases 1-145 are the 5' AAV2 ITR, bases 160-807 are two copies (2×) of a 321 bp ApoE HCR, bases 814-1103 are two copies (2×) of a 145 bp macroglobulin enhancer, bases 1111-1328 are a hAAT promoter, bases 1329-1512 are a modified human β-globin $2^{nd}$ intron, bases 1525-5898 are a codon optimized SQ FVIII, bases 5907-6130 are a bGH poly A and bases 6245-6289 are the 3' AAV2 ITR.

Construct 2× SerpinA hAAT ATG FVIII is 5430 bases in length. This construct is set forth in SEQ ID NO: 19 in which bases 1-145 are the 5' AAV2 ITR, bases 168-309 are two copies (2×) of a 71 bp SerpinA enhancer, bases 326-543 are a hAAT promoter, bases 544-727 are a modified human β-globin $2^{nd}$ intron, bases 740-5113 are a codon optimized SQ FVIII, bases 5122-5271 are a short bGH poly A, and bases 5286-5430 are the 3'AAV2 ITR.

Construct 2× SerpinA hAAT ATG FVIII 2× μ-globulin enhancer is 5779 bases in length. This construct is set forth in SEQ ID NO: 20 in which bases 1-145 are the 5' AAV2 ITR, bases 168-309 are two copies (2×) of a 71 bp SerpinA enhancer, bases 326-543 are a hAAT promoter, bases 544-727 are a modified human β-globin $2^{nd}$ intron, bases 740-5113 are a codon optimized SQ FVIII, bases 5122-5271 are a short bGH poly A, bases 5279-5618 are two copies (2×) of a 170 bp μ-globulin enhancer and bases 5635-5779 are the 3' AAV2 ITR.

Construct 100ATG short bGH poly A 2× μ-globulin enhancer is 5962 bases in length. This construct is set forth in SEQ ID NO: 21 in which bases 1-145 are the 5' AAV2 ITR, bases 160-502 are an ApoE HCR, bases 509-726 are a hAAT promoter, bases 727-910 are a modified human β-globin $2^{nd}$ intron, bases 923-5296 are a codon optimized SQ FVIII, bases 5305-5454 are a short bGH poly A, bases 5462-5801 are two copies (2×) of a 170 bp microglobulin enhancer and bases 5818-5962 are the 3' AAV2 ITR.

Construct Factor VIII-BMN001 is 5919 bases in length. This construct is set forth in SEQ ID NO: 22 in which bases 1-145 are the 5' AAV2 ITR, bases 160-480 are an ApoE HCR, bases 487-884 are a 398 bp hAAT promoter, bases 885-1145 are a truncated hAAT intron, bases 1155-5528 are a codon optimized SQ FVIII, bases 5537-5760 are a bGH poly A and bases 5775-5919 are the 3' AAV2 ITR.

Construct FVIII-BMN002 is 5306 bases in length. This construct is set forth in SEQ ID NO: 23 in which bases 1-145 are the 5' AAV2 ITR, bases 175-705 are an LP1 promoter/enhancer, bases 718-5091 are a codon optimized SQ FVIII, bases 5100-5147 are a synthetic rabbit β-globin poly A and bases 5162-5306 are the 3' AAV2 ITR.

Construct 99 is 5461 bases in length. This construct is set forth in SEQ ID NO: 24 in which bases 1-145 are the 5' AAV2 ITR, bases 169-627 are an ApoE HCR/MAR, bases 634-866 are a hAAT promoter, bases 873-5246 are a codon optimized SQ FVIII, bases 5255-5302 are a synthetic rabbit β-globin poly A and bases 5317-5461 are the 3' AAV2 ITR.

Construct 100 is 5327 bases in length. This construct is set forth in SEQ ID NO: 25 in which bases 1-145 are the 5' AAV2 ITR, bases 169-493 are an ApoE HCR, bases 509-726 are a hAAT promoter, bases 739-5112 are a codon optimized SQ FVIII, bases 5121-5168 are a synthetic rabbit β-globin poly A and bases 5183-5327 are the 3' AAV2 ITR.

Construct 100 reverse orientation is 5309 bases in length. This construct is set forth in SEQ ID NO: 26 in which bases 1-145 are the 5' AAV2 ITR, bases 160-484 are an ApoE HCR in reverse orientation, bases 491-708 are a hAAT promoter, bases 721-5094 are a codon optimized SQ FVIII, bases 5103-5150 are a synthetic rabbit β-globin poly A and bases 5165-5309 are the 3' AAV2 ITR.

Construct 100AT is 5532 bases in length. This construct is set forth in SEQ ID NO: 27 in which bases 1-145 are the 5' AAV2 ITR, bases 169-493 are an ApoE HCR, bases 509-726 are a hAAT promoter, bases 727-931 are a hAAT intron, bases 944-5317 are a codon optimized SQ FVIII, bases 5326-5373 are a synthetic rabbit β-globin poly A and bases 5388-5532 are the 3' AAV2 ITR.

Construct 100AT 2× MG is 5877 bases in length. This construct is set forth in SEQ ID NO: 28 in which bases 1-145 are the 5' AAV2 ITR, bases 169-493 are an ApoE HCR, bases 508-847 are two copies (2×) of a 170 bp μ-globulin enhancer, bases 854-1071 are a hAAT promoter, bases 1072-1276 are a hAAT intron, bases 1289-5662 are a codon optimized SQ FVIII, bases 5671-5718 are a synthetic rabbit β-globin poly A and bases 5733-5877 are the 3' AAV2 ITR.

Construct 100AT 2× MG bGH poly A is 6054 bases in length. This construct is set forth in SEQ ID NO: 29 in which bases 1-145 are the 5' AAV2 ITR, bases 169-493 are an ApoE HCR, bases 508-847 are two copies (2×) of a 170 bp μ-globulin enhancer, bases 854-1071 are a hAAT promoter, bases 1072-1276 are a hAAT intron, bases 1289-5662 are a codon optimized SQ FVIII, bases 5671-5895 are a bGH poly A and bases 5910-6054 are the 3' AAV2 ITR.

Construct 100AT 2× MG (reverse) bGH poly A is 6054 bases in length. This construct is set forth in SEQ ID NO: 30 in which bases 1-145 are the 5' AAV2 ITR, bases 169-493 are an ApoE HCR, bases 508-847 are two copies (2×) of a 170 bp μ-globulin enhancer in reverse orientation, bases 854-1071 are a hAAT promoter, bases 1072-1276 are a hAAT intron, bases 1289-5662 are a codon optimized SQ FVIII, bases 5671-5895 are a bGH poly A and bases 5910-6054 are the 3' AAV2 ITR.

Construct 100 bGH poly A is 5504 bases in length. This construct is set forth in SEQ ID NO: 31 in which bases 1-145 are the 5' AAV2 ITR, bases 169-493 are an ApoE HCR, bases 509-726 are a hAAT promoter, bases 739-5112 are a codon optimized SQ FVIII, base pairs 5121-5345 are a bGH poly A and bases 5360-5504 are the 3' AAV2 ITR.

Construct 100-400 is 5507 bases in length. This construct is set forth in SEQ ID NO: 32 in which bases 1-145 are the 5' AAV2 ITR, bases 169-493 are an ApoE HCR, bases 512-906 are a 398 bp hAAT promoter, bases 919-5292 are a codon optimized SQ FVIII, bases 5301-5348 are a synthetic rabbit β-globin poly A and bases 5363-5507 are the 3' AAV2 ITR.

Construct 101 is 5311 base in length. This construct is set forth in SEQ ID NO: 33 in which bases 1-145 are the 5' AAV2 ITR, bases 170-477 are two copies (2×) of a 154 bp ApoE HCR, bases 493-710 are a hAAT promoter, bases 723-5096 are a codon optimized SQ FVIII, bases 5105-5152 are a synthetic rabbit β-globin poly A and bases 5167-5311 are the 3' AAV2 ITR.

Construct 102 is 5156 bases in length. This construct is set forth in SEQ ID NO: 34 in which bases 1-145 are the 5' AAV2 ITR, bases 169-322 are a 154 bp ApoE HCR, bases 338-555 are a hAAT promoter, bases 568-4941 are a codon optimized SQ FVIII, bases 4950-4997 are a synthetic rabbit β-globin poly A and bases 5012-5156 are the 3' AAV2 ITR.

Construct 103 is 5178 bases in length. This construct is set forth in SEQ ID NO: 35 in which bases 1-145 are the 5' AAV2 ITR, bases 169-344 are four copies (4×) of a 44 bp ApoE HCR, bases 360-577 are a hAAT promoter, bases 590-4963 are a codon optimized SQ FVIII, bases 4972-5019 are a synthetic rabbit β-globin poly A and bases 5034-5178 are the 3' AAV2 ITR.

Construct 103 reverse orientation is 5160 bases in length. This construct is set forth in SEQ ID NO: 36 in which bases 1-145 are the 5' AAV2 ITR, bases 160-335 are four copies (4×) of a 44 bp ApoE HCR in reverse orientation, bases 342-559 are a hAAT promoter, bases 572-4945 are a codon optimized SQ FVIII, bases 4954-5001 are a synthetic rabbit β-globin poly A and bases 5016-5160 are the 3' AAV2 ITR.

Construct 103AT is 5383 bases in length. This construct is set forth in SEQ ID NO: 37 in which bases 1-145 are the 5' AAV2 ITR, bases 169-344 are four copies (4×) of a 44 bp ApoE HCR, bases 360-577 are a hAAT promoter, bases 578-782 are a hAAT intron, bases 795-4374 are a codon optimized SQ FVIII, bases 5177-5224 are a synthetic rabbit β-globin poly A and bases 5239-5383 are the 3' AAV2 ITR.

Construct 103AT 2× MG is 5728 bases in length. This construct is set forth in SEQ ID NO: 38 in which bases 1-145 are the 5' AAV2 ITR, bases 169-344 are four copies (4×) of a 44 bp ApoE HCR, bases 359-698 are two copies (2×) of a 170 bp μ-globulin enhancer, bases 705-922 are a hAAT promoter, bases 923-1127 are a hAAT intron, bases 1140-5513 are a codon optimized SQ FVIII, bases 5522-5569 are a synthetic rabbit β-globin poly A and bases 5584-5728 are the 3' AAV2 ITR.

Construct 103AT 2× MG bGH poly A is 5905 bases in length. This construct is set forth in SEQ ID NO: 39 in which bases 1-145 are the 5' AAV2 ITR, bases 169-344 are four copies (4×) of a 44 bp ApoE HCR, bases 359-698 are two copies (2×) of a 170 bp μ-globulin enhancer, bases 705-922 are a hAAT promoter, bases 923-1127 are a hAAT intron, bases 1140-5513 are a codon optimized SQ FVIII, bases 5522-5746 are a synthetic rabbit β-globin poly A and bases 5761-5905 are the 5' AAV2 ITR.

Construct 103 bGH poly A is 5355 bases in length. This construct is set forth in SEQ ID NO: 40 in which bases 1-145 are the 5' AAV2 ITR, bases 169-344 are four copies (4×) of a 44 bp ApoE HCR, bases 360-577 are a hAAT promoter, bases 590-4963 are a codon optimized SQ FVIII, bases 4972-5196 are a synthetic rabbit β-globin poly A and bases 5211-5355 are the 3' AAV2 ITR.

Construct 104 is 5618 bases in length. This construct is set forth in SEQ ID NO: 41 in which bases 1-145 are the 5' AAV2 ITR, bases 169-784 are four copies (4×) of a 154 bp ApoE HCR, bases 800-1017 are a hAAT promoter, bases 1030-5403 are a codon optimized SQ FVIII, bases 5412-5459 are a synthetic rabbit β-globin poly A and bases 5474-5618 are the 3' AAV2 ITR.

Construct 105 is 5993 bases in length. This construct is set forth in SEQ ID NO: 42 in which bases 1-145 are the 5' AAV2 ITR, bases 173-512 are two copies (2×) of a 170 bp μ-globulin enhancer, bases 519-736 are a hAAT promoter, bases 749-5122 are a codon optimized SQ FVIII, bases 5131-5178 are a synthetic rabbit β-globin poly A, bases 5185-5834 are two copies (2×) of an ApoE HCR and bases 5849-5993 are the 3' AAV2 ITR.

Construct 106 is 5337 bases in length. This construct is set forth in SEQ ID NO: 43 in which bases 1-145 are the 5' AAV2 ITR, bases 173-512 are two copies (2×) of a 170 bp μ-globulin enhancer, bases 519-736 are a hAAT promoter, bases 749-5122 are a codon optimized SQ FVIII, bases 5131-5178 are a synthetic rabbit β-globin poly A and bases 5193-5337 are the 3' AAV2 ITR.

Construct 106AT is 5542 bases in length. This construct is set forth in SEQ ID NO: 44 in which bases 1-145 are the 5' AAV2 ITR, bases 173-512 are two copies (2×) of a 170 bp μ-globulin enhancer, bases 519-736 are a hAAT promoter, bases 737-941 are a hAAT intron, bases 954-5327 are a codon optimized SQ FVIII, bases 5336-5383 are a synthetic rabbit β-globin poly A and bases 5398-5542 are the 3' AAV2 ITR.

Construct 2× SerpinA hAAT is 5126 base. This construct is set forth in SEQ ID NO: 45 in which bases 1-145 are the 5' AAV2 ITR, bases 160-301 are an ApoE HCR, bases 308-525 are a hAAT promoter, bases 538-4911 are a codon optimized SQ FVIII, bases 4920-4967 are a synthetic rabbit β-globin poly A and bases 4982-5126 are the 3' AAV2 ITR.

AAV Vectors

As used herein, the term "AAV" is a standard abbreviation for adeno-associated virus. Adeno-associated virus is a single-stranded DNA parvovirus that grows only in cells in which certain functions are provided by a co-infecting helper virus. There are currently thirteen serotypes of AAV that have been characterized, as shown below in Table 1. General information and reviews of AAV can be found in, for example, Carter, 1989, Handbook of Parvoviruses, Vol. 1, pp. 169-228, and Berns, 1990, Virology, pp. 1743-1764, Raven Press, (New York). However, it is fully expected that these same principles will be applicable to additional AAV serotypes since it is well known that the various serotypes are quite closely related, both structurally and functionally, even at the genetic level. (See, for example, Blacklowe, 1988, pp. 165-174 of Parvoviruses and Human Disease, J. R. Pattison, ed.; and Rose, Comprehensive Virology 3:1-61 (1974)). For example, all AAV serotypes apparently exhibit very similar replication properties mediated by homologous rep genes; and all bear three related capsid proteins such as those expressed in AAV 6. The degree of relatedness is further suggested by heteroduplex analysis which reveals extensive cross-hybridization between serotypes along the length of the genome; and the presence of analogous self-annealing segments at the termini that correspond to "inverted terminal repeat sequences" (ITRs). The similar infectivity patterns also suggest that the replication functions in each serotype are under similar regulatory control.

An "AAV vector" as used herein refers to a vector comprising one or more polynucleotides of interest (or transgenes) that are flanked by AAV terminal repeat sequences (ITRs). Such AAV vectors can be replicated and packaged into infectious viral particles when present in a host cell that has been transfected with a vector encoding and expressing rep and cap gene products.

An "AAV virion" or "AAV viral particle" or "AAV vector particle" refers to a viral particle composed of at least one AAV capsid protein and an encapsidated polynucleotide AAV vector. If the particle comprises a heterologous polynucleotide (i.e. a polynucleotide other than a wild-type AAV genome such as a transgene to be delivered to a mammalian cell), it is typically referred to as an "AAV vector particle" or simply an "AAV vector". Thus, production of AAV vector particle necessarily includes production of AAV vector, as such a vector is contained within an AAV vector particle.

AAV "rep" and "cap" genes are genes encoding replication and encapsidation proteins, respectively. AAV rep and cap genes have been found in all AAV serotypes examined to date, and are described herein and in the references cited. In wild-type AAV, the rep and cap genes are generally found adjacent to each other in the viral genome (i.e., they are "coupled" together as adjoining or overlapping transcriptional units), and they are generally conserved among AAV serotypes. AAV rep and cap genes are also individually and collectively referred to as "AAV packaging genes." The AAV cap gene in accordance with the present invention encodes a Cap protein which is capable of packaging AAV vectors in the presence of rep and adeno helper function and is capable of binding target cellular receptors. In some embodiments, the AAV cap gene encodes a capsid protein having an amino acid sequence derived from a particular AAV serotype, for example the serotypes shown in Table 1.

TABLE 1

AAV serotypes

| AAV Serotype | Genbank Accession No. |
| --- | --- |
| AAV-1 | NC_002077.1 |
| AAV-2 | NC_001401.2 |
| AAV-3 | NC_001729.1 |
| AAV-3B | AF028705.1 |
| AAV-4 | NC_001829.1 |
| AAV-5 | NC_006152.1 |
| AAV-6 | AF028704.1 |
| AAV-7 | NC_006260.1 |
| AAV-8 | NC_006261.1 |
| AAV-9 | AX753250.1 |
| AAV-10 | AY631965.1 |
| AAV-11 | AY631966.1 |
| AAV-12 | DQ813647.1 |
| AAV-13 | EU285562.1 |

The AAV sequences employed for the production of AAV can be derived from the genome of any AAV serotype. Generally, the AAV serotypes have genomic sequences of significant homology at the amino acid and the nucleic acid levels, provide a similar set of genetic functions, produce virions which are essentially physically and functionally equivalent, and replicate and assemble by practically identical mechanisms. For the genomic sequence of AAV serotypes and a discussion of the genomic similarities see, for example, GenBank Accession number U89790; GenBank Accession number J01901; GenBank Accession number AF043303; GenBank Accession number AF085716; Chlorini et al., J. Vir. 71: 6823-33 (1997); Srivastava et al., J. Vir. 45:555-64 (1983); Chlorini et al., J. Vir. 73:1309-1319 (1999); Rutledge et al., J. Vir. 72:309-319 (1998); and Wu et al., J. Vir. 74: 8635-47 (2000).

The genomic organization of all known AAV serotypes is very similar. The genome of AAV is a linear, single-stranded DNA molecule that is less than about 5,000 nucleotides (nt) in length. Inverted terminal repeats (ITRs) flank the unique coding nucleotide sequences for the non-structural replication (Rep) proteins and the structural (VP) proteins. The VP proteins form the capsid. The terminal 145 nt are self-complementary and are organized so that an energetically stable intramolecular duplex forming a T-shaped hairpin may be formed. These hairpin structures function as an origin for viral DNA replication, serving as primers for the cellular DNA polymerase complex. The Rep genes encode the Rep proteins, Rep78, Rep68, Rep52, and Rep40. Rep78 and Rep68 are transcribed from the p5 promoter, and Rep 52 and Rep40 are transcribed from the p19 promoter. The cap genes encode the VP proteins, VP1, VP2, and VP3. The cap genes are transcribed from the p40 promoter.

In some embodiments, a nucleic acid sequence encoding an AAV capsid protein is operably linked to expression control sequences for expression in a specific cell type, such as SD or HEK cells. Techniques known to one skilled in the art for expressing foreign genes in insect host cells or mammalian host cells can be used to practice the invention. Methodology for molecular engineering and expression of polypeptides in insect cells is described, for example, in Summers and Smith. 1986. A Manual of Methods for Baculovirus Vectors and Insect Culture Procedures, Texas Agricultural Experimental Station Bull. No. 7555, College Station, Tex.; Luckow. 1991. In Prokop et al., Cloning and Expression of Heterologous Genes in Insect Cells with Baculovirus Vectors' Recombinant DNA Technology and Applications, 97-152; King, L. A. and R. D. Possee, 1992, The baculovirus expression system, Chapman and Hall, United Kingdom; O'Reilly, D. R., L. K. Miller, V. A. Luckow, 1992, Baculovirus Expression Vectors: A Laboratory Manual, New York; W.H. Freeman and Richardson, C. D., 1995, Baculovirus Expression Protocols, Methods in Molecular Biology, volume 39; U.S. Pat. No. 4,745,051; US2003148506; and WO 03/074714. A particularly suitable promoter for transcription of a nucleotide sequence encoding an AAV capsid protein is e.g. the polyhedron promoter. However, other promoters that are active in insect cells are known in the art, e.g. the p10, p35 or IE-1 promoters and further promoters described in the above references are also contemplated.

Use of insect cells for expression of heterologous proteins is well documented, as are methods of introducing nucleic acids, such as vectors, e.g., insect-cell compatible vectors, into such cells and methods of maintaining such cells in culture. See, for example, METHODS IN MOLECULAR BIOLOGY, ed. Richard, Humana Press, N.J. (1995); O'Reilly et al., BACULOVIRUS EXPRESSION VECTORS, A LABORATORY MANUAL, Oxford Univ. Press (1994); Samulski et al., J. Vir. 63:3822-8 (1989); Kajigaya et al., Proc. Nat'l. Acad. Sci. USA 88: 4646-50 (1991); Ruffing et al., J. Vir. 66:6922-30 (1992); Kirnbauer et al., Vir. 219:37-44 (1996); Zhao et al., Vir. 272:382-93 (2000); and Samulski et al., U.S. Pat. No. 6,204,059. In some embodiments, the nucleic acid construct encoding AAV in insect cells is an insect cell-compatible vector. An "insect cell-compatible vector" or "vector" as used herein refers to a nucleic acid molecule capable of productive transformation or transfection of an insect or insect cell. Exemplary biological vectors include plasmids, linear nucleic acid molecules, and recombinant viruses. Any vector can be employed as long as it is insect cell-compatible. The vector may integrate into the insect cells genome but the presence of the vector in the insect cell need not be permanent and transient episomal vectors are also included. The vectors can be introduced by any means known, for example by chemical treatment of the cells, electroporation, or infection. In some embodiments, the vector is a baculovirus, a viral vector, or a plasmid. In a more preferred embodiment, the vector is a baculovirus, i.e. the construct is a baculoviral vector. Baculoviral vectors and methods for their use are described in the above cited references on molecular engineering of insect cells.

Baculoviruses are enveloped DNA viruses of arthropods, two members of which are well known expression vectors for producing recombinant proteins in cell cultures. Baculoviruses have circular double-stranded genomes (80-200 kbp) which can be engineered to allow the delivery of large genomic content to specific cells. The viruses used as a vector are generally *Autographa californica* multicapsid nucleopolyhedrovirus (AcMNPV) or *Bombyx mori* (Bm) NPV) (Kato et al., 2010).

Baculoviruses are commonly used for the infection of insect cells for the expression of recombinant proteins. In particular, expression of heterologous genes in insects can be accomplished as described in for instance U.S. Pat. No. 4,745,051; Friesen et al (1986); EP 127,839; EP 155,476; Vlak et al (1988); Miller et al (1988); Carbonell et al (1988); Maeda et al (1985); Lebacq-Verheyden et al (1988); Smith et al (1985); Miyajima et al (1987); and Martin et al (1988). Numerous baculovirus strains and variants and corresponding permissive insect host cells that can be used for protein production are described in Luckow et al (1988), Miller et al (1986); Maeda et al (1985) and McKenna (1989).

Methods for Producing Recombinant AAVs

The present disclosure provides materials and methods for producing recombinant AAVs in insect or mammalian cells. In some embodiments, the viral construct further comprises a promoter and a restriction site downstream of the promoter to allow insertion of a polynucleotide encoding one or more proteins of interest, wherein the promoter and the restriction site are located downstream of the 5' AAV ITR and upstream of the 3' AAV ITR. In some embodiments, the viral construct further comprises a posttranscriptional regulatory element downstream of the restriction site and upstream of the 3' AAV ITR. In some embodiments, the viral construct further comprises a polynucleotide inserted at the restriction site and operably linked with the promoter, where the polynucleotide comprises the coding region of a protein of interest. As a skilled artisan will appreciate, any one of the AAV vector disclosed in the present application can be used in the method as the viral construct to produce the recombinant AAV.

In some embodiments, the helper functions are provided by one or more helper plasmids or helper viruses comprising adenoviral or baculoviral helper genes. Non-limiting examples of the adenoviral or baculoviral helper genes include, but are not limited to, E1A, E1B, E2A, E4 and VA, which can provide helper functions to AAV packaging.

Helper viruses of AAV are known in the art and include, for example, viruses from the family Adenoviridae and the family Herpesviridae. Examples of helper viruses of AAV include, but are not limited to, SAdV-13 helper virus and SAdV-13-like helper virus described in US Publication No. 20110201088 (the disclosure of which is incorporated herein by reference), helper vectors pHELP (Applied Viromics). A skilled artisan will appreciate that any helper virus or helper plasmid of AAV that can provide adequate helper function to AAV can be used herein.

In some embodiments, the AAV cap genes are present in a plasmid. The plasmid can further comprise an AAV rep gene. The cap genes and/or rep gene from any AAV serotype (including, but not limited to, AAV1, AAV2, AAV4, AAV5, AAV6, AAV7, AAV8, AAV9, AAV10, AAV11, AAV12, AAV13 and any variants thereof) can be used herein to produce the recombinant AAV. In some embodiments, the AAV cap genes encode a capsid from serotype 1, serotype 2, serotype 4, serotype 5, serotype 6, serotype 7, serotype 8, serotype 9, serotype 10, serotype 11, serotype 12, serotype 13 or a variant thereof.

In some embodiments, the insect or mammalian cell can be transfected with the helper plasmid or helper virus, the viral construct and the plasmid encoding the AAV cap genes; and the recombinant AAV virus can be collected at various time points after co-transfection. For example, the recombinant AAV virus can be collected at about 12 hours, about 24 hours, about 36 hours, about 48 hours, about 72 hours, about 96 hours, about 120 hours, or a time between any of these two time points after the co-transfection.

Recombinant AAV can also be produced using any conventional methods known in the art suitable for producing infectious recombinant AAV. In some instances, a recombinant AAV can be produced by using an insect or mammalian cell that stably expresses some of the necessary components for AAV particle production. For example, a plasmid (or multiple plasmids) comprising AAV rep and cap genes, and a selectable marker, such as a neomycin resistance gene, can be integrated into the genome of the cell. The insect or mammalian cell can then be co-infected with a helper virus (e.g., adenovirus or baculovirus providing the helper functions) and the viral vector comprising the 5' and 3' AAV ITR (and the nucleotide sequence encoding the heterologous protein, if desired). The advantages of this method are that the cells are selectable and are suitable for large-scale production of the recombinant AAV. As another non-limiting example, adenovirus or baculovirus rather than plasmids can be used to introduce rep and cap genes into packaging cells. As yet another non-limiting example, both the viral vector containing the 5' and 3' AAV LTRs and the rep-cap genes can be stably integrated into the DNA of producer cells, and the helper functions can be provided by a wild-type adenovirus to produce the recombinant AAV.

Cell Types Used in AAV Production

The viral particles comprising the AAV vectors of the invention may be redocued using any invertebrate cell type which allows for production of AAV or biologic products and which can be maintained in culture. For example, the insect cell line used can be from *Spodoptera frupperda*, such as SF9, SF21, SF900+, drosophila cell lines, mosquito cell lines, e.g., *Aedes albopictus* derived cell lines, domestic silkworm cell lines, e.g. Bombyxmori cell lines, *Trichoplusia ni* cell lines such as High Five cells or Lepidoptera cell lines such as *Ascalapha odorata* cell lines. Preferred insect cells are cells from the insect species which are susceptible to baculovirus infection, including High Five, Sf9, Se301, SeIZD2109, SeUCR1, Sf9, Sf900+, Sf21, BTI-TN-5B1-4, MG-1, Tn368, HzAm1, BM-N, Ha2302, Hz2E5 and Ao38.

Baculoviruses are enveloped DNA viruses of arthropods, two members of which are well known expression vectors for producing recombinant proteins in cell cultures. Baculoviruses have circular double-stranded genomes (80-200 kbp) which can be engineered to allow the delivery of large genomic content to specific cells. The viruses used as a vector are generally *Autographa californica* multicapsid nucleopolyhedrovirus (AcMNPV) or *Bombyx mori* (Bm-NPV) (Kato et al., 2010).

Baculoviruses are commonly used for the infection of insect cells for the expression of recombinant proteins. In particular, expression of heterologous genes in insects can be accomplished as described in for instance U.S. Pat. No. 4,745,051; Friesen et al (1986); EP 127,839; EP 155,476; Vlak et al (1988); Miller et al (1988); Carbonell et al (1988); Maeda et al (1985); Lebacq-Verheyden et al (1988); Smith et al (1985); Miyajima et al (1987); and Martin et al (1988). Numerous baculovirus strains and variants and corresponding permissive insect host cells that can be used for protein production are described in Luckow et al (1988), Miller et al (1986); Maeda et al (1985) and McKenna (1989).

In another aspect of the invention, the methods of the invention are also carried out with any mammalian cell type which allows for replication of AAV or production of biologic products, and which can be maintained in culture. Preferred mammalian cells used can be HEK293, HeLa, CHO, NS0, SP2/0, PER.C6, Vero, RD, BHK, HT 1080, A549, Cos-7, ARPE-19 and MRC-5 cells.

Testing of AAV FVIII Vectors

Assays to test the completely packaged AAV FVIII vectors of the invention include, for example, (1) transient transfection of double-stranded DNA plasmids comprising the AAV vector nucleic acids in HepG2 cells, a cell line derived from human liver to check liver-specific mRNA expression and splicing, and FVIII protein production and secretion in vitro; (2) production of AAV virions comprising the AAV FVIII vectors in 293 cells and baculovirus-infected insect cells; (3) evaluation of the AAV vector nucleic acids by alkaline gel analysis and replication assays; and (4) evaluation of FVIII expression, FVIII activity, and FVIII specific activity in Rag2 mice. These assays are described in greater detail in the Examples.

The completely packaged AAV FVIII vectors of the invention display at least the same expression and/or activity as the UCL SQ vector, and preferably 1.5-fold, 2-fold, 3-fold, 4-fold, or 5-fold or more expression and/or activity as compared to the UCL SQ vector.

The completely packaged AAV FVIII vectors of the invention have high vector yield with little or no fragmentary genome contaminants, and preferably 1.5-fold, 2-fold, 3-fold, 4-fold, or 5-fold greater vector yield as compared to the UCL SQ vector.

Other aspects and advantages of the present invention will be understood upon consideration of the following illustrative examples.

EXAMPLES

Example 1

Generation of Proto 1, Proto 1S, Proto 2S and Proto 3S Vectors

The UCL SQ vector, which is described in detail in Nathwani et al., US Pat. App. Pub. No. 2013/0024960A1, published Jan. 24, 2013, which is incorporated herein by reference in its entirety, and McIntosh et al., Blood 121: 3335-3344, 2013, is an oversized, i.e., greater than 5.0 kb, AAV vector. As shown in FIG. 1, the UCL SQ vector comprises, from left to right, the AAV serotype 2 (AAV2) 5' ITR, wild-type AAV2 viral sequence, the 34 base human apolipoprotein E (ApoE)/C1 enhancer, the 32 base human alpha anti-trypsin (AAT) promoter distal X region, the 186 base human AAT promoter, including 42 bases of 5' untranslated region (UTR) sequence, the codon-optimized human FVIII sequence in which the B domain is replaced with the 14 amino acid SQ sequence, the 49 bases synthetic polyadenylation sequence, wild-type AAV2 viral sequence, and the AAV2 3'ITR. The UCL SQ vector is 5081 bases in length.

Figure 2A:
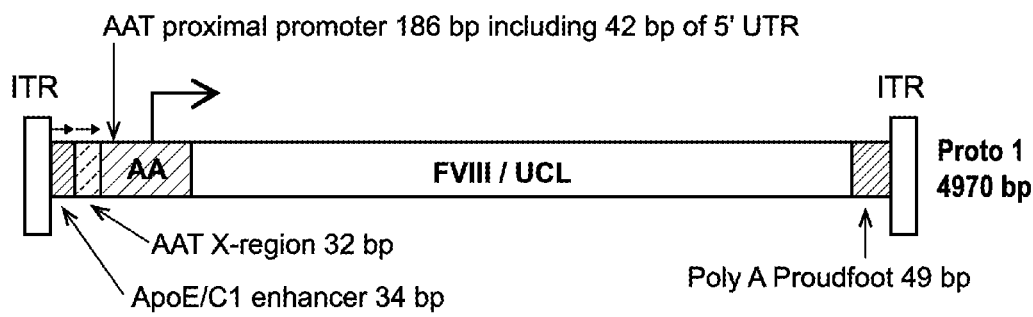
FIGS. 2A-2D provide schematics and sequences of the Proto 1, Proto 1S, Proto 2S and Proto 3S vectors.

To obtain a vector that is smaller than the UCL SQ vector, DNA sequences believed by the inventors herein to be unnecessary for FVIII expression and/or activity, or for AAV virion production, were removed from the UCL SQ vector sequence. Extraneous DNA sequence was removed, including 53 bases of AAV2 viral sequence 3' to the AAV2 5'ITR, 46 bases of AAV2 viral sequence 5' to the AAV2 3'ITR, and 11 bases adjacent to the codon-optimized FVIII SQ coding region. The resultant Proto 1 vector, which is 4970 bases in length, is shown in schematic form in FIG. 2A, and the sequence is set forth in SEQ ID NO: 1. Proto 1 produced infectious virus and encodes a functional Factor VIII polypeptide.

Sequences adjacent to the hairpin loop in the AAV2 ITR may also be dispensable in recombinant AAV vectors (see Srivastava et al., U.S. Pat. No. 6,521,225; Wang et al., J.

Figure 2B:
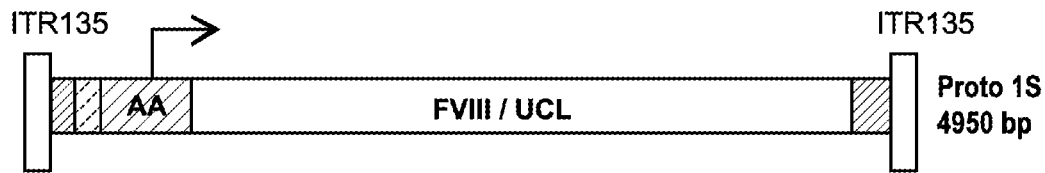

Virol. 70:1668-1677, 1996; and Wang et al., J. Virol. 71:3077-3082, 1997). To further reduce the size of the Proto 1 vector, 10 bases of AAV2 sequence was removed directly 3' to the hairpin loop in the AAV2 5'ITR and 10 bases of AAV2 sequence was removed directly 5' to the hairpin loop in the AAV2 3'ITR. The resultant Proto 1S vector, which is 4950 bases in length, is shown in schematic form in FIG. 2B, and the sequence is set forth in SEQ ID NO: 2.

In an effort to increase the expression of the FVIII SQ variant in the Proto 15 vector, a 100 base synthetic intron was inserted between exons 1 and 2 in the codon-optimized FVIII sequence. It is known that insertion of an intron can result in increased level of mRNA expression in otherwise intron-less genes, such as, for example, the interferon genes.

Enhancers are defined as working in a distance- and orientation-independent manner. The 34 base ApoE/C1 enhancer works in a distance- and orientation-independent manner with respect to FVIII expression, as exemplified by its presumptive enhancer activity in Gray et al., U.S. Pat. No. 8,030,065 (FIX expression) and in Nathwani et al., US Pat. App. Pub. No. 2013/0024960 (FVIII expression), both of which are incorporated herein by reference in their entirety. The 32 base human AAT promoter distal X region, described in Di Simone et al., EMBO J. 6:2759-2766, 1987, is located within a regulatory domain that enhances expression of a heterologous promoter.

Figure 2C:
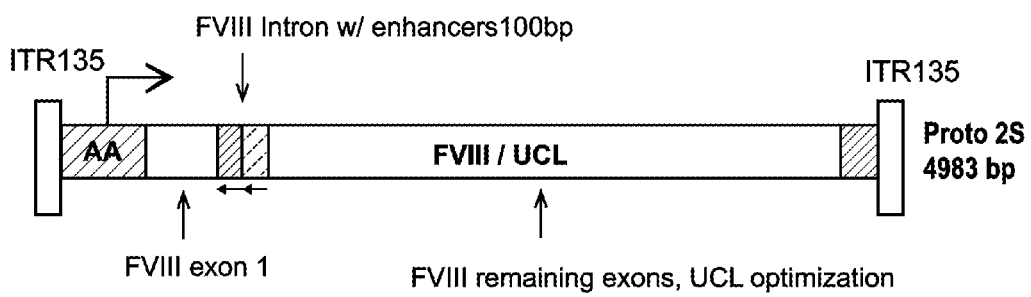

In another attempt to further increase the expression of the FVIII SQ variant in the Proto 1S vector, the synthetic intron sequence incorporated the 34 base human ApoE/C1 enhancer and 32 base human AAT promoter distal X region, which was moved from its location upstream of the human AAT promoter. These two regulatory elements were inserted in the reverse orientation with respect to their orientation in Proto 1S. The resultant Proto 2S vector, which is 4983 bases in length, is shown in schematic form in FIG. 2C, and the sequence set forth in SEQ ID NO: 3.

Figure 2D:
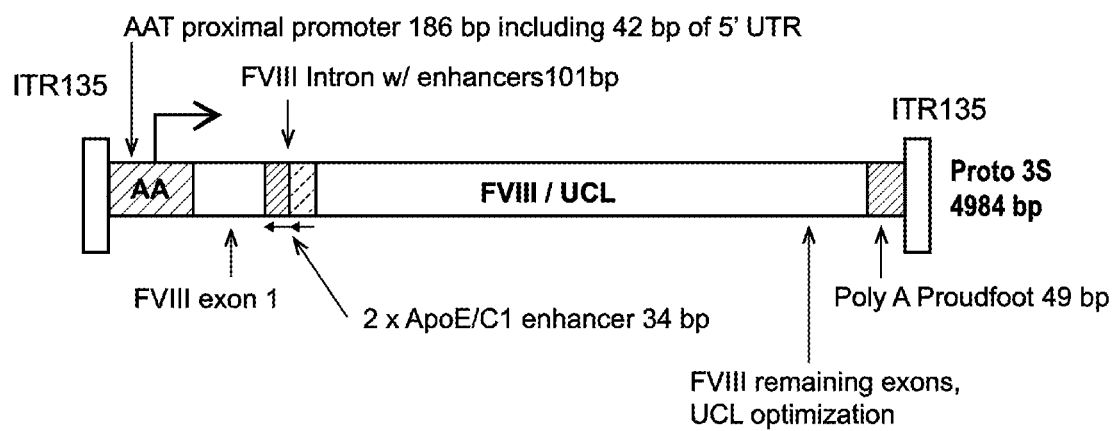

As the human AAT promoter distal X region had not previously been shown to function downstream from the transcriptional start site in an intron, this regulatory element in the Proto 2S vector was replaced with a second copy of the 34 base human ApoE/C1 enhancer in the same orientation as the first copy of the enhancer in the intron. The resultant Proto 3S vector, which is 4985 bases in length, is shown in schematic form in FIG. 2D, and the sequence is set forth in SEQ ID NO: 4.

The Proto 1, Proto 1S, Proto 2S and Proto 3S vector nucleic acids were cloned into the pUC19 bacterial expression plasmid, thereby generating double-stranded forms of the AAV FVIII vectors.

Example 2

Generation of Proto 4, Proto 5, Proto 6 and Proto 7 Vectors

To further reduce the size of the Proto 1 vector and/or increase the expression of FVIII as compared to the Proto 1 vector, the a3 domain, which is located adjacent to the light chain or C domain, was deleted. The a3 domain is involved in binding to von Willenbrand Factor, but may be dispensable for functionally active FVIII in vivo.

Figure 3A:
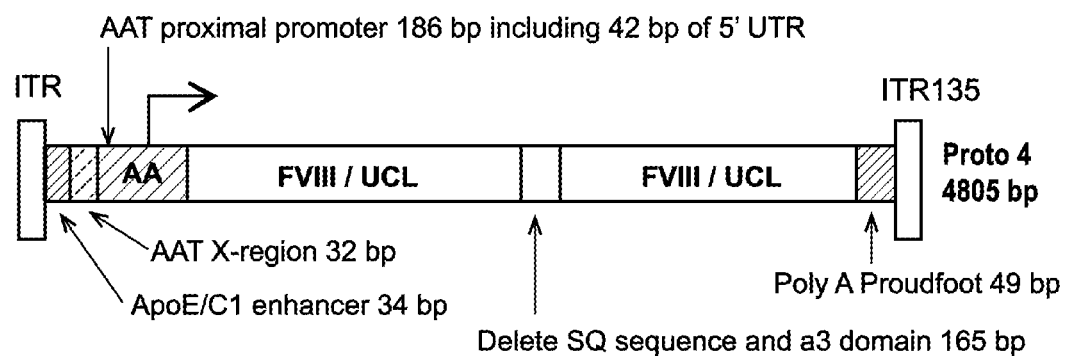
FIGS. 3A-3D provide schematics of the Proto 4, Proto 5, Proto 6 and Proto 7 vectors.

Starting from the Proto 1 vector, the 14 amino acid SQ sequence and 41 amino acids a3 domain (corresponding to amino acids 1649-1689 of wild-type FVIII) were deleted. The resultant Proto 4 vector, which is 4805 bases in length, is shown in schematic form in FIG. 3A, and the sequence is set forth in SEQ ID NO: 5.

Figure 3B:
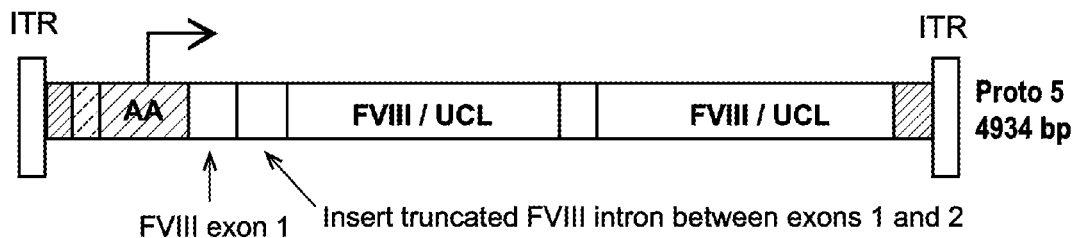

In an attempt to increase the expression of the B domain and a3 domain deleted FVIII, a 129 base, truncated FVIII intron was inserted between exons 1 and 2 in the codon-optimized FVIII sequence in the Proto 4 vector. The resultant Proto 5 vector, which is 4934 bases in length, is shown in schematic form in FIG. 3B, and the sequence is set forth in SEQ ID NO: 6.

Figure 3C:
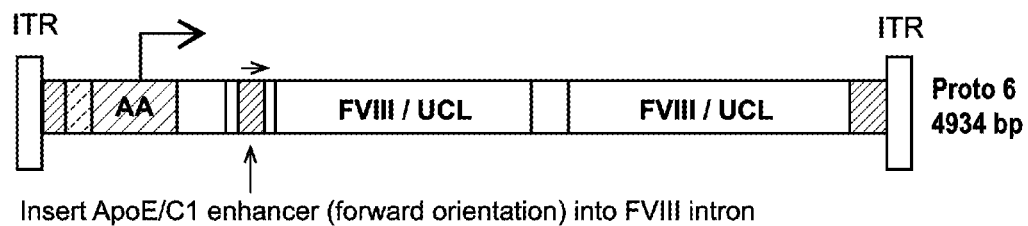

In an attempt to further increase the expression of the B domain and a3 domain deleted FVIII, a second copy of the 34 base human ApoE/C1 enhancer was inserted in either the forward or reverse orientation in the Proto 5 vector. The resultant Proto 6 vector, which is 4934 bases in length and has the intronic ApoE/C1 enhancer in the forward orientation, is shown in schematic form in FIG. 3C, and the sequence is set forth in SEQ ID NO: 7.

Figure 3D:
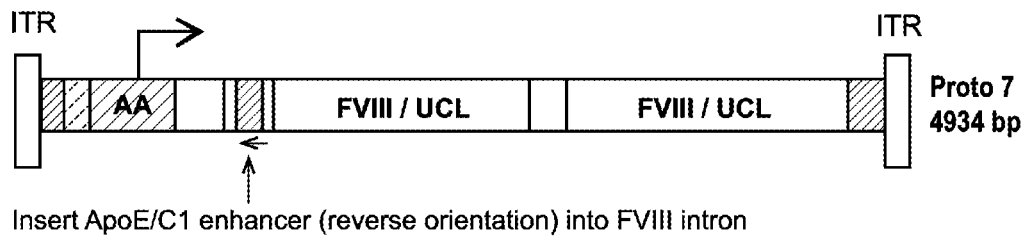
Figure 4A:
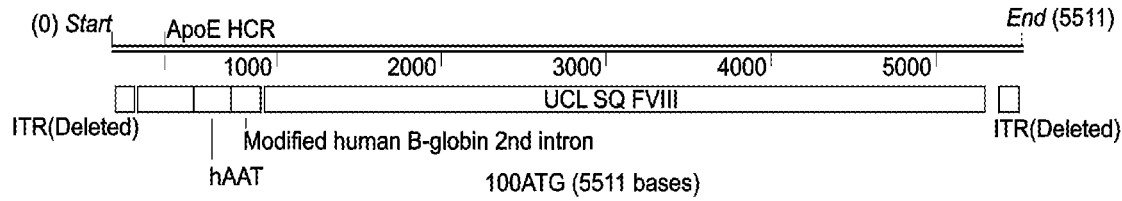
FIGS. 4A-4KK provide schematics of the AAV FVIII vectors with improved promoter/enhancer sequences.
Figure 4B:
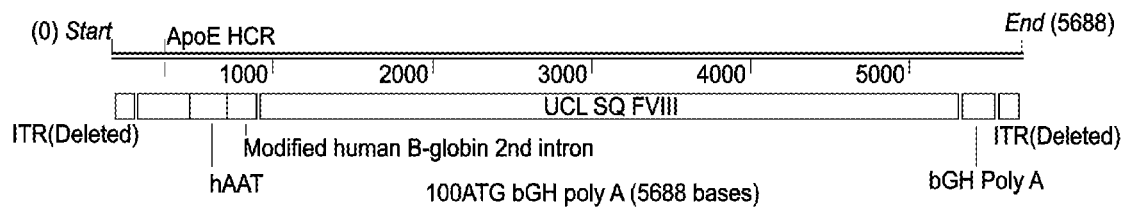
Figure 4C:
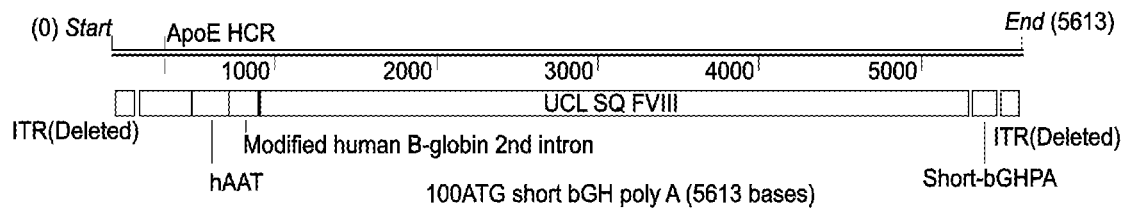
Figure 4D:
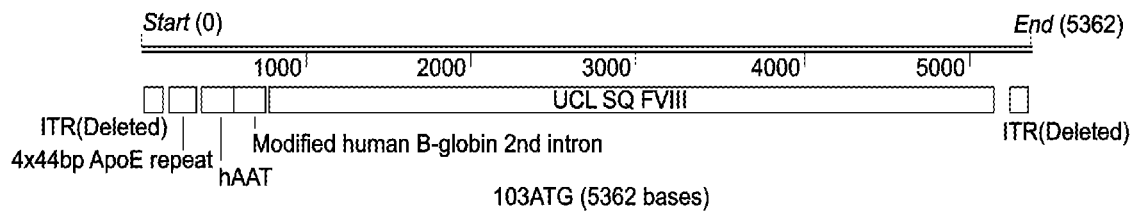
Figure 4E:
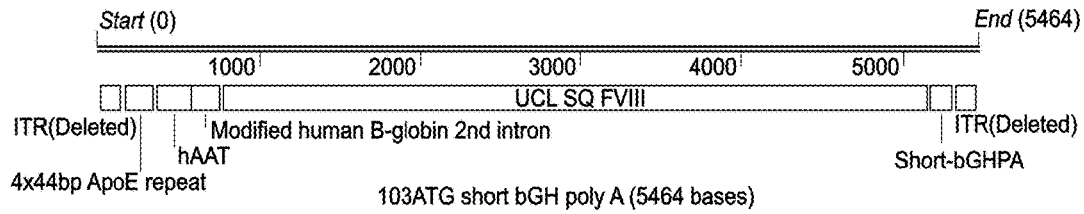
Figure 4F:
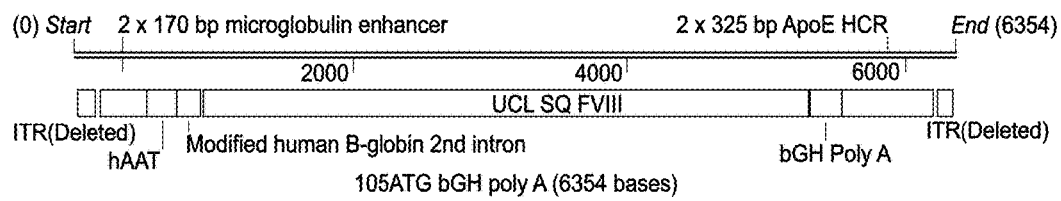
Figure 4G:
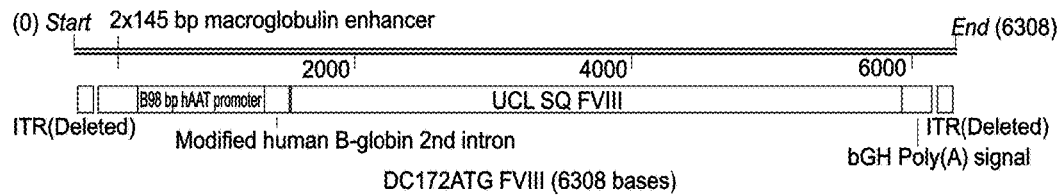
Figure 4H:
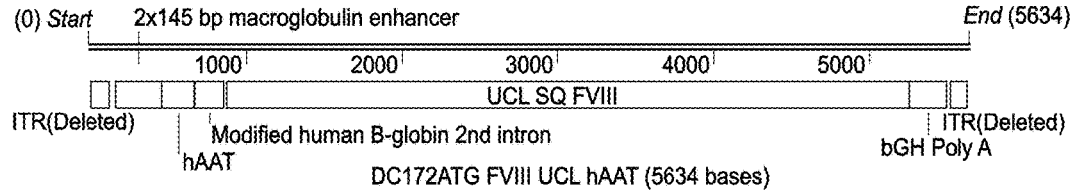
Figure 4I:
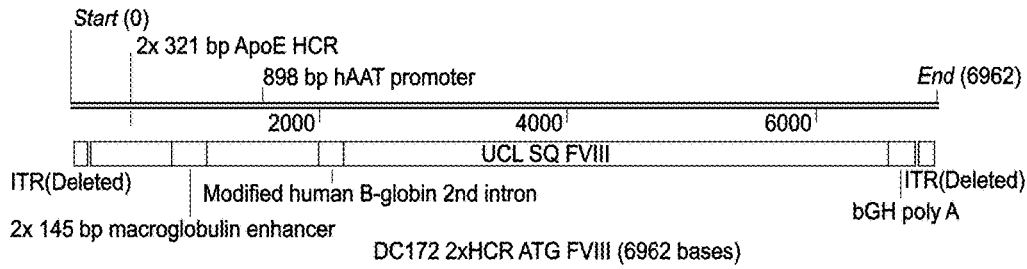
Figure 4J:
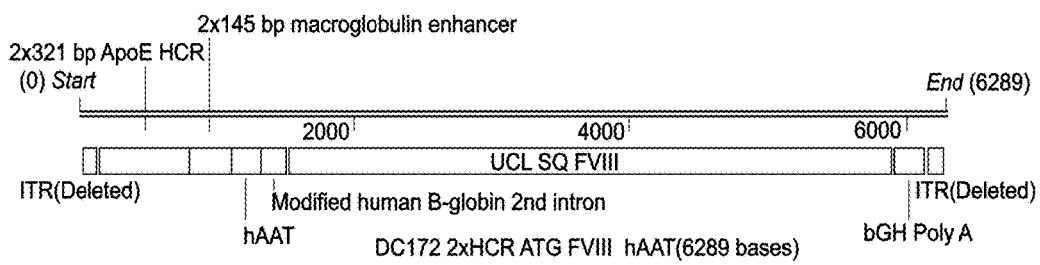
Figure 4K:
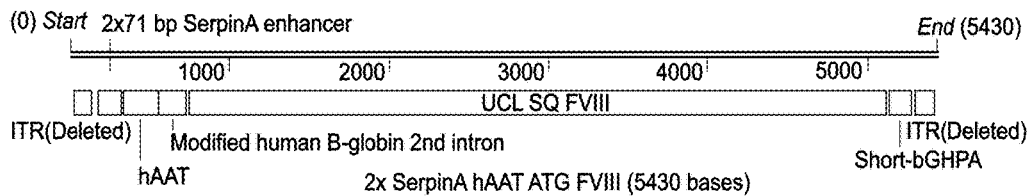
Figure 4L:
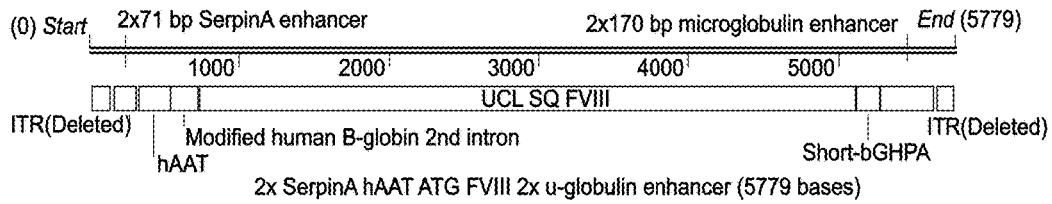
FIG. 4L provides a schematic of Construct 2× SerpinA hAAT ATG FVIII 2× μ-globulin enhancer.
Figure 4M:
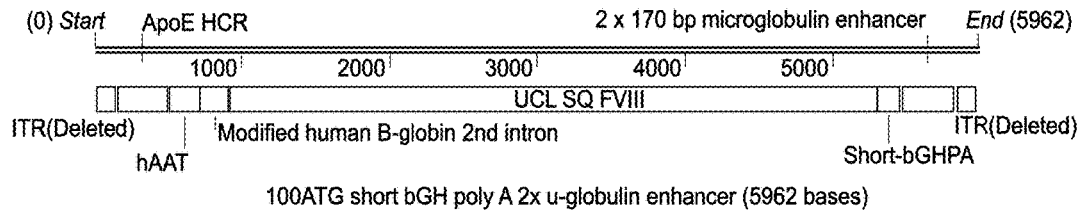
FIG. 4M provides a schematic of Construct 100ATG short bGH poly A 2× μ-globulin enhancer.
Figure 4N:
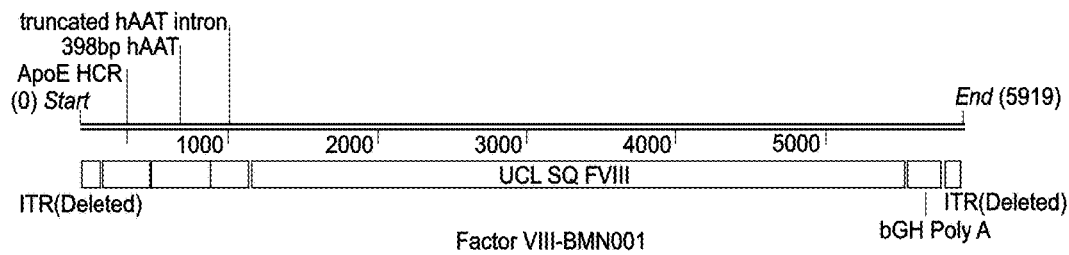
FIG. 4N provides a schematic of Construct Factor VIII-BMN001.
Figure 4O:
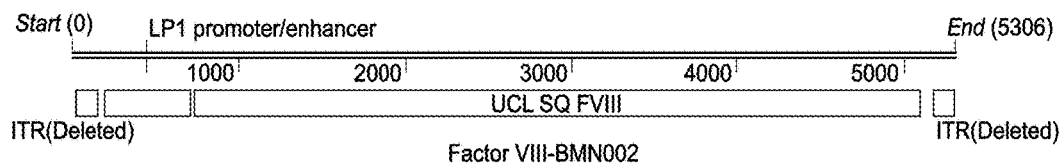
FIG. 4O provides a schematic of Construct FVIII-BMN002.
Figure 4P:
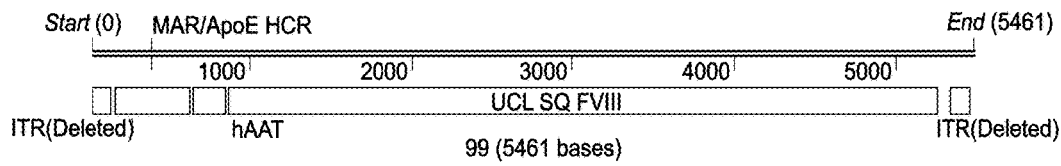
FIG. 4P provides a schematic of Construct 99.
Figure 4Q:
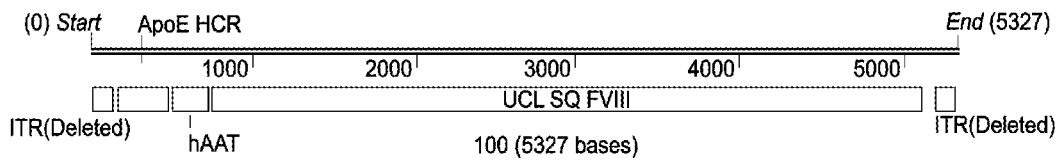
FIG. 4Q provides a schematic of Construct 100.
Figure 4R:
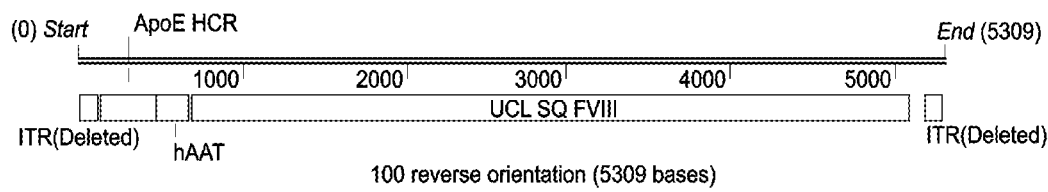
FIG. 4R provides a schematic of Construct 100 reverse orientation.
Figure 4S:
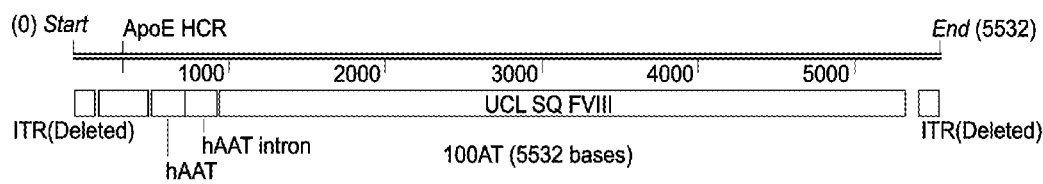
FIG. 4S provides a schematic of Construct 100AT.
Figure 4T:
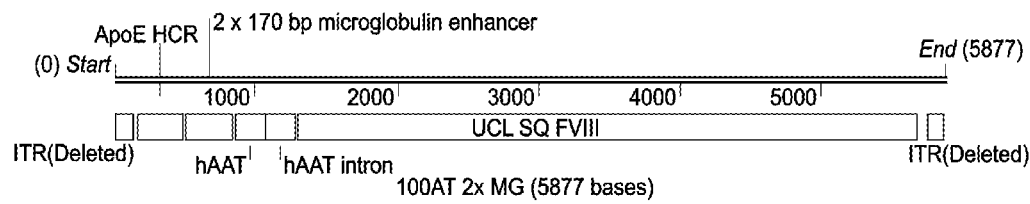
FIG. 4T provides a schematic of Construct 100AT 2× MG.
Figure 4U:
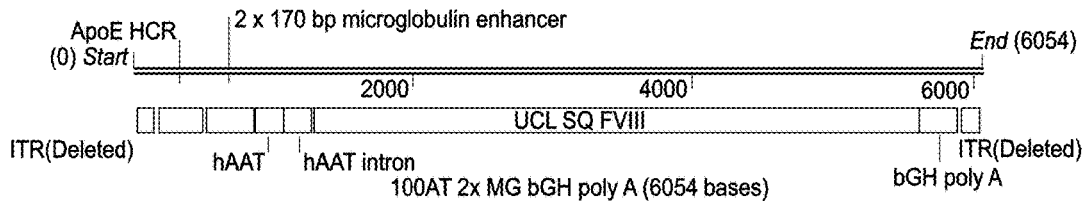
FIG. 4U provides a schematic of Construct 100AT 2× MG bGH polyA.
Figure 4V:
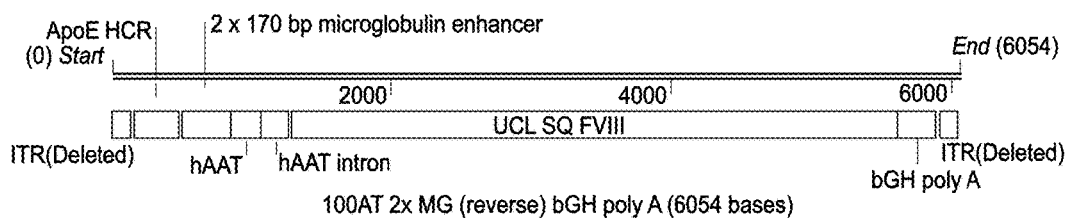
FIG. 4V provides a schematic of Construct 100AT 2× MG (reverse) bGH poly A.
Figure 4W:
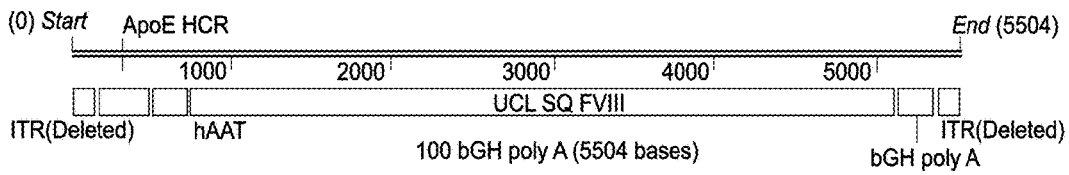
FIG. 4W provides a schematic of Construct 100 bGH poly A.
Figure 4X:
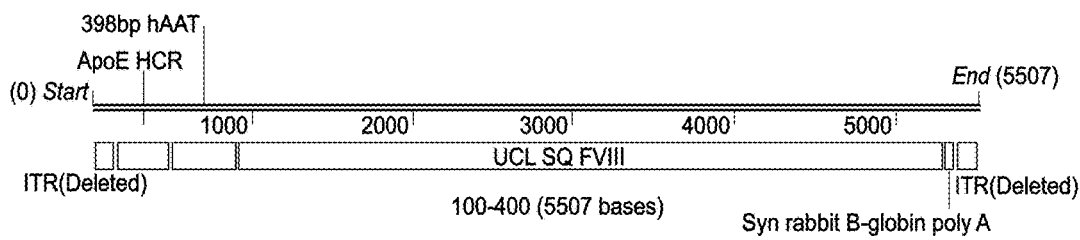
FIG. 4X provides a schematic of Construct 100-400.
Figure 4Y:
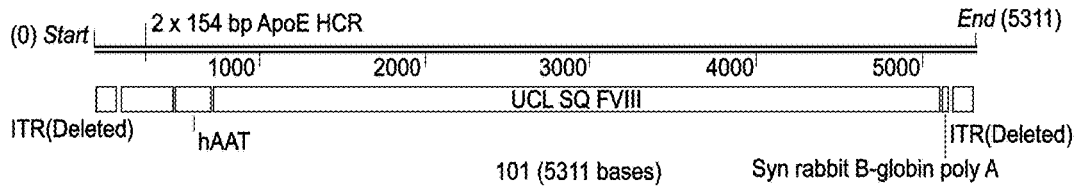
FIG. 4Y provides a schematic of Construct 101.
Figure 4Z:
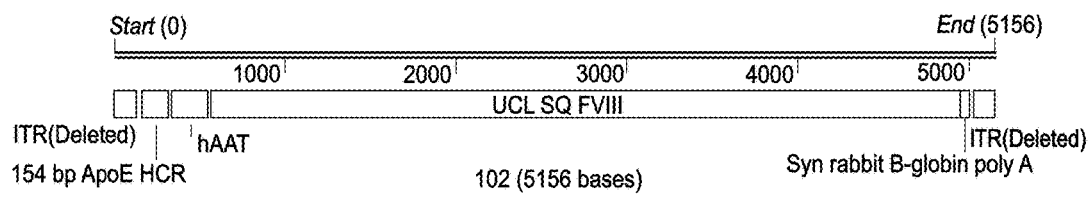
FIG. 4Z provides a schematic of Construct 102.
Figure 4A:
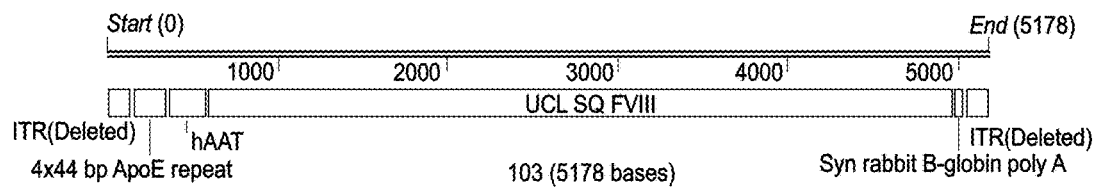
Figure 4B:
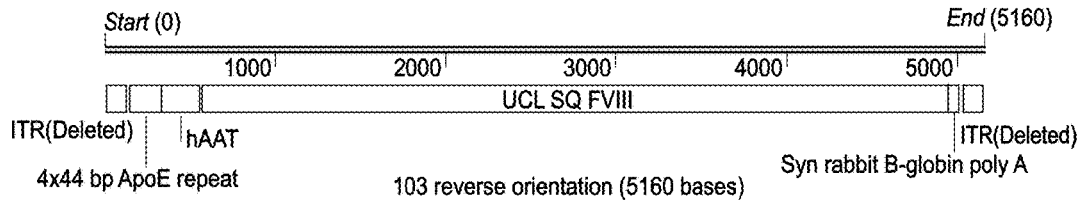
Figure 4C:
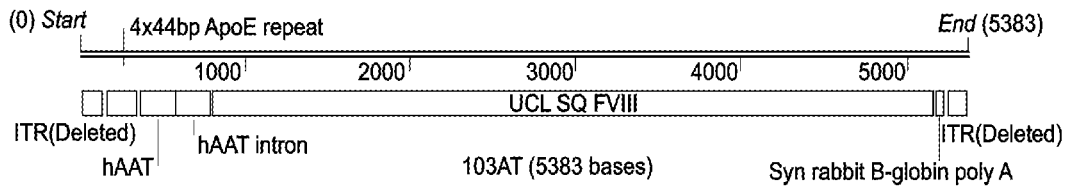
Figure 4D:
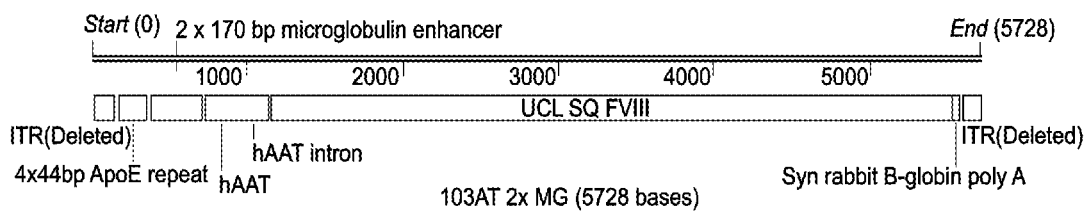
Figure 4E:
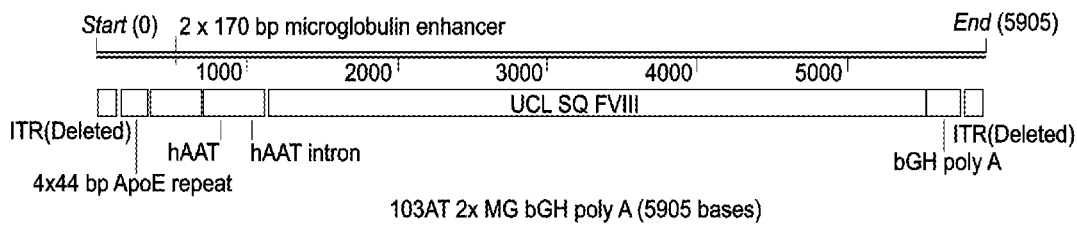
Figure 4F:
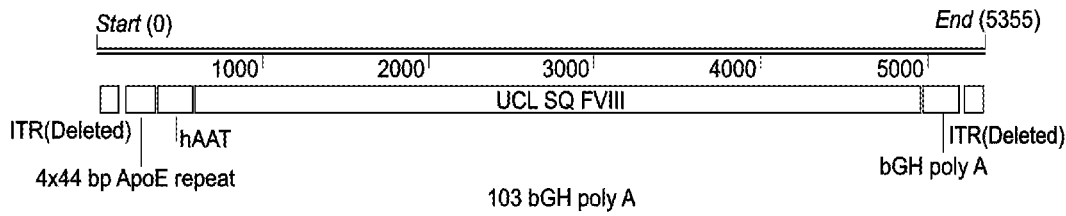
Figure 4G:
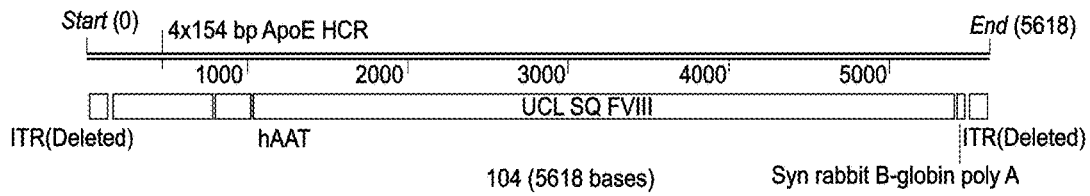
Figure 4H:
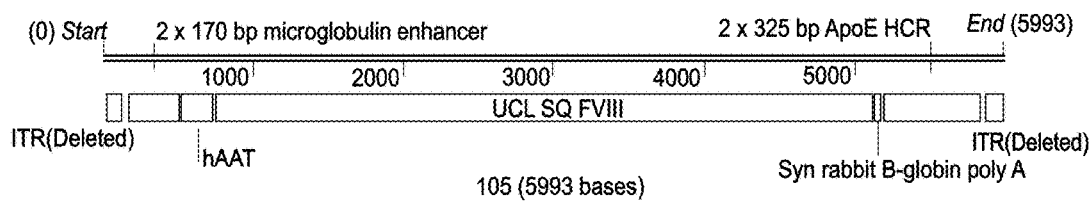
Figure 4I:
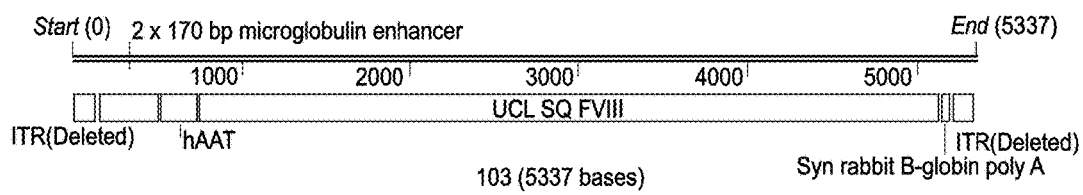
Figure 4J:
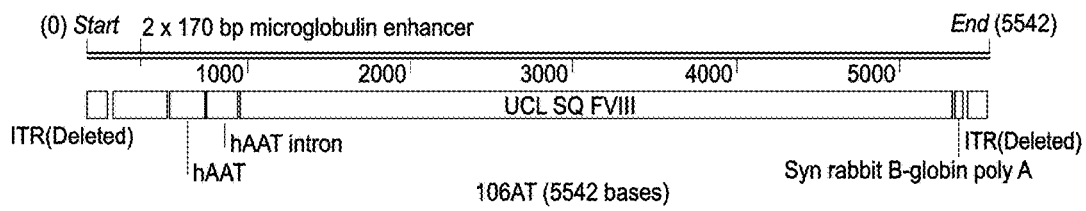
Figure 4K:
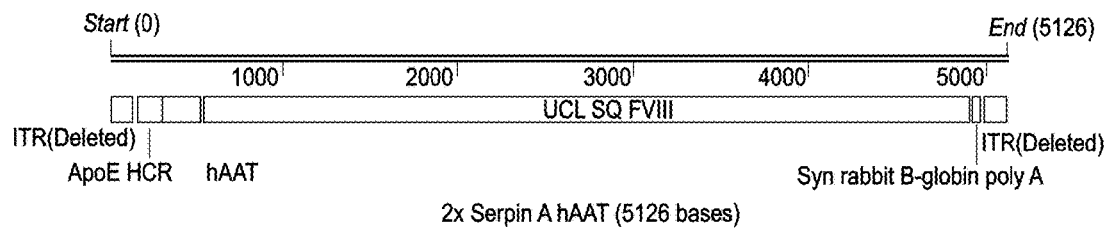

The resultant Proto 7 vector, which is 4934 bases in length and has the intronic ApoE/C1 enhancer in the reverse orientation, is shown in schematic form in FIG. 3D, and the sequence is set forth in SEQ ID NO: 8.

The Proto 4, Proto 5, Proto 6 and Proto 7 vector nucleic acids were cloned into the pUC19 bacterial expression plasmid, thereby generating double-stranded forms of the AAV FVIII vectors.

Example 3

Assays to Test the Expression and Activity of AAV FVIII Vectors

Assays to test the AAV FVIII vectors of the invention include, for example, (1) transient transfection of double-stranded DNA plasmids comprising the AAV vector nucleic acids in HepG2 cells, a cell line derived from human liver to check liver-specific mRNA expression and splicing, and FVIII protein production and secretion in vitro; (2) production of AAV virions comprising the AAV FVIII vectors in 293 cells and baculovirus-infected insect cells; (3) evaluation of the AAV vector nucleic acids by alkaline gel analysis and replication assays; and (4) evaluation of FVIII expression, FVIII activity, and FVIII specific activity in Rag2 mice.

Transient Transfection Assays.

A preliminary in vitro assay is performed to compare the FVIII expression and activity from the AAV FVIII vectors of the present invention with that from the UCL SQ vector. Double-stranded forms of the AAV FVIII vectors of the present invention are transiently transfected into the human liver cell line, HepG2. After transfection, for example, 24 or 48 hours later, FVIII antigen and activity in the culture supernatants is measured.

Using this assay, the FVIII activity in HepG2 cells transiently transfected with the Proto 1, Proto 1S and Proto 2S vectors was similar to the FVIII activity obtained using the UCL SQ vector, demonstrating that the Proto 1, Proto 1S and Proto 2S vectors were capable of expressing functional Factor VIII protein.

Production of AAV Virions in 293 Cells and Baculovirus-Infected Insect Cells.

To demonstrate that the AAV FVIII vectors of the present invention indeed package the nucleic acids encoding FVIII, the double-stranded forms of the AAV FVIII vectors generated as described in Examples 1 and 2 are introduced into cells capable of producing AAV virions. In a first AAV virus production system, plasmids comprising the AAV FVIII vector nucleic acids in double-stranded form are co-transfected into 293 cells together with a plasmid that expresses the AAV Cap and Rep proteins and a plasmid that expresses Adenovirus helper functions needed to for AAV virion production. In a second AAV virus production system, baculovirus constructs are generated expressing the AAV FVIII vector nucleic acids and the AAV Cap and Rep proteins, and then are co-infected into insect Sf9 cells. The resultant AAV virions produced in the transiently transfected 293 cells or baculovirus-infected Sf9 cells are purified and analyzed by standard methods known in the art.

Evaluation by Alkaline Gel and Replication Assay

An alkaline gel electrophoresis assay is used to determine the size of the packaged nucleic acid. A replication center assay is used to determine which AAV FVIII vectors are packaged in an intact form by both packaging methods.

A primer extension assay is used to quantify the amount of AAV FVIII vectors nucleic acids that have complete ends, i.e., terminate at the 5' end of the hairpin loop in the AAV2 5'ITR (sense strand) or 3'ITR (anti-sense strand).

Alternatively, a PCR assay is used to determine whether the AAV FVIII vectors nucleic acids have complete ends, i.e., terminate at the 5' end of the hairpin loop in the AAV2 5'ITR (sense strand) or 3'ITR (anti-sense strand).

Evaluation in Rag2 Mice

The AAV virions produced in transiently transfected 293 cells or baculovirus-infected Sf9 cells packaged vectors are tested for FVIII expression and activity in Rag2 mice at 2e11, 2e12, and 2e13 viral genomes (vg)/kg, given intravenously. Rag2 mice are used in this assay because FVIII expression and/or activity is/are not complicated by the presence of a host immune response to the AAV virus or human FVIII protein.

FVIII antigen is determined using an ELISA-based assay. FVIII activity is determined using a FXa activation assay and/or a coagulation assay. Using the FVIII antigen and activity assays, the FVIII specific activity is determined.

Numerous modifications and variations in the practice of the invention are expected to occur to those skilled in the art upon consideration of the presently preferred embodiments thereof. Consequently, the only limitations which should be placed upon the scope of the invention are those which appear in the appended claims.

Example 4

Generation of Constructs with Improved Promoter/Enhancer Sequences

To generate additional AAV vectors with strong promoters that increase expression of functional FVIII, constructs were generated with modified enhancer and/or promoter sequences. In some embodiments, the constructs comprised shortened versions of the ApoE or the μ-globulin enhancers. These constructs were generated using standard DNA cloning techniques and the sequences thereof are are shown in SEQ IS NOS: 9-45.

Example 5

Generation of AAV Viral Particles

Generation of Recombinant Bacmid

DH10 Bac competent cells were thawed on ice. Recombinant shuttle plasmid (e.g., pFB-GFP) was added and gently mixed with the competent cells and incubated on ice for 30 minutes. The competent cells were then subjected to heat at a temperature of approximately 42° C. for 30 seconds and then chilled on ice for 2 minutes. The competent cells were shocked with heat for 30 seconds at 42° C. and chilled on ice for 2 min. SOC was added to the cells and allowed to incubate at 37° C. with agitation for 4 hours to allow recombination to take place. During the incubation period, X-gal was spread onto two LB-plates (additionally containing various antibiotics (e.g., kanamycin, gentamycin and tetracycline) for transformation, is followed by IPTG.

An amount of the incubation mixture was obtained, diluted and then spread onto the two LB-plates and incubated at 37° C. for approximately 30-48 hours. Several white colonies were selected from each plate and cultured overnight in LB medium containing the same combination of antibiotics provided in the LB-plates. Next, Bacmid DNA and a glycerol stock was prepared and stored at −80° C.

Purification of Recombinant Bacmid DNA

An amount of the Bacmid glycerol stock is removed and inoculated in LB medium containing the same combination of antibiotic provided in the LB-plates described in Example 1. Cultures are allowed to grow overnight at 37° C. with shaking. Next, an amount of the culture is spun in a microfuge at full speed for approximately 30 seconds.

The pellets were resuspended in a resuspension buffer using a pipette followed by a lysis buffer, and the tube was inverted several times to mix the buffer and then incubated at room temperature for approximately 5 minutes. An exemplary resuspension buffer comprises 50 mM Tris-CL, pH 8.0, 10 mM EDTA and 100 ug/mL RNase A. An exemplary lysis buffer comprises 200 mM NaOH and 1% SDS. An amount of precipitate buffer (e.g., a buffer comprising 3.0 M potassium acetate, pH 5.5) was slowly added and the tube was inverted several times to mix the buffer and then incubated on ice for approximately 10 minutes. The tube was centrifuged for approximately 10 minutes at full speed and the supernatant is poured into a tube containing isopropanol. The tube was inverted several times to mix the solution.

Next, the solution was centrifuged at full speed for approximately 15 minutes at room temperature and the supernatant was removed immediately after centrifuge with pipette.

An amount of 70% ethanol was added to rinse the pellet and spun again at full speed for 1 minute. The ethanol was then removed and the solution is spun again to remove trace of the ethanol. An amount of TE/EB Buffer was added to each tube and the pellet is carefully dissolved by pipette. The solution was stored at −20° C. if not used immediately.

Production of P0 Stock of Recombinant Baculovirus

Sf9 cells were seeded at approximately $1\times10^6$ cells/well in a 6-well plate (or $6\times10^6$ cells in a 10-cm plate or $1.7\times10^7$ cells in a 15-cm dish) and the cells were allowed to attach for at least 1 hour before transfection.

Transfection solutions A and B are prepared as follows: Solution A: an amount of the Bacmid was diluted into an amount of serum free media without antibiotics in a 15-mL tube. Solution B: an amount of CellFectin was diluted into an amount of serum free media without antibiotics in a 15-mL tube. Solution B was added to Solution A and gently mixed by pipette approximately 3 times by pipette, and incubated at room temperature for 30–45 minutes. Next, medium from the plate was aspirated and an amount of serum free media without antibiotics was added to wash the cells. An amount of SF900II without antibiotics was added to each tube containing lipid-DNA mixtures.

The medium from the cells was aspirated, the transfection solution was added to the cells and the cells were incubated for approximately 5 hours at 28° C. The transfection solution was removed and an amount of and serum free media+ antibiotics is added, and incubated for approximately 4 days at 28° C. Media that contains the recombinant baculovirus was collected and spun for approximately 5 minutes at 1000 rpm to remove cell debris. The baculovirus was stored at 4° C. under dark.

Amplification of Baculovirus (P1)

SD cells were grown to approximately $4 \times 10^6$ cells/mL and diluted to approximately $2 \times 10^6$ cells/mL with fresh medium in shaking flasks. An amount of the SD cells were infected with an amount of the P0 stock baculovirus. The multiplicity of infection (MOI) is approximately 0.1.

The Sf9 cells were incubated for approximately 3 days and the baculovirus was harvested. The cells were spun at 2,000 rpm for 5 minutes to pellet the cells and the supernatant was collected and stored at 4° C. under dark. The titer of the baculovirus was determined according to Clontech's Rapid Titer Kit protocol.

Production of AAV Using P1 Recombinant Baculoviruses

Sf9 cells were grown to about $1 \times 10^7$ cells/mL and diluted to about $5 \times 10^6$ cells/mL. An amount of the diluted Sf9 cells were infected with Bac-vector (5Moi) and Bac-helper (15Moi) for 3 days. Cell viability was assessed on the third day (approximately 50%~70% dead cells are observed).

Cell pellets were harvested by centrifugation at 3000 rpm for 10 minutes. Media was removed and the cells lysed (or the cell pellets were stored at −20° C. if not used immediately).

Lysis and Banding Protocol

An amount of Sf9 lysis buffer plus Benzonase is added to each cell pellet and vortexed thoroughly to resuspend the cells. The resuspended Sf9 cells were incubated on ice for approximately 10 min. to cool lysate. The lysate was sonicated for approximately 20 seconds to lyse the cells thoroughly and then incubated at 37° C. for approximately 30 minutes.

An amount of 5M NaCl was added and the mixture is vortexed and then incubated for another 30 minutes at 37° C. An amount of NaCl was added to bring the salt concentration to about 500 mM, vortexed and centrifuged at 8,000 rpm for 20 minutes at 15° C. to produce a cleared lysate.

The cleared lysate proceeds to ultracentrifugation steps. A CsCl-gradient was prepared by adding the cleared lysate first, then an amount of 1.32 g/cc and an amount of 1.55 g/cc CsCl solutions through a syringe with long needle. The interface between the CsCl solutions was marked. PBS was added up to the top of the centrifuge tubes and the tubes are carefully balanced and sealed.

The tubes were centrifuged at 55,000 rpm for approximately 20 hours at 15° C. A hole was puncture on the top of each tube and the AAV band located slightly above the interface mark of the two CsCl solutions is marked.

A second CsCl centrifugation is conducted by transferring the AAV solution to centrifuge tube for 70.1 Ti rotor and an amount of CsCl solution to near top of the tube was added. The tubes were balanced and sealed. The tubes are centrifuged at 65,000 rpm for approximately 20 hours and the AAV band (lower band, the higher band is empty capsids) was collected.

Example 5

Evaluation of the Constructs in Rag2 Mice

AAV genomes which comprise a codon optimized SQ FVIII-encoding gene sequence were generated using baculovirus and 293 cells using the UCL SQ, Proto 1, Proto S1, Proto S2 and Proto S3 constructs. The packaging limits are 4800 bp for baculovirus and 4950 for 293 cells.

Figure 5:
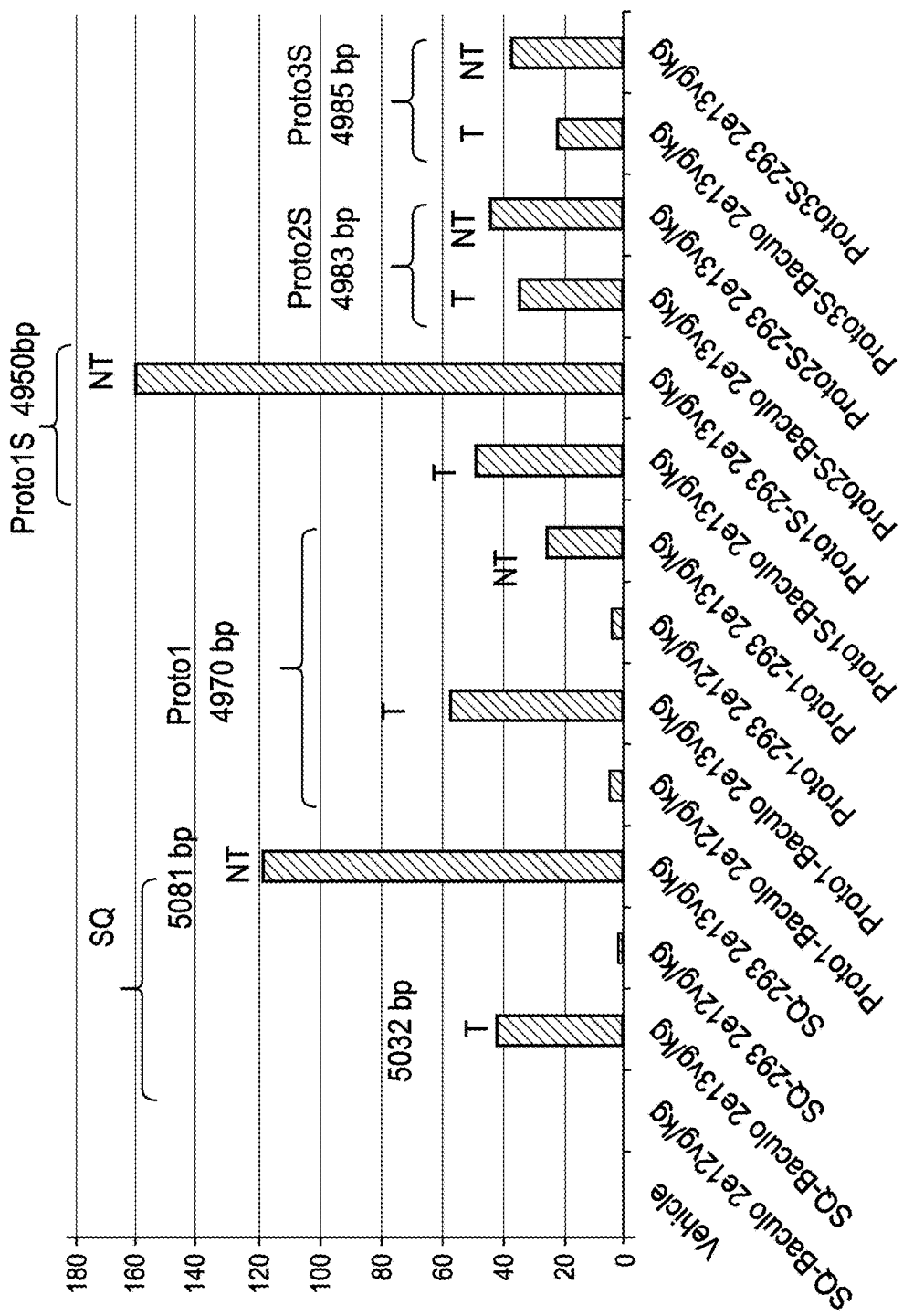
FIG. 5 provides the results of the evaluation of the Proto Constructs in Rag2 mice, and demonstrates Proto 1 transduces FVIII similarly to wild type.
Figure 6:
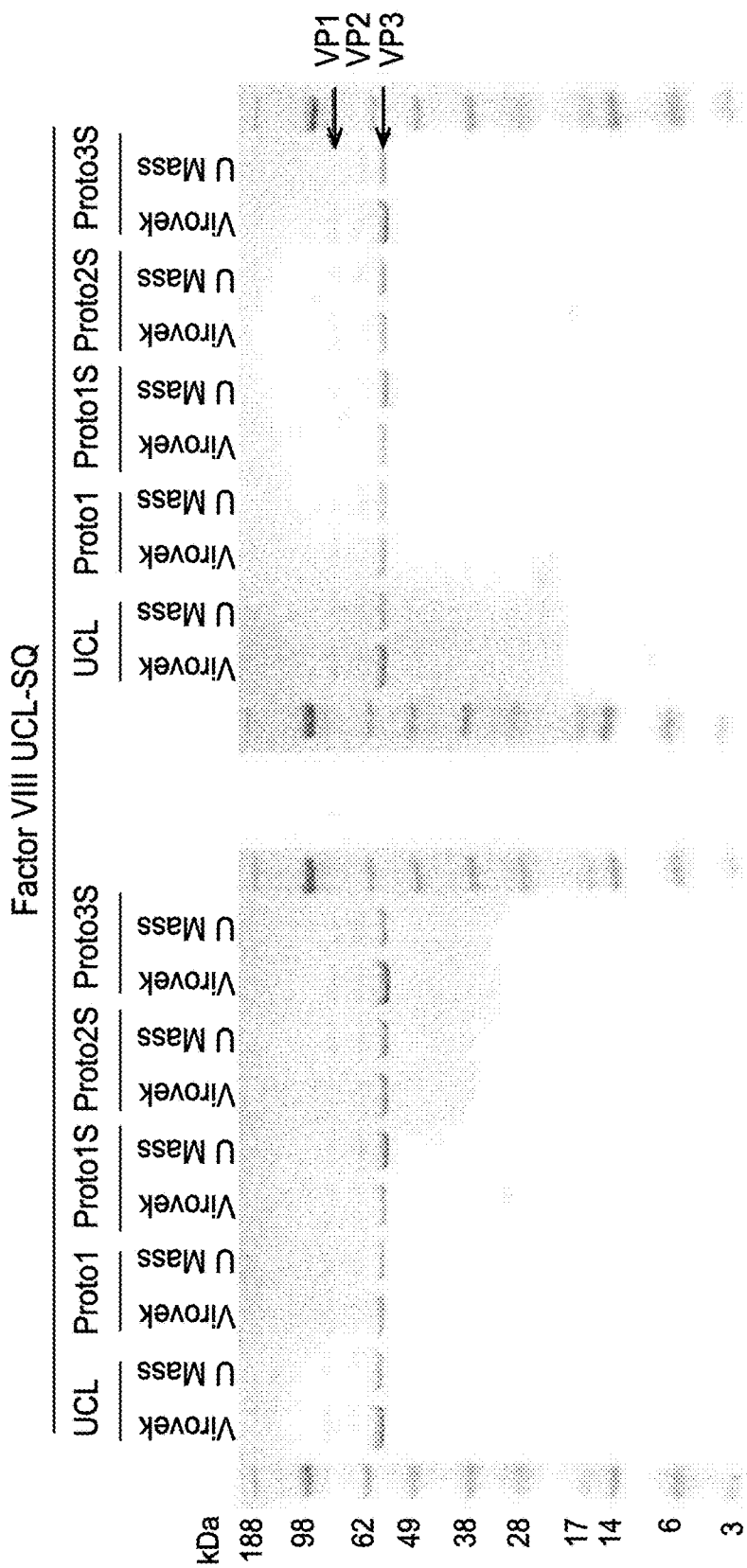
FIGS. 6 and 7 demonstrate that Proto 1, Proto 15, Proto 2S and Proto 3S express the VP1, VP2 and VP3 protein (FIG. 5) and the VP1, VP2 and VP3 DNA (FIG. 6).
Figure 7:
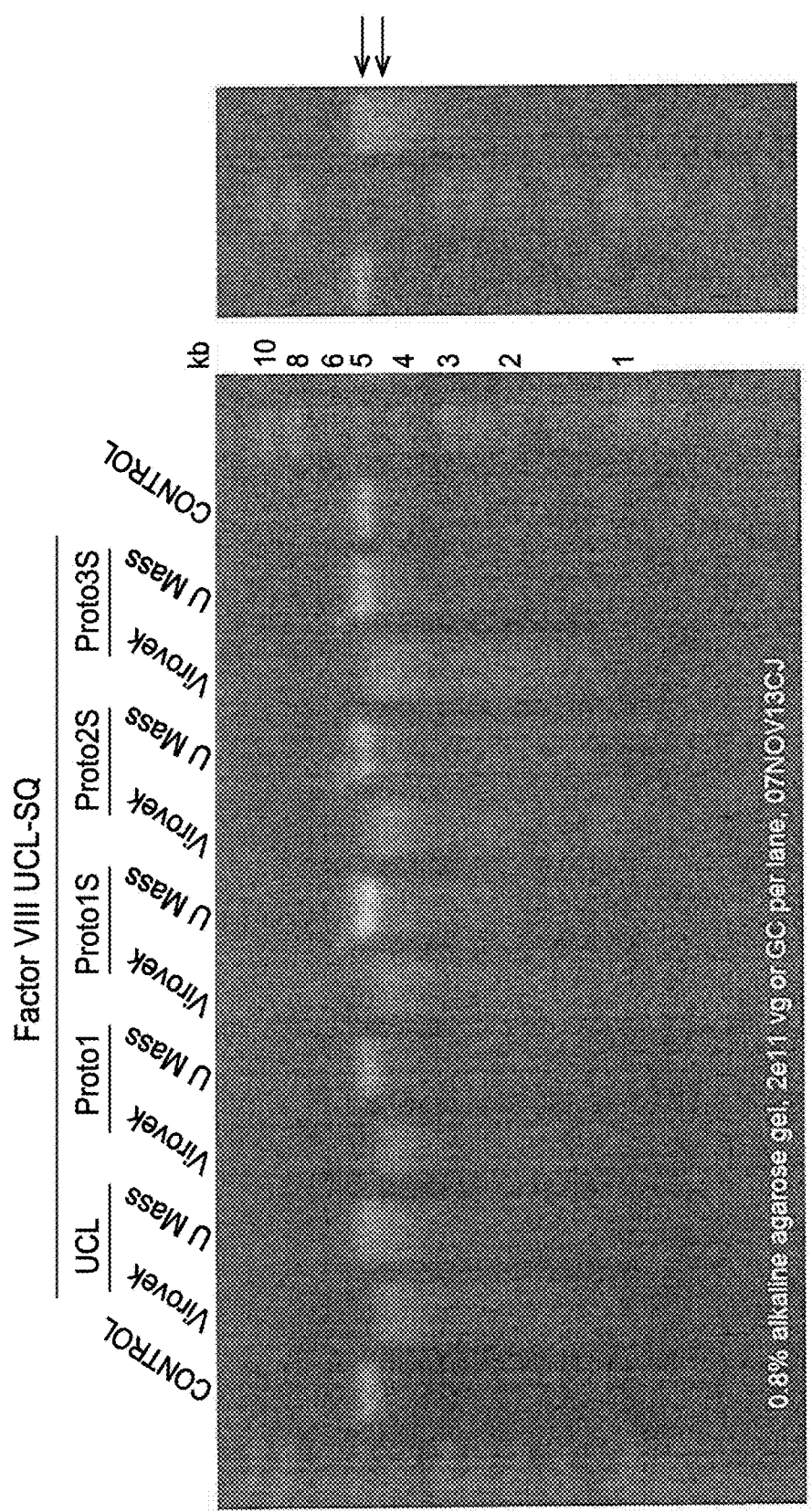

As shown in FIG. 5, Proto 1 with truncated or non-truncated genomes transduce FVIII similar to the UCL SQ construct. The AAV5.2 produced from baculovirus and 293T cell lysates as measured on a on 4-12% Bis-Tris Gel. Each samples expressed VP1, VP2 and VP3 protein, as shown in the FIG. 6. The genomic DNA from the AAV samples was run on 0.8% alkaline agarose gels, as shown in FIG. 7.

Transduction of Proto 1 was similar to the UCL SQ construct when these AAV were made by the baculovirus system. The inclusion of the intron containing Proto2S and 3S did not transduce better than Proto 1. The UCL SQ vector containing the AAV flanking sequences made in 293 cells were more potent than the UCL SQ lacking the AAV sequence made in baculovirus. As a result, additional enhancers were added to Proto 1, e.g. Construct 101, 102, 102 and 104, in an attempt to increase potency.

Example 6

Expression and Activity of AAV FVIII Vectors with Improved Promoters/Enhancer Sequences The expression and activity of AAV vectors comprising Constructs 99 to Construct 106 were tested using the hydrodynamic injection protocol. Hydrodynamic delivery is a rapid method to screen liver promoters in vivo. AAV plasmid DNA was generated using the method described in Example 5 and then diluted in TransIT-QR Hydrodynamic Delivery Solution. The plasmid DNA was injected into the tail vein of 5-6 week old C57Bl/6 mice (18-25 g) at a volume determined by (mouse weight (g)/10)=0.1 ml delivery solution). The injection time was less than 5 seconds. Plasma from each mouse was collected 48 hours after injection and the amount of FVIII antigen expressed was measured using an ELISA assay.

Increasing doses of Proto 1 plasmid (2.5, 5, 12.5 and 50 µg) were injected into the tail vein of mice. The amount of FVIII in the plasma of the injected mouse was measured using an ELISA test and recombinant FVIII (Xyntha SQ equivalents) was used as a standard for comparison.

Figure 8:
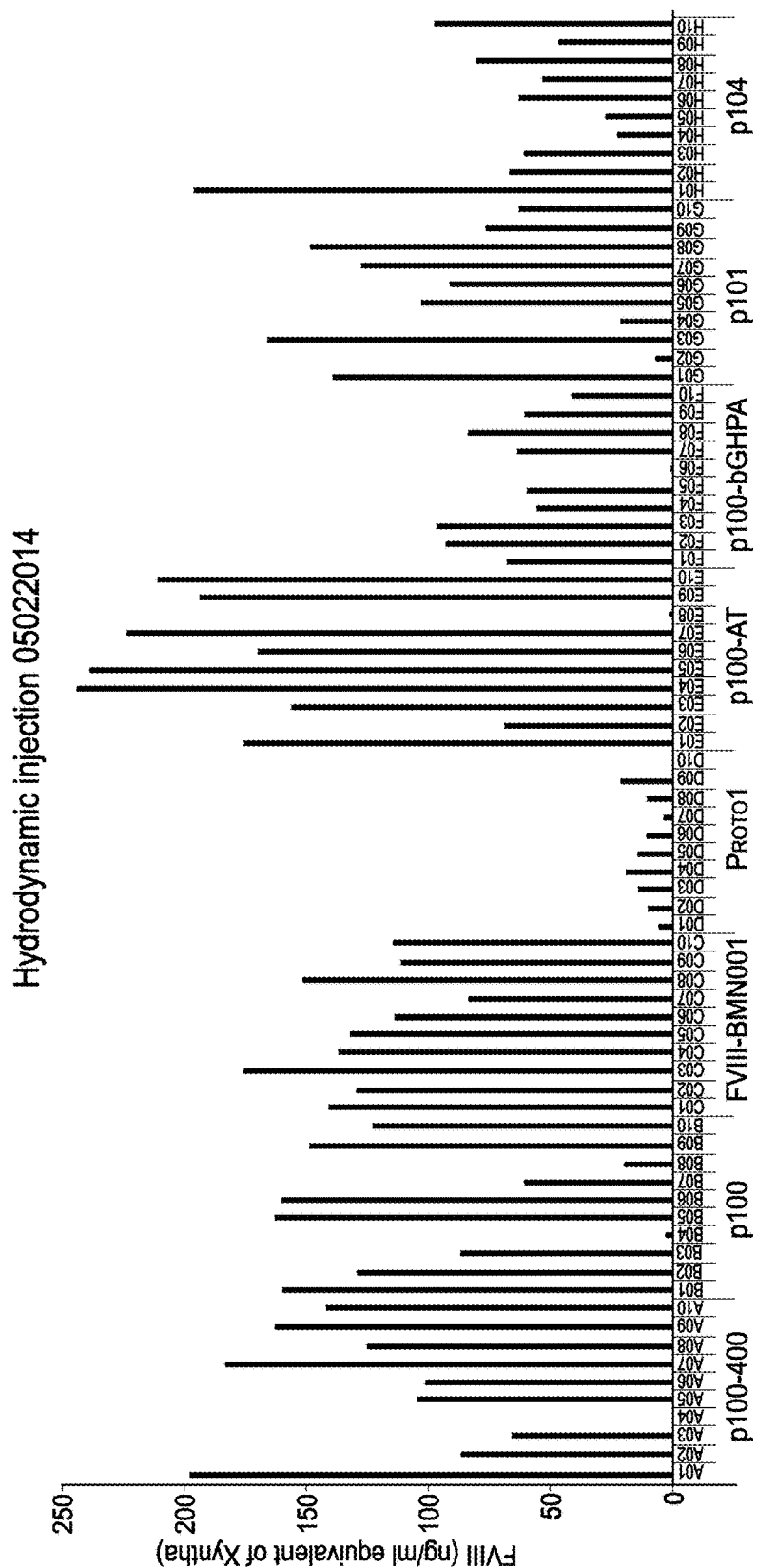
FIGS. 8-10 demonstrate that improved promoter constructs have increased expression of FVIII.

To investigate expression the improved promoter/enhancer elements of construct p100-400, Construct 100 (p100), Construct FVIII-BMN001 (pFVIII-BMN001), Protol, Construct 100AT (p100-AT), Construct 100 bGH poly A (p100-bGHPA), Construct 101 (p101) and Construct 104 (p104). As shown in FIG. 8, all constructs produced functional FVIII at varying levels of efficiency.

Figure 9:
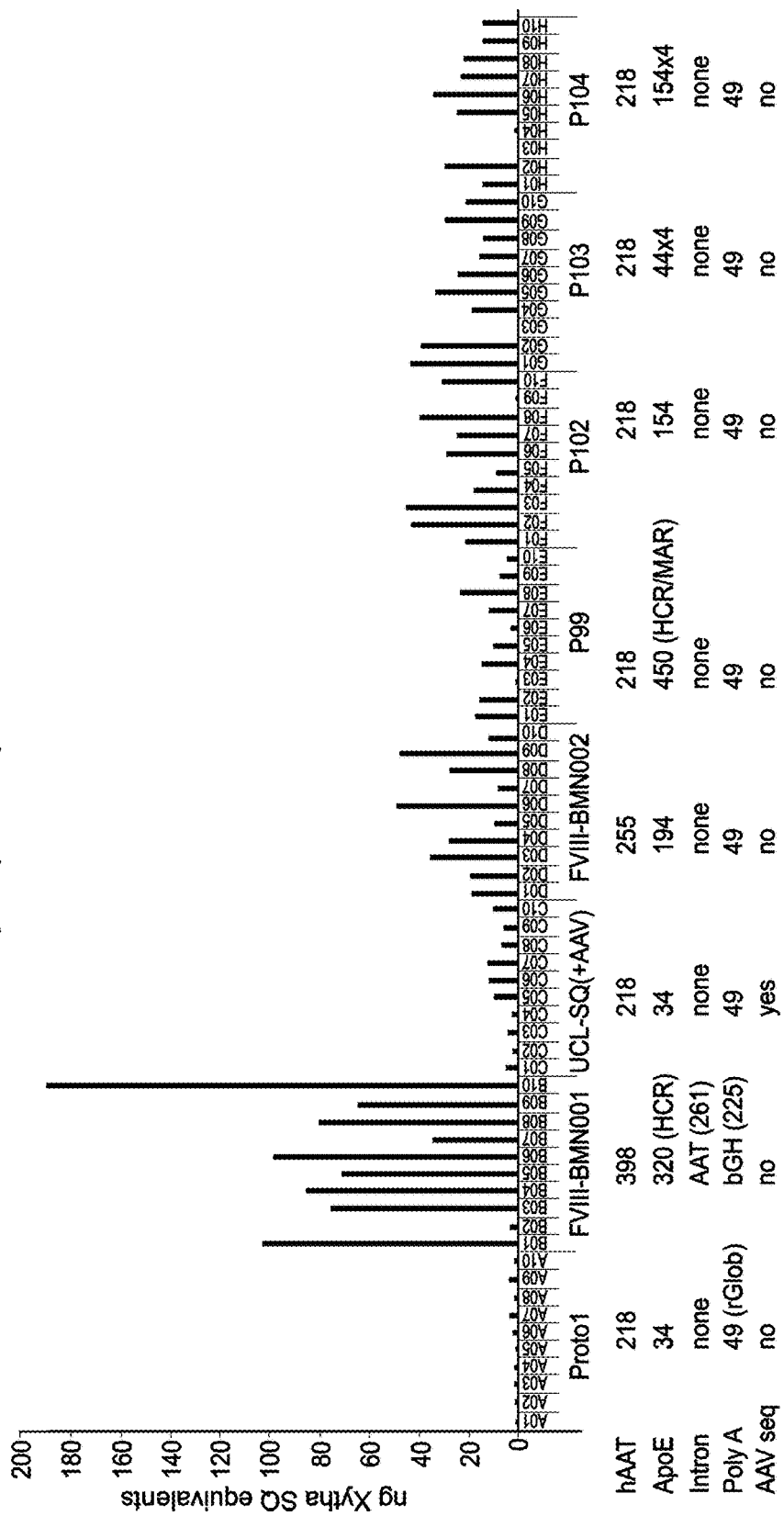
Figure 10:
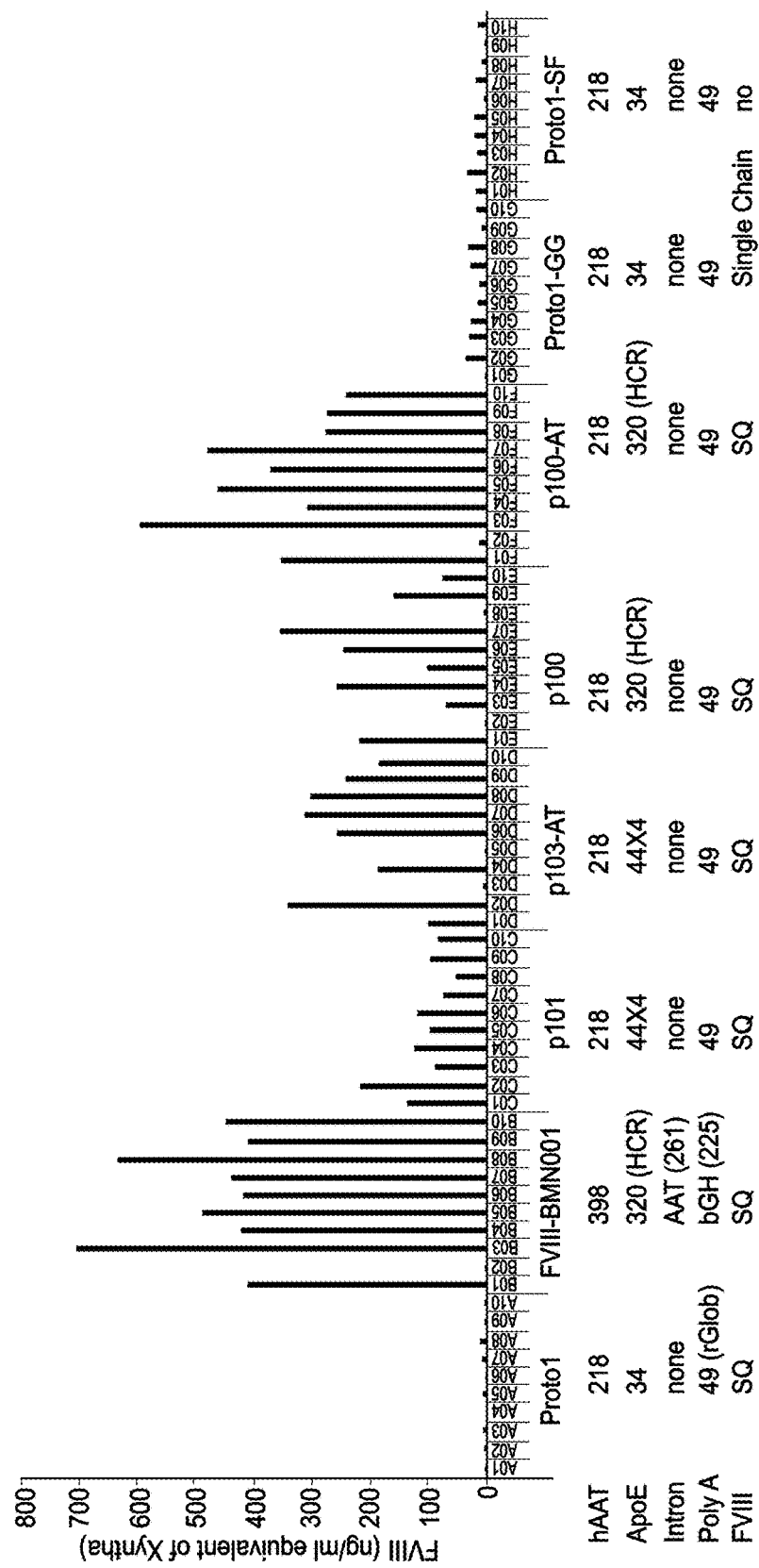

FIGS. 9 and 10 provide data for injection of 1 µg of plasmid of various constructs. As shown in FIG. 8, injection of Construct FVIII-BMN001, Constuct FVIII-BMN002, Construct 102 (p102), Construct 103 (p103) and Construct 104 (p104) resulted in expression of at least 20 ng of FVIII in 5 out of 10 mice. As shown in FIG. 9, injection of Construct FVIII-BMN001, Construct 103 (p103), Construct 103-AT (p103-AT; 398 bp hAAT promoter), Construct 100 (p100), Construct 100AT (p100-AT; 398 bp hAAT promoter) resulted in expression of at least 100 ng/ml of FVIII in 5 out of 10 mice.

What is claimed:

1. An adeno-associated virus (AAV) vector, comprising an AAV2 5' inverted terminal repeat (ITR), a liver-specific transcriptional regulatory region, a functionally active FVIII coding region, a polyadenylation sequence, an AAV2 3' ITR, and optionally one or more introns, wherein said AAV vector is less than 5.0 kb in length.

2. The AAV vector of claim 1, wherein said liver-specific transcriptional regulatory region is located immediately 3' to said AAV2 5' ITR.

3. The AAV vector of claim 2, wherein said liver-specific regulatory region comprises nucleotides 146-397 of SEQ ID NO:1.

4. The AAV vector of claim 1, which comprises nucleotides 1-397 of SEQ ID NO:1.

5. The AAV vector of claim 1, wherein said functionally active FVIII coding region comprises nucleotides 923-5296 of SEQ ID NO: 9.

6. A method of producing a recombinant adeno-associated virus (AAV) particle comprising (a) culturing a host cell that has been transfected with the AAV vector of claim 1 to provide a cell culture, and (b) recovering recombinant AAV particle from the supernatant of said cell culture.

7. A viral particle comprising the AAV vector of claim 1.

8. A composition comprising the viral particle of claim 7 for the treatment of hemophilia A.

9. A method of treating a patient suffering from hemophilia A comprising intravenously administering to the patient an effective amount of the viral particle of claim 7.

10. The AAV vector of claim 1 wherein the functionally active FVIII coding region encodes the FVIII-SQ variant.

* * * * *

SEQUENCE LISTING

<160> NUMBER OF SEQ ID NOS: 45

<210> SEQ ID NO 1
<211> LENGTH: 4970
<212> TYPE: DNA
<213> ORGANISM: Adeno-Associated Virus

<400> SEQUENCE: 1

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgtttg ctgcttgcaa tgtttgccca ttttagggtg     180
gacacaggac gctgtggttt ctgagccagg gggcgactca gatcccagcc agtggactta     240
gcccctgttt gctcctccga taactggggt gaccttggtt aatattcacc agcagcctcc     300
cccgttgccc ctctggatcc actgcttaaa tacggacgag gacagggccc tgtctcctca     360
gcttcaggca ccaccactga cctgggacag tgaatcgcca ccatgcagat tgagctgagc     420
acctgcttct tcctgtgcct gctgaggttc tgcttctctg ccaccaggag atactacctg     480
ggggctgtgg agctgagctg ggactacatg cagtctgacc tggggagct gcctgtggat      540 gccaggttcc cccccagagt gcccaagagc ttccccttca acacctctgt ggtgtacaag     600
aagaccctgt ttgtggagtt cactgaccac ctgttcaaca ttgccaagcc caggcccccc     660
tggatgggcc tgctgggccc caccatccag gctgaggtgt atgacactgt ggtgatcacc     720
ctgaagaaca tggccagcca ccctgtgagc ctgcatgctg tggggtgag ctactggaag      780 gcctctgagg gggctgagta tgatgaccag accagccaga gggagaagga ggatgacaag     840
gtgttccctg ggggcagcca cacctatgtg tggcaggtgc tgaaggagaa tggccccatg     900
gcctctgacc ccctgtgcct gacctacagc tacctgagcc atgtggacct ggtgaaggac     960
ctgaactctg gcctgattgg ggccctgctg gtgtgcaggg agggcagcct ggccaaggag    1020
aagacccaga ccctgcacaa gttcatcctg ctgtttgctg tgtttgatga gggcaagagc    1080
tggcactctg aaaccaagaa cagcctgatg caggacaggg atgctgcctc tgccagggcc    1140
tggcccaaga tgcacactgt gaatggctat gtgaacagga gcctgcctgg cctgattggc    1200
tgccacagga gtctgtgta ctggcatgtg attggcatgg gcaccacccc tgaggtgcac    1260
agcatcttcc tggagggcca caccttcctg gtcaggaacc acaggcaggc cagcctggag    1320
atcagcccca tcaccttcct gactgcccag acccttgctga tggacctggg ccagttcctg    1380
ctgttctgcc acatcagcag ccaccagcat gatggcatgg aggcctatgt gaaggtggac    1440
agctgccctg aggagcccca gctgaggat aagaacaatg aggaggctga ggactatgat    1500
gatgacctga ctgactctga gatggatgtg gtgaggtttg atgatgacaa cagccccagc    1560
ttcatccaga tcaggtctgt ggccaagaag caccccaaga cctgggtgca ctacattgct    1620
gctgaggagg aggactggga ctatgccccc ctggtgctgg cccctgatga caggagctac    1680
aagagccagt acctgaacaa tggccccag aggattggca ggaagtacaa gaaggtcagg    1740
ttcatggcct acactgatga acccttcaag accaggagg ccatccagca tgagtctggc    1800
atcctgggcc cctgctgta tgggaggtg ggggacaccc tgctgatcat cttcaagaac    1860
caggccagca ggccctacaa catctacccc catggcatca tgatgtgag gccccctgtac    1920 agcaggagg tgcccaaggg ggtgaagcac ctgaaggact ccccatcct gcctggggag    1980 atcttcaagt acaagtggac tgtgactgtg gaggatggcc caccaagtc tgaccccagg    2040 tgcctgacca gatactacag cagctttgtg aacatggaga gggacctggc ctctggcctg    2100
```

```
attggccccc tgctgatctg ctacaaggag tctgtggacc agaggggcaa ccagatcatg    2160
tctgacaaga ggaatgtgat cctgttctct gtgtttgatg agaacaggag ctggtacctg    2220
actgagaaca tccagaggtt cctgcccaac cctgctgggg tgcagctgga ggaccctgag    2280
ttccaggcca gcaacatcat gcacagcatc aatggctatg tgtttgacag cctgcagctg    2340
tctgtgtgcc tgcatgaggt ggcctactgg tacatcctga gcattggggc ccagactgac    2400
ttcctgtctg tgttcttctc tggctacacc ttcaagcaca gatggtgta tgaggacacc    2460 ctgaccctgt tcccttctc tggggagact gtgttcatga gcatggagaa ccctggcctg    2520
tggattctgg gctgccacaa ctctgacttc aggaacaggg gcatgactgc cctgctgaaa    2580
gtctccagct gtgacaagaa cactggggac tactatgagg acagctatga ggacatctct    2640
gcctacctgc tgagcaagaa caatgccatt gagcccagga gcttcagcca gaaccccca    2700 gtgctgaaga ggcaccagag ggagatcacc aggaccaccc tgcagtctga ccaggaggag    2760
attgactatg atgacaccat ctctgtggag atgaagaagg aggactttga catctacgac    2820
gaggacgaga accagagccc caggagcttc agaagaaga ccaggcacta cttcattgct    2880
gctgtggaga ggctgtggga ctatggcatg agcagcagcc cccatgtgct gaggaacagg    2940
gcccagtctg gctctgtgcc ccagttcaag aaggtggtgt tccaggagtt cactgatggc    3000
agcttcaccc agccctgta cagagggggag ctgaatgagc acctgggcct gctgggcccc    3060
tacatcaggg ctgaggtgga ggacaacatc atggtgacct caggaaacca ggccagcagg    3120
ccctacagct tctacagcag cctgatcagc tatgaggagg accagaggca gggggctgag    3180
cccaggaaga acttttgtgaa gcccaatgaa accaagacct acttctggaa ggtgcagcac    3240
cacatggccc ccaccaagga tgagtttgac tgcaaggcct gggcctactt ctctgatgtg    3300
gacctggaga aggatgtgca ctctggcctg attggccccc tgctggtgtg ccacaccaac    3360
accctgaacc ctgcccatgg caggcaggtg actgtgcagg agtttgccct gttcttcacc    3420
atctttgatg aaaccaagag ctggtacttc actgagaaca tggagaggaa ctgcagggcc    3480
ccctgcaaca tccagatgga ggaccccacc ttcaaggaga actacaggtt ccatgccatc    3540
aatggctaca tcatggacac cctgcctggc ctggtgatgg cccaggacca ggatcagg    3600 tggtacctgc tgagcatggg cagcaatgag aacatccaca gcatccactt ctctggccat    3660
gtgttcactg tgaggaagaa ggaggagtac aagatggccc tgtacaacct gtaccctggg    3720
gtgtttgaga ctgtggagat gctgcccagc aaggctggca tctggagggt ggagtgcctg    3780
attggggagc acctgcatgc tggcatgagc accctgttcc tggtgtacag caacaagtgc    3840 cagaccccc tgggcatggc ctctggccac atcagggact tccagatcac tgcctctggc    3900
cagtatggcc agtgggcccc caagctggcc aggctgcact actctggcag catcaatgcc    3960
tggagcacca aggagccctt cagctggatc aaggtggacc tgctggcccc catgatcatc    4020
catggcatca gaccagggg ggccaggcag aagttcagca gcctgtacat cagccagttc    4080
atcatcatgt acagcctgga tggcaagaag tggcagacct caggggcaa cagcactggc    4140 accctgatgg tgttcttgg caatgtggac agctctggca tcaagcacaa catcttcaac    4200 cccccatca ttgccagata catcaggctg caccccaccc actacagcat caggagcacc    4260
ctgaggatgg agctgatggg ctgtgacctg aacagctgca gcatgcccct gggcatggag    4320
agcaaggcca tctctgatgc ccagatcact gccagcagct acttcaccaa catgtttgcc    4380
acctggagcc ccagcaaggc caggctgcac ctgcagggca ggagcaatgc ctggaggccc    4440
```

```
caggtcaaca accccaagga gtggctgcag gtggacttcc agaagaccat gaaggtgact    4500
ggggtgacca cccaggggt gaagagcctg ctgaccagca tgtatgtgaa ggagttcctg     4560
atcagcagca gccaggatgg ccaccagtgg accctgttct tccagaatgg caaggtgaag    4620
gtgttccagg caaccagga cagcttcacc cctgtggtga acagcctgga ccccccctg     4680 ctgaccagat acctgaggat tcaccccag agctgggtgc accagattgc cctgaggatg     4740
gaggtgctgg gctgtgaggc ccaggacctg tactgaaata aagatctttt attttcatta    4800
gatctgtgtg ttggttttt gtgtgaggaa cccctagtga tggagttggc cactccctct     4860
ctgcgcgctc gctcgctcac tgaggccggg cgaccaaagg tcgcccgacg cccgggcttt    4920
gcccgggcgg cctcagtgag cgagcgagcg cgcagagagg gagtggccaa              4970

<210> SEQ ID NO 2
<211> LENGTH: 4950
<212> TYPE: DNA
<213> ORGANISM: Adeno-Associated Virus

<400> SEQUENCE: 2
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg    120
gccaactcca tcactgtttg ctgcttgcaa tgtttgccca ttttagggtg gacacaggac    180
gctgtggttt ctgagccagg gggcgactca gatcccagcc agtggactta gcccctgttt    240
gctcctccga taactgggt gaccttggtt aatattcacc agcagcctcc ccgttgccc     300 ctctggatcc actgcttaaa tacgacgag acagggccc tgtctcctca gcttcaggca      360
ccaccactga cctgggacag tgaatcgcca ccatgcagat tgagctgagc acctgcttct     420
tcctgtgcct gctgaggttc tgcttctctg ccaccaggag atactacctg ggggctgtgg     480
agctgagctg ggactacatg cagtctgacc tgggggagct gcctgtggat gccaggttcc     540
cccccagagt gcccaagagc ttcccttca cacctctgt ggtgtacaag aagaccctgt      600 tgtggagtt cactgaccac ctgttcaaca ttgccaagcc caggcccccc tggatgggcc     660
tgctgggccc caccatccag gctgaggtgt atgacactgt ggtgatcacc ctgaagaaca    720
tggccagcca ccctgtgagc ctgcatgctg tgggggtgag ctactggaag gcctctgagg    780
gggctgagta tgatgaccag accagccaga gggagaagga ggatgacaag gtgttccctg    840
ggggcagcca cacctatgtg tggcaggtgc tgaaggagaa tggccccatg gcctctgacc    900
ccctgtgcct gacctacagc tacctgagcc atgtggacct ggtgaaggac ctgaactctg    960
gcctgattgg ggccctgctg gtgtgcaggg agggcagcct ggccaaggag aagacccaga    1020
ccctgcacaa gttcatcctg ctgtttgctg tgtttgatga gggcaagagc tggcactctg    1080
aaaccaagaa cagcctgatg caggacaggg atgctgcctc tgccagggcc tggcccaaga    1140
tgcacactgt gaatggctat gtgaacagga gcctgcctgg cctgattggc tgccacagga    1200
agtctgtgta ctggcatgtg attggcatgg gcaccacccc tgaggtgcac agcatcttcc    1260
tggagggcca caccttcctg gtcaggaacc acaggcaggc cagcctggag atcagcccca    1320
tcaccttcct gactgcccag acctgctga tggacctggg ccagttcctg ctgttctgcc     1380
acatcagcag ccaccagcat gatggcatgg aggcctatgt gaaggtggac agctgccctg    1440
aggagcccca gctgaggatg aagaacaatg aggagctga ggactatgat gatgacctga    1500
ctgactctga gatggatgtg gtgaggtttg atgatgacaa cagccccagc ttcatccaga    1560
tcaggtctgt ggccaagaag caccccaaga cctgggtgca ctacattgct gctgaggagg    1620
```

```
aggactggga ctatgcccc ctggtgctgg cccctgatga caggagctac aagagccagt    1680
acctgaacaa tggcccccag aggattggca ggaagtacaa gaaggtcagg ttcatggcct    1740
acactgatga aaccttcaag accagggagg ccatccagca tgagtctggc atcctgggcc    1800
ccctgctgta tggggaggtg ggggacaccc tgctgatcat cttcaagaac caggccagca    1860
ggccctacaa catctacccc catggcatca ctgatgtgag gccctgtac agcaggaggc    1920
tgcccaaggg ggtgaagcac ctgaaggact tcccatcct gcctggggag atcttcaagt    1980
acaagtggac tgtgactgtg gaggatggcc ccaccaagtc tgaccccagg tgcctgacca    2040
gatactacag cagctttgtg aacatggaga gggacctggc ctctggcctg attggccccc    2100
tgctgatctg ctacaaggag tctgtggacc agaggggcaa ccagatcatg tctgacaaga    2160
ggaatgtgat cctgttctct gtgtttgatg agaacaggag ctggtacctg actgagaaca    2220
tccagaggtt cctgcccaac cctgctgggg tgcagctgga ggaccctgag ttccaggcca    2280
gcaacatcat gcacagcatc aatggctatg tgtttgacag cctgcagctg tctgtgtgcc    2340
tgcatgaggt ggcctactgg tacatcctga gcattgggc ccagactgac ttcctgtctg    2400
tgttcttctc tggctacacc ttcaagcaca agatggtgta tgaggacacc ctgaccctgt    2460
tccccttctc tggggagact gtgttcatga gcatggagaa ccctggcctg tggattctgg    2520
gctgccacaa ctctgacttc aggaacaggg gcatgactgc cctgctgaaa gtctccagct    2580
gtgacaagaa cactggggac tactatgagg acagctatga ggacatctct gcctacctgc    2640
tgagcaagaa caatgccatt gagcccagga gcttcagcca gaaccccca gtgctgaaga    2700
ggcaccagag ggagatcacc aggaccaccc tgcagtctga ccaggaggag attgactatg    2760
atgacaccat ctctgtggag atgaagaagg aggactttga catctacgac gaggacgaga    2820
accagagccc caggagcttc cagaagaaga ccaggcacta cttcattgct gctgtggaga    2880
ggctgtggga ctatgcatg agcagcagcc ccatgtgct gaggaacagg gcccagtctg    2940
gctctgtgcc ccagttcaag aaggtggtgt ccaggagtt cactgatggc agcttcaccc    3000
agccctgta cagaggggag ctgaatgagc acctgggcct gctgggcccc tacatcaggg    3060
ctgaggtgga ggacaacatc atggtgacct tcaggaacca ggccagcagg ccctacagct    3120
tctacagcag cctgatcagc tatgaggagg accagaggca gggggctgag cccaggaaga    3180
actttgtgaa gcccaatgaa accaagacct acttctggaa ggtgcagcac cacatggccc    3240
ccaccaagga tgagtttgac tgcaaggcct gggcctactt ctctgatgtg acctggagaa    3300
aggatgtgca ctctggcctg attggccccc tgctggtgtg ccacaccaac accctgaacc    3360
ctgcccatgg caggcaggtg actgtgcagg agtttgccct gttcttcacc atctttgatg    3420
aaaccaagag ctggtacttc actgagaaca tggagaggaa ctgcagggcc cctgcaaca    3480
tccagatgga ggaccccacc ttcaaggaga actacaggtt ccatgccatc aatggctaca    3540
tcatggacac cctgcctggc ctggtgatgg cccaggacca gaggatcagg tggtacctgc    3600
tgagcatggg cagcaatgag aacatccaca gcatccactt ctctggccat gtgttcactg    3660
tgaggaagaa ggaggagtac aagatggccc tgtacaacct gtaccctggg gtgtttgaga    3720
ctgtggagat gctgcccagc aaggctggca tctggagggt ggagtgcctg attggggagc    3780
acctgcatgc tggcatgagc accctgttcc tggtgtacag caacaagtgc cagaccccc    3840
tgggcatggc ctctggccac atcagggact tccagatcac tgcctctggc cagtatggcc    3900
agtgggcccc caagctggcc aggctgcact actctggcag catcaatgcc tggagcacca    3960
```

| | |
|---|---|
| aggagcccett cagctggatc aaggtggacc tgctggcccc catgatcatc catggcatca | 4020 |
| agacccaggg ggccaggcag aagttcagca gcctgtacat cagccagttc atcatcatgt | 4080 |
| acagcctgga tggcaagaag tggcagacct acagggggcaa cagcactggc accctgatgg | 4140 |
| tgttctttgg caatgtggac agctctggca tcaagcacaa catcttcaac cccccatca | 4200 |
| ttgccagata catcaggctg cacccacccc actacagcat caggagcacc ctgaggatgg | 4260 |
| agctgatggg ctgtgacctg aacagctgca gcatgcccct gggcatggag agcaaggcca | 4320 |
| tctctgatgc ccagatcact gccagcagct acttcaccaa catgtttgcc acctggagcc | 4380 |
| ccagcaaggc caggctgcac ctgcagggca ggagcaatgc ctggaggccc caggtcaaca | 4440 |
| accccaagga gtggctgcag gtggacttcc agaagaccat gaaggtgact ggggtgacca | 4500 |
| cccagggggt gaagagcctg ctgaccagca tgtatgtgaa ggagttcctg atcagcagca | 4560 |
| gccaggatgg ccaccagtgg accctgttct tccagaatgg caaggtgaag gtgttccagg | 4620 |
| gcaaccagga cagcttcacc cctgtggtga cagcctgga ccccccctg ctgaccagat | 4680 |
| acctgaggat tcaccccag agctgggtgc accagattgc cctgaggatg gaggtgctgg | 4740 |
| gctgtgaggc ccaggacctg tactgaaata aagatcttt attttcatta gatctgtgtg | 4800 |
| ttggtttttt gtgtgagtga tggagttggc cactccctct ctgcgcgctc gctcgctcac | 4860 |
| tgaggccggg cgaccaaagg tcgcccgacg cccgggcttt gcccgggcgg cctcagtgag | 4920 |
| cgagcgagcg cgcagagagg gagtggccaa | 4950 |

<210> SEQ ID NO 3
<211> LENGTH: 4983
<212> TYPE: DNA
<213> ORGANISM: Adeno-Associated Virus

<400> SEQUENCE: 3

| | |
|---|---|
| ttggccactc cctctctgcg cgctcgctcg ctcactgagg ccgcccgggc aaagcccggg | 60 |
| cgtcgggcga cctttggtcg cccggcctca gtgagcgagc gagcgcgcag agagggagtg | 120 |
| gccaactcca tcactgggcg actcagatcc cagccagtgg acttagcccc tgtttgctcc | 180 |
| tccgataact ggggtgacct tggttaatat tcaccagcag cctcccccgt tgcccctctg | 240 |
| gatccactgc ttaaatacgg acgaggacag ggccctgtct cctcagcttc aggcaccacc | 300 |
| actgacctgg gacagtgaat cgccaccatg cagattgagc tgagcacctg cttcttcctg | 360 |
| tgcctgctga gattctgctt tagtgccacc agaagatact acctgggtgc agtggaactg | 420 |
| tcatgggact atatgcaaag tgatctcggt gagctgcctg tggacgcaag gtaaatgccc | 480 |
| taaaatgggc aaacattgca agcagcaaac aacctggctc agaaaccaca gcgtcctgtg | 540 |
| tccattctaa ttttttccttt cttcacgcag atttcctcct agagtgccaa atcttttcc | 600 |
| attcaacacc tcagtcgtgt acaaaaagac tctgtttgta gaattcacgg atcacctttt | 660 |
| caacatcgct aagcccaggc cccctggat gggcctgctg ggccccacca tccaggctga | 720 |
| ggtgtatgac actgtggtga tcaccctgaa gaacatggcc agccccctg tgagcctgca | 780 |
| tgctgtgggg gtgagctact ggaaggcctc tgagggggct gagtatgatg accagaccag | 840 |
| ccagagggag aaggaggatg acaaggtgtt cctgggggc agccacacct atgtgtggca | 900 |
| ggtgctgaag gagaatggcc ccatggcctc tgaccccctg tgcctgacct acagctacct | 960 |
| gagccatgtg gacctggtga aggacctgaa ctcggcctg attggggccc tgctggtgtg | 1020 |
| cagggagggc agcctggcca aggagaagac ccagaccctg cacaagttca tcctgctgtt | 1080 |
| tgctgtgttt gatgagggca agagctggca ctctgaaacc aagaacagcc tgatgcagga | 1140 |

```
cagggatgct gcctctgcca gggcctggcc caagatgcac actgtgaatg gctatgtgaa    1200
caggagcctg cctggcctga ttggctgcca caggaagtct gtgtactggc atgtgattgg    1260
catgggcacc acccctgagg tgcacagcat cttcctggag ggccacacct tcctggtcag    1320
gaaccacagg caggccagcc tggagatcag ccccatcacc ttcctgactg cccagaccct    1380
gctgatggac ctgggccagt tcctgctgtt ctgccacatc agcagccacc agcatgatgg    1440
catggaggcc tatgtgaagg tggacagctg ccctgaggag ccccagctga ggatgaagaa    1500
caatgaggag gctgaggact atgatgatga cctgactgac tctgagatgg atgtggtgag    1560
gtttgatgat gacaacagcc ccagcttcat ccagatcagg tctgtgggcc agaagcaccc    1620
caagacctgg gtgcactaca ttgctgctga ggaggaggac tgggactatg ccccctggt    1680 gctgcccct gatgacagga gctacaagag ccagtacctg aacaatggcc cccagaggat    1740
tggcaggaag tacaagaagg tcaggttcat ggcctacact gatgaaacct tcaagaccag    1800
ggaggccatc cagcatgagt ctggcatcct gggccccctg ctgtatgggg aggtggggga    1860
caccctgctg atcatcttca agaaccaggc cagcaggccc tacaacatct acccccatgg    1920
catcactgat gtgaggcccc tgtacagcag gaggctgccc aaggggggtga agcacctgaa    1980 ggacttcccc atcctgcctg gggagatctt caagtacaag tggactgtga ctgtggagga    2040
tggccccacc aagtctgacc ccaggtgcct gaccagatac tacagcagct tgtgaacat    2100 ggagagggac ctggcctctg gcctgattgg ccccctgctg atctgctaca aggagtctgt    2160
ggaccagagg ggcaaccaga tcatgtctga caagaggaat gtgatcctgt tctctgtgtt    2220
tgatgagaac aggagctggt acctgactga gaacatccag aggttcctgc ccaaccctgc    2280
tggggtgcag ctggaggacc ctgagttcca ggccagcaac atcatgcaca gcatcaatgg    2340
ctatgtgttt gacagcctgc agctgtctgt gtgcctgcat gaggtggcct actggtacat    2400
cctgagcatt ggggcccaga ctgacttcct gtctgtgttc ttctctggct acaccttcaa    2460
gcacaagatg gtgtatgagg acaccctgac cctgttcccc ttctctgggg agactgtgtt    2520
catgagcatg gagaaccctg gcctgtggat tctgggctgc cacaactctg acttcaggaa    2580 cagggggcatg actgccctgc tgaaagtctc cagctgtgac aagaacactg ggactacta    2640 tgaggacagc tatgaggaca tctctgccta cctgctgagc aagaacaatg ccattgagcc    2700
caggagcttc agccagaacc ccccagtgct gaagaggcac cagagggaga tcaccaggac    2760
caccctgcag tctgaccagg aggagattga ctatgatgac accatctctg tggagatgaa    2820
gaaggaggac tttgacatct cgacgagga cgagaaccag agcccagga gcttccagaa    2880 gaagaccagg cactacttca ttgctgctgt ggagaggctg tgggactatg catgagcag    2940 cagcccccat gtgctgagga cagggccca gtctggctct gtgccccagt tcaagaaggt    3000
ggtgttccag gagttcactg atggcagctt cacccagccc ctgtacagag gggagctgaa    3060
tgagcacctg gcctgctgg ccccctacat cagggctgag gtggaggaca acatcatggt    3120
gaccttcagg aaccaggcca gcaggcccta cagcttctac agcagcctga tcagctatga    3180
ggaggaccag aggcagggg ctgagcccag gaagaacttt gtgaagccca tgaaaaccaa    3240
gacctacttc tggaaggtgc agcaccacat ggccccacc aaggatgagt ttgactgcaa    3300
ggcctgggcc tacttctctg atgtggacct ggagaaggat gtgcactctg cctgattgg    3360 ccccctgctg gtgtgccaca ccaacaccct gaaccctgcc catggcaggc aggtgactgt    3420
gcaggagttt gccctgttct tcaccatctt tgatgaaacc aagagctggt acttcactga    3480
```

```
gaacatggag aggaactgca gggcccctg caacatccag atggaggacc ccaccttcaa    3540
ggagaactac aggttccatg ccatcaatgg ctacatcatg acaccctgc ctggcctggt    3600
gatggcccag gaccagagga tcaggtggta cctgctgagc atgggcagca atgagaacat    3660
ccacagcatc cacttctctg ccatgtgtt cactgtgagg aagaaggagg agtacaagat    3720
ggccctgtac aacctgtacc ctggggtgtt tgagactgtg agatgctgc ccagcaaggc    3780
tggcatctgg agggtggagt gcctgattgg ggagcacctg catgctggca tgagcaccct    3840
gttcctggtg tacagcaaca agtgccagac ccccctgggc atggcctctg ccacatcag    3900
ggacttccag atcactgcct ctggccagta tggccagtgg gccccaagc tggccaggct    3960
gcactactct ggcagcatca atgcctggag caccaaggag cccttcagct ggatcaaggt    4020
ggacctgctg gcccccatga tcatccatgg catcaagacc cagggggcca ggcagaagtt    4080
cagcagcctg tacatcagcc agttcatcat catgtacagc ctggatggca agaagtggca    4140
gacctacagg ggcaacagca ctggcaccct gatggtgttc tttggcaatg tggacagctc    4200
tggcatcaag cacaacatct tcaaccccc catcattgcc agatacatca ggctgcaccc    4260
cacccactac agcatcagga gcaccctgag gatggagctg atgggctgtg acctgaacag    4320
ctgcagcatg cccctgggca tggagagcaa ggccatctct gatgcccaga tcactgccag    4380
cagctacttc accaacatgt tgccacctg gagccccagc aaggccaggc tgcacctgca    4440
gggcaggagc aatgcctgga ggccccaggt caacaacccc aaggagtggc tgcaggtgga    4500
cttccagaag accatgaagg tgactgggt gaccacccag gggtgaaga gcctgctgac    4560
cagcatgtat gtgaaggagt tcctgatcag cagcagccag gatggccacc agtggaccct    4620
gttcttccag aatggcaagg tgaaggtgtt ccagggcaac caggacagct cacccctgt    4680
ggtgaacagc ctggaccccc ccctgctgac cagatacctg aggattcacc cccagagctg    4740
ggtgcaccag attgccctga ggatggaggt gctgggctgt gaggcccagg acctgtacta    4800
ataaaagatc tttattttca ttagatctgt gtgttggttt tttgtgtgag tgatggagtt    4860
ggccactccc tctctgcgcg ctcgctcgct cactgaggcc gggcgaccaa aggtcgcccg    4920
acgcccgggc tttgcccggg cggcctcagt gagcgagcga gcgcgcagag agggagtggc    4980
caa                                                                 4983

<210> SEQ ID NO 4
<211> LENGTH: 4984
<212> TYPE: DNA
<213> ORGANISM: Adeno-Associated Virus

<400> SEQUENCE: 4
ttggccactc cctctctgcg cgctcgctcg ctcactgagg ccgccgggc aaagcccggg      60
cgtcgggcga cctttggtcg cccggcctca gtgagcgagc gagcgcgcag agagggagtg    120
gccaactcca tcactgggcg actcagatcc cagccagtgg acttagcccc tgtttgctcc    180
tccgataact ggggtgacct tggttaatat tcaccagcag cctccccccgt tgcccctctg    240
gatccactgc ttaaatacgg acgaggacag ggccctgtct cctcagcttc aggcaccacc    300
actgacctgg gacagtgaat cgccaccatg cagattgagc tgagcacctg cttcttcctg    360
tgcctgctga gattctgctt tagtgccacc agaagatact acctgggtgc agtggaactg    420
tcatgggact atatgcaaag tgatctcggt gagctgcctg tggacgcaag gtaaatgccc    480
taaaatgggc aaacattgca agcagcaaac accctaaaat gggcaaacat tgcaagcagc    540
aaacattcta attttccctt tcttcacgca gatttcctcc tagagtgcca aatctttctc    600
```

```
cattcaacac ctcagtcgtg tacaaaaaga ctctgtttgt agaattcacg gatcacctttt    660 tcaacatcgc taagcccagg ccccctgga tgggcctgct gggccccacc atccaggctg      720
aggtgtatga cactgtggtg atcaccctga agaacatggc cagccaccct gtgagcctgc     780
atgctgtggg ggtgagctac tggaaggcct ctgagggggc tgagtatgat gaccagacca     840
gccagaggga aaggaggat gacaaggtgt tccctggggg cagccacacc tatgtgtggc      900
aggtgctgaa ggagaatggc cccatggcct ctgaccccct gtgcctgacc tacagctacc     960
tgagccatgt ggacctggtg aaggacctga actctggcct gattggggcc ctgctggtgt    1020
gcagggaggg cagcctggcc aaggagaaga cccagaccct gcacaagttc atcctgctgt    1080
ttgctgtgtt tgatgagggc aagagctggc actctgaaac caagaacagc ctgatgcagg    1140
acagggatgc tgcctctgcc agggcctggc ccaagatgca cactgtgaat ggctatgtga    1200
acaggagcct gcctggcctg attggctgcc acaggaagtc tgtgtactgg catgtgattg    1260
gcatgggcac caccctgag gtgcacagca tcttcctgga gggccacacc ttcctggtca     1320
ggaaccacag gcaggccagc ctggagatca gccccatcac cttcctgact gcccagaccc    1380
tgctgatgga cctgggccag ttcctgctgt tctgccacat cagcagccac cagcatgatg    1440
gcatggaggc ctatgtgaag gtggacagct gccctgagga gccccagctg aggatgaaga    1500
acaatgagga ggctgaggac tatgatgatg acctgactga ctctgagatg gatgtggtga    1560
ggtttgatga tgacaacagc cccagcttca tccagatcag gtctgtggcc aagaagcacc    1620
ccaagacctg ggtgcactac attgctgctg aggaggagga ctgggactat gccccctgg    1680 tgctggcccc tgatgacagg agctacaaga gccagtacct gaacaatggc cccagagga    1740 ttggcaggaa gtacaagaag gtcaggttca tggcctacac tgatgaaacc ttcaagacca    1800
gggaggccat ccagcatgag tctggcatcc tgggccccct gctgtatggg gaggtggggg    1860
acaccctgct gatcatcttc aagaaccagg ccagcaggcc ctacaacatc taccccatg    1920 gcatcactga tgtgaggccc ctgtacagca ggaggctgcc caaggggtg aagcacctga    1980 aggacttccc catcctgcct ggggagatct tcaagtacaa gtggactgtg actgtggagg    2040
atggccccac caagtctgac cccaggtgcc tgaccagata ctacagcagc tttgtgaaca    2100 tggagagggga cctggcctct ggcctgattg gccccctgct gatctgctac aaggagtctg    2160
tggaccagag gggcaaccag atcatgtctg acaagagga tgtgatcctg ttctctgtgt    2220
ttgatgagaa caggagctgg tacctgactg agaacatcca gaggttcctg cccaaccctg    2280
ctggggtgca gctggaggac cctgagttcc aggccagcaa catcatgcac agcatcaatg    2340
gctatgtgtt tgacagcctg cagctgtctg tgtgcctgca tgaggtggcc tactggtaca    2400
tcctgagcat ggggcccag actgacttcc tgtctgtgtt cttctctggc tacaccttca    2460
agcacaagat ggtgtatgag gacaccctga ccctgttccc cttctctggg gagactgtgt    2520
tcatgagcat ggagaaccct ggcctgtgga ttctgggctg ccacaactct gacttcagga    2580
acaggggcat gactgccctg ctgaaagtct ccagctgtga caagaacact ggggactact    2640
atgaggacag ctatgaggac atctctgcct acctgctgag caagaacaat gccattgagc    2700
ccaggagctt cagccagaac ccccagtgc tgaagaggca ccagagggag atcaccagga    2760
ccaccctgca gtctgaccag gaggagattg actatgatga caccatctct gtggagatga    2820
agaaggagga ctttgacatc tacgacgagg acgagaacca gagcccccag gcttccaga    2880 agaagaccag gcactacttc attgctgctg tggagaggct gtgggactat ggcatgagca    2940
```

```
gcagccccca tgtgctgagg aacagggccc agtctggctc tgtgcccag ttcaagaagg    3000 tggtgttcca ggagttcact gatggcagct cacccagcc cctgtacaga ggggagctga    3060
atgagcacct gggcctgctg gcccctaca tcagggctga ggtggaggac aacatcatgg    3120
tgaccttcag gaaccaggcc agcaggccct acagcttcta cagcagcctg atcagctatg    3180
aggaggacca gaggcagggg gctgagccca ggaagaactt tgtgaagccc aatgaaacca    3240
agacctactt ctggaaggtg cagcaccaca tggcccccac caaggatgag tttgactgca    3300
aggcctgggc ctacttctct gatgtggacc tggagaagga tgtgcactct ggcctgattg    3360 gcccctgct ggtgtgccac accaacaccc tgaaccctgc ccatggcagg caggtgactg    3420
tgcaggagtt tgccctgttc ttcaccatct ttgatgaaac caagagctgg tacttcactg    3480
agaacatgga gaggaactgc agggcccct gcaacatcca gatggaggac ccaccttca    3540 aggagaacta caggttccat gccatcaatg ctacatcat ggacaccctg cctggcctgg    3600
tgatggccca ggaccagagg atcaggtggt acctgctgag catgggcagc aatgagaaca    3660
tccacagcat ccacttctct ggccatgtgt tcactgtgag gaagaaggag gagtacaaga    3720 tggcccctgta caacctgtac cctgggtgt tgagactgt ggagatgctg cccagcaagg    3780
ctggcatctg gagggtggag tgcctgattg gggagcacct gcatgctggc atgagcaccc    3840
tgttcctggt gtacagcaac aagtgccaga ccccctggg catggcctct ggccacatca    3900
gggacttcca gatcactgcc tctggccagt atggccagtg ggcccccaag ctggccaggc    3960
tgcactactc tggcagcatc aatgcctgga gcaccaagga gcccttcagc tggatcaagg    4020
tggacctgct ggcccccatg atcatccatg gcatcaagac ccaggggcc aggcagaagt    4080 tcagcagcct gtacatcagc cagttcatca tcatgtacag cctggatggc aagaagtggc    4140
agacctacag gggcaacagc actggcaccc tgatggtgtt ctttggcaat gtggacagct    4200
ctggcatcaa gcacaacatc ttcaaccccc ccatcattgc cagatacatc aggctgcacc    4260
ccacccacta cagcatcagg agcacccgta ggatggagct gatgggctgt gacctgaaca    4320
gctgcagcat gccctggggc atggagagca aggccatctc tgatgcccag atcactgcca    4380
gcagctactt caccaacatg tttgccacct ggagccccag caaggccagg ctgcacctgc    4440
agggcaggag caatgcctgg aggcccagg tcaacaaccc caaggagtgg ctgcaggtgg    4500
acttccagaa gaccatgaag gtgactgggg tgacccccca ggggtgaag agcctgctga    4560 ccagcatgta tgtgaaggag ttcctgatca gcagcagcca ggatggccac cagtggaccc    4620
tgttcttcca gaatggcaag gtgaaggtgt tccagggcaa ccaggacagc ttcaccctg    4680 tggtgaacag cctggaccc ccctgctga ccagatacct gaggattcac ccccagagct    4740
gggtgcacca gattgccctg aggatggagg tgctgggctg tgaggcccag gacctgtact    4800
aataaaagat ctttattttc attagatctg tgtgttggtt ttttgtgtga gtgatggagt    4860
tggccactcc ctctctgcgc gctcgctcg tcactgaggc cggcgaccc aaggtcgccc    4920 gacgcccggg ctttgcccgg gcggcctcag tgagcgagcg agcgcgcaga gagggagtgg    4980
ccaa                                                                4984
```

<210> SEQ ID NO 5
<211> LENGTH: 4805
<212> TYPE: DNA
<213> ORGANISM: Adeno-Associated Virus

<400> SEQUENCE: 5

```
ttggccactc cctctctgcg cgctcgctcg ctcactgagg ccgcccgggc aaagcccggg        60
```

-continued

```
cgtcgggcga cctttggtcg cccggcctca gtgagcgagc gagcgcgcag agagggagtg      120
gccaactcca tcactagggg ttcctgtttg ctgcttgcaa tgtttgccca ttttagggtg      180
gacacaggac gctgtggttt ctgagccagg gggcgactca gatcccagcc agtggactta      240
gcccctgttt gctcctccga taactggggt gaccttggtt aatattcacc agcagcctcc      300
cccgttgccc ctctggatcc actgcttaaa tacggacgag gacagggccc tgtctcctca      360
gcttcaggca ccaccactga cctgggacag tgaatcgcca ccatgcagat tgagctgagc      420
acctgcttct tcctgtgcct gctgaggttc tgcttctctg ccaccaggag atactacctg      480
ggggctgtgg agctgagctg ggactacatg cagtctgacc tggggagct  gcctgtggat      540 gccaggttcc cccccagagt gcccaagagc ttcccttca  acacctctgt ggtgtacaag      600
aagaccctgt tgtggagtt  cactgaccac ctgttcaaca ttgccaagcc caggcccccc      660
tggatgggcc tgctgggccc caccatccag gctgaggtgt atgacactgt ggtgatcacc      720
ctgaagaaca tggccagcca ccctgtgagc ctgcatgctg tggggtgag  ctactggaag      780 gcctctgagg gggctgagta tgatgaccag accagccaga gggagaagga ggatgacaag      840
gtgttccctg gggcagcca  cacctatgtg tggcaggtgc tgaaggagaa tggccccatg      900
gcctctgacc ccctgtgcct gacctacagc tacctgagcc atgtggacct ggtgaaggac      960
ctgaactctg gcctgattgg ggccctgctg gtgtgcaggg agggcagcct ggccaaggag     1020
aagacccaga ccctgcacaa gttcatcctg ctgtttgctg tgtttgatga gggcaagagc     1080
tggcactctg aaaccaagaa cagcctgatg caggacaggg atgctgcctc tgccagggcc     1140
tggcccaaga tgcacactgt gaatggctat gtgaacagga gcctgcctgg cctgattggc     1200
tgccacagga agtctgtgta ctggcatgtg attggcatgg gcaccacccc tgaggtgcac     1260
agcatcttcc tggagggcca caccttcctg gtcaggaacc acaggcaggc cagcctggag     1320
atcagcccca tcaccttcct gactgcccag accctgctga tggacctggg ccagttcctg     1380
ctgttctgcc acatcagcag ccaccagcat gatggcatgg aggcctatgt gaaggtggac     1440
agctgccctg aggagcccca gctgaggatg aagaacaatg aggaggctga ggactatgat     1500
gatgacctga ctgactctga gatggatgtg gtgaggtttg atgatgacaa cagccccagc     1560
ttcatccaga tcaggtctgt ggccaagaag caccccaaga cctgggtgca ctacattgct     1620
gctgaggagg aggactggga ctatgccccc ctggtgctgg cccctgatga caggagctac     1680
aagagccagt acctgaacaa tggcccccag aggattggca ggaagtacaa gaaggtcagg     1740
ttcatggcct acactgatga aaccttcaag accaggagg  ccatccagca tgagtctggc     1800
atcctgggcc cctgctgta  tggggaggtg ggggacaccc tgctgatcat cttcaagaac     1860
caggccagca ggccctacaa catctacccc catggcatca ctgatgtgag gccctgtac      1920 agcaggaggc tgcccaaggg ggtgaagcac ctgaaggact tccccatcct gcctggggag     1980
atcttcaagt acaagtggac tgtgactgtg gaggatggcc ccaccaagtc tgaccccagg     2040
tgcctgacca gatactacag cagctttgtg aacatggaga gggacctggc ctctggcctg     2100
attggccccc tgctgatctg ctacaaggag tctgtggacc agaggggcaa ccagatcatg     2160
tctgacaaga ggaatgtgat cctgttctct gtgtttgatg agaacaggag ctggtacctg     2220
actgagaaca tccagaggtt cctgcccaac cctgctgggg tgcagctgga ggaccctgag     2280
ttccaggcca gcaacatcat gcacagcatc aatggctatg tgtttgacag cctgcagctg     2340
tctgtgtgcc tgcatgaggt ggcctactgg tacatcctga gcattggggc ccagactgac     2400
```

```
ttcctgtctg tgttcttctc tggctacacc ttcaagcaca agatggtgta tgaggacacc   2460
ctgaccctgt tccccttctc tggggagact gtgttcatga gcatggagaa ccctggcctg   2520
tggattctgg gctgccacaa ctctgacttc aggaacaggg gcatgactgc cctgctgaaa   2580
gtctccagct gtgacaagaa cactggggac tactatgagg acagctatga ggacatctct   2640
gcctacctgc tgagcaagaa caatgccatt gagcccagga gcttccagaa aagaccagg   2700 cactacttca ttgctgctgt ggagaggctg tgggactatg gcatgagcag cagccccat   2760 gtgctgagga acagggccca gtctggctct gtgccccagt tcaagaaggt ggtgttccag   2820
gagttcactg atggcagctt cacccagccc ctgtacagag gggagctgaa tgagcacctg   2880
ggcctgctgg gcccctacat cagggctgag gtggaggaca acatcatggt gaccttcagg   2940
aaccaggcca gcaggcccta cagcttctac agcagcctga tcagctatga ggaggaccag   3000
aggcaggggg ctgagcccag gaagaacttt gtgaagccca tgaaaccaa gacctacttc   3060 tggaaggtgc agcaccacat ggccccacc aaggatgagt ttgactgcaa ggcctgggcc   3120
tacttctctg atgtggacct ggagaaggat gtgcactctg gcctgattgg ccccctgctg   3180
gtgtgccaca ccaacaccct gaaccctgcc catggcaggc aggtgactgt gcaggagttt   3240
gccctgttct tcaccatctt tgatgaaacc aagagctggt acttcactga aacatggag   3300 aggaactgca gggccccctg caacatccag atggaggacc ccaccttcaa ggagaactac   3360
aggttccatg ccatcaatgg ctacatcatg gacaccctgc ctggcctggt gatggcccag   3420
gaccagagga tcaggtggta cctgctgagc atgggcagca atgagaacat ccacagcatc   3480
cacttctctg gccatgtgtt cactgtgagg aagaaggagg agtacaagat ggccctgtac   3540
aacctgtacc ctgggtgtt tgagactgtg gagatgctgc ccagcaaggc tggcatctgg   3600
agggtggagt gcctgattgg ggagcacctg catgctggca tgagcaccct gttcctggtg   3660
tacagcaaca agtgccagac cccctgggc atggcctctg ccacatcag ggacttccag   3720 atcactgcct ctggccagta tggccagtgg gcccccaagc tggccaggct gcactactct   3780
ggcagcatca atgcctggag caccaaggag cccttcagct ggatcaaggt ggacctgctg   3840
gcccccatga tcatccatgg catcaagacc aggggggcca ggcagaagtt cagcagcctg   3900
tacatcagcc agttcatcat catgtacagc ctggatggca agaagtggca gacctacagg   3960
ggcaacagca ctggcacccct gatggtgttc tttggcaatg tggacagctc tggcatcaag   4020
cacaacatct tcaaccccc catcattgcc agatacatca ggctgcaccc cacccactac   4080
agcatcagga gcaccctgag gatggagctg atgggctgtg acctgaacag ctgcagcatg   4140
cccctgggca tggagagcaa ggccatctct gatgcccaga tcactgccag cagctacttc   4200
accaacatgt ttgccacctg gagccccagc aaggccaggc tgcacctgca gggcaggagc   4260
aatgcctgga ggccccaggt caacaacccc aaggagtggc tgcaggtgga cttccagaag   4320
accatgaagg tgactggggt gaccacccag ggggtgaaga gcctgctgac cagcatgtat   4380
gtgaaggagt tcctgatcag cagcagccag gatggccacc agtggacccct gttcttccag   4440 aatggcaagg tgaaggtgtt ccagggcaac aggacagct tcacccctgt ggtgaacagc   4500 ctggacccc cctgctgac cagatacctg aggattcacc cccagagctg ggtgcaccag   4560
attgccctga ggatggaggt gctgggctgt gaggcccagg acctgtactg aaataaaaga   4620
tctttatttt cattagatct gtgtgttggt tttttgtgtg aggaacccct agtgatggag   4680
ttggccactc cctctctgcg cgctcgctcg ctcactgagg ccgggcgacc aaaggtcgcc   4740
cgacgcccgg gctttgcccg ggcggcctca gtgagcgagc gagcgcgcag agagggagtg   4800
```

```
                                                                   gccaa                                                     4805

<210> SEQ ID NO 6
<211> LENGTH: 4934
<212> TYPE: DNA
<213> ORGANISM: Adeno-Associated Virus

<400> SEQUENCE: 6
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgtttg ctgcttgcaa tgtttgccca ttttaggggtg    180 gacacaggac gctgtggttt ctgagccagg gggcgactca gatcccagcc agtggactta    240
gccctgtttt gctcctccga taactggggt gaccttggtt aatattcacc agcagcctcc    300
cccgttgccc ctctggatcc actgcttaaa tacgacgag  acagggccc  tgtctcctca    360 gcttcaggca ccaccactga cctgggacag tgaatcgcca ccatgcagat tgagctgagc    420
acctgcttct tcctgtgcct gctgagattc tgctttagtg ccaccagaag atactacctg    480
ggtgcagtgg aactgtcatg ggactatatg caaagtgatc tcggtgagct gcctgtggac    540
gcaaggtaaa ggcatgtcct gtagggtctg atcggggcca ggattgtggg gatgtaagtc    600
tgcttggagg aaggtgcaga catcgggtta ggatggttgt gatgctattc tgactttttc    660
ctttcttcac gcagatttcc tcctagagtg ccaaaatctt ttccattcaa cacctcagtc    720
gtgtacaaaa agactctgtt tgtagaattc acggatcacc ttttcaacat cgctaagccc    780
aggcccccct ggatgggcct gctgggcccc accatccagg ctgaggtgta tgacactgtg    840
gtgatcaccc tgaagaacat ggccagccac cctgtgagcc tgcatgctgt gggggtgagc    900
tactggaagg cctctgaggg ggctgagtat gatgaccaga ccagccagag ggagaaggag    960
gatgacaagg tgttccctgg gggcagccac acctatgtgt ggcaggtgct gaaggagaat   1020
ggccccatgg cctctgaccc cctgtgcctg acctacagct acctgagcca tgtggacctg   1080
gtgaaggacc tgaactctgg cctgattggg ccctgctgg  tgtgcaggga gggcagcctg   1140
gccaaggaga gacccagac  cctgcacaag ttcatcctgc tgtttgctgt gtttgatgag   1200
ggcaagagct ggcactctga aaccaagaac agcctgatgc aggacaggga tgctgcctct   1260
gccagggcct ggcccaagat gcacactgtg aatggctatg tgaacaggag cctgcctggc   1320
ctgattggct gccacaggaa gtctgtgtac tggcatgtga ttggcatggg caccaccct   1380 gaggtgcaca gcatcttcct ggagggccac accttcctgg tcaggaacca caggcaggcc   1440
agcctggaga tcagccccat caccttcctg actgcccaga ccctgctgat ggacctgggc   1500
cagttcctgc tgttctgcca catcagcagc caccagcatg atggcatgga ggcctatgtg   1560
aaggtggaca gctgccctga ggagcccag  ctgaggatga gaacaatga  ggaggctgag   1620 gactatgatg atgacctgac tgactctgag atggatgtgg tgaggtttga tgatgacaac   1680
agccccagct tcatccagat caggtctgtg gccaagaagc accccaagac ctgggtgcac   1740
tacattgctg ctgaggagga ggactgggac tatgccccc  tggtgctggc ccctgatgac   1800
aggagctaca agagccagta cctgaacaat ggcccccaga ggattggcag gaagtacaag   1860
aaggtcaggt tcatggccta cactgatgaa accttcaaga ccagggaggc catccagcat   1920
gagtctggca tcctgggccc cctgctgtat ggggaggtgg gggacaccct gctgatcatc   1980
ttcaagaacc aggccagcag gccctacaac atctaccccc atggcatcac tgatgtgagg   2040
```

```
cccctgtaca gcaggaggct gcccaagggg gtgaagcacc tgaaggactt ccccatcctg    2100
cctggggaga tcttcaagta caagtggact gtgactgtgg aggatgggcc caccaagtct    2160
gaccccaggt gcctgaccag atactacagc agctttgtga acatggagag ggacctggcc    2220
tctggcctga ttggccccct gctgatctgc tacaaggagt ctgtggacca gaggggcaac    2280
cagatcatgt ctgacaagag gaatgtgatc ctgttctctg tgtttgatga aacaggagc     2340
tggtacctga ctgagaacat ccagaggttc ctgcccaacc ctgctggggt gcagctggag    2400
gaccctgagt tccaggccag caacatcatg cacagcatca atggctatgt gtttgacagc    2460
ctgcagctgt ctgtgtgcct gcatgaggtg gcctactggt acatcctgag cattggggcc    2520
cagactgact tcctgtctgt gttcttctct ggctacacct tcaagcacaa gatggtgtat    2580
gaggacaccc tgaccctgtt cccttctct ggggagactg tgttcatgag catggagaac     2640
cctggcctgt ggattctggg ctgccacaac tctgacttca ggaacagggg catgactgcc    2700
ctgctgaaag tctccagctg tgacaagaac actggggact actatgagga cagctatgag    2760
gacatctctg cctacctgct gagcaagaac aatgccattg agcccaggag cttccagaag    2820
aagaccaggc actacttcat tgctgctgtg gagaggctgt gggactatgg catgagcagc    2880
agcccccatg tgctgaggaa cagggcccag tctggctctg tgcccagtt caagaaggtg     2940
gtgttccagg agttcactga tggcagcttc acccagcccc tgtacagagg ggagctgaat    3000
gagcacctgg gcctgctggg ccctacatc agggctgagg tggaggacaa catcatggtg     3060
accttcagga accaggccag caggccctac agcttctaca gcagcctgat cagctatgag    3120
gaggaccaga ggcaggggc tgagcccagg aagaactttg tgaagcccaa tgaaaccaag    3180
acctacttct ggaaggtgca gcaccacatg gccccacca aggatgagtt tgactgcaag    3240
gcctgggcct acttctctga tgtggacctg agaaggatg tgcactctgg cctgattggc    3300
cccctgctgg tgtgccacac caacaccctg aaccctgccc atggcaggca ggtgactgtg    3360
caggagtttg ccctgttctt caccatcttt gatgaaacca gagctggta cttcactgag    3420
aacatggaga ggaactgcag ggccccctgc aacatccaga tggaggaccc caccttcaag    3480
gagaactaca ggttccatgc catcaatggc tacatcatgg acaccctgcc tggcctggtg    3540
atggcccagg accagaggat caggtggtac ctgctgagca tgggcagcaa tgagaacatc    3600
cacagcatcc acttctctgg ccatgtgttc actgtgagga agaaggagga gtacaagatg    3660
gccctgtaca acctgtaccc tggggtgttt gagactgtgg agatgctgcc cagcaaggct    3720
ggcatctgga gggtggagtg cctgattggg gagcacctgc atgctggcat gagcaccctg    3780
ttcctggtgt acagcaacaa gtgccagacc ccctgggca tggcctctgg ccacatcagg    3840
gacttccaga tcactgcctc tggccagtat ggccagtggg cccccaagct ggccaggctg    3900
cactactctg gcagcatcaa tgcctggagc accaaggagc ccttcagctg gatcaaggtg    3960
gacctgctgg cccccatgat catccatggc atcaagaccc aggggccag gcagaagttc    4020
agcagcctgt acatcagcca gttcatcatc atgtacagcc tggatggcaa gaagtggcag    4080
acctacaggg gcaacagcac tggcacccctg atggtgttct ttggcaatgt ggacagctct    4140
ggcatcaagc acaacatctt caaccccccc atcattgcca gatacatcag gctgcacccc    4200
acccactaca gcatcaggag caccctgagg atggagctga tgggctgtga cctgaacagc    4260
tgcagcatgc ccctgggcat ggagagcaag gccatctctg atgcccagat cactgccagc    4320
agctacttca ccaacatgtt tgccacctgg agccccagca ggccaggct gcacctgcag    4380
ggcaggagca atgcctggag gccccaggtc aacaacccca aggagtggct gcaggtggac    4440
```

-continued

```
ttccagaaga ccatgaaggt gactggggtg accacccagg gggtgaagag cctgctgacc    4500
agcatgtatg tgaaggagtt cctgatcagc agcagccagg atggccacca gtggaccctg    4560
ttcttccaga atggcaaggt gaaggtgttc cagggcaacc aggacagctt caccectgtg    4620 gtgaacagcc tggaccccccc cctgctgacc agatacctga ggattcaccc ccagagctgg    4680
gtgcaccaga ttgccctgag gatggaggtg ctgggctgtg aggcccagga cctgtactga    4740
aataaaagat ctttattttc attagatctg tgtgttggtt ttttgtgtga ggaacccta     4800 gtgatggagt tggccactcc ctctctgcgc gctcgctcgc tcactgaggc cgggcgacca    4860
aaggtcgccc gacgcccggg ctttgcccgg gcggcctcag tgagcgagcg agcgcgcaga    4920
gagggagtgg ccaa                                                      4934
```

<210> SEQ ID NO 7
<211> LENGTH: 4934
<212> TYPE: DNA
<213> ORGANISM: Adeno-Associated Virus

<400> SEQUENCE: 7

```
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgtttg ctgcttgcaa tgtttgccca ttttaggggtg   180 gacacaggac gctgtggttt ctgagccagg gggcgactca gatcccagcc agtggactta    240
gccctgtttt gctcctccga taactgggt gaccttggtt aatattcacc agcagcctcc    300 ccgttgccc ctctggatcc actgcttaaa tacgacgag acagggccc tgtctcctca    360 gcttcaggca ccaccactga cctgggacag tgaatcgcca ccatgcagat tgagctgagc    420
acctgcttct tcctgtgcct gctgagattc tgctttagtg ccaccagaag atactacctg    480
ggtgcagtgg aactgtcatg ggactatatg caaagtgatc tcggtgagct gcctgtggac    540
gcaaggtaaa ggctgtttgc tgcttgcaat gtttgcccat tttagggggg gatgtaagtc    600
tgcttggagg aaggtgcaga catcgggtta ggatggttgt gatgctattc tgacttttc    660 cttcttcac gcagatttcc tcctagagtg ccaaaatctt ttccattcaa cacctcagtc    720
gtgtacaaaa agactctgtt tgtagaattc acggatcacc ttttcaacat cgctaagccc    780
aggcccccct ggatgggcct gctgggcccc accatccagg ctgaggtgta tgacactgtg    840
gtgatcaccc tgaagaacat ggccagccac cctgtgagcc tgcatgctgt gggggtgagc    900
tactggaagg cctctgaggg ggctgagtat gatgaccaga ccagccagag ggagaaggag    960
gatgacaagg tgttccctgg gggcagccac acctatgtgt ggcaggtgct gaaggagaat   1020
ggccccatgg cctctgaccc cctgtgcctg acctacagct acctgagcca tgtggacctg    1080
gtgaaggacc tgaactctgg cctgattggg gccctgctgg tgtgcaggga gggcagcctg    1140
gccaaggaga gacccagac cctgcacaag ttcatcctgc tgtttgctgt gtttgatgag    1200
ggcaagagct ggcactctga aaccaagaac agcctgatgc aggacaggga tgctgcctct    1260
gccagggcct ggcccaagat gcacactgtg aatggctatg tgaacaggag cctgcctggc    1320
ctgattggct gccacaggaa gtctgtgtac tggcatgtga ttggcatggg caccacccct    1380
gaggtgcaca gcatcttcct ggagggccac accttcctgg tcaggaacca caggcaggcc    1440
agcctggaga tcagccccat caccttcctg actgcccaga ccctgctgat ggacctgggc    1500
cagttcctgc tgttctgcca catcagcagc caccagcatg atggcatgga ggcctatgtg    1560
```

```
aaggtggaca gctgccctga ggagcccag ctgaggatga agaacaatga ggaggctgag    1620
gactatgatg atgacctgac tgactctgag atggatgtgg tgaggtttga tgatgacaac    1680
agccccagct tcatccagat caggtctgtg gccaagaagc accccaagac ctgggtgcac    1740
tacattgctg ctgaggagga ggactgggac tatgccccc tggtgctggc ccctgatgac     1800
aggagctaca agagccagta cctgaacaat ggcccccaga ggattggcag aagtacaag     1860 aaggtcaggt tcatggccta cactgatgaa accttcaaga ccagggaggc catccagcat    1920
gagtctggca tcctgggccc cctgctgtat ggggaggtgg gggacaccct gctgatcatc    1980
ttcaagaacc aggccagcag gccctacaac atctacccc atggcatcac tgatgtgagg     2040
cccctgtaca gcaggaggct gcccaagggg gtgaagcacc tgaaggactt ccccatcctg    2100
cctggggaga tcttcaagta caagtggact gtgactgtgg aggatggccc caccaagtct    2160
gaccccaggt gcctgaccag atactacagc agctttgtga acatggagag ggacctggcc    2220
tctggcctga ttggccccct gctgatctgc tacaaggagt ctgtggacca gaggggcaac    2280
cagatcatgt ctgacaagag gaatgtgatc ctgttctctg tgtttgatga aacaggagc     2340 tggtacctga ctgagaacat ccagaggttc ctgcccaacc tgctggggt gcagctggag     2400 gaccctgagt tccaggccag caacatcatg cacagcatca atggctatgt gtttgacagc    2460
ctgcagctgt ctgtgtgcct gcatgaggtg gcctactggt acatcctgag cattggggcc    2520
cagactgact tcctgtctgt gttcttctct ggctacacct tcaagcacaa gatggtgtat    2580
gaggacaccc tgaccctgtt ccccttctct ggggagactg tgttcatgag catggagaac    2640
cctggcctgt ggattctggg ctgccacaac tctgacttca ggaacagggg catgactgcc    2700
ctgctgaaag tctccagctg tgacaagaac actggggact actatgagga cagctatgag    2760
gacatctctg cctacctgct gagcaagaac aatgccattg agcccaggag cttccagaag    2820
aagaccaggc actacttcat tgctgctgtg agaggctgt gggactatgg catgagcagc    2880
agcccccatg tgctgaggaa cagggcccag tctggctctg tgcccagtt caagaaggtg    2940 gtgttccagg agttcactga tggcagcttc acccagcccc tgtacagagg ggagctgaat    3000
gagcacctgg gcctgctggg cccctacatc agggctgagg tggaggacaa catcatggtg    3060
accttcagga accaggccag caggccctac agcttctaca gcagcctgat cagctatgag    3120
gaggaccaga ggcaggggc tgagcccagg aagaactttg tgaagcccaa tgaaaccaag    3180
acctacttct ggaaggtgca gcaccacatg gcccccacca aggatgagtt tgactgcaag    3240
gcctgggcct acttctctga tgtggacctg gagaaggatg tgcactctgg cctgattggc    3300
cccctgctgg tgtgccacac caacaccctg aaccctgccc atggcaggca ggtgactgtg    3360
caggagtttg ccctgttctt caccatcttt gatgaaacca gagctggta cttcactgag    3420 aacatggaga ggaactgcag ggccccctgc aacatccaga tggaggaccc cacttcaag    3480 gagaactaca ggttccatgc catcaatggc tacatcatgg acaccctgcc tggcctggtg    3540
atggcccagg accagaggat caggtggtac ctgctgagca tgggcagcaa tgagaacatc    3600
cacagcatcc acttctctgg ccatgtgttc actgtgagga agaaggagga gtacaagatg    3660
gccctgtaca acctgtaccc tggggtgttt gagactgtgg agatgctgcc cagcaaggct    3720
ggcatctgga gggtggagtg cctgattggg gagcacctgc atgctggcat gagcaccctg    3780
ttcctggtgt acagcaacaa gtgccagacc cccctgggca tggcctctgg ccacatcagg    3840
gacttccaga tcactgcctc tggccagtat ggccagtggg cccccaagct ggccaggctg    3900
cactactctg gcagcatcaa tgcctggagc accaaggagc ccttcagctg gatcaaggtg    3960
```

```
gacctgctgg cccccatgat catccatggc atcaagaccc aggggggccag gcagaagttc    4020
agcagcctgt acatcagcca gttcatcatc atgtacagcc tggatggcaa gaagtggcag    4080
acctacaggg gcaacagcac tggcaccctg atggtgttct ttggcaatgt ggacagctct    4140
ggcatcaagc acaacatctt caacccccc atcattgcca gatacatcag gctgcacccc     4200
acccactaca gcatcaggag caccctgagg atggagctga tgggctgtga cctgaacagc    4260
tgcagcatgc ccctgggcat ggagagcaag gccatctctg atgcccagat cactgccagc    4320
agctacttca ccaacatgtt tgccacctgg agccccagca aggccaggct gcacctgcag    4380
ggcaggagca atgcctggag gccccaggtc aacaacccca aggagtggct gcaggtggac    4440
ttccagaaga ccatgaaggt gactggggtg accacccagg gggtgaagag cctgctgacc    4500
agcatgtatg tgaaggagtt cctgatcagc agcagccagg atggccacca gtggaccctg    4560
ttcttccaga atggcaaggt gaaggtgttc caggggcaacc aggacagctt caccccctgtg  4620
gtgaacagcc tggaccccccc cctgctgacc agatacctga ggattcaccc ccagagctgg   4680
gtgcaccaga ttgccctgag gatggaggtg ctgggctgtg aggcccagga cctgtactga   4740
aataaaagat cttatttttc attagatctg tgtgttggtt ttttgtgtga ggaacccccta  4800
gtgatggagt tggccactcc ctctctgcgc gctcgctcgc tcactgaggc cgggcgacca   4860
aaggtcgccc gacgcccggg ctttgcccgg gcggcctcag tgagcgagcg agcgcgcaga   4920
gagggagtgg ccaa                                                      4934
```

<210> SEQ ID NO 8
<211> LENGTH: 4934
<212> TYPE: DNA
<213> ORGANISM: Adeno-Associated Virus

<400> SEQUENCE: 8

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg    120
gccaactcca tcactagggg ttcctgtttg ctgcttgcaa tgtttgccca ttttaggtgtg  180
gacacaggac gctgtggttt ctgagccagg gggcgactca gatcccagcc agtggactta   240
gcccctgttt gctcctccga taactggggt gaccttggtt aatattcacc agcagcctcc   300
cccgttgccc ctctggatcc actgcttaaa tacgacgag acagggccc tgtctcctca    360
gcttcaggca ccaccactga cctgggacag tgaatcgcca ccatgcagat tgagctgagc   420
acctgcttct tcctgtgcct gctgagattc tgctttagtg ccaccagaag atactacctg   480
ggtgcagtgg aactgtcatg ggactatatg caaagtgatc tcggtgagct gcctgtggac   540
gcaaggtaaa gcatgtcct gtagggtctg atcggggcca ggattgtggg gatgtaagtc   600
tgcttggagg aagccctaaa atgggcaaac attgcaagca gcaaacattc tgactttttc   660
ctttcttcac gcagatttcc tcctagagtg ccaaaatctt ttccattcaa cacctcagtc   720
gtgtacaaaa agactctgtt tgtagaattc acggatcacc ttttcaacat cgctaagccc   780
aggccccccct ggatgggcct gctgggcccc accatccagg ctgaggtgta tgacactgtg  840
gtgatcaccc tgaagaacat ggccagccac cctgtgagcc tgcatgctgt gggggtgagc    900
tactggaagg cctctgaggg ggctgagtat gatgaccaga ccagccagag ggagaaggag    960
gatgacaagg tgttccctgg gggcagccac acctatgtgt ggcaggtgct gaaggagaat   1020
ggcccccatgg cctctgaccc cctgtgcctg acctacagct acctgagcca tgtggacctg   1080
```

```
gtgaaggacc tgaactctgg cctgattggg ccctgctgg tgtgcaggga gggcagcctg    1140
gccaaggaga agacccagac cctgcacaag ttcatcctgc tgtttgctgt gtttgatgag   1200
ggcaagagct ggcactctga aaccaagaac agcctgatgc aggacaggga tgctgcctct   1260
gccagggcct ggcccaagat gcacactgtg aatggctatg tgaacaggag cctgcctggc   1320
ctgattggct gccacaggaa gtctgtgtac tggcatgtga ttggcatggg caccacccct   1380
gaggtgcaca gcatcttcct ggagggccac accttcctgg tcaggaacca caggcaggcc   1440
agcctggaga tcagccccat caccttcctg actgcccaga ccctgctgat ggacctgggc   1500
cagttcctgc tgttctgcca catcagcagc caccagcatg atggcatgga ggcctatgtg   1560
aaggtggaca gctgccctga ggagccccag ctgaggatga agaacaatga ggaggctgag   1620
gactatgatg atgacctgac tgactctgag atggatgtgg tgaggtttga tgatgacaac   1680
agccccagct tcatccagat caggtctgtg gccaagaagc accccaagac ctgggtgcac   1740
tacattgctg ctgaggagga ggactgggac tatgcccccc tggtgctggc ccctgatgac   1800
aggagctaca gagccagta cctgaacaat ggccccaga ggattggcag gaagtacaag   1860
aaggtcaggt tcatggccta cactgatgaa accttcaaga ccagggaggc catccagcat   1920
gagtctggca tcctgggccc cctgctgtat ggggaggtgg gggacaccct gctgatcatc   1980
ttcaagaacc aggccagcag gccctacaac atctaccccc atggcatcac tgatgtgagg   2040
cccctgtaca gcaggaggct gcccaagggg gtgaagcacc tgaaggactt ccccatcctg   2100
cctggggaga tcttcaagta caagtggact gtgactgtgg aggatggccc caccaagtct   2160
gaccccaggt gcctgaccag atactacagc agctttgtga acatggagag ggacctggcc   2220
tctggcctga ttggccccct gctgatctgc tacaaggagt ctgtggacca gaggggcaac   2280
cagatcatgt ctgacaagag gaatgtgatc ctgttctctg tgtttgatga gaacaggagc   2340
tggtacctga ctgagaacat ccagaggttc ctgcccaacc ctgctggggt gcagctggag   2400
gaccctgagt ccaggccag caacatcatg cacagcatca tggctatgt gtttgacagc   2460 ctgcagctgt ctgtgtgcct gcatgaggtg gcctactggt acatcctgag cattgggccc   2520
cagactgact tcctgtctgt gttcttctct ggctacacct tcaagcacaa gatggtgtat   2580
gaggacaccc tgaccctgtt ccccttctct ggggagactg tgttcatgag catggagaac   2640
cctggcctgt ggattctggg ctgccacaac tctgacttca ggaacagggg catgactgcc   2700
ctgctgaaag tctccagctg tgacaagaac actggggact actatgagga cagctatgag   2760
gacatctctg cctacctgct gagcaagaac aatgccattg agcccaggag cttccagaag   2820
aagaccaggc actacttcat tgctgctgtg agaggctgt gggactatgg catgagcagc   2880
agcccccatg tgctgaggaa cagggcccag tctggctctg tgccccagtt caagaaggtg   2940
gtgttccagg agttcactga tggcagcttc acccagcccc tgtacagagg ggagctgaat   3000
gagcacctgg gcctgctggg cccctacatc agggctgagg tggaggacaa catcatggtg   3060
accttcagga accaggccag caggcctac agcttctaca gcagcctgat cagctatgag   3120
gaggaccaga ggcaggggc tgagcccagg aagaactttg tgaagcccaa tgaaaccaag   3180
acctacttct ggaaggtgca gcaccacatg ccccccacca aggatgagtt tgactgcaag   3240
gcctgggcct acttctctga tgtggacctg gagaaggatg tgcactctgg cctgattggc   3300
cccctgctgg tgtgccacac caacacccctg aaccctgccc atggcaggca ggtgactgtg   3360
caggagtttg ccctgttctt caccatcttt gatgaaacca gagctggta cttcactgag   3420 aacatggaga ggaactgcag ggcccctgc aacatccaga tggaggaccc caccttcaag   3480
```

```
gagaactaca ggttccatgc catcaatggc tacatcatgg acaccctgcc tggcctggtg    3540
atggcccagg accagaggat caggtggtac ctgctgagca tgggcagcaa tgagaacatc    3600
cacagcatcc acttctctgg ccatgtgttc actgtgagga agaaggagga gtacaagatg    3660
gccctgtaca acctgtaccc tggggtgttt gagactgtgg agatgctgcc cagcaaggct    3720
ggcatctgga gggtggagtg cctgattggg agcacctgc atgctggcat gagcaccctg     3780
ttcctggtgt acagcaacaa gtgccagacc cccctgggca tggcctctgg ccacatcagg    3840
gacttccaga tcactgcctc tggccagtat ggccagtggg cccccaagct ggccaggctg    3900
cactactctg cagcatcaa tgcctggagc accaaggagc ccttcagctg gatcaaggtg     3960
gacctgctgg cccccatgat catccatggc atcaagaccc agggggccag gcagaagttc    4020
agcagcctgt acatcagcca gttcatcatc atgtacagcc tggatggcaa gaagtggcag    4080
acctacaggg gcaacagcac tggcacctg atggtgttct ttggcaatgt ggacagctct      4140
ggcatcaagc acaacatctt caaccccccc atcattgcca gatacatcag gctgcacccc    4200
acccactaca gcatcaggag cacccctgagg atggagctga tgggctgtga cctgaacagc   4260
tgcagcatgc ccctgggcat ggagagcaag gccatctctg atgcccagat cactgccagc   4320
agctacttca ccaacatgtt tgccacctgg agccccagca aggccaggct gcacctgcag    4380
ggcaggagca atgcctggag gccccaggtc aacaaccca aggagtggct gcaggtggac     4440
ttccagaaga ccatgaaggt gactgggtg accacccagg gggtgaagag cctgctgacc    4500
agcatgtatg tgaaggagtt cctgatcagc agcagccagg atggccacca gtggaccctg    4560
ttcttccaga atggcaaggt gaaggtgttc cagggcaacc aggacagctt caccctgtg    4620 gtgaacagcc tggaccccc cctgctgacc agatacctga ggattcaccc ccagagctgg   4680
gtgcaccaga ttgccctgag gatggaggtg ctgggctgtg aggcccagga cctgtactga    4740
aataaaagat ctttattttc attagatctg tgtgttggtt ttttgtgtga ggaacccta     4800 gtgatggagt tggccactcc ctctctgcgc gctcgctcgc tcactgaggc cgggcgacca    4860
aaggtcgccc gacgcccggg ctttgcccgg gcggcctcag tgagcgagcg agcgcgcaga    4920
gagggagtgg ccaa                                                      4934

<210> SEQ ID NO 9
<211> LENGTH: 5511
<212> TYPE: DNA
<213> ORGANISM: Adeno-Associated Virus 2

<400> SEQUENCE: 9
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgcggc cgcacgcgtg ttttcgaccc ctctcacact    180
acctaaacca cgccaggaca acctctgctc ctctccaccg aaattccaag gggtcgagtg    240
gatgttggag gtggcatggg cccagagagg tctctgacct ctgccccagc tccaaggtca    300
gcaggcaggg agggctgtgt gtttgctgtt tgctgcttgc aatgtttgcc cattttaggg    360
acatgagtag gctgaagttt gttcagtgtg gacttcagag gcagcacaca aacagctgct   420
ggaggatggg aactgagggg ttggaagggg gcagggtgag cccagaaact cctgtgtgcc   480
tctgagcctg cagacgcgaa acgtcgactg gacacaggac gctgtggttt ctgagccagg    540
gggcgactca gatcccagcc agtggactta gccctgtttt gctcctccga taactggggt     600
```

-continued

```
gaccttggtt aatattcacc agcagcctcc cccgttgccc ctctggatcc actgcttaaa    660
tacggacgag gacagggccc tgtctcctca gcttcaggca ccaccactga cctgggacag    720
tgaatcgtaa gtactagcag ctacaatcca gctaccattc tgcttttatt ttatggttgg    780
gataaggctg gattattctg agtccaagct aggcccttt gctaatcatg ttcatacctc    840
ttatcttcct cccacagctc ctgggcaacg tgctggtctg tgtgctggcc catcactttg    900
gcaaagaatt gcgatcgcca ccatgcagat tgagctgagc acctgcttct tcctgtgcct    960
gctgaggttc tgcttctctg ccaccaggag atactacctg ggggctgtgg agctgagctg   1020
ggactacatg cagtctgacc tgggggagct gcctgtggat gccaggttcc cccccagagt   1080
gcccaagagc ttccccttca cacctctgt ggtgtacaag aagaccctgt tgtggagtt    1140
cactgaccac ctgttcaaca ttgccaagcc caggcccccc tggatgggcc tgctgggccc   1200
caccatccag gctgaggtgt atgacactgt ggtgatcacc ctgaagaaca tggccagcca   1260
ccctgtgagc ctgcatgctg tgggggtgag ctactggaag gcctctgagg ggctgagta    1320
tgatgaccag accagccaga gggagaagga ggatgacaag gtgttccctg ggggcagcca   1380
cacctatgtg tggcaggtgc tgaaggagaa tggccccatg gcctctgacc ccctgtgcct   1440
gacctacagc tacctgagcc atgtggacct ggtgaaggac ctgaactctg gcctgattgg   1500
ggccctgctg gtgtgcaggg agggcagcct ggccaaggag aagacccaga ccctgcacaa   1560
gttcatcctg ctgtttgctg tgtttgatga gggcaagagc tggcactctg aaaccaagaa   1620
cagcctgatg caggacaggg atgctgcctc tgccagggcc tggccaaga tgcacactgt    1680
gaatggctat gtgaacagga gcctgcctgg cctgattggc tgccacagga agtctgtgta   1740
ctggcatgtg attggcatgg gcaccacccc tgaggtgcac agcatcttcc tggagggcca   1800
caccttcctg gtcaggaacc acaggcaggc cagcctggag atcagcccca tcaccttcct   1860
gactgcccag accctgctga tggacctggg ccagttcctg ctgttctgcc acatcagcag   1920
ccaccagcat gatggcatgg aggcctatgt gaaggtggac agctgccctg aggagcccca   1980
gctgaggatg aagaacaatg aggaggctga ggactatgat gatgacctga ctgactctga   2040
gatggatgtg tgaggttttg atgatgacaa cagccccagc ttcatccaga tcaggtctgt   2100
ggccaagaag caccccaaga cctgggtgca ctacattgct gctgaggagg aggactggga   2160
ctatgccccc ctggtgctgg cccctgatga caggagctac aagagccagt acctgaacaa   2220
tggcccccag aggattggca ggaagtacaa gaaggtcagg ttcatggcct acactgatga   2280
aaccttcaag accagggagg ccatccagca tgagtctggc atcctgggcc cctgctgta   2340
tgggaggtg ggggacaccc tgctgatcat cttcaagaac caggccagca ggccctacaa   2400
catctacccc catggcatca ctgatgtgag gcccctgtac agcaggaggc tgcccaaggg   2460
ggtgaagcac ctgaaggact tccccatcct gcctggggag atcttcaagt acaagtggac   2520
tgtgactgtg gaggatggcc ccaccaagtc tgacccagg tgcctgacca gatactacag   2580
cagctttgtg aacatggaga gggacctggc ctctggcctg attggccccc tgctgatctg   2640
ctacaaggag tctgtggacc agaggggcaa ccagatcatg tctgacaaga ggaatgtgat   2700
cctgttctct gtgtttgatg agaacaggag ctggtacctg actgagaaca tccagagggt   2760
cctgcccaac cctgctgggg tgcagctgga ggaccctgag ttccaggcca gcaacatcat   2820
gcacagcatc aatggctatg tgtttgacag cctgcagctg tctgtgtgcc tgcatgaggt   2880
ggcctactgg tacatcctga gcattggggc ccagactgac ttcctgtctg tgttcttctc   2940
tggctacacc ttcaagcaca agatggtgta tgaggacacc ctgaccctgt tcccttctc   3000
```

```
tggggagact gtgttcatga gcatggagaa ccctggcctg tggattctgg gctgccacaa    3060
ctctgacttc aggaacaggg gcatgactgc cctgctgaaa gtctccagct gtgacaagaa    3120
cactggggac tactatgagg acagctatga ggacatctct gcctacctgc tgagcaagaa    3180
caatgccatt gagcccagga gcttcagcca gaaccccca gtgctgaaga ggcaccagag    3240
ggagatcacc aggaccaccc tgcagtctga ccaggaggag attgactatg atgacaccat    3300
ctctgtggag atgaagaagg aggactttga catctacgac gaggacgaga accagagccc    3360
caggagcttc cagaagaaga ccaggcacta cttcattgct gctgtggaga ggctgtggga    3420
ctatggcatg agcagcagcc cccatgtgct gaggaacagg gcccagtctg gctctgtgcc    3480
ccagttcaag aaggtggtgt tccaggagtt cactgatggc agcttcaccc agcccctgta    3540
cagaggggag ctgaatgagc acctgggcct gctgggcccc tacatcaggg ctgaggtgga    3600
ggacaacatc atggtgacct tcaggaacca ggccagcagg ccctacagct tctacagcag    3660
cctgatcagc tatgaggagg accagaggca ggggctgag cccaggaaga actttgtgaa    3720
gcccaatgaa accaagacct acttctggaa ggtgcagcac acatggccc ccaccaagga    3780 tgagtttgac tgcaaggcct gggcctactt ctctgatgtg gacctggaga aggatgtgca    3840
ctctggcctg attggccccc tgctggtgtg ccacaccaac accctgaacc ctgcccatgg    3900
caggcaggtg actgtgcagg agtttgccct gttcttcacc atctttgatg aaaccaagag    3960
ctggtacttc actgagaaca tggagaggaa ctgcaggggcc cctgcaaca tccagatgga    4020 ggaccccacc ttcaaggaga actacaggtt ccatgccatc aatggctaca tcatggacac    4080
cctgcctggc ctggtgatgg cccaggacca gaggatcagg tggtacctgc tgagcatggg    4140
cagcaatgag aacatccaca gcatccactt ctctggccat gtgttcactg tgaggaagaa    4200
ggaggagtac aagatggccc tgtacaacct gtaccctggg gtgtttgaga ctgtggagat    4260 gctgccagc aaggctggca tctggagggt ggagtgcctg attggggagc acctgcatgc    4320
tggcatgagc accctgttcc tggtgtacag caacaagtgc cagacccccc tgggcatggc    4380
ctctggccac atcagggact tccagatcac tgcctctggc cagtatggcc agtgggcccc    4440
caagctggcc aggctgcact actctggcag catcaatgcc tggagcacca aggagccctt    4500
cagctggatc aaggtggacc tgctggcccc catgatcatc catggcatca agacccaggg    4560
ggccaggcag aagttcagca gcctgtacat cagccagttc atcatcatgt acagcctgga    4620
tggcaagaag tggcagacct acaggggcaa cagcactggc accctgatgg tgttctttgg    4680
caatgtggac agctctggca tcaagcacaa catcttcaac cccccatca ttgccagata    4740 catcaggctg cacccaccc actacagcat caggagcacc ctgaggatgg agctgatggg    4800
ctgtgacctg aacagctgca gcatgccct gggcatggag agcaaggcca tctctgatgc    4860
ccagatcact gccagcagct acttccaccaa catgtttgcc acctggagcc ccagcaaggc    4920
caggctgcac ctgcagggca ggagcaatgc ctggaggccc caggtcaaca ccccaagga    4980 gtggctgcag gtggacttcc agaagaccat gaaggtgact ggggtgacca cccagggggt    5040
gaagagcctg ctgaccagca tgtatgtgaa ggagttcctg atcagcagca gccaggatgg    5100
ccaccagtgg acccctgttct tccagaatgg caaggtgaag gtgttccagg caaccagga    5160 cagcttcacc cctgtggtga acagcctgga ccccccctg ctgaccagat acctgaggat    5220
tcacccccag agctgggtgc accagattgc cctgaggatg gaggtgctgg gctgtgaggc    5280
ccaggacctg tactgacctc gaggaataaa ggaaatttat tttcattgca atagtgtgtt    5340
```

```
ggttttttgt gtcacgtggc ggccgcagga acccctagtg atggagttgg ccactccctc   5400
tctgcgcgct cgctcgctca ctgaggccgg cgaccaaag gtcgcccgac gcccgggctt    5460
tgcccgggcg gcctcagtga gcgagcgagc gcgcagagag ggagtggcca a            5511

<210> SEQ ID NO 10
<211> LENGTH: 5688
<212> TYPE: DNA
<213> ORGANISM: Adeno-Associated Virus 2

<400> SEQUENCE: 10
ttggccactc cctctctgcg cgctcgctcg ctcactgagg ccgccccggc aaagcccggg     60
cgtcgggcga cctttggtcg cccggcctca gtgagcgagc gagcgcgcag agagggagtg    120
gccaactcca tcactagggg ttcctgcggc cgcacgcgtg ttttcgaccc ctctcacact    180 acctaaaccca cgccaggaca acctctgctc ctctccaccg aaattccaag gggtcgagtg    240
gatgttggag gtggcatggg cccagagagg tctctgacct ctgccccagc tccaaggtca    300
gcaggcaggg agggctgtgt gtttgctgtt tgctgcttgc aatgtttgcc cattttaggg    360
acatgagtag gctgaagttt gttcagtgtg gacttcagag gcagcacaca aacagctgct    420
ggaggatggg aactgagggg ttggaagggg gcagggtgag cccagaaaact cctgtgtgcc    480 tctgagcctg cagacgcgaa acgtcgactg gacacaggac gctgtggttt ctgagccagg    540
gggcgactca gatcccagcc agtggactta gcccctgttt gctcctccga taactggggt    600
gaccttggtt aatattcacc agcagcctcc cccgttgccc ctctggatcc actgcttaaa    660 tacgacgag acagggccc tgtctcctca gcttcaggca ccaccactga cctgggacag     720
tgaatcgtaa gtactagcag ctacaatcca gctaccattc tgcttttatt ttatggttgg    780
gataaggctg gattattctg agtccaagct aggcccttttt gctaatcatg ttcatacctc    840
ttatcttcct cccacagctc ctgggcaacg tgctggtctg tgtgctggcc atcactttg     900 gcaaagaatt gcgatcgcca ccatgcagat tgagctgagc acctgcttct tcctgtgcct    960
gctgaggttc tgcttctctg ccaccaggag atactacctg ggggctgtgg agctgagctg   1020
ggactacatg cagtctgacc tgggggagct gcctgtggat gccaggttcc cccccagagt   1080
gcccaagagc ttccccttca acacctctgt ggtgtacaag aagacccctgt tgtggagtt    1140 cactgaccac ctgttcaaca ttgccaagcc caggccccccc tggatgggcc tgctgggccc   1200
caccatccag gctgaggtgt atgacactgt ggtgatcacc ctgaagaaca tggccagcca   1260
ccctgtgagc ctgcatgctg ggggtgag ctactggaag gcctctgagg gggctgagta    1320
tgatgaccag accagccaga gggagaagga ggatgacaag gtgttccctg ggggcagcca   1380
cacctatgtg tggcaggtgc tgaaggagaa tggccccatg gcctctgacc cctgtgcct    1440 gacctacagc tacctgagcc atgtggacct ggtgaaggac ctgaactctg gcctgattgg   1500 ggcccctgctg gtgtgcaggg agggcagcct ggccaaggag aagacccaga ccctgcacaa   1560
gttcatcctg ctgtttgctg tgtttgatga gggcaagagc tggcactctg aaaccaagaa   1620
cagcctgatg caggacaggg atgctgcctc tgccagggcc tggccaaga tgcacactgt   1680 gaatggctat gtgaacagga gcctgcctgg cctgattggc tgccacagga agtctgtgta   1740
ctggcatgtg attggcatgg gcaccacccc tgaggtgcac agcatcttcc tggagggcca   1800
caccttcctg gtcaggaacc acaggcaggc cagcctggag atcagcccca tcaccttcct   1860
gactgcccag accctgctga tggacctggg ccagttcctg ctgttctgcc acatcagcag   1920
ccaccagcat gatggcatgg aggcctatgt gaaggtggac agctgccctg aggagcccca   1980
```

```
gctgaggatg aagaacaatg aggaggctga ggactatgat gatgacctga ctgactctga    2040
gatggatgtg gtgaggtttg atgatgacaa cagccccagc ttcatccaga tcaggtctgt    2100
ggccaagaag caccccaaga cctgggtgca ctacattgct gctgaggagg aggactggga    2160
ctatgccccc ctggtgctgg ccctgatga caggagctac aagagccagt acctgaacaa    2220
tggcccccag aggattggca ggaagtacaa gaaggtcagg ttcatggcct acactgatga    2280
aaccttcaag accagggagg ccatccagca tgagtctggc atcctgggcc cctgctgta    2340 tggggaggtg ggggacaccc tgctgatcat cttcaagaac caggccagca ggccctacaa    2400
catctacccc catggcatca ctgatgtgag gcccctgtac agcaggaggc tgcccaaggg    2460
ggtgaagcac ctgaaggact tccccatcct gcctggggag atcttcaagt acaagtggac    2520
tgtgactgtg gaggatggcc ccaccaagtc tgacccaggt gcctgacca gatactacag    2580 cagctttgtg aacatggaga gggacctggc ctctggcctg attggccccc tgctgatctg    2640
ctacaaggag tctgtggacc agaggggcaa ccagatcatg tctgacaaga ggaatgtgat    2700
cctgttctct gtgtttgatg agaacaggag ctggtacctg actgagaaca tccagaggtt    2760
cctgcccaac cctgctgggg tgcagctgga ggaccctgag ttccaggcca gcaacatcat    2820
gcacagcatc aatggctatg tgtttgacag cctgcagctg tctgtgtgcc tgcatgaggt    2880
ggcctactgg tacatcctga gcattggggc ccagactgac ttcctgtctg tgttcttctc    2940
tggctacacc ttcaagcaca gatggtgta tgaggacacc ctgaccctgt tccccttctc    3000
tggggagact gtgttcatga gcatggagaa ccctggcctg tggattctgg gctgccacaa    3060
ctctgacttc aggaacaggg gcatgactgc cctgctgaaa gtctccagct gtgacaagaa    3120
cactggggac tactatgagg acagctatga ggacatctct gcctacctgc tgagcaagaa    3180
caatgccatt gagcccagga gcttcagcca gaaccccca gtgctgaaga ggcaccagag    3240
ggagatcacc aggaccaccc tgcagtctga ccaggaggag attgactatg atgacaccat    3300
ctctgtggag atgaagaagg aggactttga catctacgac gaggacgaga accagagccc    3360
caggagcttc cagaagaaga ccaggcacta cttcattgct gctgtggaga ggctgtggga    3420
ctatggcatg agcagcagcc cccatgtgct gaggaacagg gcccagtctg gctctgtgcc    3480
ccagttcaag aaggtggtgt tccaggagtt cactgatggc agcttcaccc agcccctgta    3540
cagaggggag ctgaatgagc acctgggcct gctgggcccc tacatcaggg ctgaggtgga    3600
ggacaacatc atggtgacct tcaggaacca ggccagcagg ccctacagct tctacagcag    3660
cctgatcagc tatgaggagg accagaggca ggggctgag cccaggaaga ctttgtgaa    3720 gcccaatgaa accaagacct acttctggaa ggtgcagcac cacatggccc ccaccaagga    3780
tgagtttgac tgcaaggcct gggcctactt ctctgatgtg acctggaga aggatgtgca    3840 ctctggcctg attggccccc tgctggtgtg ccacaccaac accctgaacc ctgcccatgg    3900
caggcaggtg actgtgcagg agtttgccct gttcttcacc atctttgatg aaaccaagag    3960
ctggtacttc actgagaaca tggagaggaa ctgcagggcc cctgcaaca tccagatgga    4020 ggacccacc ttcaaggaga actacaggtt ccatgccatc aatggctaca tcatggacac    4080
cctgcctggc ctggtgatgg cccaggacca ggatcagg tggtacctgc tgagcatggg    4140
cagcaatgag aacatccaca gcatccactt ctctggccat gtgttcactg tgaggaagaa    4200
ggaggagtac aagatggccc tgtacaacct gtacctgggg gtgtttgaga ctgtggagat    4260
gctgcccagc aaggctggca tctggagggt ggagtgcctg attggggagc acctgcatgc    4320
```

```
tggcatgagc accctgttcc tggtgtacag caacaagtgc cagacccccc tgggcatggc      4380
ctctggccac atcagggact tccagatcac tgcctctggc cagtatggcc agtgggcccc      4440
caagctggcc aggctgcact actctggcag catcaatgcc tggagcacca aggagccctt      4500
cagctggatc aaggtggacc tgctggcccc catgatcatc catggcatca agacccaggg      4560
ggccaggcag aagttcagca gcctgtacat cagccagttc atcatcatgt acagcctgga      4620
tggcaagaag tggcagacct acaggggcaa cagcactggc accctgatgg tgttctttgg      4680
caatgtggac agctctggca tcaagcacaa catcttcaac ccccccatca ttgccagata      4740
catcaggctg caccccaccc actacagcat caggagcacc ctgaggatgg agctgatggg      4800
ctgtgacctg aacagctgca gcatgccct gggcatggag agcaaggcca tctctgatgc      4860
ccagatcact gccagcagct acttcaccaa catgtttgcc acctggagcc ccagcaaggc      4920
caggctgcac ctgcagggca ggagcaatgc ctggaggccc caggtcaaca accccaagga      4980
gtggctgcag gtggacttcc agaagaccat gaaggtgact ggggtgacca cccaggggagt      5040 gaagagcctg ctgaccagca tgtatgtgaa ggagttcctg atcagcagca gccaggatgg      5100
ccaccagtgg accctgttct tccagaatgg caaggtgaag gtgttccagg gcaaccagga      5160
cagcttcacc cctgtggtga acagcctgga ccccccctg ctgaccagat acctgaggat      5220 tcaccccag agctgggtgc accagattgc cctgaggatg gaggtgctgg gctgtgaggc      5280
ccaggacctg tactgacctc gaggtgtgcc ttctagttgc cagccatctg ttgtttgccc      5340
ctcccccgtg ccttccttga ccctggaagg tgccactccc actgtccttt cctaataaaa      5400
tgaggaaatt gcatcgcatt gtctgagtag gtgtcattct attctggggg gtggggtggg      5460
gcaggacagc aagggggagg attgggaaga caatagcagg catgctgggg atgcggtggg      5520
ctctatgggc acgtggcggc cgcaggaacc cctagtgatg gagttggcca ctccctctct      5580
gcgcgctcgc tcgctcactg aggccgggcg accaaaggtc gcccgacgcc cgggctttgc      5640
ccgggcggcc tcagtgagcg agcgagcgcg cagagaggga gtggccaa                  5688

<210> SEQ ID NO 11
<211> LENGTH: 5613
<212> TYPE: DNA
<213> ORGANISM: Adeno-Associated Virus 2

<400> SEQUENCE: 11
ttggccactc cctctctgcg cgctcgctcg ctcactgagg ccgcccgggc aaagcccggg       60
cgtcgggcga cctttggtcg cccggcctca gtgagcgagc gagcgcgcag agagggagtg      120
gccaactcca tcactagggg ttcctgcggc cgcacgcgtg ttttcgaccc ctctcacact      180
acctaaacca cgccaggaca acctctgctc ctctccaccg aaattccaag ggtcgagtg      240 gatgttggag gtggcatggg cccagagagg tctctgacct ctgccccagc tccaaggtca      300
gcaggcaggg agggctgtgt gtttgctgtt tgctgcttgc aatgtttgcc cattttaggg      360
acatgagtag gctgaagttt gttcagtgtg gacttcagag gcagcacaca aacagctgct      420
ggaggatggg aactgagggg ttggaagggg cagggtgag cccagaaact cctgtgtgcc      480
tctgagcctg cagacgcgaa acgtcgactg gacacaggac gctgtggttt ctgagccagg      540
gggcgactca gatcccagcc agtggactta gccctgtttt gctcctccga taactggggt      600
gaccttggtt aatattcacc agcagcctcc ccgttgccc ctctggatcc actgcttaaa      660 tacgacgag acagggccc tgtctcctca gcttcaggca ccaccactga cctgggacag      720
tgaatcgtaa gtactagcag ctacaatcca gctaccattc tgctttttatt ttatggttgg      780
```

```
gataaggctg gattattctg agtccaagct aggccctttt gctaatcatg ttcatacctc    840
ttatcttcct cccacagctc ctgggcaacg tgctggtctg tgtgctggcc catcactttg    900
gcaaagaatt gcgatcgcca ccatgcagat tgagctgagc acctgcttct tcctgtgcct    960
gctgaggttc tgcttctctg ccaccaggag atactacctg ggggctgtgg agctgagctg   1020
ggactacatg cagtctgacc tggggagct gcctgtggat gccaggttcc ccccagagt    1080 gcccaagagc ttccccttca acacctctgt ggtgtacaag aagaccctgt tgtggagtt    1140 cactgaccac ctgttcaaca ttgccaagcc caggcccccc tggatgggcc tgctgggccc   1200
caccatccag gctgaggtgt atgacactgt ggtgatcacc ctgaagaaca tggccagcca   1260
ccctgtgagc ctgcatgctg tggggtgag ctactggaag gcctctgagg gggctgagta    1320
tgatgaccaa accagccaga gggagaagga ggatgacaag gtgttccctg ggggcagcca   1380
cacctatgtg tggcaggtgc tgaaggagaa tggccccatg gcctctgacc ccctgtgcct   1440
gacctacagc tacctgagcc atgtggacct ggtgaaggac ctgaactctg gcctgattgg   1500
ggccctgctg gtgtgcaggg agggcagcct ggccaaggag aagacccaga ccctgcacaa   1560
gttcatcctg ctgtttgctg tgtttgatga gggcaagagc tggcactctg aaaccaagaa   1620
cagcctgatg caggacaggg atgctgcctc tgccagggcc tggcccaaga tgcacactgt   1680
gaatggctat gtgaacagga gcctgcctgg cctgattggc tgccacagga gtctgtgta    1740 ctggcatgtg attggcatgg gcaccaccc tgaggtgcac agcatcttcc tggagggcca    1800
caccttcctg gtcaggaacc acaggcaggc cagcctggag atcagcccca tcaccttcct   1860
gactgcccag accctgctga tggacctggg ccagttcctg ctgttctgcc acatcagcag   1920
ccaccagcat gatggcatgg aggcctatgt gaaggtggac agctgccctg aggagcccca   1980
gctgaggatg aagaacaatg aggaggctga ggactatgat gatgacctga ctgactctga   2040
gatggatgtg gtgaggtttg atgatgacaa cagccccagc ttcatccaga tcaggtctgt   2100
ggccaagaag cactcccaaga cctgggtgca ctacattgct gctgaggagg aggactggga   2160
ctatgccccc ctggtgctgg cccctgatga caggagctac aagagccagt acctgaacaa   2220
tggcccccag aggattggca ggaagtacaa gaaggtcagg ttcatggcct acactgatga   2280
aaccttcaag accagggagg ccatccagca tgagtctggc atcctgggcc ccctgctgta   2340
tggggaggtg ggggacaccc tgctgatcat cttcaagaac caggccagca ggccctacaa   2400
catctacccc catggcatca ctgatgtgag gcccctgtac agcaggaggc tgcccaaggg   2460
ggtgaagcac ctgaaggact tccccatcct gcctggggag atcttcaagt acaagtggac   2520
tgtgactgtg gaggatggcc ccaccaagtc tgaccccagg tgcctgacca gatactacag   2580
cagctttgtg aacatggaga gggacctggc ctctggcctg attggccccc tgctgatctg   2640
ctacaaggag tctgtggacc agaggggcaa ccagatcatg tctgacaaga ggaatgtgat   2700
cctgttctct gtgtttgatg agaacaggag ctggtacctg actgagaaca tccagaggtt   2760
cctgcccaac cctgctgggg tgcagctgga ggaccctgag ttccaggcca gcaacatcat   2820
gcacagcatc aatggctatg tgtttgacag cctgcagctg tctgtgtgcc tgcatgaggt   2880
ggcctactgg tacatcctga gcattgggc ccagactgac ttcctgtctg tgttcttctc    2940
tggctacacc ttcaagcaca agatggtgta tgaggacacc ctgaccctgt tccccttctc   3000
tggggagact gtgttcatga gcatggagaa ccctggcctg tggattctgg gctgccacaa   3060
ctctgacttc aggaacaggg gcatgactgc cctgctgaaa gtctccagct gtgacaagaa   3120
```

```
cactggggac tactatgagg acagctatga ggacatctct gcctacctgc tgagcaagaa    3180
caatgccatt gagcccagga gcttcagcca gaaccccca gtgctgaaga ggcaccagag     3240
ggagatcacc aggaccaccc tgcagtctga ccaggaggag attgactatg atgacaccat    3300
ctctgtggag atgaagaagg aggactttga catctacgac gaggacgaga accagagccc    3360
caggagcttc cagaagaaga ccaggcacta cttcattgct gctgtggaga ggctgtggga    3420
ctatggcatg agcagcagcc cccatgtgct gaggaacagg gcccagtctg gctctgtgcc    3480
ccagttcaag aaggtggtgt tccaggagtt cactgatggc agcttcaccc agcccctgta    3540
cagaggggag ctgaatgagc acctgggcct gctgggcccc tacatcaggg ctgaggtgga    3600
ggacaacatc atggtgacct tcaggaacca ggccagcagg ccctacagct tctacagcag    3660
cctgatcagc tatgaggagg accagaggca ggggctgag cccaggaaga cttttgtgaa     3720
gcccaatgaa accaagacct acttctggaa ggtgcagcac cacatggccc ccaccaagga    3780
tgagtttgac tgcaaggcct gggcctactt ctctgatgtg gacctggaga aggatgtgca    3840
ctctggcctg attggccccc tgctggtgtg ccacaccaac accctgaacc ctgcccatgg    3900
caggcaggtg actgtgcagg agtttgccct gttcttcacc atctttgatg aaaccaagag    3960
ctggtacttc actgagaaca tggagaggaa ctgcaggggcc ccctgcaaca tccagatgga   4020
ggaccccacc ttcaaggaga actacaggtt ccatgccatc aatggctaca tcatggacac    4080
cctgcctggc ctggtgatgg cccaggacca gaggatcagg tggtacctgc tgagcatggg    4140
cagcaatgag aacatccaca gcatccactt ctctggccat gtgttcactg tgaggaagaa    4200
ggaggagtac aagatggccc tgtacaacct gtacctgggg gtgtttgaga ctgtggagat    4260
gctgcccagc aaggctggca tctggagggt ggagtgcctg attggggagc acctgcatgc    4320
tggcatgagc accctgttcc tggtgtacag caacaagtgc cagaccccc tgggcatggc    4380 ctctggccac atcagggact tccagatcac tgcctctggc cagtatggcc agtgggcccc    4440
caagctggcc aggctgcact actctggcag catcaatgcc tggagcacca aggagccctt    4500
cagctggatc aaggtggacc tgctggcccc catgatcatc catggcatca gacccaggg    4560 ggccaggcag aagttcagca gcctgtacat cagccagtc atcatcatgt acagcctgga     4620
tggcaagaag tggcagacct acaggggcaa cagcactggc accctgatgg tgttctttgg    4680
caatgtggac agctctggca tcaagcacaa catcttcaac ccccccatca ttgccagata    4740
catcaggctg caccccaccc actacagcat caggagcacc ctgaggatgg agctgatggg    4800
ctgtgacctg aacagctgca gcatgcccct gggcatggag agcaaggcca tctctgatgc    4860
ccagatcact gccagcagct acttcaccaa catgtttgcc acctggagcc ccagcaaggc    4920
caggctgcac ctgcagggca ggagcaatgc ctggaggccc caggtcaaca ccccaagga    4980 gtggctgcag gtggacttcc agaagaccat gaaggtgact ggggtgacca cccagggggt    5040
gaagagcctg ctgaccagca tgtatgtgaa ggagttcctg atcagcagca gccaggatgg    5100
ccaccagtgg acccttgttct tccagaatgg caaggtgaag gtgttccagg caaccagga    5160 cagcttcacc cctgtggtga acagcctgga cccccccctg ctgaccagat acctgaggat    5220 tcaccccag agctgggtgc accagattgc cctgaggatg gaggtgctgg gctgtgaggc    5280
ccaggacctg tactgacctc gaggcactgt cctttcctaa taaaatgagg aaattgcatc    5340
gcattgtctg agtaggtgtc attctattct gggggtggg gtgggcagg acagcaaggg    5400 ggaggattgg gaagacaata gcaggcatgc tggggatgcg gtgggctcta tgggcacgtg    5460
gcggccgcag gaaccctag tgatggagtt ggccactccc tctctgcgcg ctcgctcgct    5520
```

```
cactgaggcc gggcgaccaa aggtcgcccg acgcccgggc tttgcccggg cggcctcagt    5580
gagcgagcga gcgcgcagag agggagtggc caa                                 5613

<210> SEQ ID NO 12
<211> LENGTH: 5362
<212> TYPE: DNA
<213> ORGANISM: Adeno-Associated Virus 2

<400> SEQUENCE: 12
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgcggc cgcacgcgtg ttttcgactg tttgctgttt     180
gctgcttgca atgtttgccc attttaggga catgtttgct gtttgctgct tgcaatgttt     240
gcccatttta gggacatgtt tgctgtttgc tgcttgcaat gtttgcccat tttagggaca     300
tgtttgctgt ttgctgcttg caatgtttgc cattttaggg acaacgcga aacgtcgact      360 ggacacagga cgctgtggtt tctgagccag ggggcgactc agatcccagc cagtggactt     420
agcccctgtt tgctcctccg ataactgggg tgaccttggt taatattcac cagcagcctc     480
ccccgttgcc cctctggatc cactgcttaa atacggacga ggacagggcc ctgtctcctc     540
agcttcaggc accaccactg acctgggaca gtgaatcgta agtactagca gctacaatcc     600
agctaccatt ctgcttttat tttatggttg ggataaggct ggattattct gagtccaagc     660
taggcccttt tgctaatcat gttcatacct cttatcttcc tcccacagct cctgggcaac     720
gtgctggtct gtgtgctggc ccatcacttt ggcaaagaat tgcgatcgcc accatgcaga     780
ttgagctgag cacctgcttc ttcctgtgcc tgctgaggtt ctgcttctct gccaccagga     840
gatactacct gggggctgtg agctgagct gggactacat gcagtctgac ctgggggagc     900
tgcctgtgga tgccaggttc ccccccagag tgcccaagag cttccccttc aacacctctg     960
tggtgtacaa gaagaccctg tttgtggagt tcactgacca cctgttcaac attgccaagc    1020
ccaggccccc ctggatgggc ctgctgggcc ccaccatcca ggctgaggtg tatgacactg    1080
tggtgatcac cctgaagaac atggccagcc acccTgtgag cctgcatgct gtgggggtga    1140
gctactggaa ggcctctgag ggggctgagt atgatgacca gaccagccag agggagaagg    1200
aggatgacaa ggtgttccct gggggcagcc acacctatgt gtggcaggtg ctgaaggaga    1260
atggccccat ggcctctgac ccctgtgcc tgacctacag ctacctgagc catgtggacc    1320
tggtgaagga cctgaactct ggcctgattg gggcctgct ggtgtgcagg gagggcagcc    1380
tggccaagga gaagacccag accctgcaca gttcatcct gctgtttgct gtgtttgatg    1440
agggcaagag ctggcactct gaaaccaaga cagcctgat gcaggacagg gatgctgcct    1500
ctgccagggc ctggcccaag atgcacactg tgaatggcta tgtgaacagg agcctgcctg    1560
gcctgattgg ctgccacagg aagtctgtgt actggcatgt gattggcatg ggcaccaccc    1620
ctgaggtgca cagcatcttc ctggagggcc acaccttcct ggtcaggaac cacaggcagg    1680
ccagcctgga gatcagcccc atcaccttcc tgactgccca gaccctgctg atggacctgg    1740
gccagttcct gctgttctgc cacatcagca gccaccagcc tgatggcatg gaggcctatg    1800
tgaaggtgga cagctgccct gaggagcccc agctgaggat gaagaacaat gaggaggctg    1860
aggactatga tgatgacctg actgactctg atggggatgt ggtgaggttt gatgatgaca    1920
acagccccag cttcatccag atcaggtctg tggccaagaa gcaccccaag acctgggtgc    1980
```

```
actacattgc tgctgaggag gaggactggg actatgcccc cctggtgctg gcccctgatg    2040
acaggagcta caagagccag tacctgaaca atggccccca gaggattggc aggaagtaca    2100
agaaggtcag gttcatggcc tacactgatg aaaccttcaa gaccagggag gccatccagc    2160
atgagtctgg catcctgggc cccctgctgt atggggaggt gggggacacc ctgctgatca    2220
tcttcaagaa ccaggccagc aggccctaca acatctaccc ccatggcatc actgatgtga    2280
ggcccctgta cagcaggagg ctgcccaagg gggtgaagca cctgaaggac ttccccatcc    2340
tgcctgggga gatcttcaag tacaagtgga ctgtgactgt ggaggatggc cccaccaagt    2400
ctgaccccag gtgcctgacc agatactaca gcagctttgt gaacatggag agggacctgg    2460
cctctggcct gattggcccc ctgctgatct gctacaagga gtctgtggac cagaggggca    2520
accagatcat gtctgacaag aggaatgtga tcctgttctc tgtgtttgat gagaacagga    2580
gctggtacct gactgagaac atccagaggt tcctgcccaa ccctgctggg gtgcagctgg    2640
aggaccctga gttccaggcc agcaacatca tgcacagcat caatggctat gtgtttgaca    2700
gcctgcagct gtctgtgtgc ctgcatgagg tggcctactg gtacatcctg agcattgggg    2760
cccagactga cttcctgtct gtgttcttct ctggctacac cttcaagcac aagatggtgt    2820
atgaggacac cctgacccty ttccccttct ctggggagac tgtgttcatg agcatggaga    2880
accctggcct gtggattctg ggctgccaca actctgactt caggaacagg ggcatgactg    2940
ccctgctgaa agtctccagc tgtgacaaga acactgggga ctactatgag acagctatg    3000 aggacatctc tgcctacctg ctgagcaaga acaatgccat tgagcccagg agcttcagcc    3060 agaaccccccc agtgctgaag aggcaccaga gggagatcac caggaccacc ctgcagtctg    3120
accaggagga gattgactat gatgacacca tctctgtgga gatgaagaag gaggactttg    3180
acatctacga cgaggacgag aaccagagcc ccaggagctt ccagaagaag accaggcact    3240
acttcattgc tgctgtggag aggctgtggg actatggcat gagcagcagc ccccatgtgc    3300
tgaggaacag ggcccagtct ggctctgtgc cccagttcaa gaaggtggtg ttccaggagt    3360
tcactgatgg cagcttcacc cagcccctgt acagagggga gctgaatgag cacctgggcc    3420
tgctgggccc ctacatcagg gctgaggtgg aggacaacat catggtgacc ttcaggaacc    3480
aggccagcag gccctacagc ttctacagca gcctgatcag ctatgaggag gaccagaggc    3540 aggggctga gccaggaag aactttgtga gcccaatga aaccaagacc tacttctgga    3600
aggtgcagca ccacatggcc cccaccaagg atgagtttga ctgcaaggcc tgggcctact    3660
tctctgatgt ggacctggag aaggatgtgc actctggcct gattggcccc ctgctggtgt    3720
gccacaccaa caccctgaac cctgcccatg gcaggcaggt gactgtgcag gagtttgccc    3780
tgttcttcac catctttgat gaaaccaaga gctggtactt cactgagaac atggagagga    3840
actgcagggc ccctgcaac atccagatgg aggaccccac cttcaaggag aactacaggt    3900
tccatgccat caatggctac atcatggaca ccctgcctgg cctggtgatg gcccaggacc    3960
agaggatcag gtggtacctg ctgagcatgg gcagcaatga gaacatccac agcatccact    4020
tctctggcca tgtgttcact gtgaggaaga ggaggagta caagatggcc ctgtacaacc    4080
tgtaccctgg ggtgtttgag actgtggaga tgctgcccag caaggctggc atctggaggg    4140
tggagtgcct gattggggag cacctgcatg ctggcatgag caccctgttc ctggtgtaca    4200
gcaacaagtg ccagacccccc ctgggcatgg cctctggcca catcaggac ttccagatca    4260 ctgcctctgg ccagtatggc cagtgggccc ccaagctggc caggctgcac tactctggca    4320
gcatcaatgc ctggagcacc aaggagccct tcagctggat caaggtggac ctgctggccc    4380
```

```
ccatgatcat ccatggcatc aagacccagg gggccaggca gaagttcagc agcctgtaca    4440
tcagccagtt catcatcatg tacagcctgg atggcaagaa gtggcagacc tacaggggca    4500
acagcactgg caccctgatg gtgttctttg gcaatgtgga cagctctggc atcaagcaca    4560
acatcttcaa cccccccatc attgccagat acatcaggct gcaccccacc cactacagca    4620
tcaggagcac cctgaggatg gagctgatgg gctgtgacct gaacagctgc agcatgcccc    4680
tgggcatgga gagcaaggcc atctctgatg cccagatcac tgccagcagc tacttcacca    4740
acatgtttgc cacctggagc cccagcaagg ccaggctgca cctgcagggc aggagcaatg    4800
cctggaggcc ccaggtcaac aaccccaagg agtggctgca ggtggacttc agaagaccca    4860
tgaaggtgac tggggtgacc acccagggg tgaagagcct gctgaccagc atgtatgtga     4920
aggagttcct gatcagcagc agccaggatg ccaccagtg gaccctgttc ttccagaatg     4980
gcaaggtgaa ggtgttccag gcaaccagg acagcttcac ccctgtggtg aacagcctgg     5040
acccccccct gctgaccaga tacctgagga ttcaccccca gagctgggtg caccagattg    5100
ccctgaggat ggaggtgctg gctgtgagg cccaggacct gtactgacct cgaggaataa     5160
aggaaattta ttttcattgc aatagtgtgt tggttttttg tgtcacgtgg cggccgcagg    5220 aaccctagt gatggagttg ccactccct ctctgcgcgc tcgctcgctc actgaggccg      5280
ggcgaccaaa ggtcgcccga cgcccgggct tgcccgggc ggcctcagtg agcgagcgag     5340
cgcgcagaga gggagtggcc aa                                             5362

<210> SEQ ID NO 13
<211> LENGTH: 5464
<212> TYPE: DNA
<213> ORGANISM: Adeno-Associated Virus 2

<400> SEQUENCE: 13
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg    120
gccaactcca tcactagggg ttcctgcggc cgcacgcgtg ttttcgactg tttgctgttt    180
gctgcttgca atgtttgccc atttaggga catgtttgct gtttgctgct tgcaatgttt    240
gcccatttta gggacatgtt tgctgtttgc tgcttgcaat gtttgcccat tttagggaca    300
tgtttgctgt ttgctgcttg caatgtttgc ccattttagg acaacgcga aacgtcgact      360 ggacacagga cgctgtggtt tctgagccag ggggcgactc agatcccagc cagtggactt    420
agcccctgtt tgctcctccg ataactgggg tgaccttggt taatattcac cagcagcctc    480
ccccgttgcc cctctggatc cactgcttaa atacggacga ggacagggcc ctgtctcctc    540
agcttcaggc accaccactg acctgggaca gtgaatcgta agtactagca gctacaatcc    600
agctaccatt ctgcttttat tttatggttg ggataaggct ggattattct gagtccaagc    660
taggcccttt tgctaatcat gttcatacct cttatcttcc tcccacagct cctgggcaac    720
gtgctggtct gtgtgctggc ccatcacttt ggcaaagaat tgcgatcgcc accatgcaga    780
ttgagctgag cacctgcttc ttcctgtgcc tgctgaggtt ctgcttctct gccaccagga    840
gatactacct gggggctgtg agctgagct gggactacat gcagtctgac ctggggagc      900 tgcctgtgga tgccaggttc ccccccagag tgcccaagag cttccccttc aacacctctg    960
tggtgtacaa gaagacctg tttgtggagt tcactgacca cctgttcaac attgccaagc    1020
ccaggccccc ctggatgggc ctgctgggcc ccaccatcca ggctgaggtg tatgacactg    1080
```

-continued

```
tggtgatcac cctgaagaac atggccagcc accctgtgag cctgcatgct gtggggtga    1140 gctactggaa ggcctctgag ggggctgagt atgatgacca gaccagccag agggagaagg    1200
aggatgacaa ggtgttccct gggggcagcc acacctatgt gtggcaggtg ctgaaggaga    1260
atggccccat ggcctctgac cccctgtgcc tgacctacag ctacctgagc catgtggacc    1320
tggtgaagga cctgaactct ggcctgattg gggccctgct ggtgtgcagg gagggcagcc    1380
tggccaagga gaagacccag accctgcaca agttcatcct gctgtttgct gtgtttgatg    1440
agggcaagag ctggcactct gaaaccaaga acagcctgat gcaggacagg gatgctgcct    1500
ctgccagggc ctggcccaag atgcacactg tgaatggcta tgtgaacagg agcctgcctg    1560
gcctgattgg ctgccacagg aagtctgtgt actggcatgt gattggcatg ggcaccaccc    1620
ctgaggtgca cagcatcttc ctggagggcc acaccttcct ggtcaggaac acacaggcagg    1680 ccagcctgga gatcagcccc atcaccttcc tgactgccca gaccctgctg atggacctgg    1740
gccagttcct gctgttctgc cacatcagca gccaccagca tgatggcatg gaggcctatg    1800
tgaaggtgga cagctgccct gaggagcccc agctgaggat gaagaacaat gaggaggctg    1860
aggactatga tgatgacctg actgactctg agatggatgt ggtgaggttt gatgatgaca    1920
acagccccag cttcatccag atcaggtctg tggccaagaa gcaccccaag acctgggtgc    1980
actacattgc tgctgaggag gaggactggg actatgcccc cctggtgctg gccctgatg     2040 acaggagcta caagagccag tacctgaaca atggcccca gaggattggc aggaagtaca    2100
agaaggtcag gttcatggcc tacactgatg aaaccttcaa gaccagggag gccatccagc    2160
atgagtctgg catcctgggc cccctgctgt atggggaggt gggggacacc ctgctgatca    2220
tcttcaagaa ccaggccagc aggccctaca acatctaccc ccatggcatc actgatgtga    2280
ggcccctgta cagcaggagg ctgcccaagg gggtgaagca cctgaaggac ttccccatcc    2340
tgcctgggga gatcttcaag tacaagtgga ctgtgactgt ggaggatggc cccaccaagt    2400
ctgaccccag gtgcctgacc agatactaca gcagctttgt gaacatggag agggacctgg    2460
cctctggcct gattggcccc ctgctgatct gctacaagga gtctgtggac cagaggggca    2520
accagatcat gtctgacaag aggaatgtga tcctgttctc tgtgtttgat gagaacagga    2580
gctggtacct gactgagaac atccagaggt tcctgcccaa ccctgctggg gtgcagctgg    2640
aggaccctga gttccaggcc agcaacatca tgcacagcat caatggctat gtgtttgaca    2700
gcctgcagct gtctgtgtgc ctgcatgagg tggcctactg gtacatcctg agcattgggg    2760
cccagactga cttcctgtct gtgttcttct ctggctacac cttcaagcac aagatggtgt    2820
atgaggacac cctgaccctg ttccccttct ctggggagac tgtgttcatg agcatggaga    2880
accctggcct gtggattctg gctgccaca actctgactt caggaacagg gcatgactg     2940 ccctgctgaa agtctccagc tgtgacaaga acactgggga ctactatgag acagctatg     3000 aggacatctc tgcctacctg ctgagcaaga caatgccat tgagcccagg agcttcagcc    3060 agaaccccc agtgctgaag aggcaccaga gggagatcac caggaccacc ctgcagtctg    3120
accaggagga gattgactat gatgacacca tctctgtgga gatgaagaag gaggactttg    3180
acatctacga cgaggacgag aaccagagcc ccaggagctt ccagaagaag accaggcact    3240
acttcattgc tgctgtggag aggctgtggg actatggcat gagcagcagc ccccatgtgc    3300
tgaggaacag ggcccagtct ggctctgtgc cccagttcaa gaaggtggtg ttccaggagt    3360
tcactgatgg cagcttcacc cagccccctg tacagagggga gctgaatgag cacctgggcc    3420
tgctgggccc ctacatcagg gctgaggtgg aggacaacat catggtgacc ttcaggaacc    3480
```

-continued

```
aggccagcag gccctacagc ttctacagca gcctgatcag ctatgaggag gaccagaggc    3540 aggggggctga gcccaggaag aactttgtga agcccaatga aaccaagacc tacttctgga    3600
aggtgcagca ccacatggcc cccaccaagg atgagtttga ctgcaaggcc tgggcctact    3660
tctctgatgt ggacctggag aaggatgtgc actctggcct gattggcccc ctgctggtgt    3720
gccacaccaa caccctgaac cctgcccatg caggcaggt gactgtgcag gagtttgccc    3780
tgttcttcac catctttgat gaaaccaaga gctggtactt cactgagaac atggagagga    3840
actgcagggc ccctgcaac atccagatgg aggaccccac cttcaaggag aactacaggt    3900
tccatgccat caatggctac atcatggaca ccctgcctgg cctggtgatg gcccaggacc    3960
agaggatcag gtggtacctg ctgagcatgg gcagcaatga aacatccac agcatccact    4020 tctctggcca tgtgttcact gtgaggaaga aggaggagta caagatgcc ctgtacaacc    4080 tgtaccctgg ggtgtttgag actgtggaga tgctgcccag caaggctggc atctggaggg    4140
tggagtgcct gattggggag cacctgcatg ctggcatgag caccctgttc ctggtgtaca    4200
gcaacaagtg ccagacccc ctgggcatgg cctctggcca catcagggac ttccagatca    4260
ctgcctctgg ccagtatggc cagtgggccc ccaagctggc caggctgcac tactctggca    4320
gcatcaatgc ctggagcacc aaggagccct tcagctggat caaggtggac ctgctggccc    4380
ccatgatcat ccatggcatc aagacccagg gggccaggca gaagttcagc agcctgtaca    4440
tcagccagtt catcatcatg tacagcctgg atggcaagaa gtggcagacc tacaggggca    4500
acagcactgg cacctgatg gtgttctttg gcaatgtgga cagctctggc atcaagcaca    4560
acatcttcaa cccccccatc attgccagat acatcaggct gcaccccacc cactacagca    4620
tcaggagcac cctgaggatg gagctgatgg gctgtgacct gaacagctgc agcatgcccc    4680
tgggcatgga gagcaaggcc atctctgatg cccagatcac tgccagcagc tacttcacca    4740
acatgtttgc cacctggagc cccagcaagg ccaggctgca cctgcagggc aggagcaatg    4800
cctggaggcc ccaggtcaac aaccccaagg agtggctgca ggtggacttc cagaagacca    4860
tgaaggtgac tgggtgacc acccagggg tgaagagcct gctgaccagc atgtatgtga    4920
aggagttcct gatcagcagc agccaggatg ccaccagtg accctgttc ttccagaatg    4980 gcaaggtgaa ggtgttccag ggcaaccagg acagcttcac ccctgtggtg aacagcctgg    5040
acccccccct gctgaccaga tacctgagga ttcaccccca gagctgggtg caccagattg    5100
ccctgaggat ggaggtgctg gctgtgagg cccaggacct gtactgacct cgaggcactg    5160 tccttccta ataaatgag gaaattgcat cgcattgtct gagtaggtgt cattctattc    5220
tggggggtgg ggtggggcag gacagcaagg gggaggattg ggaagacaat agcaggcatg    5280
ctggggatgc ggtgggctct atgggcacgt ggcggccgca ggaacccta gtgatggagt    5340 tggccactcc ctctctgcgc gctcgctcgc tcactgaggc cgggcgacca aggtcgccc    5400 gacgcccggg ctttgcccgg gcggcctcag tgagcgagcg agcgcgcaga gagggagtgg    5460
ccaa                                                               5464
```

<210> SEQ ID NO 14
<211> LENGTH: 6354
<212> TYPE: DNA
<213> ORGANISM: Adeno-Associated Virus 2

<400> SEQUENCE: 14

```
ttggccactc cctctctgcg cgctcgctcg ctcactgagg ccgcccgggc aaagcccggg     60
```

-continued

| | |
|---|---|
| cgtcgggcga cctttggtcg cccggcctca gtgagcgagc gagcgcgcag agagggagtg | 120 |
| gccaactcca tcactagggg ttcctgcggc cgcacgcgtg tttaaacgtc gacaggttaa | 180 |
| ttttaaaaa gcagtcaaaa gtccaagtgg cccttggcag catttactct ctctgtttgc | 240 |
| tctggttaat aatctcagga gcacaaacat tcctggaggc aggagaagaa atcaacatcc | 300 |
| tggacttatc ctctgggcct ctccccaccc ccaggagagg ctcaggttaa ttttaaaaa | 360 |
| gcagtcaaaa gtccaagtgg cccttggcag catttactct ctctgtttgc tctggttaat | 420 |
| aatctcagga gcacaaacat tcctggaggc aggagaagaa atcaacatcc tggacttatc | 480 |
| ctctgggcct ctccccaccc ccaggagagg ctgtcgactg gacacaggac gctgtggttt | 540 |
| ctgagccagg gggcgactca gatcccagcc agtggactta gccctgtttt gctcctccga | 600 |
| taactggggt gaccttggtt aatattcacc agcagcctcc cccgttgccc ctctggatcc | 660 |
| actgcttaaa tacggacgag gacagggccc tgtctcctca gcttcaggca ccaccactga | 720 |
| cctgggacag tgaatcgtaa gtactagcag ctacaatcca gctaccattc tgcttttatt | 780 |
| ttatggttgg gataaggctg gattattctg agtccaagct aggccctttt gctaatcatg | 840 |
| ttcatacctc ttatcttcct cccacagctc ctgggcaacg tgctggtctg tgtgctggcc | 900 |
| catcactttg gcaaagaatt gcgatcgcca ccatgcagat tgagctgagc acctgcttct | 960 |
| tcctgtgcct gctgaggttc tgcttctctg ccaccaggag atactacctg ggggctgtgg | 1020 |
| agctgagctg ggactacatg cagtctgacc tgggggagct gcctgtggat gccaggttcc | 1080 |
| cccccagagt gcccaagagc ttccccttca cacctctgt ggtgtacaag aagaccctgt | 1140 |
| ttgtggagtt cactgaccac ctgttcaaca ttgccaagcc caggcccccc tggatgggcc | 1200 |
| tgctgggccc caccatccag gctgaggtgt atgacactgt ggtgatcacc ctgaagaaca | 1260 |
| tggccagcca ccctgtgagc ctgcatgctg tgggggtgag ctactggaag gcctctgagg | 1320 |
| gggctgagta tgatgaccag accagccaga gggagaagga ggatgacaag gtgttccctg | 1380 |
| ggggcagcca cacctatgtg tggcaggtgc tgaaggagaa tggcccatg gcctctgacc | 1440 |
| ccctgtgcct gacctacagc tacctgagcc atgtggacct ggtgaaggac ctgaactctg | 1500 |
| gcctgattgg ggccctgctg gtgtgcaggg agggcagcct ggccaaggag aagacccaga | 1560 |
| ccctgcacaa gttcatcctg ctgtttgctg tgtttgatga gggcaagagc tggcactctg | 1620 |
| aaaccaagaa cagcctgatg caggacaggg atgctgcctc tgccagggcc tggcccaaga | 1680 |
| tgcacactgt gaatggctat gtgaacagga gcctgcctgg cctgattggc tgccacagga | 1740 |
| agtctgtgta ctggcatgtg attggcatgg gcaccacccc tgaggtgcac agcatcttcc | 1800 |
| tggagggcca caccttcctg gtcaggaacc acaggcaggc cagcctggag atcagcccca | 1860 |
| tcaccttcct gactgcccag accctgctga tggacctggg ccagttcctg ctgttctgcc | 1920 |
| acatcagcag ccaccagcat gatggcatgg aggcctatgt gaaggtggac agctgccctg | 1980 |
| aggagcccca gctgaggatg aagaacaatg aggaggctga ggactatgat gatgacctga | 2040 |
| ctgactctga gatggatgtg gtgaggtttg atgatgacaa cagccccagc ttcatccaga | 2100 |
| tcaggtctgt ggccaagaag caccccaaga cctgggtgca ctacattgct gctgaggagg | 2160 |
| aggactggga ctatgccccc ctggtgctgg cccctgatga caggagctac aagagccagt | 2220 |
| acctgaacaa tggccccag aggattggca ggaagtacaa gaaggtcagg ttcatggcct | 2280 |
| acactgatga aaccttcaag accagggagg ccatccagca tgagtctggc atcctgggcc | 2340 |
| ccctgctgta tggggaggtg ggggacaccc tgctgatcat cttcaagaac caggccagca | 2400 |
| ggccctacaa catctacccc catggcatca ctgatgtgag gccctgtac agcaggaggc | 2460 |

```
tgcccaaggg ggtgaagcac ctgaaggact tccccatcct gcctggggag atcttcaagt    2520
acaagtggac tgtgactgtg gaggatggcc ccaccaagtc tgaccccagg tgcctgacca    2580
gatactacag cagctttgtg aacatggaga gggacctggc ctctggcctg attggccccc    2640
tgctgatctg ctacaaggag tctgtggacc agaggggcaa ccagatcatg tctgacaaga    2700
ggaatgtgat cctgttctct gtgtttgatg agaacaggag ctggtacctg actgagaaca    2760
tccagaggtt cctgcccaac cctgctgggg tgcagctgga ggaccctgag ttccaggcca    2820
gcaacatcat gcacagcatc aatggctatg tgtttgacag cctgcagctg tctgtgtgcc    2880
tgcatgaggt ggcctactgg tacatcctga gcattgggc ccagactgac ttcctgtctg    2940
tgttcttctc tggctacacc ttcaagcaca agatggtgta tgaggacacc ctgaccctgt    3000
tccccttctc tggggagact gtgttcatga gcatggagaa ccctggcctg tggattctgg    3060
gctgccacaa ctctgacttc aggaacaggg gcatgactgc cctgctgaaa gtctccagct    3120
gtgacaagaa cactggggac tactatgagg acagctatga ggacatctct gcctacctgc    3180
tgagcaagaa caatgccatt gagcccagga gcttcagcca gaaccccca gtgctgaaga    3240 ggcaccagag ggagatcacc aggaccaccc tgcagtctga ccaggaggag attgactatg    3300
atgacaccat ctctgtggag atgaagaagg aggactttga catctacgac gaggacgaga    3360
accagagccc caggagcttc cagaagaaga ccaggcacta cttcattgct gctgtggaga    3420
ggctgtggga ctatggcatg agcagcagcc ccatgtgct gaggaacagg gcccagtctg    3480
gctctgtgcc ccagttcaag aaggtggtgt tccaggagtt cactgatggc agcttcaccc    3540
agcccctgta cagaggggag ctgaatgagc acctgggcct gctgggcccc tacatcaggg    3600
ctgaggtgga ggacaacatc atggtgacct tcaggaacca ggccagcagg ccctacagct    3660
tctacagcag cctgatcagc tatgaggagg accagaggca gggggctgag cccaggaaga    3720
actttgtgaa gcccaatgaa accaagacct acttctggaa ggtgcagcac cacatggccc    3780
ccaccaagga tgagtttgac tgcaaggcct gggcctactt ctctgatgtg gacctggaga    3840
aggatgtgca ctctggcctg attggccccc tgctggtgtg ccacaccaac ccctgaacc    3900 ctgcccatgg caggcaggtg actgtgcagg agtttgccct gttcttcacc atctttgatg    3960
aaaccaagag ctggtacttc actgagaaca tggagaggaa ctgcagggcc ccctgcaaca    4020
tccagatgga ggaccccacc ttcaaggaga actacaggtt ccatgccatc aatggctaca    4080
tcatggacac cctgcctggc ctggtgatgg cccaggacca gaggatcagg tggtacctgc    4140
tgagcatggg cagcaatgag aacatccaca gcatccactt ctctggccat gtgttcactg    4200
tgaggaagaa ggaggagtac aagatggccc tgtacaacct gtaccctggg gtgtttgaga    4260
ctgtggagat gctgcccagc aaggctgcca tctggagggt ggagtgcctg attggggagc    4320
acctgcatgc tggcatgagc acctgttcc tggtgtacag caacaagtgc cagaccccc    4380 tgggcatggc ctctggccac atcagggact tccagatcac tgcctctggc cagtatggcc    4440
agtgggcccc caagctggcc aggctgcact actctggcag catcaatgcc tggagcacca    4500
aggagccctt cagctggatc aaggtggacc tgctggcccc catgatcatc catggcatca    4560
agacccaggg ggccaggcag aagttcagca gcctgtacat cagccagttc atcatcatgt    4620
acagcctgga tggcaagaag tggcagacct acaggggcaa cagcactggc accctgatgg    4680
tgttctttgg caatgtggac agctctggca tcaagcacaa catcttcaac ccccccatca    4740
ttgccagata catcaggctg cacccccacc actacagcat caggagcacc ctgaggatgg    4800
```

```
agctgatggg ctgtgacctg aacagctgca gcatgcccct gggcatggag agcaaggcca    4860
tctctgatgc ccagatcact gccagcagct acttcaccaa catgtttgcc acctggagcc    4920
ccagcaaggc caggctgcac ctgcagggca ggagcaatgc ctggaggccc aggtcaaca     4980
accccaagga gtggctgcag gtggacttcc agaagaccat gaaggtgact ggggtgacca    5040
cccagggggt gaagagcctg ctgaccagca tgtatgtgaa ggagttcctg atcagcagca    5100
gccaggatgg ccaccagtgg accctgttct tccagaatgg caaggtgaag gtgttccagg    5160
gcaaccagga cagcttcacc cctgtggtga acagcctgga cccccccctg ctgaccagat    5220
acctgaggat tcaccccag agctgggtgc accagattgc cctgaggatg gaggtgctgg     5280
gctgtgaggc ccaggacctg tactgacctc gaggtgtgcc ttctagttgc cagccatctg    5340
ttgtttgccc ctccccgtg ccttccttga ccctggaagg tgccactccc actgtcctt     5400
cctaataaaa tgaggaaatt gcatcgcatt gtctgagtag gtgtcattct attctggggg    5460
gtggggtggg gcaggacagc aagggggagg attgggaaga caatagcagg catgctgggg    5520
atgcggtggg ctctatgggc acgtgcctc tcacactacc taaaccacgc caggacaacc     5580
tctgctcctc tccaccgaaa ttccaagggg tcgagtggat gttggaggtg catgggccc     5640
agagaggtct ctgacctctg ccccagctcc aaggtcagca ggcagggagg gctgtgtgtt    5700
tgctgtttgc tgcttgcaat gttgccat tttagggaca tgagtaggct gaagtttgtt      5760
cagtgtggac ttcagaggca gcacacaaac agctgctgga ggatgggaac tgaggggttg    5820
gaaggggca gggtgagccc agaaactcct gtgtgcctct gagcctgcag ccctctcaca     5880
ctacctaaac cacgccagga caacctctgc tcctctccac cgaaattcca aggggtcgag    5940
tggatgttgg aggtggcatg ggcccagaga ggtctctgac ctctgcccca gctccaaggt    6000
cagcaggcag gagggctgt gtgtttgctg tttgctgctt gcaatgtttg cccatttag      6060
ggacatgagt aggctgaagt tgttcagtg tggacttcag aggcagcaca caaacagctg     6120
ctggaggatg ggaactgagg ggttggaagg gggcagggtg agcccagaaa ctcctgtgtg    6180
cctctgagcc tgcagcacgt ggcggccgca ggaaccccta gtgatggagt tggccactcc    6240
ctctctgcgc gctcgctcgc tcactgaggc cgggcgacca aggtcgccc gacgcccggg    6300
ctttgcccgg gcggcctcag tgagcgagcg agcgcgcaga gagggagtgg ccaa          6354
```

<210> SEQ ID NO 15
<211> LENGTH: 6308
<212> TYPE: DNA
<213> ORGANISM: Adeno-Associated Virus 2

<400> SEQUENCE: 15

```
ttggccactc cctctctgcg cgctcgctcg ctcactgagg ccgccgggc aaagcccggg       60
cgtcgggcga cctttggtcg cccggcctca gtgagcgagc gagcgcgcag agagggagtg     120
gccaactcca tcactagggg ttcctgcggc cgcacgcgtg ttaattttta aaaagcagtc    180
aaaagtccaa gtggcccttg gcagcattta ctctctctgt ttgctctggt taataatctc    240
aggagcacaa acattcctgg aggcaggaga agaaatcaac atcctggact tatcctctgg    300
gcctgttaat ttttaaaaag cagtcaaaag tccaagtggc ccttggcagc atttactctc    360
tctgtttgct ctggttaata atctcaggag cacaaacatt cctggaggca ggagaagaaa    420
tcaacatcct ggactatcc tctgggccta ggcctgaggc tggtcaaaat tgaacctcct     480
cctgctctga gcagctgggg gggcagacta agcagagggc tgtgcagacc cacataaaga    540
gcctactgtg tgccaggcac ttcacccgag gcacttcaca agcatgcttg ggaatgaaac    600
```

| | |
|---|---|
| ttccaactct ttgggatgca ggtgaaacag ttcctggttc agagaggtga agcggcctgc | 660 |
| ctgaggcagc acagctcttc tttacagatg tgcttcccca cctctaccct gtctcacggc | 720 |
| cccccatgcc agcctgacgg ttgtgtctgc ctcagtcatg ctccattttt ccatcgggac | 780 |
| catcaagagg gtgtttgtgt ctaaggctga ctgggtaact ttggatgagc ggtctctccg | 840 |
| ctctgagcct gtttcctcat ctgtcaaatg ggctctaacc cactctgatc tcccagggcg | 900 |
| gcagtaagtc ttcagcatca ggcattttgg ggtgactcag taaatggtag atcttgctac | 960 |
| cagtggaaca gccactaagg attctgcagt gagagcagag ggccagctaa gtggtactct | 1020 |
| cccagagact gtctgactca cgccaccccc tccaccttgg acacaggacg ctgtggtttc | 1080 |
| tgagccaggt acaatgactc ctttcggtaa gtgcagtgga agctgtacac tgcccaggca | 1140 |
| aagcgtccgg gcagcgtagg cgggcgactc agatcccagc cagtggactt agcccctgtt | 1200 |
| tgctcctccg ataactgggg tgaccttggt taatattcac cagcagcctc cccgttgcc | 1260 |
| cctctggatc cactgcttaa atacggacga ggacagggcc ctgtctcctc agcttcaggc | 1320 |
| accaccactg acctgggaca gtgaatcgta agtactagca gctacaatcc agctaccatt | 1380 |
| ctgcttttat tttatggttg ggataaggct ggattattct gagtccaagc taggcccttt | 1440 |
| tgctaatcat gttcatacct cttatcttcc tcccacagct cctgggcaac gtgctggtct | 1500 |
| gtgtgctggc ccatcacttt ggcaaagaat tgcgatcgcc accatgcaga ttgagctgag | 1560 |
| cacctgcttc ttcctgtgcc tgctgaggtt ctgcttctct gccaccagga gatactacct | 1620 |
| gggggctgtg gagctgagct gggactacat gcagtctgac ctgggggagc tgcctgtgga | 1680 |
| tgccaggttc ccccccagag tgcccaagag cttcccttc aacacctctg tggtgtacaa | 1740 |
| gaagacctg tttgtggagt tcactgacca cctgttcaac attgccaagc ccaggccccc | 1800 |
| ctggatgggc ctgctgggcc ccaccatcca ggctgaggtg tatgacactg tggtgatcac | 1860 |
| cctgaagaac atggccagcc accctgtgag cctgcatgct gtggggtga gctactggaa | 1920 |
| ggcctctgag ggggctgagt atgatgacca gaccagccag agggagaagg aggatgacaa | 1980 |
| ggtgttccct gggggcagcc acacctatgt gtggcaggtg ctgaaggaga atggccccat | 2040 |
| ggcctctgac cccctgtgcc tgacctacag ctacctgagc catgtggacc tggtgaagga | 2100 |
| cctgaactct ggcctgattg ggcctgct ggtgtgcagg gagggcagcc tggccaagga | 2160 |
| gaagacccag accctgcaca gttcatcct gctgtttgct gtgtttgatg agggcaagag | 2220 |
| ctggcactct gaaaccaaga acagcctgat gcaggacagg gatgctgcct ctgccagggc | 2280 |
| ctggcccaag atgcacactg tgaatggcta tgtgaacagg agcctgcctg gcctgattgg | 2340 |
| ctgccacagg aagtctgtgt actggcatgt gattggcatg ggcaccaccc ctgaggtgca | 2400 |
| cagcatcttc ctggagggcc acaccttcct ggtcaggaac acaggcagg ccagcctgga | 2460 |
| gatcagcccc atcaccttcc tgactgccca gaccctgctg atggacctgg ccagttcct | 2520 |
| gctgttctgc cacatcagca gccaccagca tgatggcatg gaggcctatg tgaaggtgga | 2580 |
| cagctgccct gaggagcccc agctgaggat gaagaacaat gaggaggctg aggactatga | 2640 |
| tgatgacctg actgactctg agatggatgt ggtgaggttt gatgatgaca acagccccag | 2700 |
| cttcatccag atcaggtctg tggccaagaa gcaccccaag acctgggtgc actacattgc | 2760 |
| tgctgaggag gaggactggg actatgcccc cctggtgctg gcccctgatg acaggagcta | 2820 |
| caagagccca tacctgaaca tgggccccca gaggattggc aggaagtaca agaaggtcag | 2880 |
| gttcatggcc tacactgatg aaaccttcaa gaccaggag gccatccagc atgagtctgg | 2940 |

```
catcctgggc ccctgctgt atggggaggt gggggacacc ctgctgatca tcttcaagaa    3000
ccaggccagc aggccctaca acatctaccc ccatggcatc actgatgtga ggccctgta    3060 cagcaggagg ctgcccaagg gggtgaagca cctgaaggac ttccccatcc tgcctggga    3120 gatcttcaag tacaagtgga ctgtgactgt ggaggatggc cccaccaagt ctgaccccag    3180
gtgcctgacc agatactaca gcagctttgt gaacatggag agggacctgg cctctggcct    3240
gattggcccc ctgctgatct gctacaagga gtcgtggac cagaggggca accagatcat    3300
gtctgacaag aggaatgtga tcctgttctc tgtgtttgat gagaacagga gctggtacct    3360
gactgagaac atccagaggt tcctgcccaa ccctgctggg gtgcagctgg aggaccctga    3420
gttccaggcc agcaacatca tgcacagcat caatggctat gtgtttgaca gcctgcagct    3480
gtctgtgtgc ctgcatgagg tggcctactg gtacatcctg agcattgggg cccagactga    3540
cttcctgtct gtgttcttct ctggctacac cttcaagcac aagatggtgt atgaggacac    3600
cctgaccctg ttccccttct ctggggagac tgtgttcatg agcatggaga ccctggcct    3660 gtggattctg ggctgccaca actctgactt caggaacagg gcatgactg ccctgctgaa    3720 agtctccagc tgtgacaaga acactgggga ctactatgag acagctatg aggacatctc    3780 tgcctacctg ctgagcaaga acaatgccat tgagcccagg agcttcagcc agaaccccc    3840 agtgctgaag aggcaccaga gggagatcac caggaccacc ctgcagtctg accaggagga    3900
gattgactat gatgacacca tctctgtgga gatgaagaag gaggactttg acatctacga    3960
cgaggacgag aaccagagcc caggagctt ccagaagaag accaggcact acttcattgc    4020
tgctgtggag aggctgtggg actatggcat gagcagcagc ccccatgtgc tgaggaacag    4080
ggcccagtct ggctctgtgc cccagttcaa gaaggtggtg ttccaggagt tcactgatgg    4140
cagcttcacc cagcccctgt acagagggga gctgaatgag cacctgggcc tgctgggccc    4200
ctacatcagg gctgaggtgg aggacaacat catggtgacc ttcaggaacc aggccagcag    4260
gccctacagc ttctacagca gcctgatcag ctatgaggag gaccagaggc aggggctga    4320 gcccaggaag aactttgtga agcccaatga accaagaccc tacttctgga aggtgcagca    4380
ccacatggcc cccaccaagg atgagtttga ctgcaaggcc tgggcctact ctctgatgt    4440 ggacctggag aaggatgtgc actctggcct gattggcccc ctgctggtgt gccacaccaa    4500
cacccctgaa cctgcccatg gcaggcaggt gactgtgcag gagtttgccc tgttcttcac    4560
catctttgat gaaaccaaga gctggtactt cactgagaac atggagagga actgcagggc    4620
cccctgcaac atccagatgg aggacccac cttcaaggag aactacaggt tccatgccat    4680
caatggctac atcatggaca ccctgcctgg cctggtgatg gcccaggacc agaggatcag    4740
gtggtacctg ctgagcatgg gcagcaatga gaacatccac agcatccact ctctggcca    4800 tgtgttcact gtgaggaaga aggagagta caagatggcc ctgtacaacc tgtaccctgg    4860
ggtgtttgag actgtggaga tgctgcccag caaggctggc atctggaggg tggagtgcct    4920
gattggggag cacctgcatg ctggcatgag caccctgttc ctggtgtaca gcaacaagtg    4980
ccagaccccc ctgggcatgg cctctggcca catcagggac ttccagatca ctgcctctgg    5040
ccagtatggc cagtgggccc ccaagctggc caggctgcac tactctggca gcatcaatgc    5100
ctggagcacc aaggagccct tcagctggat caaggtggac ctgctggccc ccatgatcat    5160
ccatggcatc aagacccagg ggccaggca gaagttcagc agcctgtaca tcagccagtt    5220
catcatcatg tacagcctgg atggcaagaa gtggcagacc tacaggggca acagcactgg    5280
caccctgatg gtgttctttg gcaatgtgga cagctctggc atcaagcaca acatcttcaa    5340
```

```
cccccccatc attgccagat acatcaggct gcaccccacc cactacagca tcaggagcac    5400
cctgaggatg gagctgatgg gctgtgacct gaacagctgc agcatgcccc tgggcatgga    5460
gagcaaggcc atctctgatg cccagatcac tgccagcagc tacttcacca acatgtttgc    5520
cacctggagc cccagcaagg ccaggctgca cctgcagggc aggagcaatg cctggaggcc    5580
ccaggtcaac aaccccaagg agtggctgca ggtggacttc agaagacca tgaaggtgac     5640 tggggtgacc acccaggggg tgaagagcct gctgaccagc atgtatgtga aggagttcct    5700
gatcagcagc agccaggatg ccaccagtg accctgttc ttccagaatg caaggtgaa      5760 ggtgttccag gcaaccagg acagcttcac ccctgtggtg aacagcctgg accccccct     5820 gctgaccaga tacctgagga ttcaccccca gagctgggtg caccagattg ccctgaggat    5880
ggaggtgctg ggctgtgagg cccaggacct gtactgacct cgagctgtgc cttctagttg    5940
ccagccatct gttgtttgcc cctcccccgt gccttccttg accctggaag gtgccactcc    6000
cactgtcctt tcctaataaa atgaggaaat tgcatcgcat tgtctgagta ggtgtcattc     6060
tattctgggg ggtggggtgg ggcaggacag caaggggggag gattgggaag acaatagcag    6120
gcatgctggg gatgcggtgg gctctatgga ccggtgcggc cgcaggaacc cctagtgatg    6180
gagttggcca ctccctctct gcgcgctcgc tcgctcactg aggccgggcg accaaaggtc    6240
gcccgacgcc cgggctttgc ccgggcggcc tcagtgagcg agcgagcgcg cagagaggga    6300
gtggccaa                                                             6308

<210> SEQ ID NO 16
<211> LENGTH: 5635
<212> TYPE: DNA
<213> ORGANISM: Adeno-Associate Virus 2

<400> SEQUENCE: 16
ttggccactc cctctctgcg cgctcgctcg ctcactgagg ccgccgggc aaagcccggg      60 cgtcgggcga cctttggtcg cccggcctca gtgagcgagc gagcgcgcag agagggagtg    120
gccaactcca tcactagggg ttcctgcggc cgcacgcgtg ttaattttta aaaagcagtc    180
aaaagtccaa gtggcccttg gcagcattta ctctctctgt ttgctctggt taataatctc    240
aggagcacaa acattcctgg aggcaggaga agaaatcaac atcctggact tatcctctgg    300
gcctgttaat ttttaaaaag cagtcaaaag tccaagtggc ccttggcagc atttactctc    360
tctgtttgct ctggttaata atctcaggag cacaaacatt cctggaggca ggagaagaaa    420
tcaacatcct ggacttatcc tctgggccta gtcgactgga cacaggacgc tgtggtttct    480
gagccagggg gcgactcaga tcccagccag tggacttagc ccctgtttgc tcctccgata    540
actgggtgta ccttggttaa tattcaccag cagcctcccc cgttgcccct ctggatccac    600
tgcttaaata cggacgagga cagggccctg tctcctcagc ttcaggcacc accactgacc    660
tgggacagta atcgtaagt actagcagct acaatccagc taccattctg cttttatttt     720
atggttggga taaggctgga ttattctgag tccaagctag gccttttgc taatcatgtt    780 catacctctt atcttcctcc cacagctcct gggcaacgtg ctggtctgtg tgctggccca   840
tcactttggc aaagaattgc gatcgccacc atgcagatta gctgagcac ctgcttcttc     900 ctgtgcctgc tgaggttctg cttctctgcc accaggagat actacctggg ggctgtggag    960
ctgagctggg actacatgca gtctgacctg ggggagctgc ctgtggatgc caggttcccc    1020
cccagagtgc ccaagagctt cccccttcaac acctctgtgg tgtacaagaa gaccctgttt    1080
```

```
gtggagttca ctgaccacct gttcaacatt gccaagccca ggccccctg dgatgggcctg    1140
ctgggcccca ccatccaggc tgaggtgtat gacactgtgg tgatcaccct gaagaacatg    1200
gccagccacc ctgtgagcct gcatgctgtg ggggtgagct actggaaggc ctctgagggg    1260
gctgagtatg atgaccagac cagccagagg gagaaggagg atgacaaggt gttccctggg    1320
ggcagccaca cctatgtgtg gcaggtgctg aaggagaatg gccccatggc ctctgacccc    1380
ctgtgcctga cctacagcta cctgagccat gtggacctgg tgaaggacct gaactctggc    1440
ctgattgggg ccctgctggt gtgcagggag ggcagcctgg ccaaggagaa gacccagacc    1500
ctgcacaagt tcatcctgct gtttgctgtg tttgatgagg gcaagagctg gcactctgaa    1560
accaagaaca gcctgatgca ggacagggat gctgcctctg ccagggcctg gcccaagatg    1620
cacactgtga atggctatgt gaacaggagc ctgcctggcc tgattggctg ccacaggaag    1680
tctgtgtact ggcatgtgat tggcatgggc accacccctg aggtgcacag catcttcctg    1740
gagggccaca ccttcctggt caggaaccac aggcaggcca gcctggagat cagccccatc    1800
accttcctga ctgcccagac cctgctgatg gacctgggcc agttcctgct gttctgccac    1860
atcagcagcc accagcatga tggcatggag gcctatgtga aggtggacag ctgccctgag    1920
gagccccagc tgaggatgaa gaacaatgag gaggctgagg actatgatga tgacctgact    1980
gactctgaga tggatgtggt gaggtttgat gatgacaaca gccccagctt catccagatc    2040
aggtctgtgg ccaagaagca ccccaagacc tgggtgcact acattgctgc tgaggaggag    2100
gactgggact atgcccccct ggtgctggcc cctgatgaca ggagctacaa gagccagtac    2160
ctgaacaatg ccccagag gattggcagg aagtacaaga aggtcaggtt catggcctac    2220
actgatgaaa ccttcaagac cagggaggcc atccagcatg agtctggcat cctgggcccc    2280
ctgctgtatg gggaggtggg ggacaccctg ctgatcatct tcaagaacca ggccagcagg    2340
ccctacaaca tctaccccca tggcatcact gatgtgaggc ccctgtacag caggaggctg    2400
cccaaggggg tgaagcacct gaaggacttc cccatcctgc tggggagat cttcaagtac    2460
aagtggactg tgactgtgga ggatggcccc accaagtctg accccaggtg cctgaccaga    2520
tactacagca gctttgtgaa catggagagg gacctggcct ctggcctgat ggcccctg    2580
ctgatctgct acaaggagtc tgtggaccag aggggcaacc agatcatgtc tgacaagagg    2640
aatgtgatcc tgttctctgt gtttgatgag aacaggagct ggtacctgac tgagaacatc    2700
cagaggttcc tgcccaaccc tgctggggtg cagctggagg accctgagtt ccaggccagc    2760
aacatcatgc acagcatcaa tggctatgtg tttgacagcc tgcagctgtc tgtgtgcctg    2820
catgaggtgg cctactggta tcctgagc attggggccc agactgactt cctgtctgtg    2880
ttcttctctg gctacacctt caagcacaag atggtgtatg aggacaccct gaccctgttc    2940
cccttctctg gggagactgt gttcatgagc atggagaacc ctggcctgtg gattctgggc    3000
tgccacaact ctgacttcag gaacaggggc atgactgccc tgctgaaagt ctccagctgt    3060
gacaagaaca ctgggggacta ctatgaggac agctatgagg acatctctgc ctacctgctg    3120
agcaagaaca atgccattga gcccaggagc ttcagccaga accccccagt gctgaagagg    3180
caccagaggg agatcaccag gaccaccctg cagtctgacc aggaggagat tgactatgat    3240
gacaccatct ctgtggagat gaagaaggag gactttgaca tctacgacga ggacgagaac    3300
cagagcccca ggagcttcca gaagaagacc aggcactact tcattgctgc tgtggagagg    3360
ctgtgggact atggcatgag cagcagcccc catgtgctga ggaacagggc ccagtctggc    3420
tctgtgcccc agttcaagaa ggtggtgttc caggagttca ctgatggcag cttcacccag    3480
```

```
ccctgtaca gaggggagct gaatgagcac ctgggcctgc tgggccccta catcagggct    3540
gaggtggagg acaacatcat ggtgaccttc aggaaccagg ccagcaggcc ctacagcttc    3600
tacagcagcc tgatcagcta tgaggaggac cagaggcagg gggctgagcc caggaagaac    3660
tttgtgaagc ccaatgaaac caagacctac ttctggaagg tgcagcacca catggccccc    3720
accaaggatg agtttgactg caaggcctgg gcctacttct ctgatgtgga cctggagaag    3780
gatgtgcact ctggcctgat tggcccctg ctggtgtgcc acaccaacac cctgaaccct    3840
gcccatggca ggcaggtgac tgtgcaggag tttgccctgt tcttcaccat ctttgatgaa    3900
accaagagct ggtacttcac tgagaacatg gagaggaact gcagggcccc ctgcaacatc    3960
cagatggagg accccacctt caaggagaac acaggttcc atgccatcaa tggctacatc    4020
atggacaccc tgcctggcct ggtgatggcc caggaccaga ggatcaggtg gtacctgctg    4080
agcatgggca gcaatgagaa catccacagc atccacttct ctggccatgt gttcactgtg    4140
aggaagaagg aggagtacaa gatggccctg tacaacctgt accctggggt gtttgagact    4200
gtggagatgc tgcccagcaa ggctggcatc tggagggtgg agtgcctgat tggggagcac    4260
ctgcatgctg gcatgagcac cctgttcctg gtgtacagca caagtgcca gacccccctg    4320
ggcatggcct ctggccacat cagggacttc cagatcactg cctctggcca gtatggccag    4380
tgggcccca gctggccag gctgcactac tctggcagca tcaatgcctg gagcaccaag    4440
gagcccttca gctggatcaa ggtggacctg ctggccccca tgatcatcca tggcatcaag    4500
acccaggggg ccaggcagaa gttcagcagc ctgtacatca gccagttcat catcatgtac    4560
agcctggatg caagaagtg gcagacctac aggggcaaca gcactggcac cctgatggtg    4620
ttctttggca atgtggacag ctctggcatc aagcacaaca tcttcaaccc cccatcatt    4680
gccagataca tcaggctgca ccccacccac tacagcatca ggagcaccct gaggatggag    4740
ctgatgggct gtgacctgaa cagctgcagc atgcccctgg gcatggagag caaggccatc    4800
tctgatgccc agatcactgc cagcagctac ttccaccaa tgtttgccac ctggagcccc    4860
agcaaggcca ggctgcacct gcagggcagg agcaatgcct ggaggcccca ggtcaacaac    4920
cccaaggagt ggctgcaggt ggacttccag aagaccatga aggtgactgg ggtgaccacc    4980
cagggggtga gagcctgct gaccagcatg tatgtgaagg agttcctgat cagcagcagc    5040
caggatggcc accagtggac cctgttcttc cagaatggca aggtgaaggt gttccagggc    5100
aaccaggaca gcttcacccc tgtggtgaac agcctggacc cccccctgct gaccagatac    5160
ctgaggattc acccccagag ctgggtgcac cagattgccc tgaggatgga ggtgctgggc    5220
tgtgaggccc aggacctgta ctgacctcga gctgtgcctt ctagttgcca gccatctgtt    5280
gtttgcccct cccccgtgcc ttccttgacc ctggaaggtg ccactcccac tgtcctttcc    5340
taataaaatg aggaaattgc atcgcattgt ctgagtaggt gtcattctat tctggggggt    5400
ggggtgggc aggacagcaa gggggaggat tgggaagaca atagcaggca tgctgggggat    5460
gcggtgggct ctatggaccg gtgcggccgc aggaacccct agtgatggag ttggccactc    5520
cctctctgcg cgctcgctcg ctcactgagg ccgggcgacc aaaggtcgcc cgacgcccgg    5580
gctttgcccg gcggcctca gtgagcgagc gagcgcgcag agagggagtg gccaa         5635
```

<210> SEQ ID NO 17
<211> LENGTH: 6962
<212> TYPE: DNA
<213> ORGANISM: Adeno-Associated Virus 2

<400> SEQUENCE: 17

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgcggc cgcacgcgta ggctcagagg cacacaggag     180
tttctgggct caccctgccc ccttccaacc cctcagttcc catcctccag cagctgtttg     240
tgtgctgcct ctgaagtcca cactgaacaa acttcagcct actcatgtcc ctaaaatggg     300
caaacattgc aagcagcaaa cagcaaacac acagccctcc ctgcctgctg accttggagc     360
tggggcagag gtcagagacc tctctgggcc catgccacct ccaacatcca ctcgaccect     420
tggaatttcg gtggagagga gcagaggttg tcctggcgtg gtttaggtag tgtgagaggg     480
gtcgacaggc tcagaggcac acaggagttt ctgggctcac cctgccccct tccaacccct     540
cagttcccat cctccagcag ctgtttgtgt gctgcctctg aagtccacac tgaacaaact     600
tcagcctact catgtcccta aaatgggcaa acattgcaag cagcaaacag caaacacaca     660
gccctccctg cctgctgacc ttggagctgg ggcagaggtc agagacctct ctgggcccat     720
gccacctcca acatccactc gacccettgg aatttcggtg gagaggagca gaggttgtcc     780
tggcgtggtt taggtagtgt gagaggggtc gacgttaatt tttaaaaagc agtcaaaagt     840
ccaagtggcc cttggcagca tttactctct ctgtttgctc tggttaataa tctcaggagc     900
acaaacattc ctggaggcag gagaagaaat caacatcctg gacttatcct ctgggcctgt     960
taatttttaa aaagcagtca aaagtccaag tggcccttgg cagcatttac tctctctgtt    1020
tgctctggtt aataatctca ggagcacaaa cattcctgga ggcaggagaa gaaatcaaca    1080
tcctggactt atcctctggg cctaggcctg aggctggtca aaattgaacc tcctcctgct    1140
ctgagcagcc tgggggcag actaagcaga gggctgtgca gacccacata aagagcctac    1200
tgtgtgccag gcacttcacc cgaggcactt cacaagcatg cttgggaatg aaacttccaa    1260
ctctttggga tgcaggtgaa acagttcctg gttcagagag gtgaagcggc ctgcctgagg    1320
cagcacagct cttctttaca gatgtgcttc cccacctcta ccctgtctca cggccccca    1380
tgccagcctg acgttgtgt ctgcctcagt catgctccat ttttccatcg ggaccatcaa    1440
gagggtgttt gtgtctaagg ctgactgggt aactttggat gagcggtctc tccgctctga    1500
gcctgtttcc tcatctgtca aatgggctct aacccactct gatctcccag ggcggcagta    1560
agtcttcagc atcaggcatt tgggggtgac tcagtaaatg gtagatcttg ctaccagtgg    1620
aacagccact aaggattctg cagtgagagc agagggccag ctaagtggta ctctcccaga    1680
gactgtctga ctcacgccac cccctccacc ttggacacag gacgctgtgg tttctgagcc    1740
aggtacaatg actcctttcg gtaagtgcag tggaagctgt acactgccca ggcaaagcgt    1800
ccgggcagcg taggcgggcg actcagatcc cagccagtgg acttagcccc tgtttgctcc    1860
tccgataact ggggtgacct tggttaatat tcaccagcag cctcccccgt tgcccctctg    1920
gatccactgc ttaaatacgg acgaggacag ggccctgtct cctcagcttc aggcaccacc    1980
actgacctgg gacagtgaat cgtaagtact agcagctaca atccagctac cattctgctt    2040
ttattttatg gttgggataa ggctggatta ttcctgagtcc aagctaggcc ttttgctaa    2100
tcatgttcat acctcttatc ttcctcccac agctcctggg caacgtgctg gtctgtgtgc    2160
tggcccatca ctttggcaaa gaattgcgat cgccaccatg cagattgagc tgagcacctg    2220
cttcttcctg tgcctgctga ggttctgctt ctctgccacc aggagatact acctgggggc    2280
tgtggagctg agctgggact acatgcagtc tgacctgggg gagctgcctg tggatgccag    2340
```

```
gttccccccc agagtgccca agagcttccc cttcaacacc tctgtggtgt acaagaagac    2400
cctgtttgtg gagttcactg accacctgtt caacattgcc aagcccaggc ccccctggat    2460
gggcctgctg gccccacca tccaggctga ggtgtatgac actgtggtga tcaccctgaa    2520
gaacatggcc agccaccctg tgagcctgca tgctgtgggg gtgagctact ggaaggcctc    2580
tgagggggct gagtatgatg accagaccag ccagagggag aaggaggatg acaaggtgtt    2640
ccctgggggc agccacacct atgtgtggca ggtgctgaag gagaatggcc ccatggcctc    2700
tgaccccctg tgcctgacct acagctacct gagccatgtg gacctggtga aggacctgaa    2760
ctctggcctg attggggccc tgctggtgtg cagggagggc agcctggcca aggagaagac    2820
ccagaccctg cacaagttca tcctgctgtt tgctgtgttt gatgagggca gagctggca    2880 ctctgaaacc aagaacagcc tgatgcagga caggatgct gcctctgcca gggcctggcc    2940
caagatgcac actgtgaatg ctatgtgaa caggagcctg cctggcctga ttggctgcca    3000
caggaagtct gtgtactggc atgtgattgg catgggcacc accctgagg tgcacagcat    3060 cttcctggag ggccacacct tcctggtcag gaaccacagg caggccagcc tggagatcag    3120
ccccatcacc ttcctgactg cccagaccct gctgatggac ctgggccagt tcctgctgtt    3180
ctgccacatc agcagccacc agcatgatgg catggaggcc tatgtgaagg tggacagctg    3240
ccctgaggag ccccagctga ggatgaagaa caatgaggag gctgaggact atgatgatga    3300
cctgactgac tctgagatgg atgtggtgag gtttgatgat gacaacagcc ccagcttcat    3360
ccagatcagg tctgtggcca agaagcaccc caagacctgg gtgcactaca ttgctgctga    3420
ggaggaggac tgggactatg ccccctggt gctggcccct gatgacagga gctacaagag    3480
ccagtacctg aacaatggcc cccagaggat tggcaggaag tacaagaagg tcaggttcat    3540
ggcctacact gatgaaacct tcaagaccag ggaggccatc agcatgagtc tggcatcct    3600 gggcccctg ctgtatgggg aggtggggga caccctgctg atcatcttca agaaccaggc    3660
cagcaggccc tacaacatct acccccatgg catcactgat gtgaggcccc tgtacagcag    3720
gaggctgccc aagggggtga agcacctgaa ggacttcccc atcctgcctg gggagatctt    3780
caagtacaag tggactgtga ctgtggagga tggccccacc aagtctgacc ccaggtgcct    3840
gaccagatac tacagcagct tgtgaacat ggagagggac ctggcctctg gcctgattgg    3900
ccccctgctg atctgctaca aggagtctgt ggaccagagg ggcaaccaga tcatgtctga    3960
caagaggaat gtgatcctgt tctctgtgtt tgatgagaac aggagctggt acctgactga    4020
gaacatccag aggttcctgc ccaaccctgc tgggtgcag ctggaggacc ctgagttcca    4080
ggccagcaac atcatgcaca gcatcaatgg ctatgtgttt gacagcctgc agctgtctgt    4140
gtgcctgcat gaggtggcct actggtacat cctgagcatt ggggcccaga ctgacttcct    4200
gtctgtgttc ttctctggct acaccttcaa gcacaagatg gtgtatgagg acaccctgac    4260
cctgttcccc ttctctgggg agactgtgtt catgagcatg gagaaccctg cctgtggat    4320 tctgggctgc cacaactctg acttcaggaa caggggcatg actgccctgc tgaaagtctc    4380
cagctgtgac aagaacactg gggactacta tgaggacagc tatgaggaca tctctgccta    4440
cctgctgagc aagaacaatg ccattgagcc caggagcttc agccagaacc ccccagtgct    4500
gaagaggcac cagagggaga tcaccaggac caccctgcag tctgaccagg aggagattga    4560
ctatgatgac accatctctg tggagatgaa gaaggaggac tttgacatct acgacgagga    4620
cgagaaccag agcccagga gcttccagaa gaagaccagg cactacttca ttgctgctgt    4680
```

```
ggagaggctg tgggactatg gcatgagcag cagcccccat gtgctgagga acagggccca   4740
gtctggctct gtgccccagt tcaagaaggt ggtgttccag gagttcactg atggcagctt   4800
cacccagccc ctgtacagag gggagctgaa tgagcacctg ggcctgctgg cccctacat    4860
cagggctgag gtgaggaca acatcatggt gaccttcagg aaccaggcca gcaggcccta    4920
cagcttctac agcagcctga tcagctatga ggaggaccag aggcagggg ctgagcccag    4980
gaagaacttt gtgaagccca atgaaaccaa gacctacttc tggaaggtgc agcaccacat   5040
ggccccccacc aaggatgagt ttgactgcaa ggcctgggcc tacttctctg atgtggacct   5100
ggagaaggat gtgcactctg gcctgattgg cccctgctg gtgtgccaca ccaacaccct    5160
gaaccctgcc catggcaggc aggtgactgt gcaggagttt gccctgttct tcaccatctt    5220
tgatgaaacc aagagctggt acttcactga gaacatggag aggaactgca gggcccctg    5280
caacatccag atggaggacc ccaccttcaa ggagaactac aggttccatg ccatcaatgg   5340
ctacatcatg gacaccctgc ctggcctggt gatggcccag gaccagagga tcaggtggta   5400
cctgctgagc atgggcagca atgagaacat ccacagcatc cacttctctg gccatgtgtt   5460
cactgtgagg aagaaggagg agtacaagat ggccctgtac aacctgtacc tggggtgtt    5520
tgagactgtg gagatgctgc ccagcaaggc tggcatctgg agggtggagt gcctgattgg   5580
ggagcacctg catgctggca tgagcaccct gttcctggtg tacagcaaca agtgccagac   5640
ccccctgggc atggcctctg gccacatcag ggacttccag atcactgcct ctggccagta   5700
tggccagtgg gcccccaagc tggccaggct gcactactct ggcagcatca atgcctggag   5760
caccaaggag cccttcagct ggatcaaggt ggacctgctg gcccccatga tcatccatgg   5820
catcaagacc caggggggcca ggcagaagtt cagcagcctg tacatcagcc agttcatcat   5880
catgtacagc ctgatggca agaagtggca gacctacagg gcaacagca ctggcaccct    5940
gatggtgttc tttggcaatg tggacagctc tggcatcaag cacaacatct tcaaccccc    6000
catcattgcc agatacatca ggctgcaccc cacccactac agcatcagga gcaccctgag   6060
gatggagctg atgggctgtg acctgaacag ctgcagcatg cccctgggca tggagagcaa   6120
ggccatctct gatgcccaga tcactgccag cagctacttc accaacatgt ttgccacctg   6180
gagccccagc aaggccaggc tgcacctgca gggcaggagc aatgcctgga ggccccaggt   6240
caacaacccc aaggagtggc tgcaggtgga cttccagaag accatgaagg tgactggggt   6300
gaccacccag ggggtgaaga gcctgctgac cagcatgtat gtgaaggagt tcctgatcag   6360
cagcagccag gatggccacc agtggaccct gttcttccag aatggcaagg tgaaggtgtt   6420
ccagggcaac caggacagct tcaccctgt ggtgaacagc ctggaccccc cctgctgac    6480
cagatacctg aggattcacc cccagagctg ggtgcaccag attgccctga ggatggaggt   6540
gctgggctgt gaggcccagg acctgtactg acctcgagct gtgccttcta gttgccagcc   6600
atctgttgtt tgcccctccc ccgtgcctcc cttgaccctg gaaggtgcca ctcccactgt   6660
cctttcctaa taaaatgagg aaattgcatc gcattgtctg agtaggtgtc attctattct   6720
ggggggtggg gtgggcagg acagcaaggg ggaggattgg gaagacaata gcaggcatgc   6780
tggggatgcg gtgggctcta tggaccggtg cggccgcagg aacccctagt gatgagttg    6840
gccactccct ctctgcgcgc tcgctcgctc actgaggccg ggcgaccaaa ggtcgcccga   6900
cgcccgggct ttgcccgggc ggcctcagtg agcgagcgag cgcgcagaga gggagtggcc   6960
aa                                                                 6962
```

<210> SEQ ID NO 18
<211> LENGTH: 6289
<212> TYPE: DNA
<213> ORGANISM: Adeno-Associated Virus 2

<400> SEQUENCE: 18

| | | | | | |
|---|---|---|---|---|---|
| ttggccactc | cctctctgcg | cgctcgctcg | ctcactgagg | ccgcccgggc | aaagcccggg | 60 |
| cgtcgggcga | cctttggtcg | cccggcctca | gtgagcgagc | gagcgcgcag | agagggagtg | 120 |
| gccaactcca | tcactagggg | ttcctgcggc | cgcacgcgta | ggctcagagg | cacacaggag | 180 |
| tttctgggct | caccctgccc | ccttccaacc | cctcagttcc | catcctccag | cagctgtttg | 240 |
| tgtgctgcct | ctgaagtcca | cactgaacaa | acttcagcct | actcatgtcc | ctaaaatggg | 300 |
| caaacattgc | aagcagcaaa | cagcaaacac | acagccctcc | ctgcctgctg | accttggagc | 360 |
| tggggcagag | gtcagagacc | tctctgggcc | catgccacct | caacatcca | ctcgacccct | 420 |
| tggaatttcg | gtggagagga | gcagaggttg | tcctggcgtg | gtttaggtag | tgtgagaggg | 480 |
| gtcgacaggt | cagaggcac | acaggagttt | ctgggctcac | cctgcccct | tccaacccct | 540 |
| cagttcccat | cctccagcag | ctgtttgtgt | gctgcctctg | aagtccacac | tgaacaaact | 600 |
| tcagcctact | catgtcccta | aaatgggcaa | acattgcaag | cagcaaacag | caaacacaca | 660 |
| gccctccctg | cctgctgacc | ttggagctgg | gcagaggtc | agagacctct | ctgggcccat | 720 |
| gccacctcca | acatccactc | gaccccttgg | aatttcggtg | gagaggagca | gaggttgtcc | 780 |
| tggcgtggtt | taggtagtgt | gagaggggtc | gacgttaatt | tttaaaaagc | agtcaaaagt | 840 |
| ccaagtggcc | cttggcagca | tttactctct | ctgtttgctc | tggttaataa | tctcaggagc | 900 |
| acaaacattc | ctggaggcag | gagaagaaat | caacatcctg | gacttatcct | ctgggcctgt | 960 |
| taattttaa | aaagcagtca | aaagtccaag | tggcccttgg | cagcatttac | tctctctgtt | 1020 |
| tgctctggtt | aataatctca | ggagcacaaa | cattcctgga | ggcaggagaa | gaaatcaaca | 1080 |
| tcctggactt | atcctctggg | cctagtcgac | tggacacagg | acgctgtggt | ttctgagcca | 1140 |
| gggggcgact | cagatcccag | ccagtggact | tagcccctgt | ttgctcctcc | gataactggg | 1200 |
| gtgaccttgg | ttaatattca | ccagcagcct | ccccgttgc | ccctctggat | ccactgctta | 1260 |
| aatacggacg | aggacagggc | cctgtctcct | cagcttcagg | caccaccact | gacctgggac | 1320 |
| agtgaatcgt | aagtactagc | agctacaatc | cagctaccat | tctgctttta | ttttatggtt | 1380 |
| gggataaggc | tggattattc | tgagtccaag | ctaggccctt | ttgctaatca | tgttcatacc | 1440 |
| tcttatcttc | ctcccacagc | tcctgggcaa | cgtgctggtc | tgtgtgctgg | cccatcactt | 1500 |
| tggcaaagaa | ttgcgatcgc | caccatgcag | attgagctga | gcacctgctt | cttcctgtgc | 1560 |
| ctgctgaggt | tctgcttctc | tgccaccagg | agatactacc | tgggggctgt | ggagctgagc | 1620 |
| tgggactaca | tgcagtctga | cctggggag | ctgcctgtgg | atgccaggtt | ccccccagag | 1680 |
| gtgcccaaga | gcttccccct | taacacctct | gtggtgtaca | agaagaccct | gtttgtggag | 1740 |
| ttcactgacc | acctgttcaa | cattgccaag | cccaggcccc | ctggatggg | cctgctgggc | 1800 |
| cccaccatcc | aggctgaggt | gtatgacact | gtggtgatca | ccctgaagaa | catggccagc | 1860 |
| caccctgtga | gcctgcatgc | tgtgggggtg | agctactgga | aggcctctga | ggggctgag | 1920 |
| tatgatgacc | agaccagcca | gagggagaag | gaggatgaca | aggtgttccc | tgggggcagc | 1980 |
| cacacctatg | tgtggcaggt | gctgaaggag | aatggcccca | tggcctctga | ccccctgtgc | 2040 |
| ctgacctaca | gctacctgag | ccatgtggac | ctggtgaagg | acctgaactc | tggcctgatt | 2100 |
| ggggccctgc | tggtgtgcag | ggagggcagc | ctggccaagg | agaagaccca | gacccctgcac | 2160 |

```
aagttcatcc tgctgtttgc tgtgtttgat gagggcaaga gctggcactc tgaaaccaag    2220
aacagcctga tgcaggacag ggatgctgcc tctgccaggg cctggcccaa gatgcacact    2280
gtgaatggct atgtgaacag gagcctgcct ggcctgattg ctgccacag gaagtctgtg     2340 tactggcatg tgattggcat gggcaccacc cctgaggtgc acagcatctt cctggagggc    2400
cacaccttcc tggtcaggaa ccacaggcag gccagcctgg agatcagccc catcaccttc    2460
ctgactgccc agaccctgct gatggacctg ggccagttcc tgctgttctg ccacatcagc    2520
agccaccagc atgatggcat ggaggcctat gtgaaggtgg acagctgccc tgaggagccc    2580
cagctgagga tgaagaacaa tgaggaggct gaggactatg atgatgacct gactgactct    2640
gagatggatg tggtgaggtt tgatgatgac aacagcccca gcttcatcca gatcaggtct    2700
gtggccaaga agcaccccaa gacctgggtg cactacattg ctgctgagga ggaggactgg    2760
gactatgccc ccctggtgct ggcccctgat gacaggagct acaagagcca gtacctgaac    2820
aatggccccc agaggattgg caggaagtac aagaaggtca ggttcatggc ctacactgat    2880
gaaaccttca gaccaggga ggccatccag catgagtctg gcatcctggg cccctgctg      2940 tatggggagg tggggacac cctgctgatc atcttcaaga accaggccag caggccctac     3000
aacatctacc cccatggcat cactgatgtg aggcccctgt acagcaggag gctgcccaag    3060
ggggtgaagc acctgaagga cttccccatc ctgcctgggg agatcttcaa gtacaagtgg    3120
actgtgactg tggaggatgg ccccaccaag tctgaccca ggtgcctgac cagatactac     3180
agcagctttg tgaacatgga gagggacctg gcctctggcc tgattggccc cctgctgatc    3240
tgctacaagg agtctgtgga ccagaggggc aaccagatca tgtctgacaa gaggaatgtg    3300
atcctgttct ctgtgtttga tgagaacagg agctggtacc tgactgagaa catccagagg    3360
ttcctgccca accctgctgg ggtgcagctg gaggaccctg agttccaggc cagcaacatc    3420
atgcacagca tcaatggcta tgtgtttgac agcctgcagc tgtctgtgtg cctgcatgag    3480
gtggcctact ggtacatcct gagcattggg gcccagactg acttcctgtc tgtgttcttc    3540
tctggctaca ccttcaagca caagatggtg tatgaggaca ccctgaccct gttccccttc    3600
tctggggaga ctgtgttcat gagcatggag aaccctggcc tgtggattct gggctgccac    3660
aactctgact tcaggaacag gggcatgact gccctgctga aagtctccag ctgtgacaag    3720
aacactgggg actactatga ggacagctat gaggacatct ctgcctacct gctgagcaag    3780
aacaatgcca ttgagcccag gagcttcagc cagaaccccc cagtgctgaa gaggcaccag    3840
agggagatca ccaggaccac cctgcagtct gaccaggagg agattgacta tgatgacacc    3900
atctctgtgg agatgaagaa ggaggacttt gacatctacg acgaggacga gaaccagagc    3960
cccaggagct tccagaagaa gaccaggcac tacttcattg ctgctgtgga gaggctgtgg    4020
gactatggca tgagcagcag ccccatgtg ctgaggaaca gggcccagtc tggctctgtg      4080
ccccagttca agaaggtggt gttccaggag ttcactgatg gcagcttcac ccagccctg      4140 tacagagggg agctgaatga gcacctgggc ctgctgggcc cctacatcag ggctgaggtg    4200
gaggacaaca tcatggtgac cttcaggaac caggccagca ggccctacag cttctacagc    4260
agcctgatca gctatgagga ggaccagagg caggggctg agcccaggaa gaactttgtg      4320
aagcccaatg aaaccaagac ctacttctgg aaggtgcagc accacatggc ccccaccaag    4380
gatgagtttg actgcaaggc ctgggcctac ttctctgatg tggacctgga aaggatgtg     4440 cactctggcc tgattggccc cctgctggtg tgccacacca cacccctgaa ccctgcccat    4500
ggcaggcagg tgactgtgca ggagtttgcc ctgttcttca ccatctttga tgaaaccaag    4560
```

```
agctggtact tcactgagaa catggagagg aactgcaggg cccctgcaa catccagatg    4620 gaggacccca ccttcaagga gaactacagg ttccatgcca tcaatggcta catcatggac    4680
accctgcctg gcctggtgat ggcccaggac cagaggatca ggtggtacct gctgagcatg    4740
ggcagcaatg agaacatcca cagcatccac ttctctggcc atgtgttcac tgtgaggaag    4800
aaggaggagt acaagatggc cctgtacaac ctgtaccctg gggtgtttga ctgtggag     4860 atgctgccca gcaaggctgg catctggagg gtggagtgcc tgattgggga gcacctgcat    4920
gctggcatga gcaccctgtt cctggtgtac agcaacaagt gccagacccc cctgggcatg    4980
gcctctggcc acatcaggga cttccagatc actgcctctg ccagtatgg ccagtgggcc     5040 cccaagctgg ccaggctgca ctactctggc agcatcaatg cctggagcac aaggagccc     5100 ttcagctgga tcaaggtgga cctgctggcc ccatgatca tccatggcat caagacccag    5160
ggggccaggc agaagttcag cagcctgtac atcagccagt tcatcatcat gtacagcctg    5220
gatggcaaga gtggcagac ctacagggc aacagcactg gcaccctgat ggtgttcttt      5280
ggcaatgtgg acagctctgg catcaagcac aacatcttca cccccccat cattgccaga    5340 tacatcaggc tgcaccccac ccactacagc atcaggagca ccctgaggat ggagctgatg    5400
ggctgtgacc tgaacagctg cagcatgccc ctgggcatgg agagcaaggc catctctgat    5460
gcccagatca ctgccagcag ctacttcacc aacatgtttg ccacctggag ccccagcaag    5520
gccaggctgc acctgcaggg caggagcaat gcctggaggc cccaggtcaa caaccccaag    5580
gagtggctgc aggtggactt ccagaagacc atgaaggtga ctggggtgac cacccagggg    5640
gtgaagagcc tgctgaccag catgtatgtg aaggagttcc tgatcagcag cagccaggat    5700
ggccaccagt ggaccctgtt cttccagaat ggcaaggtga aggtgttcca gggcaaccag    5760
gacagcttca ccctgtggt gaacagcctg gaccccccc tgctgaccag ataccctgagg    5820 attcaccccc agagctgggt gcaccagatt gccctgagga tggaggtgct gggctgtgag    5880
gcccaggacc tgtactgacc tcgagctgtg ccttctagtt gccagccatc tgttgtttgc    5940
ccctcccccg tgccttcctt gaccctggaa ggtgccactc ccactgtcct ttcctaataa    6000
aatgaggaaa ttgcatcgca ttgtctgagt aggtgtcatt ctattctggg gggtggggtg    6060
gggcaggaca gcaaggggga ggattgggaa gacaatagca ggcatgctgg ggatgcggtg    6120
ggctctatgg accggtgcgg ccgcaggaac ccctagtgat ggagttggcc actccctctc    6180
tgcgcgctcg ctcgctcact gaggccgggc gaccaaaggt cgcccgacgc ccgggctttg    6240
cccgggcggc ctcagtgagc gagcgagcgc gcagagaggg agtggccaa                6289

<210> SEQ ID NO 19
<211> LENGTH: 5430
<212> TYPE: DNA
<213> ORGANISM: Adeno-Associated Virus 2

<400> SEQUENCE: 19
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg    120
gccaactcca tcactagggg ttcctgcggc cgcacgcgtg ttttcgacgt ggacttagcc    180
cctgtttgct cctccgataa ctggggtgac cttggttaat attcaccagc agcctcccg    240 tggacttagc cctgtttgc tcctccgata actggggtga ccttggttaa tattcaccag    300
cagcctcccc acgcgaaacg tcgactggac acaggacgct gtggtttctg agccagggg    360
```

```
cgactcagat cccagccagt ggacttagcc cctgtttgct cctccgataa ctggggtgac      420
cttggttaat attcaccagc agcctccccc gttgcccctc tggatccact gcttaaatac      480
ggacgaggac agggccctgt ctcctcagct tcaggcacca ccactgacct gggacagtga      540
atcgtaagta ctagcagcta caatccagct accattctgc ttttatttta tggttgggat      600
aaggctggat tattctgagt ccaagctagg ccctttttgct aatcatgttc atacctctta     660
tcttcctccc acagctcctg gcaacgtgc tggtctgtgt gctggcccat cactttggca       720
aagaattgcg atcgccacca tgcagattga gctgagcacc tgcttcttcc tgtgcctgct      780
gaggttctgc ttctctgcca ccaggagata ctacctgggg gctgtggagc tgagctggga      840
ctacatgcag tctgacctgg gggagctgcc tgtggatgcc aggttccccc ccagagtgcc      900
caagagcttc cccttcaaca cctctgtggt gtacaagaag accctgtttg tggagttcac      960
tgaccacctg ttcaacattg ccaagcccag gccccctggg atgggcctgc tgggcccac     1020
catccaggct gaggtgtatg acactgtggt gatcaccctg aagaacatgg ccagccaccc    1080
tgtgagcctg catgctgtgg gggtgagcta ctggaaggcc tctgaggggg ctgagtatga    1140
tgaccagacc agccagaggg agaaggagga tgacaaggtg ttccctgggg gcagccacac    1200
ctatgtgtgg caggtgctga aggagaatgg ccccatggcc tctgaccccc tgtgcctgac    1260
ctacagctac ctgagccatg tggacctggt gaaggacctg aactctggcc tgattggggc    1320
cctgctggtg tgcagggagg gcagcctggc caaggagaag acccagaccc tgcacaagtt    1380
catcctgctg tttgctgtgt ttgatgaggg caagagctgg cactctgaaa ccaagaacag    1440
cctgatgcag gacagggatg ctgcctctgc cagggcctgg cccaagatgc acactgtgaa    1500
tggctatgtg aacaggagcc tgcctggcct gattggctgc acaggaagt ctgtgtactg     1560
gcatgtgatt ggcatgggca ccaccccctga ggtgcacagc atcttcctgg agggccacac    1620
cttcctggtc aggaaccaca ggcaggccag cctggagatc agccccatca ccttcctgac    1680
tgcccagacc ctgctgatgg acctgggcca gttcctgctg ttctgccaca tcagcagcca    1740
ccagcatgat ggcatggagg cctatgtgaa ggtggacagc tgccctgagg agccccagct    1800
gaggatgaag aacaatgagg aggctgagga ctatgatgat gacctgactg actctgagat    1860
ggatgtggtg aggtttgatg atgacaacag ccccagcttc atccagatca ggtctgtggc    1920
caagaagcac cccaagacct gggtgcacta cattgctgct gaggaggagg actgggacta    1980
tgccccccctg gtgctggccc ctgatgacag gagctacaag agccagtacc tgaacaatgg    2040
cccccagagg attggcagga agtacaagaa ggtcaggttc atggcctaca ctgatgaaac    2100
cttcaagacc agggaggcca tccagcatga gtctggcatc ctgggccccc tgctgtatgg    2160
ggaggtgggg gacaccctgc tgatcatctt caagaaccag gccagcaggc cctacaacat    2220
ctaccccccat ggcatcactg atgtgaggcc cctgtacagc aggaggctgc caagggggt    2280
gaagcacctg aaggacttcc ccatcctgcc tgggggagatc ttcaagtaca agtggactgt    2340
gactgtggag gatggcccca ccaagtctga ccccaggtgc ctgaccagat actacagcag    2400
ctttgtgaac atggagaggg acctggcctc tggcctgatt ggccccctgc tgatctgcta    2460
caaggagtct gtgaccagag gggcaacca gatcatgtct gacaagagga atgtgatcct    2520
gttctctgtg tttgatgaga acaggagctg gtacctgact gagaacatcc agaggttcct    2580
gcccaaccct gctggggtgc agctggagga ccctgagttc caggccagca acatcatgca    2640
cagcatcaat ggctatgtgt ttgacagcct gcagctgtct gtgtgcctgc atgaggtggc    2700
ctactggtac atcctgagca ttggggccca gactgacttc ctgtctgtgt tcttctctgg    2760
```

```
ctacaccttc aagcacaaga tggtgtatga ggacaccctg accctgttcc ccttctctgg    2820
ggagactgtg ttcatgagca tggagaaccc tggcctgtgg attctgggct gccacaactc    2880
tgacttcagg aacaggggca tgactgccct gctgaaagtc tccagctgtg acaagaacac    2940
tggggactac tatgaggaca gctatgagga catctctgcc tacctgctga gcaagaacaa    3000
tgccattgag cccaggagct tcagccagaa cccccagtg ctgaagaggc accagaggga    3060
gatcaccagg accaccctgc agtctgacca ggaggagatt gactatgatg acaccatctc    3120
tgtggagatg aagaaggagg actttgacat ctacgacgag gacgagaacc agagccccag    3180
gagcttccag aagaagacca ggcactactt cattgctgct gtggagaggc tgtgggacta    3240
tggcatgagc agcagccccc atgtgctgag gaacagggcc cagtctggct ctgtgcccca    3300
gttcaagaag gtggtgttcc aggagttcac tgatggcagc ttcacccagc ccctgtacag    3360
aggggagctg aatgagcacc tgggcctgct gggcccctac atcagggctg aggtggagga    3420
caacatcatg gtgaccttca ggaaccaggc cagcaggccc tacagcttct acagcagcct    3480
gatcagctat gaggaggacc agaggcaggg ggctgagccc aggaagaact tgtgaagcc    3540 caatgaaacc aagacctact tctggaaggt gcagcaccac atggccccca ccaaggatga    3600
gtttgactgc aaggcctggg cctacttctc tgatgtggac ctggagaagg atgtgcactc    3660
tggcctgatt ggccccctgc tggtgtgcca caccaacacc ctgaaccctg ccatgcag    3720 gcaggtgact gtgcaggagt tgccctgtt cttcaccatc tttgatgaaa ccaagagctg    3780
gtacttcact gagaacatgg agaggaactg cagggccccc tgcaacatcc agatggagga    3840
ccccaccttc aaggagaact acaggttcca tgccatcaat ggctacatca tggacaccct    3900
gcctggcctg gtgatggccc aggaccagag gatcaggtgg tacctgctga gcatgggcag    3960
caatgagaac atccacagca tccacttctc tggccatgtg ttcactgtga ggaagaagga    4020
ggagtacaag atggccctgt acaacctgta ccctgggtgg tttgagactg tggagatgct    4080
gcccagcaag gctggcatct ggagggtgga gtgcctgatt ggggagcacc tgcatgctgg    4140
catgagcacc ctgttcctgg tgtacagcaa caagtgccag acccccctgg gcatggcctc    4200
tggccacatc agggacttcc agatcactgc ctctggccca tatggccagt gggccccaa    4260 gctggccagg ctgcactact ctggcagcat caatgcctgg agcaccaagg agcccttcag    4320
ctggatcaag gtgaccctgc tggcccccat gatcatccat ggcatcaaga cccagggggc    4380
caggcagaag ttcagcagcc tgtacatcag ccagttcatc atcatgtaca gcctggatgg    4440
caagaagtgg cagacctaca ggggcaacag cactggcacc ctgatggtgt ctttggcaa    4500 tgtggacagc tctggcatca agcacaacat cttcaacccc cccatcattg ccagatacat    4560
caggctgcac cccacccact acagcatcag gagcaccctg aggatggagc tgatgggctg    4620
tgacctgaac agctgcagca tgccctgg catggagagc aaggccatct ctgatgccca    4680
gatcactgcc agcagctact tcaccaacat gtttgccacc tggagcccca gcaaggccag    4740
gctgcacctg cagggcagga gcaatgcctg gaggcccag gtcaacaacc caaggagtg    4800 gctgcaggtg gacttccaga agaccatgaa ggtgactggg gtgaccaccc aggggtgaa    4860 gagcctgcta accagcatgt atgtgaagga gttcctgatc agcagcagcc aggatggcca    4920
ccagtggacc ctgttcttcc agaatggcaa ggtgaaggtg ttccagggca ccaggacag    4980 cttcaccccct gtggtgaaca gcctggaccc ccccctgctg accagatacc tgaggattca    5040
cccccagagc tgggtgcacc agattgccct gaggatggag gtgctgggct gtgaggccca    5100
```

-continued

| | |
|---|---|
| ggacctgtac tgacctcgag gcactgtcct ttcctaataa aatgaggaaa ttgcatcgca | 5160 |
| ttgtctgagt aggtgtcatt ctattctggg gggtggggtg gggcaggaca gcaaggggga | 5220 |
| ggattgggaa gacaatagca ggcatgctgg ggatgcggtg ggctctatgg gcacgtggcg | 5280 |
| gccgcaggaa cccctagtga tggagttggc cactccctct ctgcgcgctc gctcgctcac | 5340 |
| tgaggccggg cgaccaaagg tcgcccgacg cccgggcttt gcccgggcgg cctcagtgag | 5400 |
| cgagcgagcg cgcagagagg gagtggccaa | 5430 |

<210> SEQ ID NO 20
<211> LENGTH: 5779
<212> TYPE: DNA
<213> ORGANISM: Adeno-Associated Virus 2

<400> SEQUENCE: 20

| | |
|---|---|
| ttggccactc cctctctgcg cgctcgctcg ctcactgagg ccgcccgggc aaagcccggg | 60 |
| cgtcgggcga cctttggtcg cccggcctca gtgagcgagc gagcgcgcag agagggagtg | 120 |
| gccaactcca tcactagggg ttcctgcggc cgcacgcgtg ttttcgacgt ggacttagcc | 180 |
| cctgtttgct cctccgataa ctggggtgac cttggttaat attcaccagc agcctccccg | 240 |
| tggacttagc ccctgtttgc tcctccgata actggggtga ccttggttaa tattcaccag | 300 |
| cagcctcccc acgcgaaacg tcgactggac acaggacgct gtggtttctg agccagggg | 360 |
| cgactcagat cccagccagt ggacttagcc cctgtttgct cctccgataa ctggggtgac | 420 |
| cttggttaat attcaccagc agcctccccg ttgcccctc tggatccact gcttaaatac | 480 |
| ggacgaggac agggccctgt ctcctcagct tcaggcacca ccactgacct gggacagtga | 540 |
| atcgtaagta ctagcagcta caatccagct accattctgc ttttattta tggttgggat | 600 |
| aaggctggat tattctgagt ccaagctagg ccctttttgct aatcatgttc atacctctta | 660 |
| tcttcctccc acagctcctg ggcaacgtgc tggtctgtgt gctggcccat cactttggca | 720 |
| aagaattgcg atcgccacca tgcagattga gctgagcacc tgcttcttcc tgtgcctgct | 780 |
| gaggttctgc ttctctgcca ccaggagata ctacctgggg gctgtggagc tgagctggga | 840 |
| ctacatgcag tctgacctgg gggagctgcc tgtggatgcc aggttccccc ccagagtgcc | 900 |
| caagagcttc ccccttcaaca cctctgtggt gtacaagaag accctgtttg tggagttcac | 960 |
| tgaccacctg ttcaacattg ccaagcccag gccccctgg atgggcctgc tgggccccac | 1020 |
| catccaggct gaggtgtatg acactgtggt gatcaccctg aagaacatgg ccagccaccc | 1080 |
| tgtgagcctg catgctgtgg gggtgagcta ctggaaggcc tctgaggggg ctgagtatga | 1140 |
| tgaccagacc agccagaggg agaaggagga tgacaaggtg ttccctgggg gcagccacac | 1200 |
| ctatgtgtgg caggtgctga aggagaatgg ccccatggcc tctgaccccc tgtgcctgac | 1260 |
| ctacagctac ctgagccatg tggacctggt gaaggacctg aactctggcc tgattggggc | 1320 |
| cctgctggtg tgcagggagg gcagcctggc caaggagaag acccagaccc tgcacaagtt | 1380 |
| catcctgctg tttgctgtgt tgatgagggg caagagctgg cactctgaaa ccaagaacag | 1440 |
| cctgatgcag gacagggatg ctgcctctgc cagggcctgg cccaagatgc acactgtgaa | 1500 |
| tggctatgtg aacaggagcc tgcctggcct gattggctgc cacaggaagt ctgtgtactg | 1560 |
| gcatgtgatt ggcatgggca ccacccctga ggtgcacagc atcttcctgg agggccacac | 1620 |
| cttcctggtc aggaaccaca ggcaggccag cctggagatc agccccatca ccttcctgac | 1680 |
| tgcccagacc ctgctgatgg acctgggcca gttcctgctg ttctgccaca tcagcagcca | 1740 |
| ccagcatgat ggcatggagg cctatgtgaa ggtggacagc tgccctgagg agccccagct | 1800 |

```
gaggatgaag aacaatgagg aggctgagga ctatgatgat gacctgactg actctgagat    1860
ggatgtggtg aggtttgatg atgacaacag ccccagcttc atccagatca ggtctgtggc    1920
caagaagcac cccaagacct gggtgcacta cattgctgct gaggaggagg actgggacta    1980
tgcccccctg gtgctggccc ctgatgcag gagctacaag agccagtacc tgaacaatgg     2040
cccccagagg attggcagga agtacaagaa ggtcaggttc atggcctaca ctgatgaaac    2100
cttcaagacc agggaggcca tccagcatga gtctggcatc ctgggccccc tgctgtatgg    2160
ggaggtgggg gacaccctgc tgatcatctt caagaaccag gccagcaggc cctacaacat    2220 ctaccccat ggcatcactg atgtgaggcc cctgtacagc aggaggctgc ccaagggggt     2280
gaagcacctg aaggacttcc ccatcctgcc tgggagatc ttcaagtaca agtggactgt     2340
gactgtggag gatggcccca ccaagtctga ccccaggtgc ctgaccagat actacagcag    2400
ctttgtgaac atggagaggg acctggcctc tggcctgatt ggccccctgc tgatctgcta    2460
caaggagtct gtggaccaga ggggcaacca gatcatgtct gacaaggagaa atgtgatcct   2520 gttctctgtg tttgatgaga acaggagctg gtacctgact gagaacatcc agaggttcct    2580
gcccaaccct gctggggtgc agctggagga ccctgagttc caggccagca acatcatgca    2640
cagcatcaat ggctatgtgt tgacagcct gcagctgtct gtgtgcctgc atgaggtggc     2700
ctactggtac atcctgagca ttggggccca gactgacttc ctgtctgtgt tcttctctgg    2760
ctacaccttc aagcacaaga tggtgtatga ggacaccctg accctgttcc ccttctctgg    2820
ggagactgtg ttcatgagca tggagaaccc tggcctgtgg attctgggct gccacaactc    2880
tgacttcagg aacaggggca tgactgccct gctgaaagtc tccagctgtg acaagaacac    2940
tggggactac tatgaggaca gctatgagga catctctgcc tacctgctga gcaagaacaa    3000
tgccattgag cccaggagct tcagccagaa cccccagtg ctgaagaggc accagaggga     3060
gatcaccagg accaccctgc agtctgacca ggaggagatt gactatgatg acaccatctc    3120
tgtggagatg aagaaggagg actttgacat ctacgacgag gacgagaacc agagcccag     3180 gagcttccag aagaagacca ggcactactt cattgctgct gtggagaggc tgtgggacta    3240
tggcatgagc agcagccccc atgtgctgag gaacagggcc cagtctggct ctgtgcccca    3300
gttcaagaag gtggtgttcc aggagttcac tgatggcagc ttcacccagc cctgtacag     3360 aggggagctg aatgagcacc tgggcctgct gggcccctac atcagggctg aggtggagga    3420
caacatcatg gtgaccttca ggaaccaggc cagcaggccc tacagcttct acagcagcct    3480
gatcagctat gaggaggacc agaggcaggg ggctgagccc aggaagaact tgtgaagcc     3540 caatgaaacc aagacctact ctggaaggt gcagcaccac atggccccca ccaaggatga    3600
gtttgactgc aaggcctggg cctacttctc tgatgtggac ctggagaagg atgtgcactc    3660
tggcctgatt ggccccctgc tggtgtgcca caccaacacc ctgaaccctg cccatggcag    3720
gcaggtgact gtgcaggagt ttgccctgtt cttcaccatc tttgatgaaa ccaagagctg    3780
gtacttcact gagaacatgg agaggaactg cagggcccc tgcaacatcc agatgggagga   3840 cccccacttc aaggagaact acaggttcca tgccatcaat ggctacatca tggacaccct    3900
gcctggcctg tgtgatggcc aggaccagag gatcaggtgg tacctgctga gcatgggcag    3960
caatgagaac atccacagca tccacttctc tggccatgtg ttcactgtga ggaagaagga    4020
ggagtacaag atggccctgt acaacctgta ccctgggtg tttgagactg tggagatgct     4080
gcccagcaag gctggcatct ggaggtgga gtgcctgatt ggggagcacc tgcatgctgg     4140
```

```
catgagcacc ctgttcctgg tgtacagcaa caagtgccag accccctgg gcatggcctc      4200 tggccacatc agggacttcc agatcactgc ctctggccag tatggccagt gggcccccaa      4260
gctggccagg ctgcactact ctggcagcat caatgcctgg agcaccaagg agcccttcag      4320
ctggatcaag gtggacctgc tggcccccat gatcatccat ggcatcaaga cccaggggc       4380 caggcagaag ttcagcagcc tgtacatcag ccagttcatc atcatgtaca gcctggatgg      4440
caagaagtgg cagacctaca ggggcaacag cactggcacc ctgatggtgt tctttggcaa      4500
tgtggacagc tctggcatca agcacaacat cttcaacccc ccatcattg ccagatacat       4560 caggctgcac cccacccact acagcatcag gagcaccctg aggatggagc tgatgggctg      4620
tgacctgaac agctgcagca tgcccctggg catggagagc aaggccatct ctgatgccca      4680
gatcactgcc agcagctact tcaccaacat gtttgccacc tggagcccca gcaaggccag      4740
gctgcacctg cagggcagga gcaatgcctg gaggccccag gtcaacaacc caaggagtg       4800 gctgcaggtg gacttccaga gaccatgaa ggtgactggg gtgaccaccc aggggggtgaa      4860 gagcctgctg accagcatgt atgtgaagga gttcctgatc agcagcagcc aggatggcca      4920
ccagtggacc ctgttcttcc agaatggcaa ggtgaaggtg ttccagggca accaggacag      4980
cttcacccct gtggtgaaca gcctggaccc ccccctgctg accagatacc tgaggattca      5040
cccccagagc tgggtgcacc agattgccct gaggatggag gtgctgggct gtgaggccca      5100
ggacctgtac tgacctcgag gcactgtcct ttcctaataa aatgaggaaa ttgcatcgca      5160
ttgtctgagt aggtgtcatt ctattctggg gggtggggtg gggcaggaca gcaaggggga      5220
ggattgggaa gacaatagca ggcatgctgg ggatgcggtg ggctctatgg cactcgaca       5280 ggttaatttt taaaaagcag tcaaaagtcc aagtggccct tggcagcatt tactctctct      5340
gtttgctctg gttaataatc tcaggagcac aaacattcct ggaggcagga gaagaaatca      5400
acatcctgga cttatcctct gggcctctcc cacccccag gagaggctca ggttaatttt      5460
taaaaagcag tcaaaagtcc aagtggccct tggcagcatt tactctctct gtttgctctg      5520
gttaataatc tcaggagcac aaacattcct ggaggcagga gaagaaatca acatcctgga      5580
cttatcctct gggcctctcc cacccccag gagaggctgt cgagtggcgg ccgcaggaac      5640
ccctagtgat ggagttggcc actccctctc tgcgcgctcg ctcgctcact gaggccgggc      5700
gaccaaaggt cgcccgacgc ccgggctttg cccgggcggc ctcagtgagc gagcgagcgc      5760
gcagagaggg agtggccaa                                                  5779

<210> SEQ ID NO 21
<211> LENGTH: 5962
<212> TYPE: DNA
<213> ORGANISM: Adeno-Associated Virus 2

<400> SEQUENCE: 21
ttggccactc cctctctgcg cgctcgctcg ctcactgagg ccgcccgggc aaagcccggg       60
cgtcgggcga cctttggtcg cccggcctca gtgagcgagc gagcgcgcag agagggagtg      120
gccaactcca tcactagggg ttcctgcggc cgcacgcgtg ttttcgaccc ctctcacact      180
acctaaacca cgccaggaca acctctgctc ctccaccg aaattccaag gggtcgagtg       240
gatgttggag gtggcatggg cccagagagg tctctgacct ctgccccagc tccaaggtca      300
gcaggcaggg agggctgtgt gtttgctgtt tgctgcttgc aatgtttgcc cattttaggg      360
acatgagtag gctgaagttt gttcagtgtg gacttcagag gcagcacaca aacagctgct      420
ggaggatggg aactgagggg ttggaagggg gcagggtgag cccagaaact cctgtgtgcc      480
```

```
tctgagcctg cagacgcgaa acgtcgactg gacacaggac gctgtggttt ctgagccagg    540
gggcgactca gatcccagcc agtggactta gcccctgttt gctcctccga taactggggt    600
gaccttggtt aatattcacc agcagcctcc cccgttgccc ctctggatcc actgcttaaa    660 tacgacgag gacagggccc tgtctcctca gcttcaggca ccaccactga cctgggacag     720
tgaatcgtaa gtactagcag ctacaatcca gctaccattc tgctttttatt ttatggttgg   780 gataaggctg gattattctg agtccaagct aggccctttt gctaatcatg ttcatacctc    840
ttatcttcct cccacagctc ctgggcaacg tgctggtctg tgtgctggcc catcactttg    900
gcaaagaatt gcgatcgcca ccatgcagat tgagctgagc acctgcttct tcctgtgcct    960
gctgaggttc tgcttctctg ccaccaggag atactacctg ggggctgtgg agctgagctg   1020
ggactacatg cagtctgacc tgggggagct gcctgtggat gccaggttcc cccccagagt   1080
gcccaagagc ttccccttca cacctctgt ggtgtacaag aagaccctgt tgtggagtt     1140 cactgaccac ctgttcaaca ttgccaagcc caggcccccc tggatgggcc tgctgggccc   1200
caccatccag gctgaggtgt atgacactgt ggtgatcacc ctgaagaaca tggccagcca   1260
ccctgtgagc ctgcatgctg tggggtgag ctactggaag gcctctgagg gggctgagta    1320
tgatgaccag accagccaga gggagaagga ggatgacaag gtgttccctg ggggcagcca   1380
cacctatgtg tggcaggtgc tgaaggagaa tggcccccatg gcctctgacc cctgtgcct   1440 gacctacagc tacctgagcc atgtggacct ggtgaaggac ctgaactctg gcctgattgg   1500
ggccctgctg gtgtgcaggg agggcagcct ggccaaggaa aagacccaga ccctgcacaa   1560
gttcatcctg ctgtttgctg tgtttgatga gggcaagagc tggcactctg aaaccaagaa   1620
cagcctgatg caggacaggg atgctgcctc tgccagggcc tggccaaga tgcacactgt    1680 gaatggctat gtgaacagga gcctgcctgg cctgattggc tgccacagga agtctgtgta   1740
ctggcatgtg attggcatgg gcaccacccc tgaggtgcac agcatcttcc tggagggcca   1800
caccttcctg gtcaggaacc acaggcaggc cagcctggag atcagcccca tcaccttcct   1860
gactgcccag accctgctga tggacctggg ccagttcctg ctgttctgcc acatcagcag   1920
ccaccagcat gatggcatgg aggcctatgt gaaggtggac agctgccctg aggagcccca   1980
gctgaggatg aagaacaatg aggaggctga ggactatgat gatgacctga ctgactctga   2040
gatggatgtg gtgaggtttg atgatgacaa cagccccagc ttcatccaga tcaggtctgt   2100
ggccaagaag caccccaaga cctgggtgca ctacattgct gctgaggagg aggactggga   2160
ctatgccccc ctggtgctgg cccctgatga caggagctac aagagccagt acctgaacaa   2220
tggcccccag aggattggca ggaagtacaa gaaggtcagg ttcatggcct acactgatga   2280
aaccttcaag accaggggagg ccatccagca tgagtctggc atcctgggcc cctgctgta   2340 tggggaggtg ggggacaccc tgctgatcat cttcaagaac caggccagca ggccctacaa   2400
catctacccc catggcatca ctgatgtgag gcccctgtac agcaggaggc tgcccaaggg   2460
ggtgaagcac ctgaaggact cccccatcct gcctggggag atcttcaagt acaagtggac   2520
tgtgactgtg gaggatggcc ccaccaagtc tgacccagg tgcctgacca gatactacag    2580
cagctttgtg aacatggaga gggacctggc ctctggcctg attggccccc tgctgatctg   2640
ctacaaggag tctgtggacc agagggggcaa ccagatcatg tctgacaaga ggaatgtgat   2700
cctgttctct gtgtttgatg agaacaggag ctggtacctg actgagaaca tccagaggtt   2760
cctgcccaac cctgctgggg tgcagctgga ggaccctgag ttccaggcca gcaacatcat   2820
```

-continued

```
gcacagcatc aatggctatg tgtttgacag cctgcagctg tctgtgtgcc tgcatgaggt      2880
ggcctactgg tacatcctga gcattggggc ccagactgac ttcctgtctg tgttcttctc      2940
tggctacacc ttcaagcaca agatggtgta tgaggacacc ctgaccctgt tccccttctc      3000
tggggagact gtgttcatga gcatggagaa ccctggcctg tggattctgg gctgccacaa      3060
ctctgacttc aggaacaggg gcatgactgc cctgctgaaa gtctccagct gtgacaagaa      3120
cactggggac tactatgagg acagctatga ggacatctct gcctacctgc tgagcaagaa      3180
caatgccatt gagcccagga gcttcagcca gaaccccca gtgctgaaga ggcaccagag      3240
ggagatcacc aggaccaccc tgcagtctga ccaggaggag attgactatg atgacaccat      3300
ctctgtggag atgaagaagg aggactttga catctacgac gaggacgaga accagagccc      3360
caggagcttc cagaagaaga ccaggcacta cttcattgct gctgtggaga ggctgtggga      3420
ctatggcatg agcagcagcc cccatgtgct gaggaacagg gcccagtctg ctctgtgcc       3480
ccagttcaag aaggtggtgt tccaggagtt cactgatggc agcttcaccc agcccctgta      3540
cagagggag ctgaatgagc acctgggcct gctgggcccc tacatcaggg ctgaggtgga       3600
ggacaacatc atggtgacct tcaggaacca ggccagcagg ccctacagct tctacagcag      3660
cctgatcagc tatgaggagg accagaggca gggggctgag cccaggaaga actttgtgaa      3720
gcccaatgaa accaagacct acttctggaa ggtgcagcac cacatggccc ccaccaagga      3780
tgagtttgac tgcaaggcct gggcctactt ctctgatgtg acctggaga aggatgtgca       3840
ctctggcctg attggccccc tgctggtgtg ccacaccaac accctgaacc ctgcccatgg      3900
caggcaggtg actgtgcagg agtttgccct gttcttcacc atctttgatg aaaccaagag      3960
ctggtacttc actgagaaca tggagaggaa ctgcagggcc ccctgcaaca tccagatgga      4020
ggacccccacc ttcaaggaga actacaggtt ccatgccatc aatggctaca tcatggacac      4080
cctgcctggc ctggtgatgg cccaggacca gaggatcagg tggtacctgc tgagcatggg      4140
cagcaatgag aacatccaca gcatccactt ctctggccat gtgttcactg tgaggaagaa      4200
ggaggagtac aagatggccc tgtacaacct gtaccctggg gtgtttgaga ctgtggagat      4260
gctgcccagc aaggctggca tctggagggt ggagtgcctg attggggagc acctgcatgc      4320
tggcatgagc accctgttcc tggtgtacag caacaagtgc cagacccccc tgggcatggc      4380
ctctggccac atcagggact tccagatcac tgcctctggc cagtatggcc agtgggcccc      4440
caagctggcc aggctgcact actctggcag catcaatgcc tggagcacca aggagccctt      4500
cagctggatc aaggtggacc tgctggcccc catgatcatc catggcatca agacccaggg      4560
ggccaggcag aagttcagca gcctgtacat cagccagttc atcatcatgt acagcctgga      4620
tggcaagaag tggcagacct acagggggcaa cagcactggc accctgatgg tgttcttgg      4680
caatgtggac agctctggca tcaagcacaa catcttcaac ccccccatca ttgccagata     4740
catcaggctg caccccaccc actacagcat caggagcacc ctgaggatgg agctgatggg      4800
ctgtgacctg aacagctgca gcatgccct gggcatggag agcaaggcca tctctgatgc       4860
ccagatcact gccagcagct acttcaccaa catgtttgcc acctggagcc ccagcaaggc      4920
caggctgcac ctgcagggca ggagcaatgc ctggaggccc caggtcaaca ccccaagga       4980
gtggctgcag gtggacttcc agaagaccat gaaggtgact ggggtgacca cccaggggt      5040
gaagagcctg ctgaccagca tgtatgtgaa ggagttcctg atcagcagca gccaggatgg      5100
ccaccagtgg acccctgttct tccagaatgg caaggtgaag gtgttccagg caaccagga      5160
cagcttcacc cctgtggtga acagcctgga cccccccctg ctgaccagat acctgaggat     5220
```

```
tcaccccccag agctgggtgc accagattgc cctgaggatg gaggtgctgg gctgtgaggc    5280
ccaggacctg tactgacctc gaggcactgt cctttcctaa taaaatgagg aaattgcatc    5340
gcattgtctg agtaggtgtc attctattct gggggtggg gtggggcagg acagcaaggg     5400
ggaggattgg gaagacaata gcaggcatgc tggggatgcg gtgggctcta tgggcactcg    5460
acaggttaat ttttaaaaag cagtcaaaag tccaagtggc ccttggcagc atttactctc    5520
tctgtttgct ctggttaata atctcaggag cacaaacatt cctggaggca ggagaagaaa    5580
tcaacatcct ggacttatcc tctgggcctc tccccacccc caggagaggc tcaggttaat    5640
ttttaaaaag cagtcaaaag tccaagtggc ccttggcagc atttactctc tctgtttgct    5700
ctggttaata atctcaggag cacaaacatt cctggaggca ggagaagaaa tcaacatcct    5760
ggacttatcc tctgggcctc tccccacccc caggagaggc tgtcgagtgg cggccgcagg    5820 aaccccctagt gatggagttg ccactccct ctctgcgcgc tcgctcgctc actgaggccg    5880
ggcgaccaaa ggtcgcccga cgcccgggct tgcccgggc ggcctcagtg agcgagcgag    5940
cgcgcagaga gggagtggcc aa                                              5962

<210> SEQ ID NO 22
<211> LENGTH: 5919
<212> TYPE: DNA
<213> ORGANISM: Adeno-Associated Virus 2

<400> SEQUENCE: 22
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg    120
gccaactcca tcactagggg ttcctgcggc cgcacgcgta ggctcagagg cacacaggag    180
tttctgggct caccctgccc ccttccaacc cctcagttcc catcctccag cagctgtttg    240
tgtgctgcct ctgaagtcca cactgaacaa acttcagcct actcatgtcc ctaaaatggg    300
caaacattgc aagcagcaaa cagcaaacac acagccctcc ctgcctgctg accttggagc    360
tggggcagag gtcagagacc tctctggccc catgccacct ccaacatcca ctcgacccct    420
tggaatttcg gtggagagga gcagaggttg tcctggcgtg gtttaggtag tgtgagaggg    480
gtcgacgatc ttgctaccag tggaacagcc actaaggatt ctgcagtgag agcagagggc    540
cagctaagtg gtactctccc agagactgtc tgactcacgc caccccctcc accttggaca    600
caggacgctg tggtttctga gccaggtaca atgactcctt tcggtaagtg cagtggaagc    660
tgtacactgc ccaggcaaag cgtccgggca gcgtaggcgg gcgactcaga tcccagccag    720
tggacttagc ccctgtttgc tcctccgata actggggtga ccttggttaa tattcaccag    780
cagcctcccc cgttgcccct ctggatccac tgcttaaata cggacgagga cagggccctg    840
tctcctcagc ttcaggcacc accactgacc tgggacagtg aatcgtaagt atgcctttca    900
ctgcgagagt ttctggagag gcttctgagc tccccatggc ccaggcaggc agcaggtctg    960 ggcaggagg ggggttgtgg agtgggtatc cgcctgctga ggtgcagggc agatcatcat   1020
gtgccttgac tcggggcctg gccccccat ctctgtcttg caggacaatt gccgtcttct   1080
gtctcgtggg gcatcctcct gctggcaggc ctgtgctgcc tggtccctgt ctccctggct   1140
gaggaccggc caccatgcag attgagctga gcacctgctt cttcctgtgc ctgctgaggt   1200
tctgcttctc tgccaccagg agatactacc tgggggctgt ggagctgagc tgggactaca   1260
tgcagtctga cctgggggag ctgcctgtgg atgccaggtt ccccccaga gtgcccaaga   1320
```

```
gcttcccctt caacacctct gtggtgtaca agaagaccct gtttgtggag ttcactgacc    1380
acctgttcaa cattgccaag cccaggcccc cctggatggg cctgctgggc ccaccatcc    1440 aggctgaggt gtatgacact gtggtgatca ccctgaagaa catggccagc caccctgtga    1500
gcctgcatgc tgtggggtg agctactgga aggcctctga gggggctgag tatgatgacc    1560
agaccagcca gagggagaag gaggatgaca aggtgttccc tggggcagc cacacctatg    1620 tgtggcaggt gctgaaggag aatggcccca tggcctctga cccctgtgc ctgacctaca    1680 gctacctgag ccatgtggac ctggtgaagg acctgaactc tggcctgatt ggggccctgc    1740
tggtgtgcag ggagggcagc ctggccaagg agaagaccca gaccctgcac aagttcatcc    1800
tgctgtttgc tgtgtttgat gagggcaaga gctggcactc tgaaaccaag aacagcctga    1860
tgcaggacag ggatgctgcc tctgccaggg cctggcccaa gatgcacact gtgaatggct    1920
atgtgaacag gagcctgcct ggcctgattg gctgccacag gaagtctgtg tactggcatg    1980
tgattggcat gggcaccacc cctgaggtgc acagcatctt cctggagggc cacaccttcc    2040
tggtcaggaa ccacaggcag gccagcctgg agatcagccc catcaccttc ctgactgccc    2100
agaccctgct gatggacctg gccagttcc tgctgttctg ccacatcagc agccaccagc    2160
atgatggcat ggaggcctat gtgaaggtgg acagctgccc tgaggagccc agctgagga    2220 tgaagaacaa tgaggaggct gaggactatg atgatgacct gactgactct gagatggatg    2280
tggtgaggtt tgatgatgac aacagcccca gcttcatcca gatcaggtct gtggccaaga    2340
agcaccccaa gacctgggtg cactacattg ctgctgagga ggaggactgg gactatgccc    2400
ccctggtgct ggcccctgat gacaggagct acaagagcca gtacctgaac aatggccccc    2460
agaggattgg caggaagtac aagaaggtca ggttcatggc ctacactgat gaaaccttca    2520
agaccaggga ggccatccag catgagtctg gcatcctggg ccccctgctg tatggggagg    2580
tgggggacac cctgctgatc atcttcaaga accaggccag caggccctac aacatctacc    2640
cccatggcat cactgatgtg aggccctgt acagcaggag gctgcccaag ggggtgaagc    2700
acctgaagga cttccccatc ctgcctgggg agatcttcaa gtacaagtgg actgtgactg    2760
tggaggatgg ccccaccaag tctgacccca ggtgcctgac agatactac agcagctttg    2820 tgaacatgga gagggacctg gcctctggcc tgattggccc cctgctgatc tgctacaagg    2880
agtctgtgga ccagggggc aaccagatca tgtctgacaa gaggaatgtg atcctgttct    2940
ctgtgtttga tgagaacagg agctggtacc tgactgagaa catccagagg ttcctgccca    3000
accctgctgg ggtgcagctg gaggaccctg agttccaggc cagcaacatc atgcacagca    3060
tcaatggcta tgtgtttgac agcctgcagc tgtctgtgtg cctgcatgag gtggcctact    3120
ggtacatcct gagcattggg gcccagactg acttcctgtc tgtgttcttc tctggctaca    3180
ccttcaagca caagatggtg tatgaggaca ccctgacccct gttccccttc tctggggaga    3240
ctgtgttcat gagcatggag aaccctggcc tgtggattct gggctgccac aactctgact    3300
tcaggaacag gggcatgact gccctgctga aagtctccag ctgtgacaag aacactgggg    3360
actactatga ggacagctat gaggacatct ctgcctacct gctgagcaag aacaatgcca    3420
ttgagcccag gagcttcagc cagaaccccc cagtgctgaa gaggcaccag agggagatca    3480
ccaggaccac cctgcagtct gaccaggagg agattgacta tgatgacacc atctctgtgg    3540
agatgaagaa ggaggacttt gacatctacg acgaggacga gaaccagagc ccaggagct    3600 tccagaagaa gaccaggcac tacttcattg ctgctgtgga gaggctgtgg gactatgcca    3660
tgagcagcag ccccatgtg ctgaggaaca gggcccagtc tggctctgtg ccccagttca    3720
```

```
agaaggtggt gttccaggag ttcactgatg gcagcttcac ccagcccctg tacagagggg   3780
agctgaatga gcacctgggc ctgctgggcc cctacatcag ggctgaggtg gaggacaaca   3840
tcatggtgac cttcaggaac caggccagca ggccctacag cttctacagc agcctgatca   3900
gctatgagga ggaccagagg caggggctg agcccaggaa gaactttgtg aagcccaatg   3960
aaaccaagac ctacttctgg aaggtgcagc accacatggc ccccaccaag gatgagtttg   4020
actgcaaggc ctgggcctac ttctctgatg tggacctgga gaaggatgtg cactctggcc   4080
tgattggccc cctgctggtg tgccacacca caccctgaa ccctgcccat ggcaggcagg   4140
tgactgtgca ggagtttgcc ctgttcttca ccatctttga tgaaaccaag agctggtact   4200
tcactgagaa catggagagg aactgcaggg cccctgcaa catccagatg gaggacccca   4260
ccttcaagga gaactacagg ttccatgcca tcaatggcta catcatggac accctgcctg   4320
gcctggtgat ggcccaggac cagaggatca gtggtacct gctgagcatg ggcagcaatg   4380
agaacatcca cagcatccac ttctctggcc atgtgttcac tgtgaggaag aaggaggagt   4440
acaagatggc cctgtacaac ctgtaccctg gggtgtttga actgtggag atgctgccca   4500 gcaaggctgg catctggagg gtggagtgcc tgattgggga gcacctgcat gctggcatga   4560
gcaccctgtt cctggtgtac agcaacaagt gccagacccc cctgggcatg gcctctggcc   4620
acatcaggga cttccagatc actgcctctg gccagtatgg ccagtgggcc ccaagctgg   4680 ccaggctgca ctactctggc agcatcaatg cctggagcac caaggagccc ttcagctgga   4740
tcaaggtgga cctgctggcc cccatgatca tccatggcat caagacccag ggggccaggc   4800
agaagttcag cagcctgtac atcagccagt tcatcatcat gtacagcctg gatggcaaga   4860
agtggcagac ctacaggggc aacagcactg gcacctgat ggtgttcttt ggcaatgtgg   4920
acagctctgg catcaagcac aacatcttca accccccat cattgccaga tacatcaggc   4980 tgcacccac ccactacagc atcaggagca ccctgaggat ggagctgatg ggctgtgacc   5040
tgaacagctg cagcatgccc ctgggcatgg agagcaaggc catctctgat gcccagatca   5100
ctgccagcag ctacttcacc aacatgtttg ccacctggag ccccagcaag gccaggctgc   5160
acctgcaggg caggagcaat gcctggaggc cccaggtcaa caaccccaag gagtggctgc   5220
aggtggactt ccagaagacc atgaaggtga ctggggtgac cacccagggg gtgaagagcc   5280
tgctgaccag catgtatgtg aaggagttcc tgatcagcag cagccaggat ggccaccagt   5340
ggaccctgtt cttccagaat ggcaaggtga aggtgttcca gggcaaccag gacagcttca   5400
cccctgtggt gaacagcctg gaccccccc tgctgaccag ataccctgagg attccccc    5460 agagctgggt gcaccagatt gccctgagga tggaggtgct gggctgtgag gcccaggacc   5520
tgtactgagc tcgagctgtg ccttctagtt gccagccatc tgttgtttgc ccctccccg    5580 tgccttcctt gaccctggaa ggtgccactc ccactgtcct ttcctaataa aatgaggaaa   5640
ttgcatcgca ttgtctgagt aggtgtcatt ctattctggg gggtggggtg gggcaggaca   5700
gcaaggggga ggattgggaa gacaatagca ggcatgctgg ggatgcggtg ggctctatgg   5760
accggtgcgg ccgcaggaac ccctagtgat ggagttggcc actccctctc tgcgcgctcg   5820
ctcgctcact gaggccgggc gaccaaaggt cgcccgacgc ccgggctttg cccgggcggc   5880
ctcagtgagc gagcgagcgc gcagagaggg agtggccaa                        5919
```

<210> SEQ ID NO 23
<211> LENGTH: 5306
<212> TYPE: DNA

<213> ORGANISM: Adeno-Associated Virus 2

<400> SEQUENCE: 23

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgcggc cgcacgcgtg ttttaaacgt cgaccctaaa     180
atgggcaaac attgcaagca gcaaacagca aactgacctt ggagctgggg cagaggtcag     240
agacctctct gggcactcga ccccttggaa tttcggtgga gaggagcaga ggtacacagc     300
cctccctgcc tgcccatgc cacctccaac atctgtcctg cgtggttta ggtagtgtga      360
gaggggaatg actcctttcg gtaagtgcag tggaagctgt acactgccca ggcaaagcgt     420
ccgggcagcg taggcgggcg actcagatcc cagccagtgg acttagcccc tgtttgctcc     480
tccgataact ggggtgacct tggttaatat tcaccagcag cctcccccgt tgcccctctg     540
gatccactgc ttaaatacgg acgaggacag ggcctgtct cctcagcttc aggcaccacc      600
actgacctgg gacagtgaat cgcgatcgca ctgcttaaat acggacgagg acagggccct     660
gtctcctcag cttcaggcac caccactgac ctgggacagt gaatcgcgat cgccaccatg     720
cagattgagc tgagcacctg cttcttcctg tgcctgctga ggttctgctt ctctgccacc     780
aggagatact acctgggggc tgtggagctg agctgggact acatgcagtc tgacctgggg     840
gagctgcctg tggatgccag gttcccccc agagtgccca agagcttccc cttcaacacc      900
tctgtggtgt acaagaagac cctgtttgtg gagttcactg accacctgtt caacattgcc     960
aagcccaggc cccctggat gggcctgctg gccccacca tccaggctga ggtgtatgac      1020
actgtggtga tcaccctgaa gaacatggcc agccaccctg tgagcctgca tgctgtgggg    1080
gtgagctact ggaaggcctc tgaggggggct gagtatgatg accagaccag ccagaggag    1140
aaggaggatg acaaggtgtt ccctggggc agccacacct atgtgtggca ggtgctgaag    1200
gagaatggcc ccatggcctc tgaccccctg tgcctgacct cagctacct gagccatgtg    1260
gacctggtga aggacctgaa ctctggcctg attggggccc tgctggtgtg cagggagggc    1320
agcctggcca aggagaagac ccagaccctg cacaagttca tcctgctgtt tgctgtgttt    1380
gatgagggca gagctggca ctctgaaacc aagaacagcc tgatgcagga cagggatgct    1440
gcctctgcca gggcctggcc caagatgcac actgtgaatg ctatgtgaa caggagcctg    1500
cctggcctga ttggctgcca caggaagtct gtgtactggc atgtgattgg catgggcacc    1560
accccctgagg tgcacagcat cttcctggag ggccacacct tcctggtcag gaaccacagg    1620
caggccagcc tggagatcag ccccatcacc ttcctgactg cccagaccct gctgatggac    1680
ctgggccagt cctgctgttt ctgccacatc agcagccacc agcatgatgg catggaggcc    1740
tatgtgaagg tggacagctg ccctgaggag ccccagctga ggatgaagaa caatgaggag    1800
gctgaggact atgatgatga cctgactgac tctgagatgg atgtggtgag gtttgatgat    1860
gacaacagcc ccagcttcat ccagatcagg tctgtggcca gaagcacccc caagacctgg    1920
gtgcactaca ttgctgctga ggaggaggac tgggactatg cccccctggt gctggcccct    1980
gatgacagga gctacaagag ccagtacctg aacaatggcc cccagaggat ggcaggaag    2040
tacaagaagg tcaggttcat ggcctacact gatgaaacct caagaccag ggaggccatc    2100
cagcatgagt ctggcatcct ggggccccctg ctgtatgggg aggtggggga caccctgctg    2160
atcatcttca gaaccaggc cagcaggccc tacaacatct accccatgg catcactgat    2220
gtgaggcccc tgtacagcag gaggctgccc aaggggtga agcacctgaa ggacttcccc    2280
```

```
atcctgcctg gggagatctt caagtacaag tggactgtga ctgtggagga tggccccacc    2340
aagtctgacc ccaggtgcct gaccagatac tacagcagct ttgtgaacat ggagagggac    2400
ctggcctctg gcctgattgg cccctgctg atctgctaca aggagtctgt ggaccagagg     2460
ggcaaccaga tcatgtctga caagaggaat gtgatcctgt tctctgtgtt tgatgagaac    2520
aggagctggt acctgactga aacatccag aggttcctgc ccaaccctgc tggggtgcag     2580
ctggaggacc ctgagttcca ggccagcaac atcatgcaca gcatcaatgg ctatgtgttt    2640
gacagcctgc agctgtctgt gtgcctgcat gaggtggcct actggtacat cctgagcatt    2700
ggggcccaga ctgacttcct gtctgtgttc ttctctggct acaccttcaa gcacaagatg    2760
gtgtatgagg acaccctgac cctgttcccc ttctctgggg agactgtgtt catgagcatg    2820
gagaaccctg gctgtggat tctgggctgc acaactctg acttcaggaa caggggcatg      2880
actgccctgc tgaaagtctc cagctgtgac aagaacactg gggactacta tgaggacagc    2940
tatgaggaca tctctgccta cctgctgagc aagaacaatg ccattgagcc caggagcttc    3000
agccagaacc ccccagtgct gaagaggcac cagagggaga tcaccaggac caccctgcag    3060
tctgaccagg aggagattga ctatgatgac accatctctg tggagatgaa gaaggaggac    3120
tttgacatct acgacgagga cgagaaccag agccccagga gcttccagaa gaagaccagg    3180
cactacttca ttgctgctgt ggagaggctg tgggactatg catgagcag cagcccccat     3240 gtgctgagga cagggccca gtctggctct gtgccccagt tcaagaaggt ggtgttccag     3300
gagttcactg atggcagctt cacccagccc ctgtacagag gggagctgaa tgagcacctg    3360
ggcctgctgg gcccctacat cagggctgag gtggaggaca acatcatggt gaccttcagg    3420
aaccaggcca gcaggcccta cagcttctac agcagcctga tcagctatga ggaggaccag    3480
aggcaggggg ctgagcccag aagaactttt gtgaagccca tgaaaccaa gacctacttc    3540 tggaaggtgc agcaccacat ggccccccac aaggatgagt ttgactgcaa ggcctgggcc    3600
tacttctctg atgtggacct ggagaaggat gtgcactctg gcctgattgg cccctgctg    3660 gtgtgccaca ccaacaccct gaaccctgcc catggcaggc aggtgactgt gcaggagttt    3720
gccctgttct tcaccatctt tgatgaaacc aagagctggt acttcactga aacatggag    3780 aggaactgca gggcccctg caacatccag atggaggacc ccaccttcaa ggagaactac    3840
aggttccatg ccatcaatgg ctacatcatg gacaccctgc ctggcctggt gatggcccag    3900
gaccagagga tcaggtggta cctgctgagc atgggcagca tgagaacat ccacagcatc     3960 cacttctctg gccatgtgtt cactgtgagg aagaaggagg agtacaagat ggccctgtac    4020
aacctgtacc ctgggggtgtt tgagactgtg gagatgctgc ccagcaaggc tggcatctgg    4080
agggtggagt gcctgattgg ggagcacctg catgctggca tgagcaccct gttcctggtg    4140
tacagcaaca agtgccagac cccctgggc atggcctctg ccacatcag ggacttccag      4200 atcactgcct ctggccagta tggccagtgg gccccccaagc tggccaggct gcactactct    4260
ggcagcatca atgcctggag caccaaggag cccttcagct ggatcaaggt ggacctgctg    4320
gcccccatga tcatccatgg catcaagacc caggggggcca ggcagaagtt cagcagcctg    4380
tacatcagcc agttcatcat catgtacagc ctggatggca gaagtggca gacctacagg    4440 ggcaacagca ctggcaccct gatggtgttc tttggcaatg tggacagctc tggcatcaag    4500
cacaacatct tcaaccccc catcattgcc agatacatca ggctgcaccc caccactac     4560 agcatcagga gcacctgag gatggagctg atgggctgtg acctgaacag ctgcagcatg    4620
```

| | |
|---|---|
| cccctgggca tggagagcaa ggccatctct gatgcccaga tcactgccag cagctacttc | 4680 |
| accaacatgt ttgccacctg gagccccagc aaggccaggc tgcacctgca gggcaggagc | 4740 |
| aatgcctgga ggccccaggt caacaacccc aaggagtggc tgcaggtgga cttccagaag | 4800 |
| accatgaagg tgactggggt gaccaccag ggggtgaaga gcctgctgac cagcatgtat | 4860 |
| gtgaaggagt tcctgatcag cagcagccag gatggccacc agtggaccct gttcttccag | 4920 |
| aatggcaagt gaaggtgtt ccagggcaac caggacagct tcacccctgt ggtgaacagc | 4980 |
| ctggaccccc ccctgctgac cagatacctg aggattcacc cccagagctg ggtgcaccag | 5040 |
| attgccctga ggatggaggt gctgggctgt gaggcccagg acctgtactg acctcgagga | 5100 |
| ataaggaaa tttatttca ttgcaatagt gtgttggttt tttgtgtcac gtggcggccg | 5160 |
| caggaacccc tagtgatgga gttggccact ccctctctgc gcgctcgctc gctcactgag | 5220 |
| gccgggcgac caaaggtcgc ccgacgcccg ggctttgccc gggcggcctc agtgagcgag | 5280 |
| cgagcgcgca gagggagt ggccaa | 5306 |

<210> SEQ ID NO 24
<211> LENGTH: 5461
<212> TYPE: DNA
<213> ORGANISM: Adeno-Associated Virus 2

<400> SEQUENCE: 24

| | |
|---|---|
| ttggccactc cctctctgcg cgctcgctcg ctcactgagg ccgcccgggc aaagcccggg | 60 |
| cgtcgggcga cctttggtcg cccggcctca gtgagcgagc gagcgcgcag agggagtg | 120 |
| gccaactcca tcactagggg ttcctgcggc cgcacgcgtg ttttcgactt tatttgccac | 180 |
| aaaaaccta tcagatgggc gtctttatca tttccattgt acagatgggg aaacaggctt | 240 |
| cggggtcggg gcatagccac ttactgacga ctccccaccc agcaagtggt tttgaacccg | 300 |
| gaccctctca cactacctaa accacgccag acaacctct gctcctctcc accgaaattc | 360 |
| caaggggtcg agtggatgtt ggaggtggca tgggcccaga gaggtctctg acctctgccc | 420 |
| cagctccaag gtcagcaggc agggagggct gtgtgtttgc tgtttgctgc ttgcaatgtt | 480 |
| tgcccatttt agggacatga gtaggctgaa gtttgttcag tgtggacttc agaggcagca | 540 |
| cacaaacagc tgctggagga tgggaactga ggggttggaa gggggcaggg tgagcccaga | 600 |
| aactcctgtg tgcctctgag cctgcagacg cgaaacgtcg actggacaca ggacgctgtg | 660 |
| gtttctgagc caggggggcga ctcagatccc agccagtgga cttagccct gtttgctcct | 720 |
| ccgataactg gggtgacctt ggttaatatt caccagcagc ctccccgtt gcccctctgg | 780 |
| atccactgct taaatacgga cgaggacagg gccctgtctc ctcagcttca ggcaccacca | 840 |
| ctgacctggg acagtgaatc gcgatcgcca ccatgcagat tgagctgagc acctgcttct | 900 |
| tcctgtgcct gctgaggttc tgcttctctg ccaccaggag atactacctg ggggctgtgg | 960 |
| agctgagctg ggactacatg cagtctgacc tgggggagct gcctgtggat gccaggttcc | 1020 |
| cccccagagt gcccaagagc ttccccttca acacctctgt ggtgtacaag aagaccctgt | 1080 |
| ttgtggagtt cactgaccac ctgttcaaca ttgccaagcc caggccccc tggatgggcc | 1140 |
| tgctgggccc caccatccag gctgaggtgt atgacactgt ggtgatcacc ctgaagaaca | 1200 |
| tggccagcca ccctgtgagc ctgcatgctg tggggtgag ctactggaag gcctctgagg | 1260 |
| gggctgagta tgatgaccag accagccaga gggagaagga ggatgacaag gtgttccctg | 1320 |
| ggggcagcca cacctatgtg tggcaggtgc tgaaggagaa tggccccatg gcctctgacc | 1380 |
| ccctgtgcct gacctacagc tacctgagcc atgtggacct ggtgaaggac ctgaactctg | 1440 |

```
gcctgattgg ggccctgctg gtgtgcaggg agggcagcct ggccaaggag aagacccaga    1500
ccctgcacaa gttcatcctg ctgtttgctg tgtttgatga gggcaagagc tggcactctg    1560
aaaccaagaa cagcctgatg caggacaggg atgctgcctc tgccagggcc tggcccaaga    1620
tgcacactgt gaatggctat gtgaacagga gcctgcctgg cctgattggc tgccacagga    1680
agtctgtgta ctggcatgtg attggcatgg gcaccacccc tgaggtgcac agcatcttcc    1740
tggagggcca caccttcctg gtcaggaacc acaggcaggc cagcctggag atcagcccca    1800
tcaccttcct gactgcccag accctgctga tggacctggg ccagttcctg ctgttctgcc    1860
acatcagcag ccaccagcat gatggcatgg aggcctatgt gaaggtggac agctgccctg    1920
aggagcccca gctgaggatg aagaacaatg aggaggctga ggactatgat gatgacctga    1980
ctgactctga gatggatgtg gtgaggtttg atgatgacaa cagccccagc ttcatccaga    2040
tcaggtctgt ggccaagaag caccccaaga cctgggtgca ctacattgct gctgaggagg    2100
aggactggga ctatgccccc ctggtgctgg cccctgatga caggagctac aagagccagt    2160
acctgaacaa tggcccccag aggattggca ggaagtacaa gaaggtcagg ttcatggcct    2220
acactgatga aaccttcaag accagggagg ccatccagca tgagtctggc atcctgggcc    2280
ccctgctgta tggggaggtg ggggacaccc tgctgatcat cttcaagaac caggccagca    2340
ggccctacaa catctacccc catggcatca ctgatgtgag gccctgtac agcaggaggc    2400 tgcccaaggg ggtgaagcac ctgaaggact cccccatcct gcctggggag atcttcaagt    2460
acaagtggac tgtgactgtg gaggatggcc ccaccaagtc tgaccccagg tgcctgacca    2520
gatactacag cagctttgtg aacatggaga gggacctggc ctctggcctg attggccccc    2580
tgctgatctg ctacaaggag tctgtggacc agagggcaa ccagatcatg tctgacaaga    2640
ggaatgtgat cctgttctct gtgtttgatg agaacaggag ctggtacctg actgagaaca    2700
tccagaggtt cctgcccaac cctgctgggg tgcagctgga ggaccctgag ttccaggcca    2760
gcaacatcat gcacagcatc aatggctatg tgtttgacag cctgcagctg tctgtgtgcc    2820
tgcatgaggt ggcctactgg tacatcctga gcattgggc ccagactgac ttcctgtctg    2880
tgttcttctc tggctacacc ttcaagcaca agatggtgta tgaggacacc ctgacctgt    2940 tccccttctc tggggagact gtgttcatga gcatggagaa ccctggcctg tggattctgg    3000
gctgccacaa ctctgacttc aggaacaggg gcatgactgc cctgctgaaa gtctccagct    3060
gtgacaagaa cactggggac tactatgagg acagctatga ggacatctct gcctacctgc    3120
tgagcaagaa caatgccatt gagcccagga gcttcagcca gaaccccca gtgctgaaga    3180 ggcaccagag ggagatcacc aggaccaccc tgcagtctga ccaggaggag attgactatg    3240
atgacaccat ctctgtggag atgaagaagg aggactttga catctacgac gaggacgaga    3300
accagagccc caggagcttc cagaagaaga ccaggcacta cttcattgct gctgtggaga    3360
ggctgtggga ctatgcatg agcagcagcc ccatgtgct gaggaacagg cccagtctg    3420 gctctgtgcc ccagttcaag aaggtggtgt tccaggagtt cactgatggc agcttcaccc    3480 agccctgta cagaggggag ctgaatgagc acctgggct gctgggccc tacatcaggg    3540 ctgaggtgga ggacaacatc atggtgacct tcaggaacca ggccagcagg ccctacagct    3600
tctacagcag cctgatcagc tatgaggagg accagaggca gggggctgag cccaggaaga    3660
actttgtgaa gccaatgaa accaagacct acttctggaa ggtgcagcac cacatggccc    3720
ccaccaagga tgagtttgac tgcaaggcct gggcctactt ctctgatgtg gacctggaga    3780
```

| | |
|---|---|
| aggatgtgca ctctggcctg attggccccc tgctggtgtg ccacaccaac accctgaacc | 3840 |
| ctgcccatgg caggcaggtg actgtgcagg agtttgccct gttcttcacc atctttgatg | 3900 |
| aaaccaagag ctggtacttc actgagaaca tggagaggaa ctgcagggcc ccctgcaaca | 3960 |
| tccagatgga ggaccccacc ttcaaggaga actacaggtt ccatgccatc aatggctaca | 4020 |
| tcatggacac cctgcctggc ctggtgatgg cccaggacca gaggatcagg tggtacctgc | 4080 |
| tgagcatggg cagcaatgag aacatccaca gcatccactt ctctggccat gtgttcactg | 4140 |
| tgaggaagaa ggaggagtac aagatggccc tgtacaacct gtaccctggg gtgtttgaga | 4200 |
| ctgtggagat gctgcccagc aaggctgcac tctggagggt ggagtgcctg attggggagc | 4260 |
| acctgcatgc tggcatgagc accctgttcc tggtgtacag caacaagtgc cagaccccc | 4320 |
| tgggcatggc ctctggccac atcagggact tccagatcac tgcctctggc cagtatggcc | 4380 |
| agtgggcccc caagctggcc aggctgcact actctggcag catcaatgcc tggagcacca | 4440 |
| aggagccctt cagctggatc aaggtggacc tgctggcccc catgatcatc catggcatca | 4500 |
| agacccaggg ggccaggcag aagttcagca gcctgtacat cagccagttc atcatcatgt | 4560 |
| acagcctgga tggcaagaag tggcagacct acaggggcaa cagcactggc accctgatgg | 4620 |
| tgttcttttgg caatgtggac agctctggca tcaagcacaa catcttcaac ccccccatca | 4680 |
| ttgccagata catcaggctg cacccccacc actacagcat caggagcacc ctgaggatgg | 4740 |
| agctgatggg ctgtgacctg aacagctgca gcatgccct gggcatggag agcaaggcca | 4800 |
| tctctgatgc ccagatcact gccagcagct acttcaccaa catgtttgcc acctggagcc | 4860 |
| ccagcaaggc caggctgcac ctgcaggca ggagcaatgc ctggaggccc caggtcaaca | 4920 |
| accccaagga gtggctgcag gtggacttcc agaagaccat gaaggtgact ggggtgacca | 4980 |
| cccagggggt gaagagcctg ctgaccagca tgtatgtgaa ggagttcctg atcagcagca | 5040 |
| gccaggatgg ccaccagtgg acctgttct tccagaatgg caaggtgaag gtgttccagg | 5100 |
| gcaaccagga cagcttcacc cctgtggtga acagcctgga cccccccctg ctgaccagat | 5160 |
| acctgaggat tcaccccccag agctgggtgc accagattgc cctgaggatg gaggtgctgg | 5220 |
| gctgtgaggc ccaggacctg tactgacctc gaggaataaa ggaaatttat tttcattgca | 5280 |
| atagtgtgtt ggttttttgt gtcacgtggc ggccgcagga ccctagtg atggagttgg | 5340 |
| ccactccctc tctgcgcgct cgctcgctca ctgaggccgg gcgaccaaag gtcgcccgac | 5400 |
| gcccgggctt tgcccgggcg gcctcagtga gcgagcgagc gcgcagagag ggagtggcca | 5460 |
| a | 5461 |

<210> SEQ ID NO 25
<211> LENGTH: 5327
<212> TYPE: DNA
<213> ORGANISM: Adeno-Associated Virus 2

<400> SEQUENCE: 25

| | |
|---|---|
| ttggccactc cctctctgcg cgctcgctcg ctcactgagg ccgcccgggc aaagcccggg | 60 |
| cgtcgggcga cctttggtcg cccggcctca gtgagcgagc gagcgcgcag agagggagtg | 120 |
| gccaactcca tcactagggg ttcctgcggc cgcacgcgtg ttttcgaccc ctctcacact | 180 |
| acctaaacca cgccaggaca acctctgctc ctctccaccg aaattccaag gggtcgagtg | 240 |
| gatgttggag gtggcatggg cccagagagg tctctgacct ctgccccagc tccaaggtca | 300 |
| gcaggcaggg agggctgtgt gtttgctgtt tgctgcttgc aatgtttgcc cattttaggg | 360 |
| acatgagtag gctgaagttt gttcagtgtg gacttcagag gcagcacaca aacagctgct | 420 |

```
ggaggatggg aactgagggg ttggaagggg gcagggtgag cccagaaact cctgtgtgcc    480
tctgagcctg cagacgcgaa acgtcgactg gacacaggac gctgtggttt ctgagccagg    540
gggcgactca gatcccagcc agtggactta gccctgtttt gctcctccga taactgggt    600 gaccttggtt aatattcacc agcagcctcc cccgttgccc ctctggatcc actgcttaaa    660
tacggacgag gacagggccc tgtctcctca gcttcaggca ccaccactga cctgggacag    720
tgaatcgcga tcgccaccat gcagattgag ctgagcacct gcttcttcct gtgcctgctg    780
aggttctgct tctctgccac caggagatac tacctggggg ctgtggagct gagctgggac    840
tacatgcagt ctgacctggg ggagctgcct gtggatgcca ggttcccccc cagagtgccc    900
aagagcttcc ccttcaacac ctctgtggtg tacaagaaga ccctgttttgt ggagttcact    960 gaccacctgt tcaacattgc caagcccagg ccccccttgga tgggcctgct gggccccacc   1020
atccaggctg aggtgtatga cactgtggtg atcaccctga gaacatggc cagccaccct   1080 gtgagcctgc atgctgtggg ggtgagctac tggaaggcct ctgaggggc tgagtatgat   1140 gaccagacca gccagaggga aaggaggat gacaaggtgt ccctgggggg cagccacacc   1200
tatgtgtggc aggtgctgaa ggagaatggc cccatggcct ctgaccccct gtgcctgacc   1260
tacagctacc tgagccatgt ggacctggtg aaggacctga actctggcct gattggggcc   1320
ctgctggtgt gcagggaggg cagcctggcc aaggagaaga cccagaccct gcacaagttc   1380
atcctgctgt ttgctgtgtt tgatgagggc aagagctggc actctgaaac caagaacagc   1440
ctgatgcagg acagggatgc tgcctctgcc agggcctggc ccaagatgca cactgtgaat   1500
ggctatgtga acaggagcct gcctggcctg attggctgcc acaggaagtc tgtgtactgg   1560
catgtgattg gcatgggcac cacccctgag gtgcacagca tcttcctgga gggccacacc   1620
ttcctggtca ggaaccacag gcaggccagc ctggagatca gccccatcac cttcctgact   1680
gcccagaccc tgctgatgga cctgggccag ttcctgctgt tctgccacat cagcagccac   1740
cagcatgatg gcatggaggc ctatgtgaag gtggacagct gccctgagga gccccagctg   1800
aggatgaaga acaatgagga ggctgaggac tatgatgatg acctgactga ctctgagatg   1860
gatgtggtga ggtttgatga tgacaacagc cccagcttca tccagatcag gtctgtggcc   1920
aagaagcacc ccaagacctg ggtgcactac attgctgctg aggaggagga ctgggactat   1980
gcccccctgg tgctggcccc tgatgacagg agctacaaga gccagtaccct gaacaatggc   2040 ccccagagga ttggcaggaa gtacaagaag gtcaggttca tggcctacac tgatgaaacc   2100
ttcaagacca gggaggccat ccagcatgag tctggcatcc tgggcccct gctgtatggg   2160 gaggtggggg acaccctgct gatcatcttc aagaaccagg ccagcaggcc ctacaacatc   2220
tacccccatg gcatcactga tgtgaggccc ctgtacagca ggaggctgcc caaggggtg   2280 aagcacctga aggacttccc catcctgcct ggggagatct tcaagtacaa gtggactgtg   2340
actgtggagg atggccccac caagtctgac cccaggtgcc tgaccagata ctacagcagc   2400
tttgtgaaca tggagaggga cctggcctct ggcctgattg gccccctgct gatctgctac   2460
aaggagtctg tggaccagag gggcaaccag atcatgtctg acaagaggaa tgtgatcctg   2520
ttctctgtgt ttgatgagaa caggagctgg tacctgactg agaacatcca gaggttcctg   2580
cccaaccctg ctgggggtgca gctggaggac cctgagttcc aggccagcaa catcatgcac   2640
agcatcaatg gctatgtgtt tgacagcctg cagctgtctg tgtgcctgca tgaggtggcc   2700
tactggtaca tcctgagcat tggggcccag actgacttcc tgtctgtgtt cttctctggc   2760
```

```
tacaccttca agcacaagat ggtgtatgag gacaccctga ccctgttccc cttctctggg    2820
gagactgtgt tcatgagcat ggagaaccct ggcctgtgga ttctgggctg ccacaactct    2880
gacttcagga acaggggcat gactgccctg ctgaaagtct ccagctgtga caagaacact    2940
ggggactact atgaggacag ctatgaggac atctctgcct acctgctgag caagaacaat    3000
gccattgagc ccaggagctt cagccagaac cccccagtgc tgaagaggca ccagagggag    3060
atcaccagga ccaccctgca gtctgaccag gaggagattg actatgatga ccatctctct    3120
gtggagatga agaaggagga ctttgacatc tacgacgagg acgagaacca gagccccagg    3180
agcttccaga agaagaccag gcactacttc attgctgctg tggagaggct gtgggactat    3240
ggcatgagca gcagccccca tgtgctgagg aacagggccc agtctggctc tgtgccccag    3300
ttcaagaagg tggtgttcca ggagttcact gatggcagct tcacccagcc cctgtacaga    3360
ggggagctga atgagcacct gggcctgctg ggcccctaca tcagggctga ggtggaggac    3420
aacatcatgg tgaccttcag gaaccaggcc agcaggccct acagcttcta cagcagcctg    3480
atcagctatg aggaggacca gaggcagggg gctgagccca ggaagaactt tgtgaagccc    3540
aatgaaacca agacctactt ctggaaggtg cagcaccaca tggcccccac caaggatgag    3600
tttgactgca aggcctgggc ctacttctct gatgtggacc tggagaagga tgtgcactct    3660
ggcctgattg gcccctgct ggtgtgccac accaacaccc tgaaccctgc ccatggcagg    3720
caggtgactg tgcaggagtt tgccctgttc ttcaccatct ttgatgaaac caagagctgg    3780
tacttcactg agaacatgga gaggaactgc agggcccct gcaacatcca gatggaggac    3840
cccaccttca aggagaacta caggttccat gccatcaatg ctacatcat ggacaccctg    3900
cctggcctgg tgatggccca ggaccagagg atcaggtggt acctgctgag catgggcagc    3960
aatgagaaca tccacagcat ccacttctct ggccatgtgt tcactgtgag gaagaaggag    4020
gagtacaaga tggccctgta caacctgtac cctggggtgt ttgagactgt ggagatgctg    4080
cccagcaagg ctggcatctg gagggtggag tgcctgattg gggagcacct gcatgctggc    4140
atgagcaccc tgttcctggt gtacagcaac aagtgccaga ccccctggg catggcctct    4200
ggccacatca gggacttcca gatcactgcc tctggccagt atggccagtg ggcccccaag    4260
ctggccaggc tgcactactc tggcagcatc aatgcctgga gcaccaagga gcccttcagc    4320
tggatcaagg tggacctgct ggcccccatg atcatccatg gcatcaagac caggggggcc    4380
aggcagaagt tcagcagcct gtacatcagc cagttcatca tcatgtacag cctggatggc    4440
aagaagtggc agacctacag gggcaacagc actggcaccc tgatggtgtt ctttggcaat    4500
gtggacagct ctggcatcaa gcacaacatc ttcaaccccc ccatcattgc cagatacatc    4560
aggctgcacc ccacccacta cagcatcagg agcaccctga ggatggagct gatgggctgt    4620
gacctgaaca gctgcagcat gcccctgggc atggagagca aggccatctc tgatgcccag    4680
atcactgcca gcagctactt caccaacatg tttgccacct ggagcccag caaggccagg    4740
ctgcacctgc agggcaggag caatgcctgg aggcccagg tcaacaaccc caaggagtgg    4800
ctgcaggtgg acttccagaa gaccatgaag gtgactgggg tgaccaccca gggggtgaag    4860
agcctgctga ccagcatgta tgtgaaggag ttcctgatca gcagcagcca ggatggccac    4920
cagtggaccc tgttcttcca gaatggcaag gtgaaggtgt tccagggcaa ccaggacagc    4980
ttcacccctg tggtgaacag cctggaccc ccctgctga ccagataccc gaggattcac    5040
ccccagagct gggtgcacca gattgccctg aggatggagg tgctgggctg tgaggcccag    5100
gacctgtact gacctcgagg aataaaggaa atttatttc attgcaatag tgtgttggtt    5160
```

```
tttgtgtca cgtggcggcc gcaggaaccc ctagtgatgg agttggccac tccctctctg    5220
cgcgctcgct cgctcactga ggccgggcga ccaaaggtcg cccgacgccc gggctttgcc    5280
cgggcggcct cagtgagcga gcgagcgcgc agagagggag tggccaa                 5327
```

<210> SEQ ID NO 26
<211> LENGTH: 5309
<212> TYPE: DNA
<213> ORGANISM: Adeno-Associated Virus 2

<400> SEQUENCE: 26

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgcggc cgcacgcgtc tgcaggctca gaggcacaca    180
ggagtttctg ggctcaccct gccccttcc aaccctcag ttcccatcct ccagcagctg     240
tttgtgtgct gcctctgaag tccacactga acaaacttca gcctactcat gtccctaaaa    300
tgggcaaaca ttgcaagcag caaacagcaa acacacagcc ctccctgcct gctgaccttg    360
gagctggggc agaggtcaga gacctctctg ggcccatgcc acctccaaca tccactcgac    420
cccttggaat tcggtggag aggagcagag gttgtcctgg cgtggtttag gtagtgtgag    480
aggggtcgac tggacacagg acgctgtggt ttctgagcca gggggcgact cagatcccag    540
ccagtggact tagcccctgt tgctcctcc gataactggg gtgaccttgg ttaatattca    600
ccagcagcct ccccgttgc ccctctggat ccactgctta aatacggacg aggacagggc    660
cctgtctcct cagcttcagg caccaccact gacctgggac agtgaatcgc gatcgccacc    720
atgcagattg agctgagcac ctgcttcttc ctgtgcctgc tgaggttctg cttctctgcc    780
accaggagat actacctggg ggctgtggag ctgagctggg actacatgca gtctgacctg    840
ggggagctgc ctgtggatgc caggttcccc ccagagtgc caagagctt ccccttcaac     900 acctctgtgg tgtacaagaa gaccctgttt gtggagttca ctgaccacct gttcaacatt    960
gccaagccca ggcccccctg gatgggcctg ctgggcccca ccatccaggc tgaggtgtat   1020
gacactgtgg tgatcaccct gaagaacatg gccagccacc ctgtgagcct gcatgctgtg   1080
ggggtgagct actggaaggc ctctgagggg gctgagtatg atgaccagac cagccagagg   1140
gagaaggagg atgacaaggt gttccctggg gcagccacac cctatgtgtg gcaggtgctg   1200
aaggagaatg ccccatggc ctctgacccc ctgtgcctga cctacagcta cctgagccat   1260
gtggacctgg tgaaggacct gaactctggc ctgattgggg ccctgctggt gtgcagggag   1320
ggcagcctgg ccaaggagaa gacccagacc ctgcacaagt tcatcctgct gtttgctgtg   1380
tttgatgagg gcaagagctg gcactctgaa accaagaaca cctgatgca ggacagggat   1440 gctgcctctg ccagggcctg gcccaagatg cacactgtga atggctatgt gaacaggagc   1500
ctgcctggcc tgattggctg ccacaggaag tctgtgtact ggcatgtgat tggcatgggc   1560
accacccctg aggtgcacag catcttcctg gagggccaca ccttcctggt caggaaccac   1620
aggcaggcca gcctggagat cagccccatc accttcctga ctgccagac cctgctgatg   1680 gacctgggcc agttcctgct gttctgccac atcagcagcc accagcatga tggcatggag   1740
gcctatgtga aggtggacag ctgccctgag agccccagc tgaggatgaa gaacaatgag   1800
gaggctgagg actatgatga tgacctgact gactctgaga tggatgtggt gaggtttgat   1860
gatgacaaca gccccagctt catccagatc aggtctgtgg ccaagaagca ccccaagacc   1920
```

```
tgggtgcact acattgctgc tgaggaggag gactgggact atgcccccct ggtgctggcc    1980
cctgatgaca ggagctacaa gagccagtac ctgaacaatg cccccagag gattggcagg     2040 aagtacaaga aggtcaggtt catggcctac actgatgaaa ccttcaagac cagggaggcc    2100
atccagcatg agtctggcat cctgggcccc ctgctgtatg ggaggtggg ggacaccctg     2160 ctgatcatct tcaagaacca ggccagcagg ccctacaaca tctaccccca tggcatcact    2220
gatgtgaggc ccctgtacag caggaggctg cccaagggg tgaagcacct gaaggacttc     2280
cccatcctgc tggggagat cttcaagtac aagtggactg tgactgtgga ggatggcccc     2340
accaagtctg accccaggtg cctgaccaga tactacagca gctttgtgaa catggagagg    2400
gacctggcct ctggcctgat ggcccctg ctgatctgct acaaggagtc tgtggaccag      2460
aggggcaacc agatcatgtc tgacaagagg aatgtgatcc tgttctctgt gtttgatgag    2520
aacaggagct ggtacctgac tgagaacatc cagaggttcc tgcccaaccc tgctggggtg    2580
cagctggagg accctgagtt ccaggccagc aacatcatgc acagcatcaa tggctatgtg    2640
tttgacagcc tgcagctgtc tgtgtgcctg catgaggtgg cctactggta catcctgagc    2700
attggggccc agactgactt cctgtctgtg ttcttctctg gctacacctt caagcacaag    2760
atggtgtatg aggacaccct gaccctgttc cccttctctg gggagactgt gttcatgagc    2820
atggagaacc ctggcctgtg gattctgggc tgccacaact ctgacttcag gaacaggggc    2880
atgactgccc tgctgaaagt ctccagctgt gacaagaaca ctgggggacta ctatgaggac   2940 agctatgagg acatctctgc ctacctgctg agcaagaaca atgccattga gcccaggagc    3000
ttcagccaga accccccagt gctgaagagg caccagaggg agatcaccag gaccaccctg    3060
cagtctgacc aggaggagat tgactatgat gacaccatct ctgtggagat gaagaaggag    3120
gactttgaca tctacgacga ggacgagaac cagagcccca ggagcttcca agaagaagacc   3180 aggcactact tcattgctgc tgtggagagg ctgtgggact atggcatgag cagcagcccc    3240
catgtgctga ggaacagggc ccagtctggc tctgtgcccc agttcaagaa ggtggtgttc    3300
caggagttca ctgatggcag cttcacccag cccctgtaca gaggggagct gaatgagcac    3360
ctgggcctgc tgggccccta catcagggct gaggtggagg acaacatcat ggtgaccttc    3420
aggaaccagg ccagcaggcc ctacagcttc tacagcagcc tgatcagcta tgaggaggac    3480
cagaggcagg ggctgagcc caggaagaac tttgtgaagc ccaatgaaac caagacctac    3540
ttctggaagg tgcagcacca catggccccc accaaggatg agtttgactg caaggcctgg    3600
gcctacttct ctgatgtgga cctggagaag gatgtgcact ctggcctgat ggcccctg     3660 ctggtgtgcc acaccaacac cctgaaccct gcccatggca ggcaggtgac tgtgcaggag    3720
tttgccctgt tcttcaccat cttttgatgaa accaagagct ggtacttcac tgagaacatg   3780
gagaggaact gcagggcccc ctgcaacatc cagatggagg acccccacctt caaggagaac   3840 tacaggttcc atgccatcaa tggctacatc atggacaccc tgcctggcct ggtgatggcc    3900
caggaccaga ggatcaggtg gtacctgctg agcatgggca gcaatgagaa catccacagc    3960
atccacttct ctggccatgt gttcactgtg aggaagaagg aggagtacaa gatggccctg    4020
tacaacctgt accctgggt gtttgagact gtggagatgc tgcccagcaa ggctggcatc    4080
tggagggtgg agtgcctgat tggggagcac ctgcatgctg gcatgagcac cctgttcctg    4140
gtgtacagca acaagtgcca gacccccctg ggcatggcct ctggccacat cagggacttc    4200
cagatcactg cctctggcca gtatggccag tgggccccca gctggccag gctgcactac    4260 tctggcagca tcaatgcctg gagcaccaag gagcccttca gctggatcaa ggtggacctg    4320
```

```
ctggccccca tgatcatcca tggcatcaag acccaggggg ccaggcagaa gttcagcagc   4380
ctgtacatca gccagttcat catcatgtac agcctggatg caagaagtg gcagacctac    4440 aggggcaaca gcactggcac cctgatggtg ttctttggca atgtggacag ctctggcatc   4500
aagcacaaca tcttcaaccc ccccatcatt gccagataca tcaggctgca ccccacccac   4560
tacagcatca ggagcaccct gaggatggag ctgatgggct gtgacctgaa cagctgcagc   4620
atgcccctgg gcatggagag caaggccatc tctgatgccc agatcactgc cagcagctac   4680
ttcaccaaca tgtttgccac ctggagcccc agcaaggcca ggctgcacct gcagggcagg   4740
agcaatgcct ggaggcccca ggtcaacaac cccaaggagt ggctgcaggt ggacttccag   4800
aagaccatga aggtgactgg ggtgaccacc caggggtga agagcctgct gaccagcatg    4860
tatgtgaagg agttcctgat cagcagcagc caggatggcc accagtggac cctgttcttc   4920
cagaatggca aggtgaaggt gttccagggc aaccaggaca gcttcacccc tgtggtgaac   4980
agcctggacc ccccctgct gaccagatac ctgaggattc accccagag ctgggtgcac     5040 cagattgccc tgaggatgga ggtgctgggc tgtgaggccc aggacctgta ctgacctcga   5100
ggaataaagg aaatttattt tcattgcaat agtgtgttgg tttttttgtgt cacgtggcgg   5160 ccgcaggaac ccctagtgat ggagttggcc actccctctc tgcgcgctcg ctcgctcact   5220
gaggccgggc gaccaaaggt cgcccgacgc ccgggctttg cccgggcggc ctcagtgagc   5280
gagcgagcgc gcagagaggg agtggccaa                                    5309

<210> SEQ ID NO 27
<211> LENGTH: 5532
<212> TYPE: DNA
<213> ORGANISM: Adeno-Associated Virus 2

<400> SEQUENCE: 27
ttggccactc cctctctgcg cgctcgctcg ctcactgagg ccgcccgggc aaagcccggg     60
cgtcgggcga cctttggtcg cccggcctca gtgagcgagc gagcgcgcag agagggagtg    120
gccaactcca tcactagggg ttcctgcggc cgcacgcgtg ttttcgaccc ctctcacact    180
acctaaacca cgccaggaca acctctgctc ctctccaccg aaattccaag gggtcgagtg    240
gatgttggag gtggcatggg cccagagagg tctctgacct ctgccccagc tccaaggtca    300
gcaggcaggg agggctgtgt gtttgctgtt tgctgcttgc aatgtttgcc cattttaggg    360
acatgagtag gctgaagttt gttcagtgtg gacttcagag gcagcacaca aacagctgct    420
ggaggatggg aactgagggg ttggaagggg cagggtgag cccagaaact cctgtgtgcc     480
tctgagcctg cagacgcgaa acgtcgactg gacacaggac gctgtggttt ctgagccagg    540
gggcgactca gatcccagcc agtggactta gcccctgttt gctcctccga taactggggt    600
gaccttggtt aatattcacc agcagcctcc cccgttgccc ctctggatcc actgcttaaa    660 tacgacgag acagggccc tgtctcctca gcttcaggca ccaccactga cctgggacag     720
tgaatcgtaa gtatgccttt cactgcgaga ggttctggag aggcttctga gctccccatg    780
gcccaggcag gcagcaggtc tggggcagga gggggttgt ggagtgcctt gactcggggc     840
ctggcccccc catctctgtc ttgcaggaca attgccgtct tctgtctcgt ggggcatcct    900
cctgctggca ggcctgtgct gcctggtccc tgcgatcgcc accatgcaga ttgagctgag   960
cacctgcttc ttcctgtgcc tgctgaggtt ctgcttctct gccaccagga gatactacct   1020
gggggctgtg gagctgagct gggactacat gcagtctgac ctgggggagc tgcctgtgga   1080
```

```
tgccaggttc cccccagag tgcccaagag cttcccttc aacacctctg tggtgtacaa    1140
gaagaccctg tttgtggagt tcactgacca cctgttcaac attgccaagc ccaggccccc    1200
ctggatgggc ctgctgggcc ccaccatcca ggctgaggtg tatgacactg tggtgatcac    1260
cctgaagaac atggccagcc accctgtgag cctgcatgct gtgggggtga gctactggaa    1320
ggcctctgag ggggctgagt atgatgacca gaccagccag agggagaagg aggatgacaa    1380
ggtgttccct gggggcagcc acacctatgt gtggcaggtg ctgaaggaga atggcccccat   1440
ggcctctgac cccctgtgcc tgacctacag ctacctgagc catgtggacc tggtgaagga    1500
cctgaactct ggcctgattg gggccctgct ggtgtgcagg gagggcagcc tggccaagga    1560
gaagacccag accctgcaca agttcatcct gctgtttgct gtgtttgatg agggcaagag    1620
ctggcactct gaaaccaaga acagcctgat gcaggacagg gatgctgcct ctgccagggc    1680
ctggcccaag atgcacactg tgaatggcta tgtgaacagg agcctgcctg gcctgattgg    1740
ctgccacagg aagtctgtgt actggcatgt gattggcatg gcaccaccc ctgaggtgca     1800
cagcatcttc ctggagggcc acccttcct ggtcaggaac acaggcagg ccagcctgga     1860
gatcagcccc atcaccttcc tgactgccca accctgctg atggacctgg gccagttcct    1920
gctgttctgc cacatcagca gccaccagca tgatggcatg gaggcctatg tgaaggtgga    1980
cagctgccct gaggagcccc agctgaggat gaagaacaat gaggaggctg aggactatga    2040
tgatgacctg actgactctg agatggatgt ggtgaggttt gatgatgaca cagccccag    2100
cttcatccag atcaggtctg tggccaagaa gcaccccaag acctgggtgc actacattgc    2160
tgctgaggag gaggactggg actatgcccc cctggtgctg gcccctgatg acaggagcta    2220
caagagccag tacctgaaca atggcccca gaggattggc aggaagtaca gaaggtcag    2280
gttcatggcc tacactgatg aaaccttcaa gaccagggag gccatccagc atgagtctgg    2340
catcctgggc cccctgctgt atgggaggt gggggacacc ctgctgatca tcttcaagaa    2400
ccaggccagc aggccctaca acatctaccc ccatggcatc actgatgtga ggcccctgta    2460
cagcaggagg ctgcccaagg gggtgaagca cctgaaggac ttccccatcc tgcctgggga   2520
gatcttcaag tacaagtgga ctgtgactgt ggaggatggc cccaccaagt ctgaccccag    2580
gtgcctgacc agatactaca gcagctttgt gaacatggag agggacctgg cctctggcct    2640
gattggcccc ctgctgatct gctacaagga gtctgtggac cagaggggca accagatcat    2700
gtctgacaag aggaatgtga tcctgttctc tgtgtttgat gagaacagga gctggtacct    2760
gactgagaac atccagaggt tcctgcccaa ccctgctggg gtgcagctgg aggaccctga   2820
gttccaggcc agcaacatca tgcacagcat caatggctat gtgtttgaca gcctgcagct    2880
gtctgtgtgc ctgcatgagg tggcctactg gtacatcctg agcattgggg cccagactga    2940
cttcctgtct gtgttcttct ctggctacac cttcaagcac aagatggtgt atgaggacac    3000
cctgaccctg ttccccttct ctggggagac tgtgttcatg agcatggaga accctggcct    3060
gtggattctg gctgccaca actctgactt caggaacagg gcatgactg ccctgctgaa     3120
agtctccagc tgtgacaaga acactgggga ctactatgag acagctatg aggacatctc    3180
tgcctacctg ctgagcaaga caatgccat tgagcccagg agcttcagcc agaacccccc    3240
agtgctgaag aggcaccaga gggagatcac caggaccacc ctgcagtctg accaggagga    3300
gattgactat gatgacacca tctctgtgga gatgaagaag gaggactttg acatctacga    3360
cgaggacgag aaccagagcc caggagctt ccagaagaag accaggcact acttcattgc    3420
tgctgtggag aggctgtggg actatggcat gagcagcagc ccccatgtgc tgaggaacag    3480
```

```
ggcccagtct ggctctgtgc cccagttcaa gaaggtggtg ttccaggagt tcactgatgg   3540
cagcttcacc cagcccctgt acagagggga gctgaatgag cacctgggcc tgctgggccc   3600
ctacatcagg gctgaggtgg aggacaacat catggtgacc ttcaggaacc aggccagcag   3660
gccctacagc ttctacagca gcctgatcag ctatgaggag gaccagaggc aggggggctga  3720 gcccaggaag aactttgtga agcccaatga aaccaagacc tacttctgga aggtgcagca   3780
ccacatggcc cccaccaagg atgagtttga ctgcaaggcc tgggcctact tctctgatgt   3840
ggacctggag aaggatgtgc actctggcct gattggcccc tgctggtgt gccacaccaa    3900 cacccctgaac cctgcccatg gcaggcaggt gactgtgcag gagtttgccc tgttcttcac  3960
catctttgat gaaaccaaga gctggtactt cactgagaac atggagagga actgcagggc  4020
cccctgcaac atccagatgg aggacccccac cttcaaggag aactacaggt tccatgccat  4080
caatggctac atcatggaca ccctgcctgg cctggtgatg gcccaggacc agaggatcag  4140
gtggtacctg ctgagcatgg gcagcaatga aacatccac agcatccact tctctggcca   4200
tgtgttcact gtgaggaaga aggaggagta caagatggcc ctgtacaacc tgtaccctgg  4260
ggtgtttgag actgtggaga tgctgcccag caaggctggc atctggaggg tggagtgcct   4320
gattggggag cacctgcatg ctggcatgag caccctgttc ctggtgtaca gcaacaagtg  4380
ccagaccccc ctgggcatgg cctctggcca catcagggac ttccagatca ctgcctctgg  4440
ccagtatggc cagtgggccc ccaagctggc caggctgcac tactctggca gcatcaatgc  4500
ctggagcacc aaggagccct tcagctggat caaggtggac ctgctggccc ccatgatcat  4560
ccatggcatc aagacccagg gggccaggca gaagttcagc agcctgtaca tcagccagtt  4620
catcatcatg tacagcctgg atggcaagaa gtggcagacc tacaggggca acagcactgg  4680
caccctgatg gtgttctttg gcaatgtgga cagctctggc atcaagcaca acatcttcaa  4740 ccccccccatc attgccagat acatcaggct gcaccccacc cactacagca tcaggagcac  4800
cctgaggatg gagctgatgg gctgtgacct gaacagctgc agcatgcccc tgggcatgga  4860
gagcaaggcc atctctgatg cccagatcac tgccagcagc tacttcacca acatgtttgc  4920
cacctggagc cccagcaagg ccaggctgca cctgcagggc aggagcaatg cctggaggcc  4980
ccaggtcaac aaccccaagg agtggctgca ggtggacttc cagaagacca tgaaggtgac  5040
tggggtgacc acccagggg tgaagagcct gctgaccagc atgtatgtga aggagttcct  5100
gatcagcagc agccaggatg gccaccagtg gaccctgttc ttccagaatg gcaaggtgaa  5160
ggtgttccag ggcaaccagg acagcttcac ccctgtggtg aacagcctgg acccccccct  5220
gctgaccaga tacctgagga ttcacccccca gagctgggtg caccagattg ccctgaggat  5280
ggaggtgctg ggctgtgagg cccaggacct gtactgacct cgaggaataa ggaaatttta  5340
ttttcattgc aatagtgtgt tggttttttg tgtcacgtgg cggccgcagg aacccctagt  5400
gatggagttg gccactccct ctctcgcgcg tcgctcgctc actgaggccg ggcgaccaaa  5460
ggtcgcccga cgcccgggct tgcccgggc ggcctcagtg agcgagcgag cgcgcagaga  5520
gggagtggcc aa                                                      5532
```

<210> SEQ ID NO 28
<211> LENGTH: 5877
<212> TYPE: DNA
<213> ORGANISM: Adeno-Associated Virus 2

<400> SEQUENCE: 28

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgcggc cgcacgcgtg ttttcgaccc ctctcacact     180
acctaaacca cgccaggaca acctctgctc ctctccaccg aaattccaag gggtcgagtg     240
gatgttggag gtggcatggg cccagagagg tctctgacct ctgcccagc tccaaggtca      300
gcaggcaggg agggctgtgt gtttgctgtt tgctgcttgc aatgtttgcc cattttaggg     360
acatgagtag gctgaagttt gttcagtgtg gacttcagag gcagcacaca aacagctgct     420
ggaggatggg aactgagggg ttggaagggg gcagggtgag cccagaaact cctgtgtgcc     480
tctgagcctg cagacgcgaa acgtcgacag gttaattttt aaaaagcagt caaaagtcca     540
agtggccctt ggcagcattt actctctctg tttgctctgg ttaataatct caggagcaca     600
aacattcctg gaggcaggag aagaaatcaa catcctggac ttatcctctg ggcctctccc     660
cacccccagg agaggctcag gttaattttt aaaaagcagt caaaagtcca agtggccctt     720
ggcagcattt actctctctg tttgctctgg ttaataatct caggagcaca aacattcctg     780
gaggcaggag aagaaatcaa catcctggac ttatcctctg ggcctctccc cacccccagg     840
agaggctgtc gactggacac aggacgctgt ggtttctgag ccaggggcg actcagatcc      900
cagccagtgg acttagcccc tgtttgctcc tccgataact ggggtgacct tggttaatat     960
tcaccagcag cctcccccgt tgcccctctg gatccactgc ttaaatacgg acgaggacag    1020
ggccctgtct cctcagcttc aggcaccacc actgacctgg gacagtgaat cgtaagtatg    1080
cctttcactg cgagaggttc tggagaggct tctgagctcc ccatggccca ggcaggcagc    1140
aggtctgggg caggaggggg gttgtggagt gccttgactc ggggcctggc cccccatct     1200
ctgtcttgca ggacaattgc cgtcttctgt ctcgtgggc atcctcctgc tggcaggcct     1260
gtgctgcctg gtccctgcga tcgccaccat gcagattgag ctgagcacct gcttcttcct    1320
gtgcctgctg aggttctgct tctctgccac caggagatac tacctggggg ctgtggagct    1380
gagctgggac tacatgcagt ctgacctggg ggagctgcct gtggatgcca ggttcccccc    1440
cagagtgccc aagagcttcc ccttcaacac ctctgtggtg tacaagaaga ccctgtttgt    1500
ggagttcact gaccacctgt tcaacattgc caagcccagg ccccctgga tgggcctgct     1560
gggccccacc atccaggctg aggtgtatga cactgtggtg atcaccctga gaacatggc     1620
cagccaccct gtgagcctgc atgctgtggg ggtgagctac tggaaggcct ctgaggggc     1680
tgagtatgat gaccagacca gccagaggga aaggaggat gacaaggtgt tccctggggg    1740
cagccacacc tatgtgtggc aggtgctgaa ggagaatggc cccatggcct ctgaccccct    1800
gtgcctgacc tacagctacc tgagccatgt ggacctggtg aaggaccga actctggcct    1860
gattggggcc ctgctggtgt gcagggaggg cagcctggcc aaggagaaga cccagaccct    1920
gcacaagttc atcctgctgt ttgctgtgtt tgatgagggc aagagctggc actctgaaac    1980
caagaacagc ctgatgcagg acagggatgc tgcctctgcc agggcctggc caagatgca     2040
cactgtgaat ggctatgtga acaggagcct gcctggcctg attggctgcc acaggaagtc    2100
tgtgtactgg catgtgattg gcatgggcac caccctgag gtgcacagca tcttcctgga    2160
gggccacacc ttcctggtca ggaaccacag gcaggccagc ctggagatca gccccatcac    2220
cttcctgact gcccagaccc tgctgatgga cctgggccag ttcctgctgt tctgccacat    2280
cagcagccac cagcatgatg gcatggaggc ctatgtgaag gtggacagct gccctgagga    2340
gccccagctg aggatgaaga acaatgagga ggctgaggac tatgatgatg acctgactga    2400
```

```
ctctgagatg gatgtggtga ggtttgatga tgacaacagc cccagcttca tccagatcag   2460
gtctgtggcc aagaagcacc ccaagacctg ggtgcactac attgctgctg aggaggagga   2520
ctgggactat gcccccctgg tgctggcccc tgatgacagg agctacaaga gccagtacct   2580
gaacaatggc ccccagagga ttggcaggaa gtacaagaag gtcaggttca tggcctacac   2640
tgatgaaacc ttcaagacca gggaggccat ccagcatgag tctggcatcc tgggccccct   2700
gctgtatggg gaggtggggg acaccctgct gatcatcttc aagaaccagg ccagcaggcc   2760
ctacaacatc taccccccatg gcatcactga tgtgaggccc ctgtacagca ggaggctgcc   2820 caaggggggtg aagcacctga aggacttccc catcctgcct ggggagatct tcaagtacaa   2880
gtggactgtg actgtggagg atggccccac caagtctgac cccaggtgcc tgaccagata   2940
ctacagcagc tttgtgaaca tggagaggga cctggcctct ggcctgattg ccccctgct   3000 gatctgctac aaggagtctg tggaccagag gggcaaccag atcatgtctg acaagaggaa   3060
tgtgatcctg ttctctgtgt ttgatgagaa caggagctgg tacctgactg agaacatcca   3120
gaggttcctg cccaaccctg ctggggtgca gctggaggac cctgagttcc aggccagcaa   3180
catcatgcac agcatcaatg ctatgtgtt tgacagcctg cagctgtctg tgtgcctgca   3240
tgaggtggcc tactggtaca tcctgagcat tggggcccag actgacttcc tgtctgtgtt   3300
cttctctggc tacaccttca gcacaagat ggtgtatgag acaccctga ccctgttccc   3360 cttctctggg gagactgtgt tcatgagcat ggagaaccct ggcctgtgga ttctgggctg   3420
ccacaactct gacttcagga acaggggcat gactgccctg ctgaaagtct ccagctgtga   3480
caagaacact ggggactact atgaggacag ctatgaggac atctctgcct acctgctgag   3540
caagaacaat gccattgagc ccaggagctt cagccagaac ccccccagtgc tgaagaggca   3600 ccagagggag atcaccagga ccaccctgca gtctgaccag gaggagattg actatgatga   3660
caccatctct gtggagatga agaaggagga ctttgacatc tacgacgagg acgagaacca   3720
gagccccagg agcttccaga agaagaccag gcactacttc attgctgctg tggagaggct   3780
gtgggactat ggcatgagca gcagccccca tgtgctgagg aacagggccc agtctggctc   3840 tgtgcccag ttcaagaagg tggtgttcca ggagttcact gatggcagct tcacccagcc   3900
cctgtacaga ggggagctga atgagcacct gggcctgctg gcccctaca tcagggctga   3960 ggtggaggac aacatcatgg tgaccttcag gaaccaggcc agcaggccct acagcttcta   4020
cagcagcctg atcagctatg aggaggacca gaggcagggg gctgagccca ggaagaactt   4080
tgtgaagccc aatgaaacca agacctactt ctggaaggtg cagcaccaca tggccccccac   4140 caaggatgag tttgactgca aggcctgggc ctacttctct gatgtggacc tggagaagga   4200
tgtgcactct ggcctgattg ccccctgct ggtgtgccac accaacaccc tgaaccctgc   4260
ccatggcagg caggtgactg tgcaggagtt tgccctgttc ttcaccatct ttgatgaaac   4320
caagagctgg tacttcactg agaacatgga gaggaactgc agggcccct gcaacatcca   4380 gatggaggac cccaccttca aggagaacta caggttccat gccatcaatg gctacatcat   4440
ggacaccctg cctggcctgg tgatggccca ggaccagagg atcaggtggt acctgctgag   4500
catgggcagc aatgagaaca tccacagcat ccacttctct ggccatgtgt tcactgtgag   4560
gaagaaggag gagtacaaga tggcccctgta caacctgtac cctgggggtgt ttgagactgt   4620 ggagatgctg cccagcaagg ctggcatctg gagggtggag tgcctgattg gggagcacct   4680
gcatgctggc atgagcaccc tgttcctggt gtacagcaac aagtgccaga ccccctggg   4740
```

```
catggcctct ggccacatca gggacttcca gatcactgcc tctggccagt atggccagtg    4800 ggccccaag ctggccaggc tgcactactc tggcagcatc aatgcctgga gcaccaagga    4860
gcccttcagc tggatcaagg tggacctgct ggcccccatg atcatccatg catcaagac    4920 ccagggggcc aggcagaagt tcagcagcct gtacatcagc cagttcatca tcatgtacag    4980
cctggatggc aagaagtggc agacctacag gggcaacagc actggcaccc tgatggtgtt    5040
ctttggcaat gtggacagct ctggcatcaa gcacaacatc ttcaaccccc ccatcattgc    5100
cagatacatc aggctgcacc ccacccacta cagcatcagg agcaccctga ggatggagct    5160
gatgggctgt gacctgaaca gctgcagcat gcccctgggc atggagagca aggccatctc    5220
tgatgcccag atcactgcca gcagctactt caccaacatg tttgccacct ggagccccag    5280
caaggccagg ctgcacctgc agggcaggag caatgcctgg aggcccccag tcaacaaccc    5340
caaggagtgg ctgcaggtgg acttccagaa gaccatgaag gtgactgggg tgaccaccca    5400
gggggtgaag agcctgctga ccagcatgta tgtgaaggag ttcctgatca gcagcagcca    5460
ggatggccac cagtggaccc tgttcttcca gaatggcaag gtgaaggtgt tccagggcaa    5520
ccaggacagc ttcaccccctg tggtgaacag cctggacccc ccctgctga ccagataccct   5580 gaggattcac ccccagagct gggtgcacca gattgccctg aggatggagg tgctgggctg    5640
tgaggcccag gacctgtact gacctcgagg aataaaggaa atttatttc attgcaatag    5700 tgtgttggtt ttttgtgtca cgtggcgcc gcaggaaccc ctagtgatgg agttggccac    5760
tccctctctg cgcgctcgct cgctcactga ggccgggcga ccaaaggtcg cccgacgccc    5820
gggctttgcc cggcggcct cagtgagcga gcgagcgcgc agagagggag tggccaa       5877
```

<210> SEQ ID NO 29
<211> LENGTH: 6054
<212> TYPE: DNA
<213> ORGANISM: Adeno-Associated Virus 2

<400> SEQUENCE: 29

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgcggc cgcacgcgtg ttttcgaccc ctctcacact     180
acctaaacca cgccaggaca acctctgctc ctctccaccg aaattccaag ggtcgagtg     240 gatgttggag gtggcatggg cccagagagg tctctgacct ctgccccagc tccaaggtca    300
gcaggcaggg agggctgtgt gtttgctgtt tgctgcttgc aatgtttgcc cattttaggg    360
acatgagtag gctgaagttt gttcagtgtg gacttcagag gcagcacaca aacagctgct    420
ggaggatggg aactgagggg ttggaagggg gcagggtgag cccagaaact cctgtgtgcc    480
tctgagcctg cagacgcgaa acgtcgacag gttaattttt aaaaagcagt caaaagtcca    540
agtggccctt ggcagcattt actctctctg tttgctctgg ttaataatct caggagcaca    600 acattcctg gaggcaggag aagaaatcaa catcctggac ttatcctctg ggcctctccc    660
cacccccagg agaggctcag gttaattttt aaaaagcagt caaaagtcca agtggccctt    720
ggcagcattt actctctctg tttgctctgg ttaataatct caggagcaca acattcctg    780 gaggcaggag aagaaatcaa catcctggac ttatcctctg ggcctctccc cacccccagg    840
agaggctgtc gactgacac aggacgctgt ggtttctgag ccaggggcg actcagatcc     900 cagccagtga acttagcccc tgtttgctcc tccgataact gggtgacct tggttaatat    960 tcaccagcag cctccccccgt tgcccctctg gatccactgc ttaaatacgg acgaggacag   1020
```

```
ggccctgtct cctcagcttc aggcaccacc actgacctgg gacagtgaat cgtaagtatg   1080
cctttcactg cgagaggttc tggagaggct tctgagctcc ccatggccca ggcaggcagc   1140
aggtctgggg caggagggggg gttgtggagt gccttgactc ggggcctggc ccccccatct  1200
ctgtcttgca ggacaattgc cgtcttctgt ctcgtgggc atcctcctgc tggcaggcct    1260
gtgctgcctg gtccctgcga tcgccaccat gcagattgag ctgagcacct gcttcttcct   1320
gtgcctgctg aggttctgct tctctgccac caggagatac tacctggggg ctgtggagct   1380
gagctgggac tacatgcagt ctgacctggg ggagctgcct gtggatgcca ggttcccccc   1440
cagagtgccc aagagcttcc ccttcaacac ctctgtggtg tacaagaaga ccctgtttgt   1500
ggagttcact gaccacctgt tcaacattgc caagcccagg ccccctgga tgggcctgct    1560 gggccccacc atccaggctg aggtgtatga cactgtggtg atcaccctga gaacatggc    1620 cagccaccct gtgagcctgc atgctgtggg ggtgagctac tggaaggcct ctgagggggc   1680
tgagtatgat gaccagacca gccagaggga aaggaggat gacaaggtgt ccctgggggg    1740
cagccacacc tatgtgtggc aggtgctgaa ggagaatggc cccatggcct ctgacccct    1800 gtgcctgacc tacagctacc tgagccatgt ggacctggtg aaggacctga actctggcct   1860
gattggggcc ctgctggtgt gcagggaggg cagcctggcc aaggagaaga cccagaccct   1920
gcacaagttc atcctgctgt ttgctgtgtt tgatgagggc aagagctggc actctgaaac   1980
caagaacagc ctgatgcagg acagggatgc tgcctctgcc agggcctggc ccaagatgca   2040
cactgtgaat ggctatgtga acaggagcct gcctggcctg attggctgcc acaggaagtc   2100
tgtgtactgg catgtgattg gcatgggcac cacccctgag gtgcacagca tcttcctgga   2160
gggccacacc ttcctggtca ggaaccacag gcaggccagc ctggagatca gccccatcac   2220
cttcctgact gcccagaccc tgctgatgga cctgggccag ttcctgctgt tctgccacat   2280
cagcagccac cagcatgatg gcatggaggc ctatgtgaag gtggacagct gccctgagga   2340
gccccagctg aggatgaaga acaatgagga ggctgaggac tatgatgatg acctgactga   2400
ctctgagatg gatgtggtga ggtttgatga tgacaacagc cccagcttca tccagatcag   2460
gtctgtggcc aagaagcacc ccaagacctg ggtgcactac attgctgctg aggaggagga   2520
ctgggactat gccccctgg tgctggcccc tgatgacagg agctacaaga gccagtacct    2580
gaacaatggc ccccagagga ttggcaggaa gtacaagaag gtcaggttca tggcctacac   2640
tgatgaaacc ttcaagacca gggaggccat ccagcatgag tctggcatcc tgggccccct   2700
gctgtatggg gaggtggggg acaccctgct gatcatcttc aagaaccagg ccagcaggcc   2760
ctacaacatc tacccccatg gcatcactga tgtgaggccc ctgtacagca ggaggctgcc   2820
caagggggtg aagcacctga aggacttccc catcctgcct gggagatct caagtacaa    2880 gtggactgtg actgtggagg atggcccccac caagtctgac cccaggtgcc tgaccagata   2940
ctacagcagc tttgtgaaca tggagaggga cctggcctct ggcctgattg cccctgct    3000 gatctgctac aaggagtctg tggaccagag gggcaaccag atcatgtctg acaagaggaa   3060
tgtgatcctg ttctctgtgt ttgatgagaa caggagctgg tacctgactg agaacatcca   3120
gaggttcctg cccaaccctg ctggggtgca gctggaggac cctgagttcc aggccagcaa   3180
catcatgcac agcatcaatg gctatgtgtt tgacagcctg cagctgtctg tgtgcctgca   3240
tgaggtggcc tactggtaca tcctgagcat tggggcccag actgacttcc tgtctgtgtt   3300
cttctctggc tacaccttca gcacaagat ggtgtatgag gacaccctga ccctgttccc   3360
```

```
cttctctggg gagactgtgt tcatgagcat ggagaaccct ggcctgtgga ttctgggctg    3420
ccacaactct gacttcagga acaggggcat gactgccctg ctgaaagtct ccagctgtga    3480
caagaacact ggggactact atgaggacag ctatgaggac atctctgcct acctgctgag    3540
caagaacaat gccattgagc ccaggagctt cagccagaac cccccagtgc tgaagaggca    3600
ccagagggag atcaccagga ccaccctgca gtctgaccag gaggagattg actatgatga    3660
caccatctct gtggagatga agaaggagga ctttgacatc tacgacgagg acgagaacca    3720
gagccccagg agcttccaga agaagaccag gcactacttc attgctgctg tggagaggct    3780
gtgggactat ggcatgagca gcagccccca tgtgctgagg aacagggccc agtctggctc    3840
tgtgccccag ttcaagaagg tggtgttcca ggagttcact gatggcagct tcacccagcc    3900
cctgtacaga ggggagctga atgagcacct gggcctgctg gcccctaca tcagggctga     3960 ggtggaggac aacatcatgg tgaccttcag gaaccaggcc agcaggccct acagcttcta    4020
cagcagcctg atcagctatg aggaggacca gaggcagggg gctgagccca ggaagaactt    4080
tgtgaagccc aatgaaacca agacctactt ctggaaggtg cagcaccaca tggcccccac    4140
caaggatgag tttgactgca aggcctgggc ctacttctct gatgtggacc tggagaagga    4200
tgtgcactct ggcctgattg ccccctgct ggtgtgccac accaacaccc tgaaccctgc     4260
ccatggcagg caggtgactg tgcaggagtt tgccctgttc ttcaccatct ttgatgaaac    4320
caagagctgg tacttcactg agaacatgga aggaactgc agggcccct gcaacatcca      4380 gatggaggac cccaccttca aggagaacta caggttccat gccatcaatg ctacatcat     4440 ggacaccctg cctggcctgg tgatggccca ggaccagagg atcaggtggt acctgctgag    4500
catgggcagc aatgagaaca tccacagcat ccacttctct ggccatgtgt tcactgtgag    4560
gaagaaggag gagtacaaga tggccctgta caacctgtac cctggggtgt ttgagactgt    4620
ggagatgctg cccagcaagg ctggcatctg gagggtggag tgcctgattg gggagcacct    4680
gcatgctgga atgagcaccc tgttcctggt gtacagcaac aagtgccaga ccccctggg     4740 catggcctct ggccacatca gggacttcca gatcactgcc tctggccagt atggccagtg    4800 ggccccaag ctggccaggc tgcactactc tggcagcatc aatgcctgga gcaccaagga     4860
gcccttcagc tggatcaagg tggacctgct ggcccccatg atcatccatg gcatcaagac    4920
ccagggggcc aggcagaagt tcagcagcct gtacatcagc cagttcatca tcatgtacag    4980
cctggatggc aagaagtggc agacctacag gggcaacagc actggcaccc tgatggtgtt    5040
ctttggcaat gtggacagct ctggcatcaa gcacaacatc ttcaaccccc ccatcattgc    5100
cagatacatc aggctgcacc ccacccacta cagcatcagg agcaccctga ggatggagct    5160
gatgggctgt gacctgaaca gctgcagcat gcccctgggc atggagagca aggccatctc    5220
tgatgcccag atcactgcca gcagctactt caccaacatg tttgccacct ggagccccag    5280
caaggccagg ctgcacctgc agggcaggag caatgcctgg aggcccccag tcaacaaccc    5340
caaggagtgg ctgcaggtgg acttccagaa gaccatgaag gtgactgggg tgaccaccca    5400
gggggtgaag agcctgctga ccagcatgta tgtgaaggag ttcctgatca gcagcagcca    5460
ggatggccac cagtggaccc tgttcttcca gaatggcaag gtgaaggtgt tccagggcaa    5520
ccaggacagc ttcaccctg tggtgaacag cctggacccc ccctgctga ccagatacct      5580 gaggattcac cccagagct gggtgcacca gattgccctg aggatggagg tgctgggctg     5640
tgaggcccag gacctgtact gacctcgagg tgtgccttct agttgccagc catctgttgt    5700
ttgcccctcc cccgtgcctt ccttgaccct ggaaggtgcc actcccactg tcctttccta    5760
```

```
ataaaatgag gaaattgcat cgcattgtct gagtaggtgt cattctattc tgggggtgg    5820 ggtggggcag gacagcaagg gggaggattg ggaagacaat agcaggcatg ctggggatgc    5880
ggtgggctct atgggcacgt ggcggccgca ggaaccccta gtgatggagt tggccactcc    5940
ctctctgcgc gctcgctcgc tcactgaggc cgggcgacca aggtcgccc gacgcccggg    6000 cttTGCCCGG gcggcctcag tgagcgagcg agcgcgcaga gagggagtgg ccaa          6054
```

<210> SEQ ID NO 30
<211> LENGTH: 6054
<212> TYPE: DNA
<213> ORGANISM: Adeno-Associated Virus 2

<400> SEQUENCE: 30

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgcggc cgcacgcgtg ttttcgaccc ctctcacact     180 acctaaaacca cgccaggaca acctctgctc ctctccaccg aaattccaag gggtcgagtg    240
gatgttggag gtggcatggg cccagagagg tctctgacct ctgccccagc tccaaggtca    300
gcaggcaggg agggctgtgt gtttgctgtt tgctgcttgc aatgtttgcc cattttaggg    360
acatgagtag gctgaagttt gttcagtgtg gacttcagag gcagcacaca aacagctgct    420
ggaggatggg aactgagggg ttggaagggg gcagggtgag cccagaaact cctgtgtgcc    480
tctgagcctg cagacgcgaa acgtcgaagc ctctcctggg ggtggggaga ggcccagagg    540
ataagtccag gatgttgatt tcttctcctg cctccaggaa tgtttgtgct cctgagatta    600
ttaaccagag caaacagaga gagtaaatgc tgccaagggc cacttggact tttgactgct    660
ttttaaaaat taacctgagc ctctcctggg ggtggggaga ggcccagagg ataagtccag    720
gatgttgatt tcttctcctg cctccaggaa tgtttgtgct cctgagatta ttaaccagag    780
caaacagaga gagtaaatgc tgccaagggc cacttggact tttgactgct ttttaaaaat    840
taacctggtc gactggacac aggacgctgt ggtttctgag ccaggggcg actcagatcc     900 cagccagtgg acttagcccc tgtttgctcc tccgataact ggggtgacct tggttaatat    960
tcaccagcag cctcccccgt tgcccctctg gatccactgc ttaaatacgg acgaggacag   1020
ggccctgtct cctcagcttc aggcaccacc actgacctgg gacagtgaat cgtaagtatg   1080
cctttcactg cgagaggttc tggagaggct tctgagctcc ccatggccca ggcaggcagc   1140
aggtctgggg caggaggggg gttgtggagt gccttgactc ggggcctggc cccccatct   1200 ctgtcttgca ggacaattgc cgtcttctgt ctcgtgggc atcctcctgc tggcaggcct   1260
gtgctgcctg gtccctgcga tcgccaccat gcagattgag ctgagcacct gcttcttcct   1320
gtgcctgctg aggttctgct tctctgccac caggagatac tacctggggg ctgtggagct   1380
gagctgggac tacatgcagt ctgacctggg ggagctgcct gtggatgcca ggttcccccc   1440
cagagtgccc aagagcttcc ccttcaacac ctctgtggtg tacaagaaga cctgttttgt   1500
ggagttcact gaccacctgt tcaacattgc caagccaagg ccccctgga tgggcctgct   1560 gggccccacc atccaggctg aggtgtatga cactgtggtg atcaccctga gaacatggc   1620 cagccaccct gtgagcctgc atgctgtggg ggtgagctac tggaaggcct ctgaggggc   1680 tgagtatgat gaccagacca gccagaggga aaggaggat gacaaggtgt ccctggggg   1740 cagccacacc tatgtgtggc aggtgctgaa ggagaatggc cccatggcct ctgaccccct   1800
```

```
gtgcctgacc tacagctacc tgagccatgt ggacctggtg aaggacctga actctggcct   1860
gattggggcc ctgctggtgt gcagggaggg cagcctggcc aaggagaaga cccagaccct   1920
gcacaagttc atcctgctgt ttgctgtgtt tgatgagggc aagagctggc actctgaaac   1980
caagaacagc ctgatgcagg acagggatgc tgcctctgcc agggcctggc ccaagatgca   2040
cactgtgaat ggctatgtga acaggagcct gcctggcctg attggctgcc acaggaagtc   2100
tgtgtactgg catgtgattg gcatgggcac caccctgag gtgcacagca tcttcctgga   2160
gggccacacc ttcctggtca ggaaccacag gcaggccagc ctggagatca gccccatcac   2220
cttcctgact gcccagaccc tgctgatgga cctgggccag ttcctgctgt tctgccacat   2280
cagcagccac cagcatgatg gcatggaggc ctatgtgaag gtggacagct gccctgagga   2340
gccccagctg aggatgaaga caatgaggag ggctgaggac tatgatgatg acctgactga   2400
ctctgagatg gatgtggtga ggtttgatga tgacaacagc cccagcttca tccagatcag   2460
gtctgtggcc aagaagcacc ccaagacctg ggtgcactac attgctgctg aggaggagga   2520
ctgggactat gcccccctgg tgctggcccc tgatgacagg agctacaaga gccagtacct   2580
gaacaatggc ccccagagga ttggcaggaa gtacaagaag gtcaggttca tggcctacac   2640
tgatgaaacc ttcaagacca gggaggcat ccagcatgag tctggcatcc tgggcccct   2700
gctgtatggg gaggtggggg acaccctgct gatcatcttc aagaaccagg ccagcaggcc   2760
ctacaacatc tacccccatg gcatcactga tgtgaggccc ctgtacagca ggaggctgcc   2820
caagggggtg aagcacctga aggacttccc catcctgcct ggggagatct caagtacaa   2880
gtggactgtg actgtggagg atggcccac caagtctgac cccaggtgcc tgaccagata   2940
ctacagcagc tttgtgaaca tggagaggga cctggcctct ggcctgattg gcccctgct   3000
gatctgctac aaggagtctg tggaccagag gggcaaccag atcatgtctg acaagaggaa   3060
tgtgatcctg ttctctgtgt ttgatgagaa caggagctgg tacctgactg agaacatcca   3120
gaggttcctg cccaaccctg ctgggggtgca gctggaggac cctgagttcc aggccagcaa   3180
catcatgcac agcatcaatg gctatgtgtt tgacagcctg cagctgtctg tgcctgca   3240
tgaggtggcc tactgtgtaca tcctgagcat gggcccag actgacttcc tgtctgtgtt   3300
cttctctggc tacacttca agcacaagat ggtgatgag acaccctga ccctgttccc   3360
cttctctggg gagactgtgt tcatgagcat ggagaaccct ggcctgtgga ttctgggctg   3420
ccacaactct gacttcagga acaggggcat gactgccctg ctgaaagtct ccagctgtga   3480
caagaacact ggggactact atgaggacag ctatgaggac atctctgcct acctgctgag   3540
caagaacaat gccattgagc ccaggagctt cagccagaac ccccagtgc tgaagaggca   3600
ccagagggag atcaccagga ccaccctgca gtctgaccag gaggagattg actatgatga   3660
caccatctct gtggagatga agaaggagga cttgacatc tacgacgagg acgagaacca   3720
gagccccagg agcttccaga agaagaccag gcactactc attgctgctg tggagaggct   3780
gtgggactat ggcatgagca gcagccccca tgtgctgagg aacagggccc agtctggctc   3840
tgtgccccag ttcaagaagg tggtgttcca ggagttcact gatggcagct tcacccagcc   3900
cctgtacaga ggggagctga tgagcacct gggcctgctg gcccctaca tcagggctga   3960
ggtggaggac aacatcatgg tgaccttcag gaaccaggcc agcaggccct acagcttcta   4020
cagcagcctg atcagctatg aggaggacca gaggcagggg gctgagccca ggaagaactt   4080
tgtgaagccc aatgaaacca gacctactt ctggaaggtg cagcaccaca tggcccccac   4140
caaggatgag tttgactgca aggcctgggc ctacttctct gatgtggacc tggagaagga   4200
```

-continued

```
tgtgcactct ggcctgattg gccccctgct ggtgtgccac accaacaccc tgaaccctgc    4260
ccatggcagg caggtgactg tgcaggagtt tgccctgttc ttcaccatct ttgatgaaac    4320
caagagctgg tacttcactg agaacatgga gaggaactgc agggcccct gcaacatcca    4380 gatggaggac cccaccttca aggagaacta caggttccat gccatcaatg ctacatcat    4440 ggacaccctg cctggcctgg tgatggccca ggaccagagg atcaggtggt acctgctgag    4500
catgggcagc aatgagaaca tccacagcat ccacttctct ggccatgtgt tcactgtgag    4560
gaagaaggag gagtacaaga tggccctgta caacctgtac cctggggtgt ttgagactgt    4620
ggagatgctg cccagcaagg ctggcatctg gagggtggag tgcctgattg gggagcacct    4680
gcatgctggc atgagcaccc tgttcctggt gtacagcaac aagtgccaga cccccctggg    4740
catggcctct ggccacatca gggacttcca gatcactgcc tctggccagt atggccagtg    4800 ggccccccaag ctggccaggc tgcactactc tggcagcatc aatgcctgga gcaccaagga    4860
gcccttcagc tggatcaagg tggacctgct ggccccatg atcatccatg catcaagac    4920 ccagggggcc aggcagaagt tcagcagcct gtacatcagc cagttcatca tcatgtacag    4980
cctggatggc aagaagtggc agacctacag gggcaacagc actggcaccc tgatggtgtt    5040
ctttggcaat gtggacagct ctggcatcaa gcacaacatc ttcaaccccc ccatcattgc    5100
cagatacatc aggctgcacc ccacccacta cagcatcagg agcaccctga ggatggagct    5160
gatgggctgt gacctgaaca gctgcagcat gcccctgggc atggagagca aggccatctc    5220
tgatgcccag atcactgcca gcagctactt caccaacatg tttgccacct ggagccccag    5280
caaggccagg ctgcacctgc agggcaggag caatgcctgg aggccccagg tcaacaaccc    5340
caaggagtgg ctgcaggtgg acttccagaa gaccatgaag gtgactgggg tgaccaccca    5400
gggggtgaag agcctgctga ccagcatgta tgtgaaggag ttcctgatca gcagcagcca    5460
ggatggccac cagtggaccc tgttcttcca gaatggcaag gtgaaggtgt tccagggcaa    5520
ccaggacagc ttcacccctg tggtgaacag cctggacccc cccctgctga ccagataccc    5580
gaggattcac ccccagagct gggtgcacca gattgccctg aggatggagg tgctgggctg    5640
tgaggcccag gacctgtact gacctcgagg tgtgccttct agttgccagc catctgttgt    5700
ttgcccctcc cccgtgcctt ccttgaccct ggaaggtgcc actcccactg tcctttccta    5760
ataaaatgag gaaattgcat cgcattgtct gagtaggtgt cattctattc tggggggtgg    5820 ggtgggcag acagcaagg gggaggattg ggaagacaat agcaggcatg ctggggatgc    5880
ggtgggctct atgggcacgt ggcggccgca ggaaccccta gtgatggagt tggccactcc    5940
ctctctgcgc gctcgctcgc tcactgaggc cgggcgacca aaggtcgccc gacgcccggg    6000
ctttgcccgg gcggcctcag tgagcgagcg agcgcgcaga gagggagtgg ccaa          6054
```

<210> SEQ ID NO 31
<211> LENGTH: 5504
<212> TYPE: DNA
<213> ORGANISM: Adeno-Associated Virus 2

<400> SEQUENCE: 31

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgcggc cgcacgcgtg ttttcgaccc ctctcacact     180
acctaaacca cgccaggaca acctctgctc ctctccaccg aaattccaag gggtcgagtg     240
```

```
gatgttggag gtggcatggg cccagagagg tctctgacct ctgccccagc tccaaggtca    300
gcaggcaggg agggctgtgt gtttgctgtt tgctgcttgc aatgtttgcc cattttaggg    360
acatgagtag gctgaagttt gttcagtgtg gacttcagag gcagcacaca aacagctgct    420
ggaggatggg aactgagggg ttggaagggg gcagggtgag cccagaaact cctgtgtgcc    480
tctgagcctg cagacgcgaa acgtcgactg gacacaggac gctgtggttt ctgagccagg    540
gggcgactca gatcccagcc agtggactta gcccctgttt gctcctccga taactggggt    600
gaccttggtt aatattcacc agcagcctcc cccgttgccc ctctggatcc actgcttaaa    660
tacggacgag gacagggccc tgtctcctca gcttcaggca ccaccactga cctgggacag    720
tgaatcgcga tcgccaccat gcagattgag ctgagcacct gcttcttcct gtgcctgctg    780
aggttctgct tctctgccac caggagatac tacctggggg ctgtggagct gagctgggac    840
tacatgcagt ctgacctggg ggagctgcct gtggatgcca ggttcccccc cagagtgccc    900
aagagcttcc ccttcaacac ctctgtggtg tacaagaaga ccctgtttgt ggagttcact    960
gaccacctgt tcaacattgc caagcccagg ccccccctgga tgggcctgct gggccccacc   1020
atccaggctg aggtgtatga cactgtggtg atcaccctga gaacatggc cagccaccct   1080 gtgagcctgc atgctgtggg ggtgagctac tggaaggcct ctgaggggc tgagtatgat   1140 gaccagacca gccagaggga aaggaggat gacaaggtgt ccctgggggg cagccacacc   1200
tatgtgtggc aggtgctgaa ggagaatggc cccatgcct ctgaccccct gtgcctgacc   1260
tacagctacc tgagccatgt ggacctggtg aaggacctga actctggcct gattggggcc   1320
ctgctggtgt gcagggaggg cagcctggcc aaggagaaga cccagaccct gcacaagttc   1380
atcctgctgt ttgctgtgtt tgatgagggc aagagctggc actctgaaac caagaacagc   1440
ctgatgcagg acagggatgc tgcctctgcc agggcctggc caagatgca cactgtgaat   1500 ggctatgtga acaggagcct gcctggcctg attggctgcc acaggaagtc tgtgtactgg   1560
catgtgattg gcatgggcac cacccctgag gtgcacagca tcttcctgga gggccacacc   1620
ttcctggtca ggaaccacag gcaggccagc ctggagatca gccccatcac cttcctgact   1680
gcccagaccc tgctgatgga cctgggccag ttcctgctgt tctgccacat cagcagccac   1740
cagcatgatg gcatggaggc ctatgtgaag gtggacagct gccctgagga gccccagctg   1800
aggatgaaga acaatgagga ggctgaggac tatgatgatg acctgactga ctctgagatg   1860
gatgtggtga ggtttgatga tgacaacagc cccagcttca tccagatcag gtctgtggcc   1920
aagaagcacc ccaagacctg ggtgcactac attgctgctg aggaggagga ctgggactat   1980
gcccccctgg tgctggcccc tgatgacagg agctacaaga gccagtacct gaacaatggc   2040
ccccagagga ttggcaggaa gtacaagaag gtcaggttca tggcctacac tgatgaaacc   2100
ttcaagacca gggaggccat ccagcatgag tctggcatcc tgggcccct gctgtatggg   2160 gaggtggggg acaccctgct gatcatcttc aagaaccagg ccagcaggcc ctacaacatc   2220
tacccccatg gcatcactga tgtgaggccc ctgtacagca ggaggctgcc caaggggtg   2280 aagcacctga aggacttccc catcctgcct ggggagatct tcaagtacaa gtggactgtg   2340
actgtggagg atggccccac caagtctgac cccaggtgcc tgaccagata ctacagcagc   2400
tttgtgaaca tggagaggga cctggcctct ggcctgattg gcccctgct gatctgctac   2460 aaggagtctg tggaccagag gggcaaccag atcatgtctg acaagaggaa tgtgatcctg   2520
ttctctgtgt ttgatgagaa caggagctgg tacctgactg agaacatcca gaggttcctg   2580
cccaaccctg ctggggtgca gctggaggac cctgagttcc aggccagcaa catcatgcac   2640
```

-continued

```
agcatcaatg gctatgtgtt tgacagcctg cagctgtctg tgtgcctgca tgaggtggcc   2700
tactggtaca tcctgagcat tggggcccag actgacttcc tgtctgtgtt cttctctggc   2760
tacaccttca agcacaagat ggtgtatgag acaccctga ccctgttccc cttctctggg    2820
gagactgtgt tcatgagcat ggagaaccct ggcctgtgga ttctgggctg ccacaactct   2880
gacttcagga acaggggcat gactgccctg ctgaaagtct ccagctgtga caagaacact   2940
ggggactact atgaggacag ctatgaggac atctctgcct acctgctgag caagaacaat   3000
gccattgagc ccaggagctt cagccagaac cccccagtgc tgaagaggca ccagagggag   3060
atcaccagga ccacccctgca gtctgaccag gaggagattg actatgatga ccatcatctct  3120
gtggagatga agaaggagga ctttgacatc tacgacgagg acgagaacca gagccccagg   3180
agcttccaga agaagaccag gcactacttc attgctgctg tggagaggct gtgggactat   3240
ggcatgagca gcagccccca tgtgctgagg aacagggccc agtctggctc tgtgccccag   3300
ttcaagaagg tggtgttcca ggagttcact gatggcagct tcacccagcc cctgtacaga   3360
ggggagctga atgagcacct gggcctgctg ggcccctaca tcagggctga ggtggaggac   3420
aacatcatgg tgaccttcag gaaccaggcc agcaggccct acagcttcta cagcagcctg   3480
atcagctatg aggaggacca gaggcagggg gctgagccca ggaagaactt tgtgaagccc   3540
aatgaaacca agacctactt ctggaaggtg cagcaccaca tggcccccac caaggatgag   3600
tttgactgca aggcctgggc ctacttctct gatgtggacc tggagaagga tgtgcactct   3660
ggcctgattg cccccctgct ggtgtgccac accaacaccc tgaaccctgc ccatggcagg   3720
caggtgactg tgcaggagtt tgccctgttc ttcaccatct ttgatgaaac caagagctgg   3780
tacttcactg agaacatgga gaggaactgc agggcccct gcaacatcca gatggaggac   3840
cccaccttca aggagaacta caggttccat gccatcaatg gctacatcat ggacaccctg   3900
cctggcctgg tgatggccca ggaccagagg atcaggtggt acctgctgag catgggcagc   3960
aatgagaaca tccacagcat ccacttctct ggccatgtgt tcactgtgag gaagaaggag   4020
gagtacaaga tggcccctgta caacctgtac cctggggtgt ttgagactgt ggagatgctg   4080
cccagcaagg ctggcatctg gagggtggag tgcctgattg gggagcacct gcatgctggc   4140
atgagcaccc tgttcctggt gtacagcaac aagtgccaga ccccctggg catggcctct   4200
ggccacatca gggacttcca gatcactgcc tctggccagt atggccagtg ggccccaag   4260
ctggccaggc tgcactactc tggcagcatc aatgcctgga gcaccaagga gcccttcagc   4320
tggatcaagg tggacctgct ggcccccatg atcatccatg gcatcaagac ccaggggcc   4380
aggcagaagt tcagcagcct gtacatcagc cagttcatca tcatgtacag cctggatggc   4440
aagaagtgg agacctacag gggcaacagc actggcaccc tgatggtgtt ctttggcaat   4500
gtggacagct ctggcatcaa gcacaacatc ttcaaccccc ccatcattgc cagatacatc   4560
aggctgcacc ccacccacta cagcatcagg agcaccctga ggatggagct gatgggctgt   4620
gacctgaaca gctgcagcat gcccctgggc atggagagca aggccatctc tgatgcccag   4680
atcactgcca gcagctactt caccaacatg tttgccacct ggagcccag caaggccagg   4740
ctgcacctgc agggcaggag caatgcctgg aggcccaggg tcaacaaccc caaggagtgg   4800
ctgcaggtgg acttccagaa gaccatgaag gtgactgggg tgaccaccca gggggtgaag   4860
agcctgctga ccagcatgta tgtgaaggag ttcctgatca gcagcagcca ggatggccac   4920
cagtggaccc tgttcttcca gaatggcaag gtgaaggtgt tccagggcaa ccaggacagc   4980
```

```
ttcaccctg tggtgaacag cctggacccc ccctgctga ccagatacct gaggattcac      5040
ccccagagct gggtgcacca gattgccctg aggatggagg tgctgggctg tgaggcccag      5100
gacctgtact gacctcgagg tgtgccttct agttgccagc catctgttgt ttgcccctcc      5160
cccgtgcctt ccttgaccct ggaaggtgcc actcccactg tcctttccta ataaaatgag      5220
gaaattgcat cgcattgtct gagtaggtgt cattctattc tggggggtgg ggtggggcag      5280
gacagcaagg gggaggattg ggaagacaat agcaggcatg ctggggatgc ggtgggctct      5340
atgggcacgt ggcggccgca ggaaccccta gtgatggagt tggccactcc ctctctgcgc      5400
gctcgctcgc tcactgaggc cgggcgacca aggtcgcccc gacgcccggg ctttgcccgg      5460
gcggcctcag tgagcgagcg agcgcgcaga gagggagtgg ccaa                       5504

<210> SEQ ID NO 32
<211> LENGTH: 5507
<212> TYPE: DNA
<213> ORGANISM: Adeno-Associated Virus 2

<400> SEQUENCE: 32
ttggccactc cctctctgcg cgctcgctcg ctcactgagg ccgcccgggc aaagcccggg        60
cgtcgggcga cctttggtcg cccggcctca gtgagcgagc gagcgcgcag agagggagtg       120
gccaactcca tcactagggg ttcctgcggc cgcacgcgtg ttttcgaccc ctctcacact       180
acctaaacca cgccaggaca acctctgctc ctctccaccg aaattccaag gggtcgagtg       240
gatgttggag gtggcatggg cccagagagg tctctgacct ctgccccagc tccaaggtca       300
gcaggcaggg agggctgtgt gtttgctgtt tgctgcttgc aatgtttgcc cattttaggg       360
acatgagtag gctgaagttt gttcagtgtg gacttcagag gcagcacaca aacagctgct       420
ggaggatggg aactgagggg ttggaagggg cagggtgagc ccagaaaact cctgtgtgcc       480
tctgagcctg cagacgcgaa acgtcgacga tcttgctacc agtggaacag ccactaagga       540
ttctgcagtg agagcagagg gccagctaag tggtactctc ccagagactg tctgactcac       600
gccaccccct ccaccttgga cacaggacgc tgtggtttct gagccaggta caatgactcc       660
tttcggtaag tgcagtggaa gctgtacact gcccaggcaa agcgtccggg cagcgtaggc       720
gggcgactca gatcccagcc agtggactta gcccctgttt gctcctccga taactggggt       780
gaccttggtt aatattcacc agcagcctcc ccgttgccc tctggatcc actgcttaaa       840 tacggacgag gacagggccc tgtctcctca gcttcaggca ccaccactga cctgggacag       900
tgaatcgcga tcgccaccat gcagattgag ctgagcacct gcttcttcct gtgcctgctg       960
aggttctgct tctctgccac caggagatac tacctggggg ctgtggagct gagctgggac      1020
tacatgcagt ctgacctggg ggagctgcct gtggatgcca ggttcccccc cagagtgccc      1080
aagagcttcc ccttcaacac ctctgtggtg tacaagaaga cctgtttgt ggagttcact      1140 gaccacctgt tcaacattgc caagcccagg ccccctgga tgggcctgct gggccccacc      1200
atccaggctg aggtgtatga cactgtggtg atcaccctga gaacatggc cagccaccct      1260 gtgagcctgc atgctgtggg ggtgagctac tggaaggcct ctgagggggc tgagtatgat      1320
gaccagacca gccagaggga aaggaggat acaaggtgt ccctggggg cagccacacc      1380 tatgtgtggc aggtgctgaa ggagaatggc cccatggcct ctgacccct gtgcctgacc      1440 tacagctacc tgagccatgt ggacctggtg aaggacctga actctggcct gattggggcc      1500
ctgctggtgt gcagggaggg cagcctgcc aaggagaaga cccagaccct gcacaagttc      1560
atcctgctgt tgctgtgtt tgatgagggc aagagctggc actctgaaac caagaacagc      1620
```

```
ctgatgcagg acagggatgc tgcctctgcc agggcctggc ccaagatgca cactgtgaat   1680
ggctatgtga acaggagcct gcctggcctg attggctgcc acaggaagtc tgtgtactgg   1740
catgtgattg gcatgggcac caccoctgag gtgcacagca tcttcctgga gggccacacc   1800
ttcctggtca ggaaccacag gcaggccagc ctggagatca gccccatcac cttcctgact   1860
gcccagaccc tgctgatgga cctgggccag ttcctgctgt tctgccacat cagcagccac   1920
cagcatgatg gcatggaggc ctatgtgaag gtggacagct gccctgagga gccccagctg   1980
aggatgaaga acaatgagga ggctgaggac tatgatgatg acctgactga ctctgagatg   2040
gatgtggtga ggtttgatga tgacaacagc cccagcttca tccagatcag gtctgtggcc   2100
aagaagcacc ccaagacctg ggtgcactac attgctgctg aggaggagga ctgggactat   2160
gccccctgg tgctggcccc tgatgacagg agctacaaga ccagtacct gaacaatggc   2220
ccccagagga ttggcaggaa gtacaagaag gtcaggttca tggcctacac tgatgaaacc   2280
ttcaagacca gggaggccat ccagcatgag tctggcatcc tgggccccct gctgtatggg   2340
gaggtggggg acaccctgct gatcatcttc aagaaccagg ccagcaggcc ctacaacatc   2400
tacccccatg gcatcactga tgtgaggccc ctgtacagca ggaggctgcc caagggggtg   2460
aagcacctga aggacttccc catcctgcct ggggagatct tcaagtacaa gtggactgtg   2520
actgtggagg atggccccac caagtctgac cccaggtgcc tgaccagata ctacagcagc   2580
tttgtgaaca tggagaggga cctggcctct ggcctgattg gcccctgct gatctgctac   2640
aaggagtctg tggaccagag gggcaaccag atcatgtctg acaagaggaa tgtgatcctg   2700
ttctctgtgt ttgatgagaa caggagctgg tacctgactg agaacatcca gaggttcctg   2760
cccaaccctg ctggggtgca gctggaggac cctgagttcc aggccagcaa catcatgcac   2820
agcatcaatg gctatgtgtt tgacagcctg cagctgtctg tgtgcctgca tgaggtggcc   2880
tactggtaca tcctgagcat tggggcccag actgacttcc tgtctgtgtt cttctctggc   2940
tacaccttca agcacaagat ggtgtatgag gacaccctga ccctgttccc cttctctggg   3000
gagactgtgt tcatgagcat ggagaaccct ggcctgtgga ttctgggctg ccacaactct   3060
gacttcagga cagggcat gactgccctg ctgaaagtct ccagctgtga caagaacact   3120
ggggactact atgaggacag ctatgaggac atctctgcct acctgctgag caagaacaat   3180
gccattgagc caggagcttt cagccagaac cccccagtgc tgaagaggca ccagagggag   3240
atcaccagga ccaccctgca gtctgaccag gaggagattg actatgatga caccatctct   3300
gtggagatga agaggagga ctttgacatc tacgacgagg acgagaacca gagccccagg   3360
agcttccaga agaaaccag gcactacttc attgctgctg tggagaggct gtgggactat   3420
ggcatgagca gcagccccca tgtgctgagg aacaggccc agtctggctc tgtgccccag   3480
ttcaagaagg tggtgttcca ggagttcact gatggcagct tcacccagcc cctgtacaga   3540
ggggagctga tgagcacct gggcctgctg gcccctaca tcagggctga ggtggaggac   3600
aacatcatgg tgaccttcag gaaccaggcc agcaggccct acagcttcta cagcagcctg   3660
atcagctatg aggaggacca gaggcagggg gctgagccca ggaagaactt tgtgaagccc   3720
aatgaaacca gacctactt ctggaaggtg cagcaccaca tggcccccac caaggatgag   3780
tttgactgca aggcctggc ctacttctct gatgtggacc tggagaagga tgtgcactct   3840
ggcctgattg gcccctgct ggtgtgccac accaacaccc tgaaccctgc ccatggcagg   3900
caggtgactg tgcaggagtt tgccctgttc ttcaccatct ttgatgaaac caagagctgg   3960
```

```
tacttcactg agaacatgga gaggaactgc agggccccct gcaacatcca gatggaggac    4020
cccaccttca aggagaacta caggttccat gccatcaatg ctacatcat ggacaccctg     4080 cctggcctgg tgatggccca ggaccagagg atcaggtggt acctgctgag catgggcagc   4140
aatgagaaca tccacagcat ccacttctct ggccatgtgt tcactgtgag gaagaaggag   4200
gagtacaaga tggccctgta caacctgtac cctggggtgt tgagactgt ggagatgctg    4260 cccagcaagg ctggcatctg gagggtggag tgcctgattg gggagcacct gcatgctggc   4320
atgagcaccc tgttcctggt gtacagcaac aagtgccaga ccccctggg catggcctct    4380 ggccacatca gggacttcca gatcactgcc tctggccagt atggccagtg gcccccaag    4440 ctggccaggc tgcactactc tggcagcatc aatgcctgga gcaccaagga gcccttcagc   4500
tggatcaagg tggacctgct ggcccccatg atcatccatg gcatcaagac caggggggcc   4560
aggcagaagt tcagcagcct gtacatcagc cagttcatca tcatgtacag cctggatggc   4620
aagaagtggc agacctacag gggcaacagc actggcaccc tgatggtgtt ctttggcaat   4680
gtggacagct ctggcatcaa gcacaacatc ttcaaccccc ccatcattgc cagatacatc   4740
aggctgcacc ccacccacta cagcatcagg agcaccctga ggatggagct gatgggctgt   4800
gacctgaaca gctgcagcat gccctgggc atggagagca aggccatctc tgatgcccag   4860
atcactgcca gcagctactt caccaacatg tttgccacct ggagcccag caaggccagg    4920 ctgcacctgc agggcaggag caatgcctgg aggcccagg tcaacaaccc caaggagtgg    4980
ctgcaggtgg acttccagaa gaccatgaag gtgactgggg tgaccaccca gggggtgaag   5040
agcctgctga ccagcatgta tgtgaaggag ttcctgatca gcagcagcca ggatggccac   5100
cagtggaccc tgttcttcca gaatggcaag gtgaaggtgt tccagggcaa ccaggacagc   5160 ttcaccctg tggtgaacag cctggacccc cccctgctga ccagatacct gaggattcac    5220
ccccagagct gggtgcacca gattgccctg aggatggagg tgctgggctg tgaggcccag   5280
gacctgtact gacctcgagg aataaaggaa atttattttc attgcaatag tgtgttggtt   5340
ttttgtgtca cgtggcggcc gcaggaaccc ctagtgatgg agttggccac tccctctctg   5400
cgcgctcgct cgctcactga ggccgggcga ccaaaggtcg cccgacgccc gggctttgcc   5460
cgggcggcct cagtgagcga gcgagcgcgc agagagggag tggccaa                5507
```

<210> SEQ ID NO 33
<211> LENGTH: 5311
<212> TYPE: DNA
<213> ORGANISM: Adeno-Associated Virus 2

<400> SEQUENCE: 33

```
ttggccactc cctctctgcg cgctcgctcg ctcactgagg ccgccgggc aaagcccggg      60 cgtcgggcga cctttggtcg cccggcctca gtgagcgagc gagcgcgcag agagggagtg    120
gccaactcca tcactagggg ttcctgcggc cgcacgcgtg ttttcgacgc agagaggtct    180
ctgacctctg ccccagctcc aaggtcagca ggcaggagg gctgtgtgtt tgctgtttgc    240
tgcttgcaat gttttgcccat tttagggaca tgagtaggct gaagtttgtt cagtgtggac   300
ttcagaggca gcacacaaac agccagagag gtctctgacc tctgccccag ctccaaggtc   360
agcaggcagg gagggctgtg tgtttgctgt ttgctgcttg caatgtttgc ccattttagg    420
gacatgagta ggctgaagtt tgttcagtgt ggacttcaga ggcagcacac aaacagcacg   480
cgaaacgtcg actggacaca ggacgctgtg gtttctgagc caggggggcga ctcagatccc    540 agccagtgga cttagccct gtttgctcct ccgataactg gggtgacctt ggttaatatt    600
```

```
caccagcagc ctcccccgtt gccctctgg atccactgct taaatacgga cgaggacagg    660
gccctgtctc ctcagcttca ggcaccacca ctgacctggg acagtgaatc gcgatcgcca    720
ccatgcagat tgagctgagc acctgcttct tcctgtgcct gctgaggttc tgcttctctg    780
ccaccaggag atactacctg ggggctgtgg agctgagctg ggactacatg cagtctgacc    840
tgggggagct gcctgtggat gccaggttcc cccccagagt gcccaagagc ttccccttca    900
acacctctgt ggtgtacaag aagaccctgt ttgtggagtt cactgaccac ctgttcaaca    960
ttgccaagcc caggccccc tggatgggcc tgctgggccc caccatccag gctgaggtgt   1020
atgacactgt ggtgatcacc ctgaagaaca tggccagcca ccctgtgagc ctgcatgctg   1080
tgggggtgag ctactggaag gcctctgagg gggctgagta tgatgaccag accagccaga   1140
gggagaagga ggatgacaag gtgttccctg ggggcagcca cacctatgtg tggcaggtgc   1200
tgaaggagaa tggcccatg gcctctgacc ccctgtgcct gacctacagc tacctgagcc   1260
atgtggacct ggtgaaggac ctgaactctg gcctgattgg ggccctgctg gtgtgcaggg   1320
agggcagcct ggccaaggag aagacccaga ccctgcacaa gttcatcctg ctgtttgctg   1380
tgtttgatga gggcaagagc tggcactctg aaaccaagaa cagcctgatg caggacaggg   1440
atgctgcctc tgccagggcc tggcccaaga tgcacactgt gaatggctat gtgaacagga   1500
gcctgcctgg cctgattggc tgccacagga agtctgtgta ctggcatgtg attggcatgg   1560
gcaccacccc tgaggtgcac agcatcttcc tggagggcca caccttcctg gtcaggaacc   1620
acaggcaggc cagcctggag atcagcccca tcaccttcct gactgcccag accctgctga   1680
tggacctggg ccagttcctg ctgttctgcc acatcagcag ccaccagcat gatggcatgg   1740
aggcctatgt gaaggtggac agctgccctg aggagcccca gctgaggatg aagaacaatg   1800
aggaggctga ggactatgat gatgacctga ctgactctga gatggatgtg gtgaggtttg   1860
atgatgacaa cagcccccagc ttcatccaga tcaggtctgt ggccaagaag caccccaaga   1920
cctgggtgca ctacattgct gctgaggagg aggactggga ctatgccccc ctggtgctgg   1980
cccctgatga caggagctac aagagccagt acctgaacaa tggcccccag aggattggca   2040
ggaagtacaa gaaggtcagg ttcatggcct acactgatga aaccttcaag accagggagg   2100
ccatccagca tgagtctggc atcctggggcc ccctgctgta tggggaggtg ggggacacccc   2160 tgctgatcat cttcaagaac caggccagca ggccctacaa catctacccc catggcatca   2220
ctgatgtgag gcccctgtac agcaggaggc tgcccaaggg ggtgaagcac ctgaaggact   2280
tccccatcct gcctggggag atcttcaagt acaagtggac tgtgactgtg gaggatggcc   2340
ccaccaagtc tgaccccagg tgcctgacca gatactacag cagctttgtg aacatggaga   2400
gggacctggc ctctggcctg attggccccc tgctgatctg ctacaaggag tctgtggacc   2460
agagggggca accagatcatg tctgacaaga ggaatgtgat cctgttctct gtgtttgatg   2520
agaacaggag ctggtacctg actgagaaca tccagaggtt cctgcccaac cctgctgggg   2580
tgcagctgga ggaccctgag ttccaggcca gcaacatcat gcacagcatc aatggctatg   2640
tgtttgacag cctgcagctg tctgtgtgcc tgcatgaggt ggcctactgg tacatcctga   2700
gcattggggc ccagactgac ttcctgtctg tgttcttctc tggctacacc ttcaagcaca   2760
agatggtgta tgaggacacc ctgaccctgt tccccttctc tggggagact gtgttcatga   2820
gcatggagaa ccctggcctg tggattctgg gctgccacaa ctctgacttc aggaacaggg   2880
gcatgactgc cctgctgaaa gtctccagct gtgacaagaa cactgggac tactatgagg   2940
```

```
acagctatga ggacatctct gcctacctgc tgagcaagaa caatgccatt gagcccagga    3000
gcttcagcca gaacccccca gtgctgaaga ggcaccagag ggagatcacc aggaccaccc    3060
tgcagtctga ccaggaggag attgactatg atgacaccat ctctgtggag atgaagaagg    3120
aggactttga catctacgac gaggacgaga accagagccc caggagcttc cagaagaaga    3180
ccaggcacta cttcattgct gctgtggaga ggctgtggga ctatggcatg agcagcagcc    3240
cccatgtgct gaggaacagg gcccagtctg gctctgtgcc ccagttcaag aaggtggtgt    3300
tccaggagtt cactgatggc agcttcaccc agcccctgta cagaggggag ctgaatgagc    3360
acctgggcct gctgggcccc tacatcaggg ctgaggtgga ggacaacatc atggtgacct    3420
tcaggaacca ggccagcagg ccctacagct tctacagcag cctgatcagc tatgaggagg    3480
accagaggca gggggctgag cccaggaaga actttgtgaa gcccaatgaa accaagacct    3540
acttctggaa ggtgcagcac cacatggccc ccaccaagga tgagtttgac tgcaaggcct    3600
gggcctactt ctctgatgtg gacctggaga aggatgtgca ctctggcctg attggccccc    3660
tgctggtgtg ccacaccaac accctgaacc ctgcccatgg caggcaggtg actgtgcagg    3720
agtttgccct gttcttcacc atctttgatg aaaccaagag ctggtacttc actgagaaca    3780
tggagaggaa ctgcagggcc ccctgcaaca tccagatgga ggaccccacc ttcaaggaga    3840
actacaggtt ccatgccatc aatggctaca tcatggacac cctgcctggc ctggtgatgg    3900
cccaggacca gaggatcagg tggtacctgc tgagcatggg cagcaatgag aacatccaca    3960
gcatccactt ctctggccat gtgttcactg tgaggaagaa ggaggagtac aagatggccc    4020
tgtacaacct gtaccctggg gtgtttgaga ctgtggagat gctgcccagc aaggctggca    4080
tctggagggt ggagtgcctg attggggagc acctgcatgc tggcatgagc accctgttcc    4140
tggtgtacag caacaagtgc cagaccccc tgggcatggc ctctggccac atcagggact    4200
tccagatcac tgcctctggc cagtatggcc agtgggcccc caagctggcc aggctgcact    4260
actctggcag catcaatgcc tggagcacca aggagccctt cagctggatc aaggtggacc    4320
tgctggcccc catgatcatc catggcatca agacccaggg ggccaggcag aagttcagca    4380
gcctgtacat cagccagttc atcatcatgt acagcctgga tggcaagaag tggcagacct    4440
acaggggcaa cagcactggc acctgatgg tgttctttgg caatgtggac agctctggca    4500
tcaagcacaa catcttcaac cccccatca ttgccagata catcaggctg cacccacccc    4560
actacagcat caggagcacc ctgaggatgg agctgatggg ctgtgacctg aacagctgca    4620
gcatgcccct gggcatggag agcaaggcca tctctgatgc ccagatcact gccagcagct    4680
acttcaccaa catgtttgcc acctggagcc ccagcaaggc caggctgcac ctgcagggca    4740
ggagcaatgc ctggaggccc caggtcaaca accccaagga gtggctgcag gtggacttcc    4800
agaagaccat gaaggtgact ggggtgacca cccagggggt gaagagcctg ctgaccagca    4860
tgtatgtgaa ggagttcctg atcagcagca gccaggatgg ccaccagtgg acctgttct    4920 tccagaatgg caaggtgaag gtgttccagg caaccagga cagcttcacc cctgtggtga    4980
acagcctgga ccccccctg ctgaccagat acctgaggat tcacccccag agctgggtgc    5040
accagattgc cctgaggatg gaggtgctgg gctgtgaggc ccaggacctg tactgacctc    5100
gaggaataaa ggaaatttat tttcattgca atagtgtgtt ggttttttgt gtcacgtggc    5160
ggccgcagga accctagtg atggagttgg ccactccctc tctgcgcgct cgctcgctca    5220
ctgaggccgg gcgaccaaag gtcgcccgac gcccgggctt tgcccgggcg gcctcagtga    5280
gcgagcgagc gcgcagagag ggagtggcca a                                  5311
```

<210> SEQ ID NO 34
<211> LENGTH: 5156
<212> TYPE: DNA
<213> ORGANISM: Adeno-Associated Virus 2

<400> SEQUENCE: 34

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgcggc cgcacgcgtg ttttcgacca gagaggtctc     180
tgacctctgc cccagctcca aggtcagcag gcagggagtg ctgtgtgttt gctgtttgct     240
gcttgcaatg tttgcccatt ttagggacat gagtaggctg aagtttgttc agtgtggact     300
tcagaggcag cacacaaaca gcacgcgaaa cgtcgactgg acacaggacg ctgtggtttc     360
tgagccaggg ggcgactcag atcccagcca gtggacttag cccctgtttg ctcctccgat     420
aactggggtg accttggtta atattcacca gcagcctccc ccgttgcccc tctggatcca     480
ctgcttaaat acggacgagg acagggccct gtctcctcag cttcaggcac caccactgac     540
ctgggacagt gaatcgcgat cgccaccatg cagattgagc tgagcacctg cttcttcctg     600
tgcctgctga ggttctgctt ctctgccacc aggagatact acctgggggc tgtggagctg     660
agctgggact acatgcagtc tgacctgggg gagctgcctg tggatgccag gttccccccc     720
agagtgccca agagcttccc cttcaacacc tctgtggtgt acaagaagac cctgtttgtg     780
gagttcactg accacctgtt caacattgcc aagcccaggc cccctggat gggcctgctg     840
ggccccacca tccaggctga ggtgtatgac actgtggtga tcaccctgaa gaacatggcc     900
agccaccctg tgagcctgca tgctgtgggg gtgagctact ggaaggcctc tgagggggct     960
gagtatgatg accagaccag ccagagggag aaggaggatg acaaggtgtt ccctgggggc    1020
agccacacct atgtgtggca ggtgctgaag gagaatggcc ccatggcctc tgacccctg    1080
tgcctgacct acagctacct gagccatgtg gacctggtga aggacctgaa ctctggcctg    1140
attgggccc tgctggtgtg cagggagggc agcctggcca aggagaagac ccagaccctg    1200
cacaagttca tcctgctgtt tgctgtgttt gatgagggca gagctggca ctctgaaacc    1260
aagaacagcc tgatgcagga cagggatgct gcctctgcca gggcctggcc aagatgcac    1320
actgtgaatg gctatgtgaa caggagcctg cctggcctga ttggctgcca caggaagtct    1380
gtgtactggc atgtgattgg catgggcacc accctgagg tgcacagcat cttcctggag    1440
ggccacacct tcctggtcag gaaccacagg caggccagcc tggagatcag ccccatcacc    1500
ttcctgactg cccagaccct gctgatggac ctgggccagt cctgctgttt ctgccacatc    1560
agcagccacc agcatgatgg catggaggcc tatgtgaagg tggacagctg ccctgaggag    1620
ccccagctga ggatgaagaa caatgaggag gctgaggact atgatgatga cctgactgac    1680
tctgagatgg atgtggtgag gtttgatgat gacaacagcc cagcttcat ccagatcagg    1740
tctgtggcca agaagcaccc caagacctgg gtgcactaca ttgctgctga ggaggaggac    1800
tgggactatg cccccctggt gctggccct gatgacagga gctacaagag ccagtacctg    1860
aacaatggcc cccagaggat tggcaggaag tacaagaagg tcaggttcat ggcctacact    1920
gatgaaacct tcaagaccag ggaggccatc cagcatgagt ctggcatcct ggccccctg    1980
ctgtatgggg aggtggggga caccctgctg atcatcttca agaaccaggc cagcaggccc    2040
tacaacatct acccccatgg catcactgat gtgaggcccc tgtacagcag gaggctgccc    2100
```

```
aaggggggtga agcacctgaa ggacttcccc atcctgcctg ggagatcttc aagtacaag     2160
tggactgtga ctgtggagga tggccccacc aagtctgacc ccaggtgcct gaccagatac     2220
tacagcagct ttgtgaacat ggagagggac ctggcctctg gcctgattgg cccctgctg      2280
atctgctaca aggagtctgt ggaccagagg ggcaaccaga tcatgtctga caagaggaat     2340
gtgatcctgt tctctgtgtt tgatgagaac aggagctggt acctgactga gaacatccag     2400
aggttcctgc ccaaccctgc tggggtgcag ctggaggacc ctgagttcca ggccagcaac     2460
atcatgcaca gcatcaatgg ctatgtgttt gacagcctgc agctgtctgt gtgcctgcat     2520
gaggtggcct actggtacat cctgagcatt ggggcccaga ctgacttcct gtctgtgttc     2580
ttctctggct acaccttcaa gcacaagatg gtgtatgagg acaccctgac cctgttcccc     2640
ttctctgggg agactgtgtt catgagcatg agaaccctg gcctgtggat ctgggctgc       2700
cacaactctg acttcaggaa cagggcatg actgccctgc tgaaagtctc cagctgtgac     2760
aagaacactg gggactacta tgaggacagc tatgaggaca tctctgccta cctgctgagc     2820
aagaacaatg ccattgagcc caggagcttc agccagaacc cccagtgct gaagaggcac      2880
cagagggaga tcaccaggac caccctgcag tctgaccagg aggagattga ctatgatgac    2940
accatctctg tggagatgaa gaaggaggac tttgacatct acgacgagga cgagaaccag    3000
agccccagga gcttccagaa gaagaccagg cactacttca ttgctgctgt ggagaggctg     3060
tgggactatg gcatgagcag cagcccccat gtgctgagga caggggccca gtctggctct    3120
gtgccccagt tcaagaaggt ggtgttccag gagttcactg atggcagctt cacccagccc    3180
ctgtacagag gggagctgaa tgagcacctg ggcctgctgg gcccctacat cagggctgag    3240
gtggaggaca acatcatggt gaccttcagg aaccaggcca gcaggcccta cagcttctac    3300
agcagcctga tcagctatga ggaggaccag aggcagggg ctgagcccag gaagaacttt     3360
gtgaagccca atgaaaccaa gacctacttc tggaaggtgc agcaccacat ggcccccacc    3420
aaggatgagt ttgactgcaa ggcctgggcc tacttctctg atgtggacct ggagaaggat    3480
gtgcactctg gcctgattgg ccccctgctg gtgtgccaca ccaacaccct gaaccctgcc    3540
catggcaggc aggtgactgt gcaggagttt gccctgttct tcaccatctt tgatgaaacc    3600
aagagctggt acttcactga gaacatggag aggaactgca gggcccctg caacatccag    3660
atggaggacc ccaccttcaa ggagaactac aggttccatg ccatcaatgg ctacatcatg    3720
gacacccctg ctggcctggt gatggcccag accagagga tcaggtggta cctgctgagc    3780
atgggcagca tgagaacat ccacagcatc cacttctctg gccatgtgtt cactgtgagg    3840
aagaaggagg agtacaagat ggccctgtac aacctgtacc ctgggtgtt tgagactgtg    3900
gagatgctgc ccagcaaggc tggcatctgg agggtggagt gcctgattgg ggagcacctg    3960
catgctggca tgagcacccct gttcctggtg tacagcaaca agtgccagac ccccctgggc    4020
atggcctctg ccacatcag ggacttccag atcactgcct ctggccagta tggccagtgg    4080
gcccccaagc tggccaggct gcactactct ggcagcatca atgcctggag caccaaggag    4140
cccttcagct ggatcaaggt ggacctgctg gccccccatga tcatccatgg catcaagacc    4200
cagggggcca ggcagaagtt cagcagcctg tacatcagcc agttcatcat catgtacagc    4260
ctggatggca agaagtggca gacctacagg ggcaacagca ctggcacccct gatggtgttc    4320
tttggcaatg tggacagctc tggcatcaag cacaacatct tcaacccccc catcattgcc    4380
agatacatca ggctgcaccc cacccactac agcatcagga gcacctgag gatggagctg    4440
atgggctgtg acctgaacag ctgcagcatg cccctgggca tggagagcaa ggccatctct    4500
```

```
gatgcccaga tcactgccag cagctacttc accaacatgt ttgccacctg gagcccagc      4560 aaggccaggc tgcacctgca gggcaggagc aatgcctgga ggcccaggt caacaacccc      4620 aaggagtggc tgcaggtgga cttccagaag accatgaagg tgactggggt gaccacccag    4680
ggggtgaaga gcctgctgac cagcatgtat gtgaaggagt tcctgatcag cagcagccag    4740
gatggccacc agtggaccct gttcttccag aatggcaagg tgaaggtgtt ccagggcaac    4800
caggacagct tcacccctgt ggtgaacagc ctgaccccc ccctgctgac cagatacctg      4860
aggattcacc cccagagctg ggtgcaccag attgccctga ggatggaggt gctgggctgt    4920
gaggcccagg acctgtactg acctcgagga ataaaggaaa tttattttca ttgcaatagt    4980
gtgttggttt tttgtgtcac gtggcggccg caggaacccc tagtgatgga gttggccact    5040
ccctctctgc gcgctcgctc gctcactgag gccgggcgac caaaggtcgc ccgacgcccg    5100
ggctttgccc gggcggcctc agtgagcgag cgagcgcgca gagagggagt ggccaa        5156
```

<210> SEQ ID NO 35
<211> LENGTH: 5178
<212> TYPE: DNA
<213> ORGANISM: Adeno-Associated Virus 2

<400> SEQUENCE: 35

```
ttggccactc cctctctgcg cgctcgctcg ctcactgagg ccgccgggc aaagcccggg       60 cgtcgggcga cctttggtcg cccggcctca gtgagcgagc gagcgcgcag agagggagtg    120
gccaactcca tcactagggg ttcctgcggc cgcacgcgtg ttttcgactg tttgctgttt    180
gctgcttgca atgtttgccc attttaggga catgtttgct gtttgctgct tgcaatgttt    240
gcccatttta gggacatgtt tgctgtttgc tgcttgcaat gtttgcccat tttaggaca    300 tgtttgctgt ttgctgcttg caatgtttgc ccattttagg acaacgcga aacgtcgact      360 ggacacagga cgctgtggtt tctgagccag ggggcgactc agatcccagc cagtggactt    420
agcccctgtt tgctcctccg ataactgggg tgaccttggt taatattcac cagcagcctc    480
ccccgttgcc cctctggatc cactgcttaa atacgacga ggacagggcc ctgtctcctc      540
agcttcaggc accaccactg acctgggaca gtgaatcgcg atcgccacca tgcagattga    600
gctgagcacc tgcttcttcc tgtgcctgct gaggttctgc ttctctgcca ccaggagata    660
ctacctgggg gctgtggagc tgagctggga ctacatgcag tctgacctgg gggagctgcc    720
tgtggatgcc aggttccccc ccagagtgcc caagagcttc ccccttcaaca cctctgtggt    780 gtacaagaag accctgtttg tggagttcac tgaccacctg ttcaacattg ccaagccag    840 gcccccctgg atgggcctgc tgggccccac catccaggct gaggtgtatg acactgtggt    900 gatcacctg aagaacatgg ccagccaccc tgtgagcctg catgctgtgg gggtgagcta    960
ctggaaggcc tctgaggggg ctgagtatga tgaccagacc agccagaggg agaaggagga    1020
tgacaaggtg ttccctgggg gcagccacac ctatgtgtgg caggtgctga ggagaatgg      1080 ccccatggcc tctgaccccc tgtgcctgac ctacagctac ctgagccatg tggacctggt    1140
gaaggacctg aactctggcc tgattggggc cctgctggtg tgcagggagg cagcctggc     1200 caaggagaag acccagaccc tgcacaagtt catcctgctg tttgctgtgt ttgatgaggg    1260
caagagctgg cactctgaaa ccaagaacag cctgatgcag acagggatg ctgcctctgc     1320 cagggcctgg cccaagatgc acactgtgaa tggctatgtg aacaggagcc tgcctggcct    1380
gattggctgc cacaggaagt ctgtgtactg gcatgtgatt ggcatgggca ccaccctga    1440
```

```
ggtgcacagc atcttcctgg agggccacac cttcctggtc aggaaccaca ggcaggccag    1500
cctggagatc agccccatca ccttcctgac tgcccagacc ctgctgatgg acctgggcca    1560
gttcctgctg ttctgccaca tcagcagcca ccagcatgat ggcatggagg cctatgtgaa    1620
ggtggacagc tgccctgagg agccccagct gaggatgaag aacaatgagg aggctgagga    1680
ctatgatgat gacctgactg actctgagat ggatgtggtg aggtttgatg atgacaacag    1740
ccccagcttc atccagatca ggtctgtggc caagaagcac cccaagacct gggtgcacta    1800
cattgctgct gaggaggagg actgggacta tgccccctg gtgctggccc ctgatgacag     1860
gagctacaag agccagtacc tgaacaatgg cccccagagg attggcagga agtacaagaa    1920
ggtcaggttc atggcctaca ctgatgaaac cttcaagacc agggaggcca tccagcatga    1980
gtctggcatc ctgggccccc tgctgtatgg ggaggtgggg gacaccctgc tgatcatctt    2040
caagaaccag gccagcaggc cctacaacat ctacccccat ggcatcactg atgtgaggcc    2100
cctgtacagc aggaggctgc caaggggggt gaagcacctg aaggacttcc ccatcctgcc    2160
tggggagatc ttcaagtaca gtggactgt gactgtggag gatggcccca ccaagtctga     2220
ccccaggtgc ctgaccagat actacagcag cttttgtgaac atggagaggg acctggcctc   2280
tggcctgatt ggcccctgc tgatctgcta caaggagtct gtggaccaga ggggcaacca     2340
gatcatgtct gacaagagga atgtgatcct gttctctgtg tttgatgaga caggagctg     2400 gtacctgact gagaacatcc agaggttcct gcccaaccct gctggggtgc agctggagga   2460
ccctgagttc caggccagca acatcatgca cagcatcaat ggctatgtgt tgacagcct    2520 gcagctgtct gtgtgcctgc atgaggtggc ctactggtac atcctgagca ttggggccca    2580
gactgacttc ctgtctgtgt tcttctctgg ctacaccttc aagcacaaga tggtgtatga    2640
ggacaccctg accctgttcc ccttctctgg ggagactgtg ttcatgagca tggagaaccc    2700
tggcctgtgg attctgggct gccacaactc tgacttcagg aacaggggca tgactgccct    2760
gctgaaagtc tccagctgtg acaagaacac tggggactac tatgaggaca gctatgagga    2820
catctctgcc tacctgctga gcaagaacaa tgccattgag cccaggagct tcagccagaa    2880
ccccccagtg ctgaagaggc accagaggga gatcaccagg accaccctgc agtctgacca    2940
ggaggagatt gactatgatg acaccatctc tgtggagatg aagaaggagg actttgacat    3000
ctacgacgag gacgagaacc agagcccag gagcttccag aagaagacca ggcactactt    3060
cattgctgct gtggagaggc tgtgggacta tggcatgagc agcagccccc atgtgctgag    3120
gaacagggcc cagtctggct ctgtgcccca gttcaagaag gtggtgttcc aggagttcac    3180
tgatggcagc ttcacccagc ccctgtacag aggggagctg aatgagcacc tgggcctgct    3240
gggcccctac atcagggctg aggtggagga caacatcatg gtgaccttca ggaaccaggc    3300
cagcaggccc tacagcttct acagcagcct gatcagctat gaggaggacc agaggcaggg    3360
ggctgagccc aggaagaact tgtgaagcc aatgaaacc aagacctact tctgaaggt      3420 gcagcaccac atggccccca ccaaggatga gtttgactgc aaggcctggg cctacttctc    3480
tgatgtggac ctggagaagg atgtgcactc tggcctgatt ggcccctgc tggtgtgcca    3540 caccaacacc ctgaaccctg cccatggcag gcaggtgact gtgcaggagt ttgccctgtt    3600
cttcaccatc tttgatgaaa ccaagagctg gtacttcact gagaacatgg agaggaactg    3660
cagggccccc tgcaacatcc agatggagga ccccaccttc aaggagaact acaggttcca    3720
tgccatcaat ggctacatca tggacaccct gcctggcctg gtgatggccc aggaccagag    3780
gatcaggtgg tacctgctga gcatgggcag caatgagaac atccacagca tccacttctc    3840
```

| | |
|---|---|
| tggccatgtg ttcactgtga ggaagaagga ggagtacaag atggccctgt acaacctgta | 3900 |
| ccctggggtg tttgagactg tggagatgct gcccagcaag gctggcatct ggagggtgga | 3960 |
| gtgcctgatt ggggagcacc tgcatgctgg catgagcacc ctgttcctgg tgtacagcaa | 4020 |
| caagtgccag acccccctgg gcatggcctc tggccacatc agggacttcc agatcactgc | 4080 |
| ctctggccag tatggccagt gggcccccaa gctggccagg ctgcactact ctggcagcat | 4140 |
| caatgcctgg agcaccaagg agcccttcag ctggatcaag gtggacctgc tggcccccat | 4200 |
| gatcatccat ggcatcaaga cccagggggc caggcagaag ttcagcagcc tgtacatcag | 4260 |
| ccagttcatc atcatgtaca gcctggatgg caagaagtgg cagacctaca ggggcaacag | 4320 |
| cactggcacc ctgatggtgt tctttggcaa tgtggacagc tctggcatca agcacaacat | 4380 |
| cttcaacccc cccatcattg ccagatacat caggctgcac cccacccact acagcatcag | 4440 |
| gagcaccctg aggatggagc tgatgggctg tgacctgaac agctgcagca tgccccctggg | 4500 |
| catggagagc aaggccatct ctgatgccca gatcactgcc agcagctact tcaccaacat | 4560 |
| gtttgccacc tggagcccca gcaaggccag gctgcacctg cagggcagga gcaatgcctg | 4620 |
| gaggcccccag gtcaacaacc ccaaggagtg gctgcaggtg gacttccaga agaccatgaa | 4680 |
| ggtgactggg gtgaccaccc aggggggtgaa gagcctgctg accagcatgt atgtgaagga | 4740 |
| gttcctgatc agcagcagcc aggatggcca ccagtggacc ctgttcttcc agaatggcaa | 4800 |
| ggtgaaggtg ttccagggca accaggacag cttcacccct gtggtgaaca gcctggaccc | 4860 |
| cccccctgctg accagatacc tgaggattca ccccccagagc tgggtgcacc agattgccct | 4920 |
| gaggatggag gtgctgggct gtgaggccca ggacctgtac tgacctcgag gaataaagga | 4980 |
| aatttatttt cattgcaata gtgtgttggt tttttgtgtc acgtggcggc cgcaggaacc | 5040 |
| cctagtgatg gagttggcca ctccctctct gcgcgctcgc tcgctcactg aggccgggcg | 5100 |
| accaaaggtc gcccgacgcc cgggctttgc ccgggcggcc tcagtgagcg agcgagcgcg | 5160 |
| cagagaggga gtggccaa | 5178 |

<210> SEQ ID NO 36
<211> LENGTH: 5160
<212> TYPE: DNA
<213> ORGANISM: Adeno-Associated Virus 2

<400> SEQUENCE: 36

| | |
|---|---|
| ttggccactc cctctctgcg cgctcgctcg ctcactgagg ccgcccgggc aaagcccggg | 60 |
| cgtcgggcga cctttggtcg cccggcctca gtgagcgagc gagcgcgcag agagggagtg | 120 |
| gccaactcca tcactagggg ttcctgcggc cgcacgcgtt gtccctaaaa tgggcaaaca | 180 |
| ttgcaagcag caaacagcaa acatgtccct aaaatgggca acattgcaa gcagcaaaca | 240 |
| gcaaacatgt ccctaaaatg gcaaacatt gcaagcagca acagcaaac atgtccctaa | 300 |
| aatgggcaaa cattgcaagc agcaaacagc aaacagtcga ctggacacag acgctgtgg | 360 |
| tttctgagcc aggggcgac tcagatccca gccagtggac ttagcccctg tttgctcctc | 420 |
| cgataactgg ggtgaccttg gttaatattc accagcagcc tccccgttg ccctctgga | 480 |
| tccactgctt aaatacggac gaggacaggg ccctgtctcc tcagcttcag gcaccaccac | 540 |
| tgacctggga cagtgaatcg cgatcgccac catgcagatt gagctgagca cctgcttctt | 600 |
| cctgtgcctg ctgaggttct gcttctctgc caccaggaga tactacctgg gggctgtgga | 660 |
| gctgagctgg gactacatgc agtctgacct ggggagctg cctgtggatg ccaggttccc | 720 |

```
ccccagagtg cccaagagct tccccttcaa cacctctgtg gtgtacaaga agaccctgtt    780
tgtggagttc actgaccacc tgttcaacat tgccaagccc aggccccccct ggatgggcct   840
gctgggcccc accatccagg ctgaggtgta tgacactgtg gtgatcaccc tgaagaacat   900
ggccagccac cctgtgagcc tgcatgctgt gggggtgagc tactggaagg cctctgaggg   960
ggctgagtat gatgaccaga ccagccagag ggagaaggag gatgacaagg tgttccctgg  1020
gggcagccac acctatgtgt ggcaggtgct gaaggagaat ggccccatgg cctctgaccc  1080
cctgtgcctg acctacagct acctgagcca tgtggacctg gtgaaggacc tgaactctgg  1140
cctgattggg gccctgctgg tgtgcaggga gggcagcctg gccaaggaga gacccagac   1200
cctgcacaag ttcatcctgc tgtttgctgt gtttgatgag ggcaagagct ggcactctga  1260
aaccaagaac agcctgatgc aggacaggga tgctgcctct gccagggcct ggcccaagat  1320
gcacactgtg aatggctatg tgaacaggag cctgcctggc ctgattggct gccacaggaa  1380
gtctgtgtac tggcatgtga ttggcatggg caccaccccct gaggtgcaca gcatcttcct  1440
ggagggccac accttcctgg tcaggaacca caggcaggcc agcctggaga tcagccccat  1500
caccttcctg actgcccaga ccctgctgat ggacctgggc cagttcctgc tgttctgcca  1560
catcagcagc caccagcatg atggcatgga ggcctatgtg aaggtggaca gctgccctga  1620
ggagccccag ctgaggatga agaacaatga ggaggctgag gactatgatg atgacctgac  1680
tgactctgag atggatgtgg tgaggtttga tgatgacaac agcccagct catccagat   1740
caggtctgtg gccaagaagc accccaagac ctgggtgcac tacattgctg ctgaggagga  1800
ggactgggac tatgcccccc tggtgctggc ccctgatgac aggagctaca agagccagta  1860
cctgaacaat ggcccccaga ggattggcag gaagtacaag aaggtcaggt tcatggccta  1920
cactgatgaa accttcaaga ccagggaggc catccagcat gagtctggca tcctgggccc  1980
cctgctgtat gggagggtgg gggacaccct gctgatcatc ttcaagaacc aggccagcag  2040
gccctacaac atctacccccc atggcatcac tgatgtgagg cccctgtaca gcaggaggct  2100
gcccaagggg gtgaagcacc tgaaggactt ccccatcctg cctggggaga tcttcaagta  2160
caagtggact gtgactgtgg aggatggccc caccaagtct gacccaggt gcctgaccag  2220
atactacagc agctttgtga acatggagag ggacctggcc tctggcctga ttggcccct   2280
gctgatctgc tacaaggagt ctgtggacca gaggggcaac cagatcatgt ctgacaagag  2340
gaatgtgatc ctgttctctg tgtttgatga aaacaggagc tggtacctga ctgagaacat  2400
ccagagggttc ctgcccaacc tgctgggggt gcagctggag gacctgagtt ccaggccag  2460
caacatcatg cacagcatca atggctatgt gtttgacagc ctgcagctgt ctgtgtgcct  2520
gcatgaggtg gcctactggt acatcctgag cattggggcc cagactgact tcctgtctgt  2580
gttcttctct ggctacacct tcaagcacaa gatggtgtat gaggacaccc tgaccctgtt  2640
ccccttctct ggggagactg tgttcatgag catggagaac cctggcctgt ggattctggg  2700
ctgccacaac tctgacttca ggaacagggg catgactgcc ctgctgaaag tctccagctg  2760
tgacaagaac actggggact actatgagga cagctatgag gacatctctg cctacctgct  2820
gagcaagaac aatgccattg agcccaggag cttcagccag aacccccag tgctgaagag  2880
gcaccagagg gagatcacca ggaccacccct gcagtctgac caggaggaga ttgactatga  2940
tgacaccatc tctgtggaga tgaagaagga ggactttgac atctacgacg aggacgagaa  3000
ccagagcccc aggagcttcc agaagaagac caggcactac ttcattgctg ctgtggagag  3060
gctgtgggac tatggcatga gcagcagccc ccatgtgctg aggaacaggg cccagtctgg  3120
```

```
ctctgtgccc cagttcaaga aggtggtgtt ccaggagttc actgatggca gcttcaccca    3180 gccctgtac  agaggggagc tgaatgagca cctgggcctg ctgggcccct acatcagggc    3240
tgaggtggag gacaacatca tggtgacctt caggaaccag gccagcaggc cctacagctt    3300
ctacagcagc ctgatcagct atgaggagga ccagaggcag ggggctgagc ccaggaagaa    3360
ctttgtgaag cccaatgaaa ccaagaccta cttctggaag gtgcagcacc acatggcccc    3420
caccaaggat gagtttgact gcaaggcctg ggcctacttc tctgatgtgg acctggagaa    3480
ggatgtgcac tctggcctga ttggcccccct gctggtgtgc cacaccaaca ccctgaaccc    3540
tgcccatggc aggcaggtga ctgtgcagga gtttgccctg ttcttcacca tctttgatga    3600
aaccaagagc tggtacttca ctgagaacat ggagaggaac tgcagggccc cctgcaacat    3660
ccagatggag gaccccacct tcaaggagaa ctacaggttc catgccatca atggctacat    3720
catggacacc ctgcctggcc tggtgatggc ccaggaccag aggatcaggt ggtacctgct    3780
gagcatgggc agcaatgaga acatccacag catccacttc tctggccatg tgttcactgt    3840
gaggaagaag gaggagtaca gatggcccct gtacaacctg taccctgggg tgtttgagac    3900
tgtggagatg ctgcccagca aggctggcat ctggagggtg gagtgcctga ttggggagca    3960
cctgcatgct ggcatgagca ccctgttcct ggtgtacagc aacaagtgcc agaccccct    4020 gggcatggcc tctggccaca tcagggactt ccagatcact gcctctggcc agtatggcca    4080 gtgggcccc  aagctggcca ggctgcacta ctctggcagc atcaatgcct ggagcaccaa    4140
ggagcccttc agctggatca aggtggacct gctggccccc atgatcatcc atggcatcaa    4200
gacccagggg gccaggcaga gttcagcag cctgtacatc agccagttca tcatcatgta    4260
cagcctggat ggcaagaagt ggcagaccta caggggcaac agcactgcca ccctgatggt    4320 gttcttggc  aatgtggaca gctctggcat caagcacaac atcttcaacc cccccatcat    4380
tgccagatac atcaggctgc accccaccca ctacagcatc aggagcaccc tgaggatgga    4440
gctgatgggc tgtgacctga acagctgcag catgcccctg ggcatggaga gcaaggccat    4500
ctctgatgcc cagatcactg ccagcagcta cttcaccaac atgtttgcca cctggagccc    4560
cagcaaggcc aggctgcacc tgcagggcag gagcaatgcc tggaggcccc aggtcaacaa    4620
ccccaaggag tggctgcagg tggacttcca gaagaccatg aaggtgactg gggtgaccac    4680 ccaggggggtg aagagcctgc tgaccagcat gtatgtgaag gagttcctga tcagcagcag    4740
ccaggatggc caccagtgga ccctgttctt ccagaatggc aaggtgaagg tgttccaggg    4800
caaccaggac agcttcaccc ctgtggtgaa cagcctggac ccccccctgc tgaccagata    4860
cctgaggatt caccccagga gctgggtgca ccagattgcc ctgaggatgg aggtgctggg    4920
ctgtgaggcc caggacctgt actgacctcg aggaataaag gaaatttatt ttcattgcaa    4980
tagtgtgttg gttttttgtg tcacgtggcg gccgcaggaa ccctagtgat ggagttggc    5040 cactccctct ctgcgcgctc gctcgctcac tgaggccggg cgaccaaagg tcgcccgacg    5100
cccgggcttt gcccgggcgg cctcagtgag cgagcgagcg cgcagagagg gagtggccaa    5160
```

<210> SEQ ID NO 37
<211> LENGTH: 5383
<212> TYPE: DNA
<213> ORGANISM: Adeno-Associated Virus 2

<400> SEQUENCE: 37

```
ttggccactc cctctctgcg cgctcgctcg ctcactgagg ccgcccgggc aaagcccggg    60
```

-continued

| | |
|---|---|
| cgtcgggcga cctttggtcg cccggcctca gtgagcgagc gagcgcgcag agagggagtg | 120 |
| gccaactcca tcactagggg ttcctgcggc cgcacgcgtg ttttcgactg tttgctgttt | 180 |
| gctgcttgca atgtttgccc attttaggga catgtttgct gtttgctgct tgcaatgttt | 240 |
| gcccatttta gggacatgtt tgctgtttgc tgcttgcaat gtttgcccat tttagggaca | 300 |
| tgtttgctgt ttgctgcttg caatgtttgc ccattttagg acaacgcga aacgtcgact | 360 |
| ggacacagga cgctgtggtt tctgagccag ggggcgactc agatcccagc cagtggactt | 420 |
| agcccctgtt tgctcctccg ataactgggg tgaccttggt taatattcac cagcagcctc | 480 |
| ccccgttgcc cctctggatc cactgcttaa atacggacga ggacagggcc ctgtctcctc | 540 |
| agcttcaggc accaccactg acctgggaca gtgaatcgta agtatgcctt tcactgcgag | 600 |
| aggtctgga gaggcttctg agctccccat ggcccaggca ggcagcaggt ctggggcagg | 660 |
| aggggggttg tggagtgcct tgactcgggg cctggccccc ccatctctgt cttgcaggac | 720 |
| aattgccgtc ttctgtctcg tggggcatcc tcctgctggc aggcctgtgc tgcctggtcc | 780 |
| ctgcgatcgc caccatgcag attgagctga gcacctgctt cttcctgtgc ctgctgaggt | 840 |
| tctgcttctc tgccaccagg agatactacc tgggggctgt ggagctgagc tgggactaca | 900 |
| tgcagtctga cctgggggag ctgcctgtgg atgccaggtt ccccccaga gtgcccaaga | 960 |
| gcttcccctt caacacctct gtggtgtaca agaagaccct gtttgtggag ttcactgacc | 1020 |
| acctgttcaa cattgccaag cccaggcccc cctggatggg cctgctgggc ccaccatcc | 1080 |
| aggctgaggt gtatgacact gtggtgatca ccctgaagaa catggccagc caccctgtga | 1140 |
| gcctgcatgc tgtgggggtg agctactgga aggcctctga gggggctgag tatgatgacc | 1200 |
| agaccagcca gagggagaag gaggatgaca aggtgttccc tgggggcagc cacacctatg | 1260 |
| tgtggcaggt gctgaaggag aatggcccca tggcctctga ccccctgtgc ctgacctaca | 1320 |
| gctacctgag ccatgtggac ctggtgaagg acctgaactc tggcctgatt ggggccctgc | 1380 |
| tggtgtgcag ggagggcagc ctggccaagg agaagaccca gaccctgcac aagttcatcc | 1440 |
| tgctgtttgc tgtgtttgat gagggcaaga gctggcactc tgaaaccaag aacagcctga | 1500 |
| tgcaggacag ggatgctgcc tctgccaggg cctggcccaa gatgcacact gtgaatggct | 1560 |
| atgtgaacag gagcctgcct ggctgattg gctgccacag gaagtctgtg tactggcatg | 1620 |
| tgattggcat gggcaccacc cctgaggtgc acagcatctt cctggagggc acacccttcc | 1680 |
| tggtcaggaa ccacaggcag gccagcctgg agatcagccc catcaccttc ctgactgccc | 1740 |
| agaccctgct gatggacctg gccagttcc tgctgttctg ccacatcagc agccaccagc | 1800 |
| atgatggcat ggaggcctat gtgaaggtgg acagctgccc tgaggagccc cagctgagga | 1860 |
| tgaagaacaa tgaggaggct gaggactatg atgatgacct gactgactct gagatggatg | 1920 |
| tggtgaggtt tgatgatgac aacagcccca gcttcatcca gatcaggtct gtggccaaga | 1980 |
| agcaccccaa gacctgggtg cactacattg ctgctgagga ggaggactgg gactatgccc | 2040 |
| ccctggtgct ggcccctgat gacaggagct acaagagcca gtacctgaac aatggccccc | 2100 |
| agaggattgg caggaagtac aagaaggtca ggttcatggc ctacactgat gaaaccttca | 2160 |
| agaccaggga ggccatccag catgagtctg gcatcctggg ccccctgctg tatggggagg | 2220 |
| tgggggacac cctgctgatc atcttcaaga accaggccag caggccctac aacatctacc | 2280 |
| ccatggcat cactgatgtg aggccctgt acagcaggag ctgcccaag ggggtgaagc | 2340 |
| acctgaagga cttccccatc ctgcctgggg agatcttcaa gtacaagtgg actgtgactg | 2400 |
| tggaggatgg ccccaccaag tctgaccccc ggtgcctgac cagatactac agcagctttg | 2460 |

```
tgaacatgga gagggacctg gcctctggcc tgattggccc cctgctgatc tgctacaagg    2520
agtctgtgga ccagaggggc aaccagatca tgtctgacaa gaggaatgtg atcctgttct    2580
ctgtgtttga tgagaacagg agctggtacc tgactgagaa catccagagg ttcctgccca    2640
accctgctgg ggtgcagctg gaggaccctg agttccaggc cagcaacatc atgcacagca    2700
tcaatggcta tgtgtttgac agcctgcagc tgtctgtgtg cctgcatgag gtggcctact    2760
ggtacatcct gagcattggg gcccagactg acttcctgtc tgtgttcttc tctggctaca    2820
ccttcaagca caagatggtg tatgaggaca ccctgaccct gttccccttc tctggggaga    2880
ctgtgttcat gagcatggag aaccctgccc tgtggattct gggctgccac aactctgact    2940
tcaggaacag gggcatgact gccctgctga agtctccag ctgtgacaag aacactgggg    3000
actactatga ggacagctat gaggacatct ctgcctacct gctgagcaag aacaatgcca    3060
ttgagcccag gagcttcagc cagaaccccc cagtgctgaa gaggcaccag agggagatca    3120
ccaggaccac cctgcagtct gaccaggagg agattgacta tgatgacacc atctctgtgg    3180
agatgaagaa ggaggacttt gacatctacg acgaggacga gaaccagagc cccaggagct    3240
tccagaagaa gaccaggcac tacttcattg ctgctgtgga gaggctgtgg gactatggca    3300
tgagcagcag cccccatgtg ctgaggaaca gggcccagtc tggctctgtg ccccagttca    3360
agaaggtggt gttccaggag ttcactgatg gcagcttcac ccagcccctg tacagagggg    3420
agctgaatga gcacctgggc ctgctgggcc cctacatcag ggctgaggtg gaggacaaca    3480
tcatggtgac cttcaggaac caggccagca ggccctacag cttctacagc agcctgatca    3540
gctatgagga ggaccagagg caggggctg agcccaggaa gaactttgtg aagcccaatg    3600
aaaccaagac ctacttctgg aaggtgcagc accacatggc cccaccaag gatgagtttg    3660 actgcaaggc ctgggcctac ttctctgatg tggacctgga aaggatgtg cactctggcc    3720 tgattggccc cctgctggtg tgccacacca cacccctgaa ccctgccat ggcaggcagg    3780 tgactgtgca ggagtttgcc ctgttcttca ccatctttga tgaaaccaag agctggtact    3840
tcactgagaa catggagagg aactgcaggg cccctgcaa catccagatg gaggacccca    3900
ccttcaagga gaactacagg ttccatgcca tcaatggcta catcatggac accctgcctg    3960
gcctggtgat ggcccaggac cagaggatca ggtggtacct gctgagcatg ggcagcaatg    4020
agaacatcca cagcatccac ttctctggcc atgtgttcac tgtgaggaag aaggaggagt    4080
acaagatggc cctgtacaac ctgtaccctg gggtgtttga gactgtggag atgctgccca    4140
gcaaggctgg catctggagg gtggagtgcc tgattgggga gcacctgcat gctggcatga    4200
gcaccctgtt cctggtgtac agcaacaagt gccagacccc cctgggcatg gcctctggcc    4260
acatcaggga cttccagatc actgcctctg ccagtatgg ccagtgggcc ccaagctgg    4320 ccaggctgca ctactctggc agcatcaatg cctggagcac caaggagccc ttcagctgga    4380
tcaaggtgga cctgctggcc cccatgatca tccatggcat caagacccag ggggccaggc    4440
agaagttcag cagcctgtac atcagccagt tcatcatcat gtacagcctg gatggcaaga    4500
agtggcagac ctacaggggc aacagcactg gcaccctgat ggtgttcttt ggcaatgtgg    4560
acagctctgg catcaagcac aacatcttca acccccccat cattgccaga tacatcaggc    4620
tgcaccccac ccactacagc atcaggagca cctgaggat ggagctgatg ggctgtgacc    4680
tgaacagctg cagcatgccc ctgggcatgg agagcaaggc catctctgat gcccagatca    4740
ctgccagcag ctacttcacc aacatgtttg ccacctggag ccccagcaag gccaggctgc    4800
```

```
acctgcaggg caggagcaat gcctggaggc cccaggtcaa caaccccaag gagtggctgc    4860
aggtggactt ccagaagacc atgaaggtga ctggggtgac cacccagggg gtgaagagcc    4920
tgctgaccag catgtatgtg aaggagttcc tgatcagcag cagccaggat ggccaccagt    4980
ggaccctgtt cttccagaat ggcaaggtga aggtgttcca gggcaaccag acagcttca    5040 cccctgtggt gaacagcctg accccccccc tgctgaccag atacctgagg attcaccccc    5100
agagctgggt gcaccagatt gccctgagga tggaggtgct gggctgtgag gcccaggacc    5160
tgtactgacc tcgaggaata aggaaatttt attttcattg caatagtgtg ttggtttttt    5220
gtgtcacgtg gcggccgcag gaaccctag tgatggagtt ggccactccc tctctgcgcg    5280
ctcgctcgct cactgaggcc gggcgaccaa aggtcgcccg acgcccgggc tttgcccggg    5340
cggcctcagt gagcgagcga gcgcgcagag agggagtggc caa                     5383
```

<210> SEQ ID NO 38
<211> LENGTH: 5728
<212> TYPE: DNA
<213> ORGANISM: Adeno-Associated Virus 2

<400> SEQUENCE: 38

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgcggc cgcacgcgtg ttttcgactg tttgctgttt     180
gctgcttgca atgtttgccc attttaggga catgtttgct gtttgctgct tgcaatgttt     240
gcccatttta gggacatgtt tgctgtttgc tgcttgcaat gtttgcccat tttagggaca     300
tgtttgctgt ttgctgcttg caatgtttgc ccattttagg acaacgcga aacgtcgaca      360 ggttaatttt taaaaagcag tcaaaagtcc aagtggccct tggcagcatt tactctctct     420
gtttgctctg gttaataatc tcaggagcac aaacattcct ggaggcagga agaaaatca      480 acatcctgga cttatcctct gggcctctcc ccacccccag gagaggctca ggttaatttt     540
taaaaagcag tcaaaagtcc aagtggccct tggcagcatt tactctctct gtttgctctg     600
gttaataatc tcaggagcac aaacattcct ggaggcagga agaaaatca acatcctgga     660 cttatcctct gggcctctcc ccacccccag gagaggctgt cgactggaca caggacgctg     720
tggtttctga gccaggggc gactcagatc ccagccagtg gacttagccc ctgtttgctc      780
ctccgataac tggggtgacc ttggttaata ttcaccagca gcctccccg ttgcccctct     840 ggatccactg cttaaatacg gacgaggaca gggccctgtc tcctcagctt caggcaccac     900
cactgacctg ggacagtgaa tcgtaagtat gcctttcact gcgagaggtt ctggagaggc     960
ttctgagctc cccatggccc aggcaggcag caggtctggg gcaggagggg ggttgtggag    1020
tgccttgact cggggcctgg cccccccatc tctgtcttgc aggacaattg ccgtcttctg    1080
tctcgtgggg catcctcctg ctggcaggcc tgtgctgcct ggtccctgcg atcgccacca    1140
tgcagattga gctgagcacc tgcttcttcc tgtgcctgct gaggttctgc ttctctgcca    1200
ccaggagata ctacctgggg gctgtggagc tgagctggga ctacatgcag tctgacctgg    1260
gggagctgcc tgtggatgcc aggttccccc ccagagtgcc caagagcttc ccctttcaaca    1320 cctctgtggt gtacaagaag accctgtttg tggagttcac tgaccacctg ttcaacattg    1380
ccaagcccag gccccctgg atgggcctgc tgggccccac catccaggct gaggtgtatg    1440
acactgtggt gatcacctg aagaacatgg ccagccaccc tgtgagcctg catgctgtgg    1500
gggtgagcta ctggaaggcc tctgaggggg ctgagtatga tgaccagacc agccagaggg    1560
```

```
agaaggagga tgacaaggtg ttccctgggg gcagccacac ctatgtgtgg caggtgctga    1620
aggagaatgg ccccatggcc tctgaccccc tgtgcctgac ctacagctac ctgagccatg    1680
tggacctggt gaaggacctg aactctggcc tgattggggc cctgctggtg tgcagggagg    1740
gcagcctggc caaggagaag acccagaccc tgcacaagtt catcctgctg tttgctgtgt    1800
ttgatgaggg caagagctgg cactctgaaa ccaagaacag cctgatgcag gacagggatg    1860
ctgcctctgc cagggcctgg cccaagatgc acactgtgaa tggctatgtg aacaggagcc    1920
tgcctggcct gattggctgc acaggaagt ctgtgtactg gcatgtgatt ggcatgggca    1980
ccaccccctga ggtgcacagc atcttcctgg agggccacac cttcctggtc aggaaccaca    2040
ggcaggccag cctggagatc agccccatca ccttcctgac tgcccagacc ctgctgatgg    2100
acctgggcca gttcctgctg ttctgccaca tcagcagcca ccagcatgat ggcatggagg    2160
cctatgtgaa ggtggacagc tgccctgagg agccccagct gaggatgaag aacaatgagg    2220
aggctgagga ctatgatgat gacctgactg actctgagat ggatgtggtg aggtttgatg    2280
atgacaacag ccccagcttc atccagatca ggtctgtggc caagaagcac cccaagacct    2340
gggtgcacta cattgctgct gaggaggagg actgggacta tgccccccctg gtgctggccc    2400
ctgatgacag gagctacaag agccagtacc tgaacaatgg cccccagagg attggcagga    2460
agtacaagaa ggtcaggttc atggcctaca ctgatgaaac cttcaagacc agggaggcca    2520
tccagcatga gtctggcatc ctgggccccc tgctgtatgg ggaggtgggg gacaccctgc    2580
tgatcatctt caagaaccag gccagcaggc cctacaacat ctaccccccat ggcatcactg    2640
atgtgaggcc cctgtacagc aggaggctgc ccaagggggt gaagcacctg aaggacttcc    2700
ccatcctgcc tgggagatc ttcaagtaca agtggactgt gactgtggag gatggcccca    2760
ccaagtctga ccccaggtgc ctgaccagat actacagcag ctttgtgaac atggagaggg    2820
acctggcctc tggcctgatt ggcccccctgc tgatctgcta caaggagtct gtggaccaga    2880
ggggcaacca gatcatgtct gacaagagga atgtgatcct gttctctgtg tttgatgaga    2940
acaggagctg gtacctgact gagaacatcc agaggttcct gcccaaccct gctggggtgc    3000
agctggagga ccctgagttc caggccagca acatcatgca cagcatcaat ggctatgtgt    3060
ttgacagcct gcagctgtct gtgtgcctgc atgaggtggc ctactggtac atcctgagca    3120
ttggggccca gactgacttc ctgtctgtgt cttctctgg ctacaccttc aagcacaaga    3180
tggtgtatga ggacacccctg accctgttcc ccttctctgg ggagactgtg ttcatgagca    3240
tggagaaccc tggcctgtgg attctgggct gccacaactc tgacttcagg aacaggggca    3300
tgactgccct gctgaaagtc tccagctgtg acaagaacac tggggactac tatgaggaca    3360
gctatgagga catctctgcc tacctgctga gcaagaacaa tgccattgag cccaggagct    3420
tcagccagaa ccccccagtg ctgaagaggc accagaggga gatcaccagg accaccctgc    3480
agtctgacca ggaggagatt gactatgatg acaccatctc tgtggagatg aagaaggagg    3540
actttgacat ctacgacgag gacgagaacc agagcccag agcttccag aagaagacca    3600
ggcactactt cattgctgct gtggagaggc tgtgggacta tggcatgagc agcagccccc    3660
atgtgctgag gaacagggcc cagtctggct ctgtgcccca gttcaagaag gtggtgttcc    3720
aggagttcac tgatggcagc ttcacccagc ccctgtacag aggggagctg aatgagcacc    3780
tgggcctgct gggcccctac atcagggctg aggtggagga caacatcatg gtgaccttca    3840
ggaaccaggc cagcaggccc tacagcttct acagcagcct gatcagctat gaggaggacc    3900
```
agaggcaggg ggctgagccc aggaagaact ttgtgaagcc caatgaaacc aagacctact    3960
tctggaaggt gcagcaccac atggcccca ccaaggatga gtttgactgc aaggcctggg    4020
cctacttctc tgatgtggac ctggagaagg atgtgcactc tggcctgatt ggccccctgc    4080
tggtgtgcca caccaacacc ctgaaccctg cccatggcag gcaggtgact gtgcaggagt    4140
ttgccctgtt cttcaccatc tttgatgaaa ccaagagctg gtacttcact gagaacatgg    4200
agaggaactg cagggccccc tgcaacatcc agatggagga ccccaccttc aaggagaact    4260
acaggttcca tgccatcaat ggctacatca tggacaccct gcctggcctg gtgatggccc    4320
aggaccagag gatcaggtgg tacctgctga gcatgggcag caatgagaac atccacagca    4380
tccacttctc tggccatgtg ttcactgtga ggaagaagga ggagtacaag atggccctgt    4440
acaacctgta ccctgggtg tttgagactg tggagatgct gcccagcaag gctggcatct    4500
ggagggtgga gtgcctgatt ggggagcacc tgcatgctgg catgagcacc ctgttcctgg    4560
tgtacagcaa caagtgccag accccctgg gcatggcctc tggccacatc agggacttcc    4620
agatcactgc ctctggccag tatggccagt gggcccccaa gctggccagg ctgcactact    4680
ctggcagcat caatgcctgg agcaccaagg agcccttcag ctggatcaag gtggacctgc    4740 tggccccat gatcatccat ggcatcaaga cccaggggc caggcagaag ttcagcagcc    4800
tgtacatcag ccagttcatc atcatgtaca gcctggatgg caagaagtgg cagacctaca    4860
ggggcaacag cactggcacc ctgatggtgt tctttggcaa tgtggacagc tctggcatca    4920
agcacaacat cttcaacccc ccatcattg ccagatacat caggctgcac cccacccact    4980
acagcatcag gagcacctg aggatggagc tgatgggctg tgacctgaac agctgcagca    5040 tgccctggg catggagagc aaggccatct ctgatgccca gatcactgcc agcagctact    5100
tcaccaacat gtttgccacc tggagccca gcaaggccag gctgcacctg cagggcagga    5160
gcaatgcctg gaggcccag gtcaacaacc caaggagtg gctgcaggtg gacttccaga    5220
agaccatgaa ggtgactggg gtgaccaccc aggggggtgaa gagcctgctg accagcatgt    5280
atgtgaagga gttcctgatc agcagcagcc aggatggcca ccagtggacc ctgttcttcc    5340
agaatggcaa ggtgaaggtg ttccagggca accaggacac cttcaccct gtggtgaaca    5400 gcctggaccc ccccctgctg accagatacc tgaggattca ccccagagc tgggtgcacc    5460 agattgccct gaggatggag gtgctgggct gtgaggccca ggacctgtac tgacctcgag    5520
gaataaagga aatttatttt cattgcaata gtgtgttggt tttttgtgtc acgtggcggc    5580
cgcaggaacc cctagtgatg gagttggcca ctccctctct gcgcgctcgc tcgctcactg    5640
aggccgggcg accaaaggtc gcccgacgcc cgggctttgc ccgggcggcc tcagtgagcg    5700
agcgagcgcg cagagaggga gtggccaa    5728

<210> SEQ ID NO 39
<211> LENGTH: 5905
<212> TYPE: DNA
<213> ORGANISM: Adeno-Associated Virus 2

<400> SEQUENCE: 39
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgcggc cgcacgcgtg ttttcgactg tttgctgttt     180
gctgcttgca atgtttgccc attttaggga catgttgct gtttgctgct tgcaatgttt     240 gcccattta gggacatgtt tgctgtttgc tgcttgcaat gtttgcccat tttagggaca     300

-continued

```
tgtttgctgt tgctgcttg caatgtttgc ccatttagg gacaacgcga aacgtcgaca    360
ggttaatttt taaaaagcag tcaaaagtcc aagtgggcct tggcagcatt tactctctct    420
gtttgctctg gttaataatc tcaggagcac aaacattcct ggaggcagga aagaaatca     480
acatcctgga cttatcctct gggcctctcc cacccccag gagaggctca ggttaattt     540
taaaaagcag tcaaaagtcc aagtggccct tggcagcatt tactctctct gtttgctctg    600
gttaataatc tcaggagcac aaacattcct ggaggcagga gaagaaatca acatcctgga    660
cttatcctct gggcctctcc cacccccag gagaggctgt cgactggaca caggacgctg    720
tggtttctga gccagggggc gactcagatc ccagccagtg gacttagccc ctgtttgctc    780
ctccgataac tggggtgacc ttggttaata ttcaccagca gcctccccg ttgcccctct     840
ggatccactg cttaaaatacg gacgaggaca gggccctgtc tcctcagctt caggcaccac    900
cactgacctg gacagtgaa tcgtaagtat gcctttcact gcgagaggtt ctggagaggc    960
ttctgagctc cccatggccc aggcaggcag caggtctggg gcaggagggg ggttgtggag   1020
tgccttgact cggggcctgg ccccccatc tctgtcttgc aggacaattg ccgtcttctg    1080
tctcgtgggg catcctcctg ctggcaggcc tgtgctgcct ggtccctgcg atcgccacca   1140
tgcagattga gctgagcacc tgcttcttcc tgtgcctgct gaggttctgc ttctctgcca   1200
ccaggagata ctacctgggg gctgtggagc tgagctggga ctacatgcag tctgacctgg   1260
gggagctgcc tgtggatgcc aggttccccc ccagagtgcc caagagcttc cccttcaaca   1320
cctctgtggt gtacaagaag accctgtttt tggagttcac tgaccacctg ttcaacattg   1380
ccaagcccag gccccctgg atgggcctgc tgggccccac catccaggct gaggtgtatg    1440
acactgtggt gatcaccctg aagaacatgg ccagccaccc tgtgagcctg catgctgtgg   1500
gggtgagcta ctggaaggcc tctgaggggg ctgagtatga tgaccagacc agccagaggg   1560
agaaggagga tgacaaggtg ttccctgggg gcagccacac ctatgtgtgg caggtgctga   1620
aggagaatgg ccccatggcc tctgacccc tgtgcctgac ctacagctac ctgagccatg   1680
tggacctggt gaaggacctg aactctggcc tgattgggc cctgctggtg tgcagggagg   1740
gcagcctggc caaggagaag acccagaccc tgcacaagtt catcctgctg tttgctgtgt   1800
ttgatgaggg caagagctgg cactctgaaa ccaagaacag cctgatgcag gacagggatg   1860
ctgcctctgc cagggcctgg cccaagatgc acactgtgaa tggctatgtg aacaggagcc   1920
tgcctggcct gattggctgc cacaggaagt ctgtgtactg gcatgtgatt ggcatgggca   1980
ccacccctga ggtgcacagc atcttcctgg agggccacac cttcctggtc aggaaccaca   2040
ggcaggccag cctggagatc agccccatca ccttcctgac tgcccagacc ctgctgatgg   2100
acctgggcca gttcctgctg ttctgccaca tcagcagcca ccagcatgat ggcatggagg   2160
cctatgtgaa ggtggacagc tgccctgagg agccccagct gaggatgaag aacaatgagg   2220
aggctgagga ctatgatgat gacctgactg actctgagat ggatgtggtg aggtttgatg   2280
atgacaacag ccccagcttc atccagatca ggtctgtggc caagaagcac cccaagacct   2340
gggtgcacta cattgctgct gaggaggagg actgggacta tgccccctg gtgctggccc   2400
ctgatgacag gagctacaag agccagtacc tgaacaatgg ccccagagg attggcagga   2460
agtacaagaa ggtcaggttc atggcctaca ctgatgaaac cttcaagacc agggaggcca   2520
tccagcatga gtctgcatc ctgggccccc tgctgtatgg ggaggtgggg gacacctgc    2580
tgatcatctt caagaaccag gccagcaggc cctacaacat ctaccccat ggcatcactg    2640
```

```
atgtgaggcc cctgtacagc aggaggctgc ccaagggggt gaagcacctg aaggacttcc    2700
ccatcctgcc tggggagatc ttcaagtaca agtggactgt gactgtggag gatggcccca    2760
ccaagtctga ccccaggtgc ctgaccagat actacagcag ctttgtgaac atggagaggg    2820
acctggcctc tggcctgatt ggccccctgc tgatctgcta caaggagtct gtggaccaga    2880
ggggcaacca gatcatgtct gacaagagga atgtgatcct gttctctgtg tttgatgaga    2940
acaggagctg gtacctgact gagaacatcc agaggttcct gcccaaccct gctggggtgc    3000
agctggagga ccctgagttc caggccagca acatcatgca cagcatcaat ggctatgtgt    3060
ttgacagcct gcagctgtct gtgtgcctgc atgaggtggc ctactggtac atcctgagca    3120
ttggggccca gactgacttc ctgtctgtgt cttctctgg ctacaccttc aagcacaaga    3180
tggtgtatga ggacaccctg accctgttcc ccttctctgg ggagactgtg ttcatgagca    3240
tggagaaccc tggcctgtgg attctgggct gccacaactc tgacttcagg aacaggggca    3300
tgactgccct gctgaaagtc tccagctgtg acaagaacac tggggactac tatgaggaca    3360
gctatgagga catctctgcc tacctgctga gcaagaacaa tgccattgag cccaggagct    3420
tcagccagaa ccccccagtg ctgaagaggc ccagaggga gatcaccagg accaccctgc    3480
agtctgacca ggaggagatt gactatgatg acaccatctc tgtggagatg aagaaggagg    3540
actttgacat ctacgacgag gacgagaacc agagccccag gagcttccag aagaagacca    3600
ggcactactt cattgctgct gtggagaggc tgtgggacta tggcatgagc agcagccccc    3660
atgtgctgag gaacagggcc cagtctggct ctgtgcccca gttcaagaag gtggtgttcc    3720
aggagttcac tgatggcagc ttcacccagc ccctgtacag aggggagctg aatgagcacc    3780
tgggcctgct gggcccctac atcagggctg aggtggagga caacatcatg gtgaccttca    3840
ggaaccaggc cagcaggccc tacagcttct acagcagcct gatcagctat gaggaggacc    3900
agaggcaggg ggctgagccc aggaagaact tgtgaagcc caatgaaacc aagacctact    3960
tctgaaggt gcagcaccac atggccccca ccaaggatga gtttgactgc aaggcctggg    4020
cctacttctc tgatgtggac ctggagaagg atgtgcactc tggcctgatt ggccccctgc    4080
tggtgtgcca caccaacacc ctgaaccctg cccatggcag gcaggtgact gtgcaggagt    4140
ttgccctgtt cttcaccatc tttgatgaaa ccaagagctg gtacttcact gagaacatgg    4200
agaggaactg cagggccccc tgcaacatcc agatggagga ccccaccttc aaggagaact    4260
acaggttcca tgccatcaat ggctacatca tggacaccct gcctggcctg gtgatggccc    4320
aggaccagag gatcaggtgg tacctgctga gcatgggcag caatgagaac atccacagca    4380
tccacttctc tggccatgtg ttcactgtga ggaagaagga ggagtacaag atggcctgt    4440
acaacctgta ccctgggggtg tttgagactg tggagatgct gcccagcaag gctggcatct    4500
ggagggtgga gtgcctgatt ggggagcacc tgcatgctgg catgagcacc ctgttcctgg    4560
tgtacagcaa caagtgccag acccccctgg catggcctc tggccacatc agggacttcc    4620
agatcactgc ctctggccag tatggccagt gggcccccaa gctggccagg ctgcactact    4680
ctggcagcat caatgcctgg agcaccaagg agcccttcag ctggatcaag gtggacctgc    4740
tggcccccat gatcatccat ggcatcaaga cccaggggc caggcagaag ttcagcagcc    4800
tgtacatcag ccagttcatc atcatgtaca gcctggatgg caagaagtgg cagacctaca    4860
ggggcaacag cactggcacc ctgatggtgt tctttggcaa tgtggacagc tctggcatca    4920
agcacaacat cttcaacccc cccatcattg ccagatacac caggctgcac cccacccact    4980
acagcatcag gagcacccctg aggatggagc tgatgggctg tgacctgaac agctgcagca    5040
```

```
tgcccctggg catggagagc aaggccatct ctgatgccca gatcactgcc agcagctact    5100
tcaccaacat gtttgccacc tggagcccca gcaaggccag gctgcacctg cagggcagga    5160
gcaatgcctg gaggcccag gtcaacaacc ccaaggagtg gctgcaggtg gacttccaga     5220
agaccatgaa ggtgactggg gtgaccaccc aggggtgaa gagcctgctg accagcatgt     5280
atgtgaagga gttcctgatc agcagcagcc aggatggcca ccagtggacc ctgttcttcc    5340
agaatggcaa ggtgaaggtg ttccagggca accaggacgc cttcacccct gtggtgaaca    5400
gcctggaccc ccccctgctg accagatacc tgaggattca ccccagagc tgggtgcacc     5460 agattgccct gaggatggag gtgctgggct gtgaggccca ggacctgtac tgacctcgag    5520
gtgtgccttc tagttgccag ccatctgttg tttgcccctc cccgtgcct tccttgaccc      5580 tggaaggtgc cactcccact gtcctttcct aataaaatga ggaaattgca tcgcattgtc    5640
tgagtaggtg tcattctatt ctggggggtg gggtggggca ggacagcaag ggggaggatt    5700
gggaagacaa tagcaggcat gctggggatg cggtgggctc tatgggcacg tggcggccgc    5760
aggaacccct agtgatggag ttggccactc cctctctgcg cgctcgctcg ctcactgagg    5820
ccgggcgacc aaaggtcgcc cgacgcccgg gctttgcccg gcggcctca gtgagcgagc     5880 gagcgcgcag agagggagtg gccaa                                          5905
```

<210> SEQ ID NO 40
<211> LENGTH: 5355
<212> TYPE: DNA
<213> ORGANISM: Adeno-Associated Virus 2

<400> SEQUENCE: 40

```
ttggccactc cctctctgcg cgctcgctcg ctcactgagg ccgcccgggc aaagcccggg      60
cgtcgggcga ccttttggtcg cccggcctca gtgagcgagc gagcgcgcag agagggagtg   120
gccaactcca tcactagggg ttcctgcggc cgcacgcgtg ttttcgactg tttgctgttt    180
gctgcttgca atgtttgccc attttaggga catgtttgct gtttgctgct tgcaatgttt    240
gcccatttta gggacatgtt tgctgtttgc tgcttgcaat gtttgcccat tttaggaca     300 tgtttgctgt tgctgcttg caatgtttgc ccatttagg acaacgcga aacgtcgact       360 ggacacagga cgctgtggtt tctgagccag ggggcgactc agatcccagc cagtggactt    420
agcccctgtt tgctcctccg ataactgggg tgaccttggt taatattcac cagcagcctc    480
ccccgttgcc cctctggatc cactgcttaa atacggacga ggacagggcc ctgtctcctc    540
agcttcaggc accaccactg acctgggaca gtgaatcgcg atcgccacca tgcagattga    600
gctgagcacc tgcttcttcc tgtgcctgct gaggttctgc ttctctgcca ccaggagata    660
ctacctgggg gctgtggagc tgagctggga ctacatgcag tctgacctgg ggagctgcc     720 tgtggatgcc aggttcccc ccagagtgcc caagagcttc cccttcaaca cctctgtggt     780
gtacaagaag accctgtttg tggagttcac tgaccacctg ttcaacattg ccaagcccag    840
gcccccctgg atgggcctgc tgggccccac catccaggct gaggtgtatg acactgtggt    900
gatcaccctg aagaacatgg ccagccaccc tgtgagcctg catgctgtgg gggtgagcta    960
ctggaaggcc tctgagggg ctgagtatga tgaccagacc agccagaggg agaaggagga    1020
tgacaaggtg ttccctgggg gcagccacac ctatgtgtgg caggtgctga aggagaatgg   1080
ccccatggcc tctgacccc tgtgcctgac ctacagctac ctgagccatg tggacctggt   1140
gaaggacctg aactctggcc tgattggggc cctgctggtg tgcaggagg gcagcctggc   1200
```

```
caaggagaag acccagaccc tgcacaagtt catcctgctg tttgctgtgt ttgatgaggg      1260
caagagctgg cactctgaaa ccaagaacag cctgatgcag gacagggatg ctgcctctgc      1320
cagggcctgg cccaagatgc acactgtgaa tggctatgtg aacaggagcc tgcctggcct      1380
gattggctgc cacaggaagt ctgtgtactg catgtgatt ggcatgggca ccacccctga       1440
ggtgcacagc atcttcctgg agggccacac cttcctggtc aggaaccaca ggcaggccag      1500
cctggagatc agccccatca ccttcctgac tgcccagacc ctgctgatgg acctgggcca      1560
gttcctgctg ttctgccaca tcagcagcca ccagcatgat ggcatggagg cctatgtgaa      1620
ggtggacagc tgccctgagg agccccagct gaggatgaag aacaatgagg aggctgagga      1680
ctatgatgat gacctgactg actctgagat ggatgtggtg aggtttgatg atgacaacag      1740
cccccagctt catccagatca ggtctgtggc caagaagcac cccaagacct gggtgcacta      1800
cattgctgct gaggaggagg actgggacta tgcccccctg gtgctggccc ctgatgacag      1860
gagctacaag agccagtacc tgaacaatgg cccccagagg attggcagga agtacaagaa      1920
ggtcaggttc atggcctaca ctgatgaaac cttcaagacc agggaggcca tccagcatga      1980
gtctggcatc ctgggccccc tgctgtatgg ggaggtgggg gacaccctgc tgatcatctt      2040
caagaaccag gccagcaggc cctacaacat ctaccccat ggcatcactg atgtgaggcc       2100
cctgtacagc aggaggctgc ccaagggggt gaagcacctg aaggacttcc ccatcctgcc      2160
tgggagatc ttcaagtaca gtggactgt gactgtggag gatggcccca ccaagtctga       2220
ccccaggtgc ctgaccagat actacagcag ctttgtgaac atggagaggg acctggcctc      2280
tggcctgatt ggccccctgc tgatctgcta caaggagtct gtggaccaga ggggcaacca      2340
gatcatgtct gacaagagga atgtgatcct gttctctgtg tttgatgaga acaggagctg      2400
gtacctgact gagaacatcc agaggttcct gcccaacccct gctgggtgc agctggagga     2460
ccctgagttc caggccagca acatcatgca cagcatcaat ggctatgtgt ttgacagcct      2520
gcagctgtct gtgtgcctgc atgaggtggc ctactggtac atcctgagca ttggggccca      2580
gactgacttc ctgtctgtgt tcttctctgg ctacaccttc aagcacaaga tggtgtatga      2640
ggacaccctg accctgttcc ccttctctgg ggagactgtg ttcatgagca tggagaaccc      2700
tggcctgtgg attctgggct gccacaactc tgacttcagg aacaggggca tgactgccct      2760
gctgaaagtc tccagctgtg acaagaacac tggggactac tatgaggaca gctatgagga      2820
catctctgcc tacctgctga gcaagaacaa tgccattgag cccaggagct tcagccagaa      2880
ccccccagtg ctgaagaggc accagaggga gatcaccagg accaccctgc agtctgacca      2940
ggaggagatt gactatgatg acaccatctc tgtggagatg aagaaggagg acttgacat       3000
ctacgacgag gacgagaacc agagcccag gagcttccag aagaagacca ggcactactt       3060
cattgctgct gtggagaggc tgtgggacta tggcatgagc agcagccccc atgtgctgag      3120
gaacagggcc cagtctggct ctgtgcccca gttcaagaag gtggtgttcc aggagttcac      3180
tgatggcagc ttcacccagc ccctgtacag aggggagctg aatgagcacc tgggcctgct      3240
gggcccctac atcagggctg aggtggagga caacatcatg gtgaccttca ggaaccaggc      3300
cagcaggccc tacagcttct acagcagcct gatcagctat gaggaggacc agaggcaggg      3360
ggctgagccc aggaagaact tgtgaagcc caatgaaacc aagacctact tctggaaggt       3420
gcagcaccac atggccccca ccaaggatga gtttgactgc aaggcctggg cctacttctc      3480
tgatgtggac ctggagaagg atgtgcactc tggcctgatt ggccccctgc tggtgtgcca      3540
caccaacacc ctgaaccctg cccatggcag gcaggtgact gtgcaggagt tgccctgtt       3600
```

-continued

```
cttcaccatc tttgatgaaa ccaagagctg gtacttcact gagaacatgg agaggaactg    3660
cagggccccc tgcaacatcc agatggagga ccccaccttc aaggagaact acaggttcca    3720
tgccatcaat ggctacatca tggacaccct gcctggcctg gtgatggccc aggaccagag    3780
gatcaggtgg tacctgctga gcatgggcag caatgagaac atccacagca tccacttctc    3840
tggccatgtg ttcactgtga ggaagaagga ggagtacaag atggccctgt acaacctgta    3900
ccctggggtg tttgagactg tggagatgct gcccagcaag ctggcatctg gagggtgga    3960 gtgcctgatt ggggagcacc tgcatgctgg catgagcacc ctgttcctgg tgtacagcaa    4020
caagtgccag accccctgg gcatggcctc tggccacatc agggacttcc agatcactgc    4080
ctctggccag tatggccagt gggccccaa gctggccagg ctgcactact ctggcagcat    4140
caatgcctgg agcaccaagg agcccttcag ctggatcaag gtggacctgc tggccccat    4200 gatcatccat ggcatcaaga cccaggggc caggcagaag ttcagcagcc tgtacatcag    4260
ccagttcatc atcatgtaca gcctggatgg caagaagtgg cagacctaca ggggcaacag    4320
cactggcacc ctgatggtgt tctttggcaa tgtggacagc tctggcatca gcacaacat    4380 cttcaaccc cccatcattg ccagatacat caggctgcac cccacccact acagcatcag    4440
gagcaccctg aggatggagc tgatgggctg tgacctgaac agctgcagca tgccccctggg   4500 catggagagc aaggccatct ctgatgccca gatcactgcc agcagctact tcaccaacat    4560
gtttgccacc tggagcccca gcaaggccag gctgcacctg cagggcagga gcaatgcctg    4620 gaggcccag gtcaacaacc ccaaggagtg gctgcaggtg gacttccaga gaccatgaa    4680 ggtgactggg gtgaccaccc aggggtgaa gagcctgctg accagcatgt atgtgaagga    4740
gttcctgatc agcagcagcc aggatggcca ccagtggacc ctgttcttcc agaatggcaa    4800
ggtgaaggtg ttccagggca accaggacag cttcaccct gtggtgaaca gcctggaccc    4860 cccctgctg accagatacc tgaggattca ccccagagc tgggtgcacc agattgccct    4920
gaggatggag gtgctgggct gtgaggccca ggacctgtac tgacctcgag gtgtgccttc    4980
tagttgccag ccatctgttg tttgcccctc cccgtgcct tccttgaccc tggaaggtgc    5040
cactcccact gtcctttcct aataaaatga ggaaattgca tcgcattgtc tgagtaggtg    5100
tcattctatt ctgggggtg gggtgggca ggacagcaag ggggaggatt gggaagacaa    5160
tagcaggcat gctggggatg cggtgggctc tatgggcacg tggcggccgc aggaacccct    5220
agtgatggag ttggccactc cctctctgcg cgctcgctcg ctcactgagg ccgggcgacc    5280
aaaggtcgcc cgacgcccgg gctttgcccg ggcggcctca gtgagcgagc gagcgcgcag    5340
agagggagtg gccaa                                                    5355
```

```
<210> SEQ ID NO 41
<211> LENGTH: 5618
<212> TYPE: DNA
<213> ORGANISM: Adeno-Associated Virus 2

<400> SEQUENCE: 41
```

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg    120
gccaactcca tcactagggg ttcctgcggc cgcacgcgtg ttttcgacca gagaggtctc    180
tgacctctgc cccagctcca aggtcagcag gcagggaggg ctgtgtgttt gctgtttgct    240
gcttgcaatg tttgcccatt ttagggacat gagtaggctg aagtttgttc agtgtggact    300
```

```
tcagaggcag cacacaaaca gccagagagg tctctgacct ctgccccagc tccaaggtca    360
gcaggcaggg agggctgtgt gtttgctgtt tgctgcttgc aatgtttgcc cattttaggg    420
acatgagtag gctgaagttt gttcagtgtg gacttcagag gcagcacaca aacagccaga    480
gaggtctctg acctctgccc cagctccaag gtcagcaggc agggagggct gtgtgtttgc    540
tgtttgctgc ttgcaatgtt tgcccatttt agggacatga gtaggctgaa gtttgttcag    600
tgtggacttc agaggcagca cacaaacagc cagagaggtc tctgacctct gccccagctc    660
caaggtcagc aggcagggag ggctgtgtgt ttgctgtttg ctgcttgcaa tgtttgccca    720
ttttagggac atgagtaggc tgaagtttgt tcagtgtgga cttcagaggc agcacacaaa    780
cagcacgcga acgtcgact ggacacagga cgctgtggtt tctgagccag ggggcgactc    840
agatcccagc cagtggactt agcccctgtt tgctcctccg ataactgggg tgaccttggt    900
taatattcac cagcagcctc ccccgttgcc cctctggatc cactgcttaa atacggacga    960
ggacagggcc ctgtctcctc agcttcaggc accaccactg acctgggaca gtgaatcgcg   1020
atcgccacca tgcagattga gctgagcacc tgcttcttcc tgtgcctgct gaggttctgc   1080
ttctctgcca ccaggagata ctacctgggg gctgtggagc tgagctggga ctacatgcag   1140
tctgacctgg gggagctgcc tgtggatgcc aggttccccc ccagagtgcc caagagcttc   1200
cccttcaaca cctctgtggt gtacaagaag accctgtttg tggagttcac tgaccacctg   1260
ttcaacattg ccaagcccag gcccccctgg atgggcctgc tgggcccac catccaggct   1320 gaggtgtatg acactgtggt gatcaccctg aagaacatgg ccagccaccc tgtgagcctg   1380
catgctgtgg gggtgagcta ctggaaggcc tctgaggggg ctgagtatga tgaccagacc   1440
agccagaggg agaaggagga tgacaaggtg ttccctgggg gcagccacac ctatgtgtgg   1500
caggtgctga aggagaatgg ccccatggcc tctgaccccc tgtgcctgac ctacagctac   1560
ctgagccatg tggacctggt gaaggacctg aactctggcc tgattggggc cctgctggtg   1620
tgcagggagg cagcctggc caaggagaag acccagaccc tgcacaagtt catcctgctg   1680
tttgctgtgt ttgatgaggg caagagctgg cactctgaaa ccaagaacag cctgatgcag   1740
gacagggatg ctgcctctgc cagggcctgg cccaagatgc acactgtgaa tggctatgtg   1800
aacaggagcc tgcctggcct gattggctgc cacaggaagt ctgtgtactg gcatgtgatt   1860
ggcatgggca ccaccctga ggtgcacagc atcttcctgg agggccacac cttcctggtc   1920
aggaaccaca ggcaggccag cctggagatc agccccatca ccttcctgac tgcccagacc   1980
ctgctgatgg acctgggcca gttcctgctg ttctgccaca tcagcagcca ccagcatgat   2040
ggcatggagg cctatgtgaa ggtggacagc tgccctgagg agcccagct gaggatgaag   2100 aacaatgagg aggctgagga ctatgatgat gacctgactg actctgagat ggatgtggtg   2160
aggtttgatg atgacaacag ccccagcttc atccagatca ggtctgtggc caagaagcac   2220
cccaagacct gggtgcacta cattgctgct gaggaggagg actgggacta tgcccccctg   2280
gtgctggccc ctgatgacag gagctacaag agccagtacc tgaacaatgg ccccccagagg  2340 attggcagga agtacaagaa ggtcaggttc atggcctaca ctgatgaaac cttcaagacc   2400
agggaggcca tccagcatga gtctggcatc ctgggccccc tgctgtatgg ggaggtgggg   2460
gacaccctgc tgatcatctt caagaaccag gccagcaggc cctacaacat ctaccccat    2520 ggcatcactg atgtgaggcc cctgtacagc aggaggctgc caagggggt gaagcacctg   2580 aaggacttcc ccatcctgcc tggggagatc ttcaagtaca gtggactgt gactgtggag   2640 gatggccca ccaagtctga ccccaggtgc ctgaccagat actacagcag ctttgtgaac   2700
```

```
atggagaggg acctggcctc tggcctgatt ggcccctgc tgatctgcta caaggagtct      2760
gtggaccaga ggggcaacca gatcatgtct gacaagagga atgtgatcct gttctctgtg      2820
tttgatgaga acaggagctg gtacctgact gagaacatcc agaggttcct gcccaaccct      2880
gctggggtgc agctggagga ccctgagttc caggccagca acatcatgca cagcatcaat      2940
ggctatgtgt ttgacagcct gcagctgtct gtgtgcctgc atgaggtggc ctactggtac      3000
atcctgagca ttggggccca gactgacttc ctgtctgtgt tcttctctgg ctacaccttc      3060
aagcacaaga tggtgtatga ggacaccctg accctgttcc ccttctctgg ggagactgtg      3120
ttcatgagca tggagaaccc tggcctgtgg attctgggct gccacaactc tgacttcagg      3180
aacaggggca tgactgccct gctgaaagtc tccagctgtg acaagaacac tggggactac      3240
tatgaggaca gctatgagga catctctgcc tacctgctga gcaagaacaa tgccattgag      3300
cccaggagct tcagccagaa ccccccagtg ctgaagaggc accagaggga gatcaccagg      3360
accaccctgc agtctgacca ggaggagatt gactatgatg acaccatctc tgtggagatg      3420
aagaaggagg actttgacat ctacgacgag gacgagaacc agagccccag gagcttccag      3480
aagaagacca ggcactactt cattgctgct gtggagaggc tgtgggacta ggcatgagc       3540 agcagccccc atgtgctgag gaacagggcc cagtctggct ctgtgcccca gttcaagaag      3600
gtggtgttcc aggagttcac tgatggcagc ttcacccagc ccctgtacag aggggagctg      3660
aatgagcacc tgggcctgct gggcccctac atcagggctg aggtggagga caacatcatg      3720
gtgaccttca ggaaccaggc cagcaggccc tacagcttct acagcagcct gatcagctat      3780
gaggaggacc agaggcaggg ggctgagccc aggaagaact ttgtgaagcc caatgaaacc      3840
aagacctact tctggaaggt gcagcaccac atggccccca ccaaggatga gtttgactgc      3900
aaggcctggg cctacttctc tgatgtggac ctggagaagg atgtgcactc tggcctgatt      3960 ggcccctgc tggtgtgcca caccaacacc ctgaaccctg cccatggcag gcaggtgact       4020
gtgcaggagt ttgccctgtt cttcaccatc tttgatgaaa ccaagagctg gtacttcact      4080
gagaacatgg agaggaactg cagggccccc tgcaacatcc agatggagga ccccaccttc      4140
aaggagaact acaggttcca tgccatcaat ggctacatca tggacaccct gcctggcctg      4200
gtgatggccc aggaccagag gatcaggtgg tacctgctga gcatgggcag caatgagaac      4260
atccacagca tccacttctc tggccatgtg ttcactgtga ggaagaagga ggagtacaag      4320 atggcctgt acaacctgta ccctggggtg tttgagactg tggagatgct gcccagcaag       4380
gctggcatct ggagggtgga gtgcctgatt ggggagcacc tgcatgctgg catgagcacc      4440
ctgttcctgg tgtacagcaa caagtgccag accccctgg gcatggcctc tggccacatc       4500
agggacttcc agatcactgc ctctggccag tatggccagt gggccccaa gctggccagg       4560 ctgcactact ctggcagcat caatgcctgg agcaccaagg agcccttcag ctggatcaag      4620
gtggacctgc tggcccccat gatcatccat ggcatcaaga cccaggggc caggcagaag       4680 ttcagcagcc tgtacatcag ccagttcatc atcatgtaca gcctggatgg caagaagtgg      4740
cagacctaca gggcaacag cactggcacc ctgatggtgt ctttggcaa tgtggacagc        4800 tctggcatca agcacaacat cttcaacccc ccatcattg ccagatacat caggctgcac       4860
cccacccact acagcatcag gagcaccctg aggatggagc tgatgggctg tgacctgaac      4920
agctgcagca tgcccctggg catggagagc aaggccatct ctgatgccca gatcactgcc      4980
agcagctact tcaccaacat gtttgccacc tggagcccca gcaaggccag gctgcacctg      5040
```

-continued

| | |
|---|---|
| caggggcagga gcaatgcctg gaggccccag gtcaacaacc ccaaggagtg gctgcaggtg | 5100 |
| gacttccaga agaccatgaa ggtgactggg gtgaccaccc aggggtgaa gagcctgctg | 5160 |
| accagcatgt atgtgaagga gttcctgatc agcagcagcc aggatggcca ccagtggacc | 5220 |
| ctgttcttcc agaatggcaa ggtgaaggtg ttccagggca accaggacag cttcacccct | 5280 |
| gtggtgaaca gcctggaccc ccccctgctg accagatacc tgaggattca cccccagagc | 5340 |
| tgggtgcacc agattgccct gaggatgag gtgctgggct gtgaggccca ggacctgtac | 5400 |
| tgacctcgag gaataaagga aatttatttt cattgcaata gtgtgttggt tttttgtgtc | 5460 |
| acgtggcggc cgcaggaacc cctagtgatg gagttggcca ctccctctct gcgcgctcgc | 5520 |
| tcgctcactg aggccgggcg accaaaggtc gcccgacgcc cgggctttgc ccgggcggcc | 5580 |
| tcagtgagcg agcgagcgcg cagagaggga gtggccaa | 5618 |

<210> SEQ ID NO 42
<211> LENGTH: 5993
<212> TYPE: DNA
<213> ORGANISM: Adeno-Associated Virus 2

<400> SEQUENCE: 42

| | |
|---|---|
| ttggccactc cctctctgcg cgctcgctcg ctcactgagg ccgcccgggc aaagcccggg | 60 |
| cgtcgggcga cctttggtcg cccggcctca gtgagcgagc gagcgcgcag agagggagtg | 120 |
| gccaactcca tcactagggg ttcctgcggc cgcacgcgtt tttaaacgtc gacaggttaa | 180 |
| tttttaaaaa gcagtcaaaa gtccaagtgg cccttggcag catttactct ctctgtttgc | 240 |
| tctggttaat aatctcagga gcacaaacat tcctggaggc aggagaagaa atcaacatcc | 300 |
| tggacttatc ctctgggcct ctccccaccc ccaggagagg ctcaggttaa ttttttaaaa | 360 |
| gcagtcaaaa gtccaagtgg cccttggcag catttactct ctctgtttgc tctggttaat | 420 |
| aatctcagga gcacaaacat tcctggaggc aggagaagaa atcaacatcc tggacttatc | 480 |
| ctctgggcct ctccccaccc ccaggagagg ctgtcgactg gacacaggac gctgtggttt | 540 |
| ctgagccagg gggcgactca gatcccagcc agtggactta gcccctgttt gctcctccga | 600 |
| taactggggt gaccttggtt aatattcacc agcagcctcc cccgttgccc ctctggatcc | 660 |
| actgcttaaa tacggacgag gacagggccc tgtctcctca gcttcaggca ccaccactga | 720 |
| cctgggacag tgaatcgcga tcgccaccat gcagattgag ctgagcacct gcttcttcct | 780 |
| gtgcctgctg aggttctgct tctctgccac caggagatac tacctggggg ctgtggagct | 840 |
| gagctgggac tacatgcagt ctgacctggg ggagctgcct gtggatgcca ggttcccccc | 900 |
| cagagtgccc aagagcttcc ccttcaacac ctctgtggtg tacaagaaga cctgttttgt | 960 |
| ggagttcact gaccaccctg tcaacattgc caagcccagg ccccctga tgggcctgct | 1020 |
| gggccccacc atccaggctg aggtgtatga cactgtggtg atcaccctga agaacatggc | 1080 |
| cagccaccct gtgagcctgc atgctgtggg ggtgagctac tggaaggcct gaggggggc | 1140 |
| tgagtatgat gaccagacca gccagaggga aaggaggat gacaaggtgt ccctgggggg | 1200 |
| cagccacacc tatgtgtggc aggtgctgaa ggagaatggc cccatggcct ctgaccccct | 1260 |
| gtgcctgacc tacagctacc tgagccatgt ggacctggtg aaggacctga actctggcct | 1320 |
| gattggggcc ctgctggtgt gcaggaggg cagcctggcc aaggagaaga cccagaccct | 1380 |
| gcacaagttc atcctgctgt ttgctgtgtt tgatgagggc aagagctggc actctgaaac | 1440 |
| caagaacagc ctgatgcagg acagggatgc tgcctctgcc agggcctggc caagatgca | 1500 |
| cactgtgaat ggctatgtga acaggagcct gcctggcctg attggctgcc acaggaagtc | 1560 |

```
tgtgtactgg catgtgattg gcatgggcac cacccctgag gtgcacagca tcttcctgga   1620
gggccacacc ttcctggtca ggaaccacag gcaggccagc ctggagatca gccccatcac   1680
cttcctgact gcccagaccc tgctgatgga cctgggccag ttcctgctgt tctgccacat   1740
cagcagccac cagcatgatg gcatggaggc ctatgtgaag gtggacagct gccctgagga   1800
gccccagctg aggatgaaga caatgagga ggctgaggac tatgatgatg acctgactga   1860
ctctgagatg gatgtggtga ggtttgatga tgacaacagc cccagcttca tccagatcag   1920
gtctgtggcc aagaagcacc ccaagacctg ggtgcactac attgctgctg aggaggagga   1980
ctgggactat gccccctgg tgctggcccc tgatgacagg agctacaaga gccagtacct   2040
gaacaatggc ccccagagga ttggcaggaa gtacaagaag gtcaggttca tggcctacac   2100
tgatgaaacc ttcaagacca gggaggccat ccagcatgag tctggcatcc tgggcccct   2160
gctgtatggg gaggtggggg acaccctgct gatcatcttc aagaaccagg ccagcaggcc   2220
ctacaacatc taccccatg gcatcactga tgtgaggccc ctgtacagca ggaggctgcc   2280
caaggggtg aagcacctga aggacttccc catcctgcct ggggagatct tcaagtacaa   2340
gtggactgtg actgtggagg atggccccac caagtctgac cccaggtgcc tgaccagata   2400
ctacagcagc tttgtgaaca tggagaggga cctggcctct ggcctgattg cccctgct    2460
gatctgctac aaggagtctg tggaccagag gggcaaccag atcatgtctg acaagaggaa   2520
tgtgatcctg ttctctgtgt ttgatgagaa caggagctgg tacctgactg agaacatcca   2580
gaggttcctg cccaaccctg ctggggtgca gctggaggac cctgagttcc aggccagcaa   2640
catcatgcac agcatcaatg gctatgtgtt tgacagcctg cagctgtctg tgtgcctgca   2700
tgaggtggcc tactggtaca tcctgagcat tggggcccag actgacttcc tgtctgtgtt   2760
cttctctggc tacaccttca gcacaagat ggtgtatgag gacaccctga ccctgttccc   2820
cttctctggg gagactgtgt tcatgagcat ggagaaccct ggcctgtgga ttctgggctg   2880
ccacaactct gacttcagga acaggggcat gactgccctg ctgaaagtct ccagctgtga   2940
caagaacact ggggactact atgaggacag ctatgaggac atctctgcct acctgctgag   3000
caagaacaat gccattgagc ccaggagctt cagccagaac cccccagtgc tgaagaggca   3060
ccagagggag atcaccagga ccaccctgca gtctgaccag gaggagattg actatgatga   3120
caccatctct gtggagatga agaaggagga ctttgacatc tacgacgagg acgagaacca   3180
gagccccagg agcttccaga agaagaccag gcactacttc attgctgctg tggagaggct   3240
gtgggactat ggcatgagca gcagccccca tgtgctgagg aacagggccc agtctggctc   3300
tgtgccccag ttcaagaagg tggtgttcca ggagttcact gatggcagct tcacccagcc   3360
cctgtacaga ggggagctga atgagcacct gggcctgctg ggccctaca tcagggctga   3420
ggtggaggac aacatcatgg tgaccttcag gaaccaggcc agcaggccct acagcttcta   3480
cagcagcctg atcagctatg aggaggacca ggagcagggg ctgagcccca ggaagaactt   3540
tgtgaagccc aatgaaacca gacctacttc tggaaggtg cagcaccaca tggccccac    3600
caaggatgag tttgactgca aggcctgggc ctacttctct gatgtggacc tggagaagga   3660
tgtgcactct ggcctgattg ccccctgct ggtgtgccac accaacaccc tgaaccctgc   3720
ccatggcagg caggtgactg tgcaggagtt tgccctgttc ttcaccatct ttgatgaaac   3780
caagagctgg tacttcactg agaacatgga gaggaactgc agggcccct gcaacatcca   3840
gatggaggac cccaccttca aggagaacta caggttccat gccatcaatg gctacatcat   3900
```

```
ggacaccctg cctggcctgg tgatggccca ggaccagagg atcaggtggt acctgctgag    3960
catgggcagc aatgagaaca tccacagcat ccacttctct ggccatgtgt tcactgtgag    4020
gaagaaggag gagtacaaga tggccctgta caacctgtac cctggggtgt ttgagactgt    4080
ggagatgctg cccagcaagg ctggcatctg gagggtggag tgcctgattg gggagcacct    4140
gcatgctggc atgagcaccc tgttcctggt gtacagcaac aagtgccaga cccccctggg    4200
catggcctct ggccacatca gggacttcca gatcactgcc tctggccagt atggccagtg    4260
ggcccccaag ctggccaggc tgcactactc tggcagcatc aatgcctgga gcaccaagga    4320
gcccttcagc tggatcaagg tggacctgct ggcccccatg atcatccatg gcatcaagac    4380
ccagggggcc aggcagaagt tcagcagcct gtacatcagc cagttcatca tcatgtacag    4440
cctggatggc aagaagtggc agacctacag gggcaacagc actggcaccc tgatggtgtt    4500
ctttggcaat gtggacagct ctggcatcaa gcacaacatc ttcaaccccc ccatcattgc    4560
cagatacatc aggctgcacc ccacccacta cagcatcagg agcacctga ggatggagct    4620 gatgggctgt gacctgaaca gctgcagcat gcccctgggc atggagagca aggccatctc    4680
tgatgcccag atcactgcca gcagctactt caccaacatg tttgccacct ggagccccag    4740
caaggccagg ctgcacctgc agggcaggag caatgcctgg aggcccagg tcaacaaccc    4800 caaggagtgg ctgcaggtgg acttccagaa gaccatgaag gtgactgggg tgaccaccca    4860
gggggtgaag agcctgctga ccagcatgta tgtgaaggag ttcctgatca gcagcagcca    4920
ggatggccac cagtggacccc tgttcttcca gaatggcaag gtgaaggtgt ccagggcaa    4980 ccaggacagc ttcaccctg tggtgaacag cctggacccc ccctgctga ccagatacct    5040 gaggattcac ccccagagct gggtgcacca gattgccctg aggatggagg tgctgggctg    5100
tgaggcccag gacctgtact gacctcgagg aataaaggaa atttattttc attgcaatag    5160
tgtgttggtt ttttgtgtca cgtgccctct cacactacct aaaccacgcc aggacaacct    5220
ctgctcctct ccaccgaaat tccaagggg cgagtggatg ttggaggtgg catgggccca    5280
gagaggtctc tgacctctgc cccagctcca aggtcagcag gcagggaggg ctgtgtgttt    5340
gctgtttgct gcttgcaatg tttgcccatt ttagggacat gagtaggctg aagtttgttc    5400
agtgtggact tcagaggcag cacacaaaca gctgctggag gatgggaact gagggggttgg    5460 aagggggcag ggtgagccca gaaactcctg tgtgcctctg agcctgcagc cctctcacac    5520
tacctaaacc acgccaggac aacctctgct cctctccacc gaaattccaa ggggtcgagt    5580
ggatgttgga ggtggcatgg gcccagagag gtctctgacc tctgccccag ctccaaggtc    5640
agcaggcagg gagggctgtg tgtttgctgt ttgctgcttg caatgtttgc ccattttagg    5700
gacatgagta ggctgaagtt tgttcagtgt ggacttcaga ggcagcacac aaacagctgc    5760
tggaggatgg gaactgaggg gttggaaggg gcagggtga gcccagaaac tcctgtgtgc    5820
ctctgagcct gcagcacgtg gcggccgcag gaacccctag tgatggagtt ggccactccc    5880
tctctgcgcg ctcgctcgct cactgaggcc gggcgaccaa aggtcgcccg acgcccgggc    5940
tttgcccggg cggcctcagt gagcgagcga gcgcgcagag agggagtggc caa          5993
```

<210> SEQ ID NO 43
<211> LENGTH: 5337
<212> TYPE: DNA
<213> ORGANISM: Adeno-Associated Virus 2

<400> SEQUENCE: 43

```
ttggccactc cctctctgcg cgctcgctcg ctcactgagg ccgcccgggc aaagcccggg      60
```

-continued

```
cgtcgggcga cctttggtcg cccggcctca gtgagcgagc gagcgcgcag agagggagtg    120
gccaactcca tcactagggg ttcctgcggc cgcacgcgtg tttaaacgtc gacaggttaa    180
tttttaaaaa gcagtcaaaa gtccaagtgg cccttggcag catttactct ctctgtttgc    240
tctggttaat aatctcagga gcacaaacat tcctggaggc aggagaagaa atcaacatcc    300
tggacttatc ctctgggcct ctccccaccc ccaggagagg ctcaggttaa tttttaaaaa    360
gcagtcaaaa gtccaagtgg cccttggcag catttactct ctctgtttgc tctggttaat    420
aatctcagga gcacaaacat tcctggaggc aggagaagaa atcaacatcc tggacttatc    480
ctctgggcct ctccccaccc ccaggagagg ctgtcgactg gacacaggac gctgtggttt    540
ctgagccagg gggcgactca gatcccagcc agtggactta gcccctgttt gctcctccga    600
taactggggt gaccttggtt aatattcacc agcagcctcc cccgttgccc ctctggatcc    660
actgcttaaa tacgacgag acagggccc tgtctcctca gcttcaggca ccaccactga     720
cctgggacag tgaatcgcga tcgccaccat gcagattgag ctgagcacct gcttcttcct    780
gtgcctgctg aggttctgct tctctgccac caggagatac tacctggggg ctgtggagct    840
gagctgggac tacatgcagt ctgacctggg ggagctgcct gtggatgcca ggttcccccc    900
cagagtgccc aagagcttcc ccttcaacac ctctgtggtg tacaagaaga ccctgtttgt    960
ggagttcact gaccacctgt tcaacattgc caagcccagg ccccctggga tgggcctgct   1020 gggcccccacc atccaggctg aggtgtatga cactgtggtg atcaccctga gaacatggc   1080 cagccacccct gtgagcctgc atgctgtggg ggtgagctac tggaaggcct ctgaggggc    1140 tgagtatgat gaccagacca ccagaggga aaggaggat gacaaggtgt ccctgggggg     1200
cagccacacc tatgtgtggc aggtgctgaa ggagaatggc cccatggcct ctgacccct    1260 gtgcctgacc tacagctacc tgagccatgt ggacctggtg aaggacctga actctggcct   1320
gattggggcc ctgctggtgt gcagggaggg cagcctggcc aaggagaaga cccagaccct   1380
gcacaagttc atcctgctgt ttgctgtgtt tgatgagggc aagagctggc actctgaaac   1440
caagaacagc ctgatgcagg acagggatgc tgcctctgcc agggcctggc caagatgca   1500 cactgtgaat ggctatgtga acaggagcct gcctggcctg attggctgcc acaggaagtc   1560
tgtgtactgg catgtgattg gcatgggcac caccctgag gtgcacagca tcttcctgga   1620
gggccacacc ttcctggtca ggaaccacag gcaggccagc ctggagatca gccccatcac   1680
cttcctgact gcccagaccc tgctgatgga cctgggccag ttcctgctgt tctgccacat   1740
cagcagccac cagcatgatg gcatggaggc ctatgtgaag gtggacagct gcctgagga   1800 gccccagctg aggatgaaga acaatgagga ggctgaggac tatgatgatg acctgactga   1860
ctctgagatg gatgtggtga ggtttgatga tgacaacagc cccagcttca tccagatcag   1920
gtctgtggcc aagaagcacc ccaagacctg ggtgcactac attgctgctg aggaggagga   1980
ctgggactat gccccctgg tgctggcccc tgatgacagg agctacaaga gccagtacct   2040
gaacaatggc ccccagagga ttggcaggaa gtacaagaag gtcaggttca tggcctacac   2100
tgatgaaacc ttcaagacca gggaggccat ccagcatgag tctggcatcc tgggcccct    2160 gctgtatggg gaggtggggg acaccctgct gatcatcttc aagaaccagg ccagcaggcc   2220
ctacaacatc taccccatg gcatcactga tgtgaggccc ctgtacagca ggaggctgcc   2280 caaggggggta aagcacctga aggacttccc catcctgcct ggggagatct tcaagtacaa   2340
gtggactgtg actgtggagg atggccccac caagtctgac cccaggtgcc tgaccagata   2400
```

```
ctacagcagc tttgtgaaca tggagaggga cctggcctct ggcctgattg gcccctgct      2460
gatctgctac aaggagtctg tggaccagag gggcaaccag atcatgtctg acaagaggaa      2520
tgtgatcctg ttctctgtgt ttgatgagaa caggagctgg tacctgactg agaacatcca      2580
gaggttcctg cccaaccctg ctggggtgca gctggaggac cctgagttcc aggccagcaa      2640
catcatgcac agcatcaatg ctatgtgtt tgacagcctg cagctgtctg tgtgcctgca       2700
tgaggtggcc tactggtaca tcctgagcat tggggcccag actgacttcc tgtctgtgtt      2760
cttctctggc tacaccttca gcacaagat ggtgtatgag gacaccctga ccctgttccc       2820
cttctctggg gagactgtgt tcatgagcat ggagaaccct ggcctgtgga ttctgggctg      2880
ccacaactct gacttcagga cagggggcat gactgccctg ctgaaagtct ccagctgtga      2940
caagaacact ggggactact atgaggacag ctatgaggac atctctgcct acctgctgag      3000
caagaacaat gccattgagc ccaggagctt cagccagaac cccccagtgc tgaagaggca      3060
ccagagggag atcaccagga ccaccctgca gtctgaccag gaggagattg actatgatga      3120
caccatctct gtggagatga agaaggagga ctttgacatc tacgacgagg acgagaacca      3180
gagccccagg agcttccaga agaagaccag gcactacttc attgctgctg tggagaggct      3240
gtgggactat ggcatgagca gcagccccca tgtgctgagg aacagggccc agtctggctc      3300
tgtgccccag ttcaagaagg tggtgttcca ggagttcact gatggcagct tcacccagcc      3360
cctgtacaga ggggagctga atgagcacct gggcctgctg gcccctaca tcagggctga       3420
ggtggaggac aacatcatgg tgaccttcag gaaccaggcc agcaggccct acagcttcta      3480
cagcagcctg atcagctatg aggaggacca gaggcagggg gctgagccca ggaagaactt      3540
tgtgaagccc aatgaaacca agacctactt ctggaaggtg cagcaccaca tggcccccac      3600
caaggatgag tttgactgca aggcctgggc ctacttctct gatgtggacc tggagaagga      3660
tgtgcactct ggcctgattg gcccctgct ggtgtgccac accaacaccc tgaaccctgc       3720
ccatggcagg caggtgactg tgcaggagtt tgccctgttc ttcaccatct ttgatgaaac      3780
caagagctgg tacttcactg agaacatgga gaggaactgc agggcccct gcaacatcca       3840
gatggaggac cccaccttca aggagaacta caggttccat gccatcaatg ctacatcat       3900
ggacaccctg cctggcctgg tgatggccca ggaccagagg atcaggtggt acctgctgag      3960
catgggcagc aatgagaaca tccacagcat ccacttctct ggccatgtgt tcactgtgag      4020
gaagaaggag gagtacaaga tggcctgta caacctgtac cctggggtgt ttgagactgt       4080
ggagatgctg cccagcaagg ctggcatctg gagggtggag tgcctgattg gggagcacct      4140
gcatgctggc atgagcaccc tgttcctggt gtacagcaac aagtgccaga ccccctggg      4200
catgcctct ggccacatca gggacttcca gatcactgcc tctggccagt atggccagtg      4260
ggccccaag ctggccaggc tgcactactc tggcagcatc aatgcctgga gcaccaagga      4320
gcccttcagc tggatcaagg tggacctgct ggccccatg atcatccatg catcaagac       4380
ccaggggggcc aggcagaagt tcagcagcct gtacatcagc cagttcatca tcatgtacag      4440
cctggatggc aagaagtggc agacctacag gggcaacagc actggcaccc tgatggtgtt      4500
ctttggcaat gtggacagct ctggcatcaa gcacaacatc ttcaaccccc ccatcattgc      4560
cagatacatc aggctgcacc ccaccccacta cagcatcagg agcaccctga ggatggagct      4620
gatgggctgt gacctgaaca gctgcagcat gcccctgggc atggagagca aggccatctc      4680
tgatgcccag atcactgcca gcagctactt caccaacatg tttgccacct ggagcccag       4740
caaggccagg ctgcacctgc agggcaggag caatgcctgg aggccccagg tcaacaaccc      4800
```

-continued

```
caaggagtgg ctgcaggtgg acttccagaa gaccatgaag gtgactgggg tgaccaccca    4860
gggggtgaag agcctgctga ccagcatgta tgtgaaggag ttcctgatca gcagcagcca    4920
ggatggccac cagtggaccc tgttcttcca gaatggcaag gtgaaggtgt tccagggcaa    4980
ccaggacagc ttcacccctg tggtgaacag cctggacccc ccctgctga ccagatacct    5040 gaggattcac ccccagagct gggtgcacca gattgccctg aggatggagg tgctgggctg    5100
tgaggcccag gacctgtact gacctcgagg aataaaggaa atttattttc attgcaatag    5160
tgtgttggtt ttttgtgtca cgtggcggcc gcaggaaccc ctagtgatgg agttggccac    5220
tccctctctg cgcgctcgct cgctcactga ggccgggcga ccaaaggtcg cccgacgccc    5280
gggctttgcc cggcggcct cagtgagcga gcgagcgcgc agagagggag tggccaa      5337
```

<210> SEQ ID NO 44
<211> LENGTH: 5542
<212> TYPE: DNA
<213> ORGANISM: Adeno-Associated Virus 2

<400> SEQUENCE: 44

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgcggc cgcacgcgtg tttaaacgtc gacaggttaa     180
tttttaaaaa gcagtcaaaa gtccaagtgg cccttggcag catttactct ctctgtttgc     240
tctggttaat aatctcagga gcacaaacat tcctggaggc aggagaagaa atcaacatcc     300
tggacttatc ctctgggcct ctccccaccc ccaggagagg ctcaggttaa tttttaaaaa     360
gcagtcaaaa gtccaagtgg cccttggcag catttactct ctctgtttgc tctggttaat     420
aatctcagga gcacaaacat tcctggaggc aggagaagaa atcaacatcc tggacttatc     480
ctctgggcct ctccccaccc ccaggagagg ctgtcgactg acacaggac gctgtggttt     540 ctgagccagg gggcgactca gatcccagcc agtggactta gcccctgttt gctcctccga     600
taactggggt gaccttggtt aatattcacc agcagcctcc cccgttgccc ctctggatcc     660
actgcttaaa tacggacgag gacagggccc tgtctcctca gcttcaggca ccaccactga     720
cctgggacag tgaatcgtaa gtatgccttt cactgcgaga ggttctggag aggcttctga     780
gctccccatg gccaggcag gcagcaggtc tggggcagga ggggggttgt ggagtgcctt     840
gactcggggc ctggcccccc catctctgtc ttgcaggaca attgccgtct tctgtctcgt     900
ggggcatcct cctgctggca ggcctgtgct gcctggtccc tgcgatcgcc accatgcaga    960
ttgagctgag cacctgcttc ttcctgtgcc tgctgaggtt ctgcttctct gccaccagga   1020
gatactacct gggggctgtg gagctgagct gggactacat gcagtctgac ctgggggagc   1080
tgcctgtgga tgccaggttc ccccccagag tgcccaagag cttccccttc aacacctctg   1140
tggtgtacaa gaagaccctg tttgtggagt tcactgacca cctgttcaac attgccaagc   1200
ccaggccccc ctggatgggc ctgctgggcc ccaccatcca ggctgaggtg tatgacactg   1260
tggtgatcac cctgaagaac atggccagcc accctgtgag cctgcatgct gtgggggtga   1320
gctactggaa ggcctctgag ggggctgagt atgatgacca gaccagccag agggagaagg   1380
aggatgacaa ggtgttccct ggggcagcc acacctatgt gtggcaggtg ctgaaggaga   1440
atggccccat ggcctctgac cccctgtgcc tgacctacag ctacctgagc catgtggacc   1500
tggtgaagga cctgaactct ggcctgattg gggccctgct ggtgtgcagg gagggcagcc   1560
```

```
tggccaagga gaagacccag accctgcaca agttcatcct gctgtttgct gtgtttgatg    1620
agggcaagag ctggcactct gaaaccaaga acagcctgat gcaggacagg gatgctgcct    1680
ctgccagggc ctggcccaag atgcacactg tgaatggcta tgtgaacagg agcctgcctg    1740
gcctgattgg ctgccacagg aagtctgtgt actggcatgt gattggcatg ggcaccaccc    1800
ctgaggtgca cagcatcttc ctggagggcc acaccttcct ggtcaggaac acaggcagg    1860 ccagcctgga gatcagcccc atcaccttcc tgactgccca gaccctgctg atggacctgg    1920
gccagttcct gctgttctgc cacatcagca gccaccagca tgatggcatg gaggcctatg    1980
tgaaggtgga cagctgccct gaggagcccc agctgaggat gaagaacaat gaggaggctg    2040
aggactatga tgatgacctg actgactctg agatggatgt ggtgaggttt gatgatgaca    2100
acagccccag cttcatccag atcaggtctg tggccaagaa gcaccccaag acctgggtgc    2160
actacattgc tgctgaggag gaggactggg actatgcccc cctggtgctg gcccctgatg    2220
acaggagcta caagagccag tacctgaaca atgcccccca gaggattggc aggaagtaca    2280
agaaggtcag gttcatggcc tacactgatg aaaccttcaa gaccagggag gccatccagc    2340
atgagtctgg catcctgggc cccctgctgt atggggaggt ggggacacc ctgctgatca    2400 tcttcaagaa ccaggccagc aggccctaca acatctaccc ccatggcatc actgatgtga    2460
ggcccctgta cagcaggagg ctgcccaagg gggtgaagca cctgaaggac ttccccatcc    2520
tgcctgggga gatcttcaag tacaagtgga ctgtgactgt ggaggatggc cccaccaagt    2580
ctgaccccag gtgcctgacc agatactaca gcagctttgt gaacatggag agggacctgg    2640
cctctggcct gattggcccc ctgctgatct gctacaagga gtctgtggac cagaggggca    2700
accagatcat gtctgacaag aggaatgtga tcctgttctc tgtgtttgat gagaacagga    2760
gctggtacct gactgagaac atccagaggt tcctgcccaa ccctgctggg gtgcagctgg    2820
aggaccctga gttccaggcc agcaacatca tgcacagcat caatggctat gtgtttgaca    2880
gcctgcagct gtctgtgtgc ctgcatgagg tggcctactg gtacatcctg agcattgggg    2940
cccagactga cttcctgtct gtgttcttct ctggctacac cttcaagcac aagatggtgt    3000
atgaggacac cctgaccctg ttccccttct ctggggagac tgtgttcatg agcatggaga    3060
accctggcct gtggattctg ggctgccaca actctgactt caggaacagg ggcatgactg    3120
ccctgctgaa agtctccagc tgtgacaaga cactgggga ctactatgag acagcctatg    3180
aggacatctc tgcctacctg ctgagcaaga caatgccat tgagcccagg agcttcagcc    3240 agaaccccc agtgctgaag aggcaccaga gggagatcac caggaccacc ctgcagtctg    3300
accaggagga gattgactat gatgacacca tctctgtgga gatgaagaag gaggactttg    3360
acatctacga cgaggacgag aaccagagcc caggagctt ccagaagaag accaggcact    3420
acttcattgc tgctgtggag aggctgtggg actatggcat gagcagcagc ccccatgtgc    3480
tgaggaacag ggcccagtct ggctctgtgc cccagttcaa gaaggtggtg ttccaggagt    3540
tcactgatgg cagcttcacc cagcccctgt acagagggga gctgaatgag cacctgggcc    3600
tgctgggccc ctacatcagg gctgaggtgg aggacaacat catggtgacc ttcaggaacc    3660
aggccagcag gccctacagc ttctacagca gcctgatcag ctatgaggag gaccagaggc    3720 aggggctga gccaggaag aactttgtga agcccaatga aaccaagacc tacttctgga    3780
aggtgcagca ccacatggcc cccaccaagg atgagtttga ctgcaaggcc tgggcctact    3840
tctctgatgt ggacctggag aaggatgtgc actctggcct gattggcccc ctgctggtgt    3900
gccacaccaa caccctgaac cctgcccatg gcaggcaggt gactgtgcag gagtttgccc    3960
```

```
tgttcttcac catctttgat gaaaccaaga gctggtactt cactgagaac atggagagga    4020
actgcagggc ccctgcaac atccagatgg aggaccccac cttcaaggag aactacaggt    4080
tccatgccat caatggctac atcatggaca ccctgcctgg cctggtgatg gcccaggacc    4140
agaggatcag gtggtacctg ctgagcatgg gcagcaatga gaacatccac agcatccact    4200
tctctggcca tgtgttcact gtgaggaaga aggaggagta caagatggcc ctgtacaacc    4260
tgtaccctgg ggtgtttgag actgtggaga tgctgcccag caaggctggc atctggaggg    4320
tggagtgcct gattggggag cacctgcatg ctggcatgag caccctgttc ctggtgtaca    4380
gcaacaagtg ccagaccccc ctgggcatgg cctctggcca catcagggac ttccagatca    4440
ctgcctctgg ccagtatggc cagtgggccc caagctggc caggctgcac tactctggca    4500
gcatcaatgc ctggagcacc aaggagccct cagctggat caaggtggac ctgctggccc    4560
ccatgatcat ccatggcatc aagacccagg ggccaggca aagttcagc agcctgtaca    4620 tcagccagtt catcatcatg tacagcctgg atggcaagaa gtggcagacc tacaggggca    4680
acagcactgg caccctgatg gtgttctttg gcaatgtgga cagctctggc atcaagcaca    4740
acatcttcaa ccccccatc attgccagat acatcaggct gcaccccacc cactacagca    4800
tcaggagcac cctgaggatg gagctgatgg gctgtgacct gaacagctgc agcatgcccc    4860
tgggcatgga gagcaaggcc atctctgatg cccagatcac tgccagcagc tacttccacc    4920
acatgtttgc cacctggagc cccagcaagg ccaggctgca cctgcagggc aggagcaatg    4980
cctggaggcc ccaggtcaac aaccccaagg agtggctgca ggtggacttc cagaagacca    5040
tgaaggtgac tggggtgacc acccaggggg tgaagagcct gctgaccagc atgtatgtga    5100
aggagttcct gatcagcagc agccaggatg ccaccagtg gaccctgttc ttccagaatg    5160
gcaaggtgaa ggtgttccag ggcaaccagg acagcttcac ccctgtggtg aacagcctgg    5220
acccccccct gctgaccaga tacctgagga ttcaccccca gagctgggtg caccagattg    5280
ccctgaggat ggaggtgctg gctgtgagg cccaggacct gtactgacct cgaggaataa    5340
aggaaattta ttttcattgc aatagtgtgt tggttttttg tgtcacgtgg cggccgcagg    5400
aacccctagt gatggagttg gccactccct ctctgcgcgc tcgctcgctc actgaggccg    5460
ggcgaccaaa ggtcgcccga cgcccgggct tgcccgggc ggcctcagtg agcgagcgag    5520
cgcgcagaga gggagtggcc aa                                            5542
```

<210> SEQ ID NO 45
<211> LENGTH: 5126
<212> TYPE: DNA
<213> ORGANISM: Adeno-Associated Virus 2

<400> SEQUENCE: 45

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgcggc cgcacgcgtg ggaggctgct ggtgaatatt     180
aaccaaggtc accccagtta tcggaggagc aaacaggggc taagtccacg ggaggctgc     240 tggtgaatat taaccaaggt caccccagtt atcggaggag caaacagggg ctaagtccac     300
ggtcgactgg acacaggacg ctgtggtttc tgagccaggg ggcgactcag atcccagcca     360
gtggacttag cccctgtttg ctcctccgat aactggggtg accttggtta atattcacca     420
gcagcctccc ccgttgcccc tctggatcca ctgcttaaat acggacgagg acagggccct     480
```

```
gtctcctcag cttcaggcac caccactgac ctgggacagt gaatcgcgat cgccaccatg    540
cagattgagc tgagcacctg cttcttcctg tgcctgctga ggttctgctt ctctgccacc    600
aggagatact acctggggc tgtggagctg agctgggact acatgcagtc tgacctgggg     660
gagctgcctg tggatgccag gttcccccc agagtgccca agagcttccc cttcaacacc     720
tctgtggtgt acaagaagac cctgtttgtg gagttcactg accacctgtt caacattgcc    780
aagcccaggc cccctggat gggcctgctg gccccacca tccaggctga ggtgtatgac      840
actgtggtga tcaccctgaa gaacatggcc agccaccctg tgagcctgca tgctgtgggg    900
gtgagctact ggaaggcctc tgaggggct gagtatgatg accagaccag ccagagggag     960
aaggaggatg acaaggtgtt ccctgggggc agccacacct atgtgtggca ggtgctgaag   1020
gagaatggcc ccatggcctc tgaccccctg tgcctgacct acagctacct gagccatgtg   1080
gacctggtga aggacctgaa ctctggcctg attggggccc tgctggtgtg cagggagggc   1140
agcctggcca aggagaagac ccagaccctg cacaagttca tcctgctgtt tgctgtgttt   1200
gatgagggca gagctggca ctctgaaacc aagaacagcc tgatgcagga cagggatgct    1260
gcctctgcca gggcctggcc caagatgcac actgtgaatg ctatgtgaa caggagcctg    1320 cctggcctga ttggctgcca caggaagtct gtgtactggc atgtgattgg catgggcacc   1380 accctgagg tgcacagcat cttcctggag ggccacacct tcctggtcag gaaccacagg    1440
caggccagcc tggagatcag ccccatcacc ttcctgactg cccagaccct gctgatggac   1500
ctgggccagt cctgctgtt ctgccacatc agcagccacc agcatgatgg catggaggcc    1560
tatgtgaagg tggacagctg ccctgaggag ccccagctga ggatgaagaa caatgaggag   1620
gctgaggact atgatgatga cctgactgac tctgagatgg atgtggtgag gtttgatgat   1680
gacaacagcc ccagcttcat ccagatcagg tctgtggcca agaagcaccc caagacctgg   1740
gtgcactaca ttgctgctga ggaggaggac tgggactatg cccccctggt gctggcccct   1800
gatgacagga gctacaagag ccagtacctg aacaatggcc cccagaggat tggcaggaag   1860
tacaagaagg tcaggttcat ggcctacact gatgaaacct tcaagaccag ggaggccatc   1920
cagcatgagt ctggcatcct gggccccctg ctgtatgggg aggtggggga cccctgctg   1980 atcatcttca gaaccaggc cagcaggccc tacaacatct accccatgg catcactgat    2040 gtgaggcccc tgtacagcag gaggctgccc aaggggtga agcacctgaa ggacttcccc   2100
atcctgcctg gggagatctt caagtacaag tggactgtga ctgtggagga tggccccacc   2160
aagtctgacc ccaggtgcct gaccagatac tacagcagct tgtgaacat ggagagggac    2220 ctggcctctg gcctgattgg ccccctgctg atctgctaca aggagtctgt ggaccagagg   2280
ggcaaccaga tcatgtctga caagaggaat gtgatcctgt tctctgtgtt tgatgagaac   2340
aggagctggt acctgactga gaacatccag aggttcctgc ccaaccctgc tggggtgcag   2400
ctggaggacc ctgagttcca ggccagcaac atcatgcaca gcatcaatgg ctatgtgttt   2460
gacagcctgc agctgtctgt gtgcctgcat gaggtggcct actggtacat cctgagcatt   2520
ggggcccaga ctgacttcct gtctgtgttc ttctctggct acaccttcaa gcacaagatg   2580
gtgtatgagg acaccctgac cctgttcccc ttctctgggg agactgtgtt catgagcatg   2640
gagaaccctg gcctgtggat tctgggctgc cacaactctg acttcaggaa caggcatg     2700 actgccctgc tgaaagtctc cagctgtgac aagaacactg ggactactat gaggacagc    2760 tatgaggaca tctctgccta cctgctgagc aagaacaatg ccattgagcc caggagcttc   2820
agccagaacc ccccagtgct gaagaggcac cagagggaga tcaccaggac caccctgcag   2880
```

```
tctgaccagg aggagattga ctatgatgac accatctctg tggagatgaa gaaggaggac    2940
tttgacatct acgacgagga cgagaaccag agccccagga gcttccagaa gaagaccagg    3000
cactacttca ttgctgctgt ggagaggctg tgggactatg gcatgagcag cagcccccat    3060
gtgctgagga acagggccca gtctggctct gtgccccagt tcaagaaggt ggtgttccag    3120
gagttcactg atggcagctt cacccagccc ctgtacagag gggagctgaa tgagcacctg    3180
ggcctgctgg gccctacat cagggctgag gtggaggaca acatcatggt gaccttcagg    3240
aaccaggcca gcaggcccta cagcttctac agcagcctga tcagctatga ggaggaccag    3300
aggcaggggg ctgagcccag gaagaacttt gtgaagccca tgaaaccaa gacctacttc    3360 tggaaggtgc agcaccacat ggcccccacc aaggatgagt ttgactgcaa ggcctgggcc    3420
tacttctctg atgtggacct ggagaaggat gtgcactctg gcctgattgg cccctgctg    3480 gtgtgccaca ccaacaccct gaaccctgcc catggcaggc aggtgactgt gcaggagttt    3540
gccctgttct tcaccatctt tgatgaaacc aagagctggg acttcactga gaacatggag    3600
aggaactgca gggcccctg caacatccag atggaggacc ccaccttcaa ggagaactac    3660
aggttccatg ccatcaatgg ctacatcatg gacaccctgc ctggcctggt gatggcccag    3720
gaccagagga tcaggtggta cctgctgagc atgggcagca atgagaacat ccacagcatc    3780
cacttctctg gccatgtgtt cactgtgagg aagaaggagg agtacaagat ggccctgtac    3840
aacctgtacc ctggggtgtt tgagactgtg agatgctgc ccagcaaggc tggcatctgg    3900
agggtggagt gcctgattgg ggagcacctg catgctggca tgagcaccct gttcctggtg    3960
tacagcaaca agtgccagac ccccctgggc atggcctctg ccacatcag ggacttccag    4020 atcactgcct ctggccagta tggccagtgg gcccccaagc tggccaggct gcactactct    4080
ggcagcatca atgcctggag caccaaggag cccttcagct ggatcaaggt ggacctgctg    4140
gcccccatga tcatccatgg catcaagacc caggggccca ggcagaagtt cagcagcctg    4200
tacatcagcc agttcatcat catgtacagc ctggatggca gaagtggca gacctacagg    4260 ggcaacagca ctggcaccct gatggtgttc tttggcaatg tggacagctc tggcatcaag    4320
cacaacatct tcaacccccc catcattgcc agatacatca ggctgcaccc cacccactac    4380
agcatcagga gcaccctgag gatggagctg atgggctgtg acctgaacag ctgcagcatg    4440
cccctgggca tggagagcaa ggccatctct gatgcccaga tcactgccag cagctacttc    4500
accaacatgt ttgccacctg gagccccagc aaggccaggc tgcacctgca gggcaggagc    4560
aatgcctgga ggccccaggt caacaacccc aaggagtggc tgcaggtgga cttccagaag    4620
accatgaagg tgactggggt gaccacccag ggggtgaaga gcctgctgac cagcatgtat    4680
gtgaaggagt tcctgatcag cagcagccag gatggccacc agtggaccct gttcttccag    4740
aatggcaagg tgaaggtgtt ccagggcaac caggacagct tcacccctgt ggtgaacagc    4800 ctggacccc cctgctgac cagatacctg aggattcacc cccagagctg ggtgcaccag    4860
attgccctga ggatggaggt gctgggctgt gaggcccagg acctgtactg acctcgagga    4920
ataaaggaaa tttatttca ttgcaatagt gtgttggttt tttgtgtcac gtggcggccg    4980
caggaacccc tagtgatgga gttggccact ccctctctgc gcgctcgctc gctcactgag    5040
gccgggcgac caaaggtcgc ccgacgcccg ggctttgccc gggcggcctc agtgagcgag    5100
cgagcgcgca gagagggagt ggccaa    5126
```